US011827711B2

(12) United States Patent
Dengl et al.

(10) Patent No.: US 11,827,711 B2
(45) Date of Patent: Nov. 28, 2023

(54) ANTIBODIES BINDING TO NKG2D

(71) Applicant: Hoffmann-La Roche Inc., Little Falls, NJ (US)

(72) Inventors: Stefan Dengl, Geretsried (DE); Guy Georges, Habach (DE); Ralf Hosse, Mettmenstetten (CH); Inja Waldhauer, Urdorf (CH); Christian Klein, Bonstetten (CH); Pablo Umana, Wollerau (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 283 days.

(21) Appl. No.: 16/929,000

(22) Filed: Jul. 14, 2020

(65) Prior Publication Data
US 2021/0032349 A1 Feb. 4, 2021

(30) Foreign Application Priority Data
Jul. 15, 2019 (EP) ..................................... 19186265

(51) Int. Cl.
C07K 16/28 (2006.01)
(52) U.S. Cl.
CPC ...... C07K 16/2851 (2013.01); C07K 16/2809 (2013.01); *C07K 2317/31* (2013.01); *C07K 2317/55* (2013.01); *C07K 2317/565* (2013.01)

(58) Field of Classification Search
CPC ............ C07K 16/2851; C07K 2317/55; C07K 2317/565; C07K 2317/56
USPC .................................................... 424/133.1
See application file for complete search history.

(56) References Cited

FOREIGN PATENT DOCUMENTS

| WO | 00/46251 A2 | 8/2000 |
|---|---|---|
| WO | 01/71005 A2 | 9/2001 |
| WO | 02/12437 A2 | 2/2002 |
| WO | 2005/007696 A2 | 1/2005 |
| WO | 2006/047367 A2 | 5/2006 |
| WO | 2007/019223 | 2/2007 |
| WO | 2008/027986 A2 | 3/2008 |
| WO | 2009/077483 A1 | 6/2009 |
| WO | 2010/017103 A2 | 2/2010 |
| WO | 2016/134371 A2 | 8/2016 |
| WO | 2018/148445 A1 | 8/2018 |
| WO | 2018/148447 A1 | 8/2018 |
| WO | 2018/157147 A1 | 8/2018 |
| WO | 2019/157366 A1 | 8/2019 |

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Hosomi et al (Front Immunol Jun. 18, 2018;9:1324. doi: 10.3389/fimmu.2018.01324. eCollection 2018).*
Banfield, M.J., et al., "VL: VH domain rotations in engineered antibodies: crystal structures of the Fab fragments from two murine antitumor antibodies and their engineered human constructs" Proteins 29(2):161-171 (Oct. 1, 1997).
Bauer et al., "Activation of NK Cells and T Cells by NKG2D, A Receptor for Stress-Inducible MICA" Science 285:727-729 ( 1999).
Haun et al., "Rapid, reliable ligation-independent cloning of PCR products using modified plasmid vectors" Biotechniques 13(4):515-518 (Oct. 1992).
Houchins et al., "DNA Sequence Analysis of NKG2, a Family of Related CDNA Clones Encoding Type II Integral Membrane Proteins on Human Natural Killer Cells" J Exp Med 173:1017-1020 ( 1991).
Kwong et al., "Generation, affinity maturation, and characterization of a human anti-human NKG2D monoclonal antibody with dual antagonistic and agonistic activity" J Mol Biol 384(5):1143-1156 (2008).
Li et al., "Harnessing homologous recombination in vitro to generate recombinant DNA via SLIC" Nature Methods 4(3):251-256 (Mar. 2007).
Pace, C., et al., "How to measure and predict the molar absorption coefficient of a protein" Protein Sci 4(11):2411-2423 (Nov. 1, 1995).
Seeber. S., et al., "A robust high throughput platform to generate functional recombinant monoclonal antibodies using rabbit B cells from peripheral blood" PLOS ONE 9(2):e86184-14 (Feb. 4, 2014).
Steigerwald et al., "Human IgG1 Antibodies Antagonizing Activating Receptor NKG2D on Natural Killer Cells" MAbs 1(2):115-127 (2009).
International Search Report for PCT/EP2020/069813 dated Sep. 14, 2020.
Weiner et al., "Engineered Antibodies to Promote Cytotoxicity and Tumor Inflammation" Targeted Therapy Internet Citation (Nov. 23, 2005).

* cited by examiner

*Primary Examiner* — Lynn A Bristol
(74) *Attorney, Agent, or Firm* — Yan Qi

(57) ABSTRACT

The present invention generally relates to antibodies that bind to NKG2D, including multispecific antigen binding molecules e.g. for activation of T cells and/or NK cells. In addition, the present invention relates to polynucleotides encoding such antibodies, and vectors and host cells comprising such polynucleotides. The invention further relates to methods for producing the antibodies, and to methods of using them in the treatment of disease.

27 Claims, 35 Drawing Sheets
Specification includes a Sequence Listing.

Figure 11

ANTIBODIES BINDING TO NKG2D

CROSS-REFERENCE TO RELATED APPLICATIONS

This application claims priority from European Patent Application No. 19186265.5, filed Jul. 15, 2019, the contents of which are incorporated herein by reference in its entirety.

SEQUENCE LISTING

This application contains a Sequence Listing which has been submitted electronically in ASCII format and is hereby incorporated by reference in its entirety. Said ASCII copy, created on Jul. 8, 2020, is named P35642-US_SeqListing.txt and is 229,310 bytes in size.

FIELD OF THE INVENTION

The present invention generally relates to antibodies that bind to NKG2D, including multispecific antigen binding molecules e.g. for activation of T cells and/or NK cells. In addition, the present invention relates to polynucleotides encoding such antibodies, and vectors and host cells comprising such polynucleotides. The invention further relates to methods for producing the antibodies, and to methods of using them in the treatment of disease.

BACKGROUND

Cancer immunotherapy is a very active area of research and cancer immunotherapies are now being used to treat many different types of cancer. Despite promising clinical results that were obtained with immune checkpoint inhibitors, still only a low percentage of patients respond to these novel therapies. This clearly demonstrates a high need for novel and differentiated therapeutic approaches activating the immune system, beyond checkpoint inhibition, to improve clinical benefit of a greater number of patients with advanced cancer.

NKG2D is an activating receptor expressed on cytotoxic effector cells described for the first time in 1991 (Houchnins et al. (1991) J Exp Med 173, 1017-1020). It has no own signaling motif in the cytoplasmic tail but associates via charged amino acids with the adapter protein DNAX activating protein of 10 kDa (DAP10). DAP10 has a cytoplasmic YxxM motif which recruits phosphatidylinositol 3-kinase (PI3K) after phosphorylation at its tyrosine residue eventually resulting in the activation of NK cells, cytotoxicity and CD8 T cell co-stimulation. NKG2D is constitutively expressed on almost all NK cells, CD8 T cells, γδ T cells and on a subset of NKT cells but not in normal tissues (Bauer et al. (1999) Science 285, 727-729). NKG2D expression can be modulated by different cytokines; IL-2 and IL-15 induce upregulation whereas TGFβ and IL-21 were shown to down-modulate NKG2D. Also on tumor infiltrating lymphocytes NKG2D can be detected.

NKG2D serves as a sensor for transformed cells via the upregulation of NKG2D ligands (NKG2DL). Many viruses and tumors have developed mechanisms to evade the sensing via NKG2D, suggesting that this receptor plays an important role in the immunosurveillance of tumors and virus infections and making it a compelling target for cancer immunotherapy.

An anti-NKG2D antibody with dual antagonistic and agonistic activity, KYK-2.0, has been reported by Kwong et al. (Kwong et al. (2008) J Mol Biol 384, 1143-1156; WO 2010/017103). A bispecific antibody derived therefrom has been reported in WO 2016/134371. Trispecific antibodies targeting NKG2D, CD16 and a tumor-associated antigen have been reported e.g. in WO 2018/148445.

There remains a need, however, for antibodies targeting NKG2D with improved efficacy and/or safety, e.g. for use in cancer immunotherapy.

SUMMARY OF THE INVENTION

The present invention provides novel antibodies, including multispecific antibodies, that bind NKG2D and have particularly favorable properties for therapeutic purposes.

The present inventors have developed novel antibodies with unexpected, improved properties, that bind to NKG2D. For example, the antibodies bind to NKG2D—both human and cynomolgus monkey—with high affinity, and specifically show binding to as well as agonistic activity (i.e. activation or co-stimulation) on NKG2D-expressing immune cells. The invention also encompasses multispecific antigen binding molecules that bind to NKG2D and a second antigen, incorporating the novel NKG2D antibodies and combining good efficacy and produceability with low toxicity and favorable pharmacokinetic properties. These (multispecific) antibodies may be used for therapeutic purposes, particularly in the therapy of cancer, specifically cancer immunotherapy. Importantly, (multispecific) antibodies of the invention are particularly suitable for combining with other immunotherapeutic agents, such as T-cell activating agents.

In a first aspect the present invention provides an antibody that binds to NKG2D, wherein the antibody comprises a first antigen binding domain, comprising (i) a heavy chain variable region (VH) comprising a heavy chain complementary determining region (HCDR) 1 of SEQ ID NO: 73, a HCDR 2 selected from the group consisting of SEQ ID NO: 74, SEQ ID NO: 102, SEQ ID NO: 103, SEQ ID NO: 104 and SEQ ID NO: 105, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78;

(ii) a VH comprising a HCDR 1 of SEQ ID NO: 65, a HCDR 2 of SEQ ID NO: 66, and a HCDR 3 of SEQ ID NO: 67, and a VL comprising a LCDR 1 of SEQ ID NO: 68, a LCDR 2 of SEQ ID NO: 69 and a LCDR 3 of SEQ ID NO: 70;

(iii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;

(iv) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;

(v) a VH comprising a HCDR 1 of SEQ ID NO: 49, a HCDR 2 of SEQ ID NO: 50, and a HCDR 3 of SEQ ID NO: 51, and a VL comprising a LCDR 1 of SEQ ID NO: 52, a LCDR 2 of SEQ ID NO: 53 and a LCDR 3 of SEQ ID NO: 54;

(vi) a VH comprising a HCDR 1 of SEQ ID NO: 57, a HCDR 2 of SEQ ID NO: 58, and a HCDR 3 of SEQ ID NO: 59, and a VL comprising a LCDR 1 of SEQ ID NO: 60, a LCDR 2 of SEQ ID NO: 61 and a LCDR 3 of SEQ ID NO: 62;

(vii) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;

(viii) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22;

(ix) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38; or (x) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46.

In one aspect, the present invention provides an antibody that binds to NKG2D, wherein the antibody comprises a first antigen binding domain, comprising (i) a VH comprising an amino acid sequence that is at least about 95%, 96%, 97%, 98%, 99% or 100% identical to an amino acid sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, and/or a VL comprising an amino acid sequence that is at least about 95%, 96%, 97%, 98%, 99% or 100% identical to the amino acid sequence of SEQ ID NO: 80;

(ii) a VH comprising an amino acid sequence that is at least about 95%, 96%, 97%, 98%, 99% or 100% identical to the amino acid sequence of SEQ ID NO: 71, and/or a VL comprising an amino acid sequence that is at least about 95%, 96%, 97%, 98%, 99% or 100% identical to the amino acid sequence of SEQ ID NO: 72;

(iii) a VH comprising an amino acid sequence that is at least about 95%, 96%, 97%, 98%, 99% or 100% identical to the amino acid sequence of SEQ ID NO: 7, and/or a VL comprising an amino acid sequence that is at least about 95%, 96%, 97%, 98%, 99% or 100% identical to the amino acid sequence of SEQ ID NO: 8;

(iv) a VH comprising an amino acid sequence that is at least about 95%, 96%, 97%, 98%, 99% or 100% identical to the amino acid sequence of SEQ ID NO: 31, and/or a VL comprising an amino acid sequence that is at least about 95%, 96%, 97%, 98%, 99% or 100% identical to the amino acid sequence of SEQ ID NO: 32;

(v) a VH comprising an amino acid sequence that is at least about 95%, 96%, 97%, 98%, 99% or 100% identical to the amino acid sequence of SEQ ID NO: 55, and/or a VL comprising an amino acid sequence that is at least about 95%, 96%, 97%, 98%, 99% or 100% identical to the amino acid sequence of SEQ ID NO: 56;

(vi) a VH comprising an amino acid sequence that is at least about 95%, 96%, 97%, 98%, 99% or 100% identical to the amino acid sequence of SEQ ID NO: 63, and/or a VL comprising an amino acid sequence that is at least about 95%, 96%, 97%, 98%, 99% or 100% identical to the amino acid sequence of SEQ ID NO: 64;

(vii) a VH comprising an amino acid sequence that is at least about 95%, 96%, 97%, 98%, 99% or 100% identical to the amino acid sequence of SEQ ID NO: 15, and/or a VL comprising an amino acid sequence that is at least about 95%, 96%, 97%, 98%, 99% or 100% identical to the amino acid sequence of SEQ ID NO: 16;

(viii) a VH comprising an amino acid sequence that is at least about 95%, 96%, 97%, 98%, 99% or 100% identical to the amino acid sequence of SEQ ID NO: 23, and/or a VL comprising an amino acid sequence that is at least about 95%, 96%, 97%, 98%, 99% or 100% identical to the amino acid sequence of SEQ ID NO: 24;

(ix) a VH comprising an amino acid sequence that is at least about 95%, 96%, 97%, 98%, 99% or 100% identical to the amino acid sequence of SEQ ID NO: 39, and/or a VL comprising an amino acid sequence that is at least about 95%, 96%, 97%, 98%, 99% or 100% identical to the amino acid sequence of SEQ ID NO: 40; or (x) a VH comprising an amino acid sequence that is at least about 95%, 96%, 97%, 98%, 99% or 100% identical to the amino acid sequence of SEQ ID NO: 47, and/or a VL comprising an amino acid sequence that is at least about 95%, 96%, 97%, 98%, 99% or 100% identical to the amino acid sequence of SEQ ID NO: 48.

In one aspect, the antibody is an IgG, particularly an IgG$_1$, antibody. In one embodiment, the antibody is a full-length antibody. In another aspect, the antibody is an antibody fragment selected from the group of an Fv molecule, a scFv molecule, a Fab molecule, and a F(ab')$_2$ molecule.

In one aspect, the antibody is a multispecific, particularly a bispecific, antibody. In one aspect, the antibody comprises a second antigen binding domain that binds to a second antigen. In one aspect, the second antigen is a target cell antigen, particularly a tumor cell antigen.

In one aspect, the antibody comprises an Fc domain composed of a first and a second subunit. In one aspect, the Fc domain is an IgG, particularly an IgG$_1$, Fc domain. In one aspect the Fc domain is a human Fc domain. In one aspect, the Fc domain comprises one or more amino acid substitution that reduces binding to an Fc receptor and/or effector function. In one aspect, the antibody does not bind to FcγRIIIa (CD16a).

In one aspect, the first and/or the second antigen binding domain is a Fab molecule.

In some aspects, the first antigen binding domain is a Fab molecule wherein the variable domains VL and VH or the constant domains CL and CH1, particularly the variable domains VL and VH, of the Fab light chain and the Fab heavy chain are replaced by each other. In one such aspect, the second antigen binding domain is a conventional Fab molecule. In a further such aspect, the second antigen binding domain is a Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In alternative aspects, the second antigen binding domain is a Fab molecule wherein the variable domains VL and VH or the constant domains CL and CH1, particularly the variable domains VL and VH, of the Fab light chain and the Fab heavy chain are replaced by each other. In one such aspect the first antigen binding domain is a conventional Fab molecule. In a further such aspect, the first antigen binding domain is a Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one aspect, the first and the second antigen binding domain are each a Fab molecule and the antibody comprises an Fc domain composed of a first and a second subunit; and either (i) the first antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or (ii) the second antigen binding domain is fused at the C-terminus of the Fab heavy chain to the N-terminus of the first subunit of the Fc domain and the first antigen binding domain is fused at the C-terminus of the Fab heavy chain to the N-terminus of the second subunit of the Fc domain.

In one aspect, the Fc domain comprises a modification promoting the association of the first and the second subunit of the Fc domain. In one aspect, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable.

According to a further aspect of the invention there is provided an isolated polynucleotide encoding an antibody of the invention, and a host cell comprising the isolated polynucleotide of the invention. In another aspect is provided a method of producing an antibody that binds to NKG2D, comprising the steps of (a) culturing the host cell of the invention under conditions suitable for the expression of the antibody and optionally (b) recovering the antibody. The invention also encompasses an antibody that binds to NKG2D produced by the method of the invention.

The invention further provides a pharmaceutical composition comprising the antibody of the invention and a pharmaceutically acceptable carrier.

Also encompassed by the invention are methods of using the antibody and pharmaceutical composition of the invention. In one aspect, the invention provides an antibody or pharmaceutical composition according to the invention for use as a medicament. In one aspect is provided an antibody or pharmaceutical composition according to the invention for use in the treatment of a disease. In a specific aspect, the disease is cancer. In a specific aspect, the use is in combination with a T-cell activating agent, such as an antibody that binds to CD3, particularly a bispecific antibody that binds to CD3 and a target cell antigen, particularly a tumor cell antigen.

Also provided is the use of an antibody or pharmaceutical composition according to the invention in the manufacture of a medicament, the use of an antibody or pharmaceutical composition according to the invention in the manufacture of a medicament for the treatment of a disease, particularly cancer. In a specific aspect, the treatment is in combination with a T-cell activating agent, such as an antibody that binds to CD3, particularly a bispecific antibody that binds to CD3 and a target cell antigen, particularly a tumor cell antigen. The invention also provides a method of treating a disease, particularly cancer, in an individual, comprising administering to said individual an effective amount of the antibody or pharmaceutical composition according to the invention. In a specific aspect, the method further comprises administration of a T-cell activating agent, such as an antibody that binds to CD3, particularly a bispecific antibody that binds to CD3 and a target cell antigen, particularly a tumor cell antigen.

BRIEF DESCRIPTION OF THE DRAWINGS

FIG. 11. Alignment of humanized VH-domains of anti-NKG2D antibody 395 (i.e., P1AE4973, SEQ ID NO: 107; P1AE4975, SEQ ID NO: 108; P1AE4977, SEQ ID NO: 109; P1AE4978, SEQ ID NO: 110; P1AE4979, SEQ ID NO: 111; P1AE4980, SEQ ID NO: 112; and P1AE4981, SEQ ID NO: 113) in comparison to non-humanized parental rabbit sequence 395 (P1AE4972, SEQ ID NO: 106) with the unpaired cysteine in HCDR2 replaced by a serine (position indicated by asterisk).

DETAILED DESCRIPTION OF THE INVENTION

I. Definitions

Figure 1:
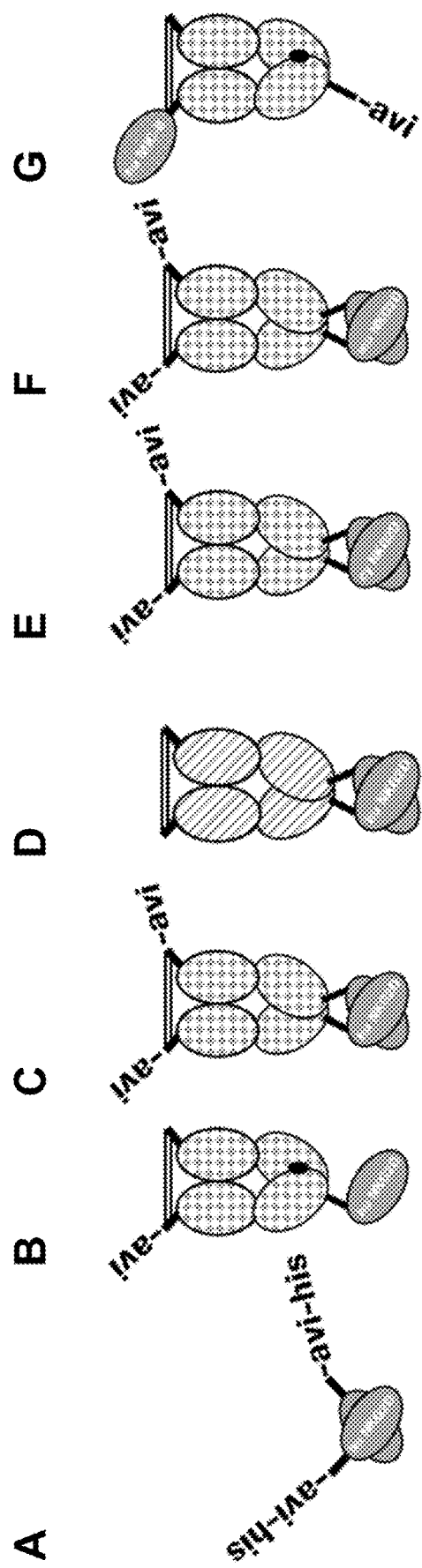
FIG. 1. Schematic illustration of NKG2D receptors and MIC-B ligand constructed in Example 1. NKG2D receptors and MIC-B ligand were cloned with or without fusion to a human or murine Fc domain as monomers ('mono') or dimers ('di') with respect to the receptor or ligand portion of the construct. All constructs, except for di huNKG2D ECD mu IgG1 Fc, carry at least one avi-tag for site-directed biotinylation. (A) his avi huNKG2D ECD, (B) mono huNKG2D ECD Fc kh avi, (C) di huNKG2D ECD Fc avi, (D) di huNKG2D ECD mu IgG1 Fc, (E) di cyNKG2D ECD Fc avi, (F) di muNKG2D ECD Fc avi, (G) ECD FL MIC-B Fc avi.

Terms are used herein as generally used in the art, unless otherwise defined in the following.

As used herein, the terms "first", "second" or "third" with respect to antigen binding domains etc., are used for convenience of distinguishing when there is more than one of each type of moiety. Use of these terms is not intended to confer a specific order or orientation of the moiety unless explicitly so stated.

The terms "anti-NKG2D antibody" and "an antibody that binds to NKG2D" refer to an antibody that is capable of binding NKG2D with sufficient affinity such that the antibody is useful as a diagnostic and/or therapeutic agent in targeting NKG2D. In one aspect, the extent of binding of an anti-NKG2D antibody to an unrelated, non-NKG2D protein is less than about 10% of the binding of the antibody to NKG2D as measured, e.g., by surface plasmon resonance (SPR). In certain aspects, an antibody that binds to NKG2D has a dissociation constant ($K_D$) of ≤1 μM, ≤500 nM, ≤200 nM, or ≤100 nM. An antibody is said to "specifically bind" to NKG2D when the antibody has a $K_D$ of 1 μM or less, as measured, e.g., by SPR. In certain aspects, an anti-NKG2D antibody binds to an epitope of NKG2D that is conserved among NKG2D from different species.

Conversely, an antibody that "does not bind" to a certain antigen is not capable of binding said antigen with sufficient affinity such that the antibody is useful as a diagnostic and/or therapeutic agent in targeting said antigen. In certain aspects, an antibody that does not bind to a certain antigen has a dissociation constant ($K_D$) of >1 μM to said antigen.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv and scFab), single-domain antibodies, and multispecific antibodies formed from antibody fragments. For a review of certain antibody fragments, see Hollinger and Hudson, Nature Biotechnology 23:1126-1136 (2005).

The terms "full-length antibody," "intact antibody," and "whole antibody" are used herein interchangeably to refer to an antibody having a structure substantially similar to a native antibody structure.

The term "monoclonal antibody" as used herein refers to an antibody obtained from a population of substantially homogeneous antibodies, i.e. the individual antibodies comprised in the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "isolated" antibody is one which has been separated from a component of its natural environment. In some aspects, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC, affinity chromatography, size exclusion chromatography) methods. For review of methods for assessment of antibody purity, see, e.g., Flatman et al., *J. Chromatogr. B* 848:79-87 (2007). In some aspects, the antibodies provided by the present invention are isolated antibodies.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. Such variable domains are referred to herein as "humanized variable region". A humanized antibody optionally may comprise at least a portion of an antibody constant region derived from a human antibody. In some aspects, some FR residues in a humanized antibody are substituted with corresponding residues from a non-human antibody (e.g., the antibody from which the CDR residues are derived), e.g., to restore or improve antibody specificity or affinity. A "humanized form" of an antibody, e.g. of a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. In certain aspects, a human antibody is derived from a non-human transgenic mammal, for example a mouse, a rat, or a rabbit. In certain aspects, a human antibody is derived from a hybridoma cell line. Antibodies or antibody fragments isolated from human antibody libraries are also considered human antibodies or human antibody fragments herein.

The term "antigen binding domain" refers to the part of an antibody that comprises the area which binds to and is complementary to part or all of an antigen. An antigen binding domain may be provided by, for example, one or more antibody variable domains (also called antibody variable regions). In preferred aspects, an antigen binding domain comprises an antibody light chain variable domain (VL) and an antibody heavy chain variable domain (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and complementarity determining regions (CDRs). See, e.g., Kindt et al., *Kuby Immunology*, 6$^{th}$ ed., W.H. Freeman & Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991). As used herein in connection with variable region sequences, "Kabat numbering" refers to the numbering system set forth by Kabat et al., *Sequences of Proteins of Immunological Interest*, 5th Ed. Public Health Service, National Institutes of Health, Bethesda, MD (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991), referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, MD (1991)) is used for the light chain constant domain CL of kappa and lambda isotype and the Kabat EU index numbering system (see pages 661-723) is used for the heavy chain constant domains (CH1, hinge, CH2 and CH3), which is herein further clarified by referring to "numbering according to Kabat EU index" or "Kabat EU index numbering" in this case.

The term "hypervariable region" or "HVR", as used herein, refers to each of the regions of an antibody variable domain which are hypervariable in sequence and which determine antigen binding specificity, for example "complementarity determining regions" ("CDRs"). Generally, antibodies comprise six CDRs; three in the VH (HCDR1, HCDR2, HCDR3), and three in the VL (LCDR1, LCDR2, LCDR3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

"Framework" or "FR" refers to variable domain residues other than complementarity determining regions (CDRs). The FR of a variable domain generally consists of four FR domains: FR1, FR2, FR3, and FR4. Accordingly, the HVR and FR sequences generally appear in the following order in VH (or VL): FR1-HCDR1(LCDR1)-FR2-HCDR2 (LCDR2)-FR3-HCDR3(LCDR3)-FR4.

Unless otherwise indicated, CDR residues and other residues in the variable domain (e.g., FR residues) are numbered herein according to Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some aspects, the number of amino acid changes is 10 or less, 9 or less, 8 or less, 7 or less, 6 or less, 5 or less, 4 or less, 3 or less, or 2 or less. In some aspects, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3.

The term "immunoglobulin molecule" herein refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ ($IgG_1$), $\gamma_2$ ($IgG_2$), $\gamma_3$ ($IgG_3$), $\gamma_4$ ($IgG_4$), $\alpha_1$ ($IgA_1$) and $\alpha_2$ ($IgA_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

A "Fab molecule" refers to a protein consisting of the VH and CH1 domain of the heavy chain (the "Fab heavy chain") and the VL and CL domain of the light chain (the "Fab light chain") of an immunoglobulin.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and alight chain composed of the light chain variable and constant domains (VL-CL, in N- to C-terminal direction).

The term "Fc domain" or "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (Lys447), of the Fc region may or may not be present. Amino acid sequences of heavy chains including an Fc region (or a subunit of an Fc domain as defined herein) are denoted herein without C-terminal glycine-lysine dipeptide if not indicated otherwise. In one aspect, a heavy chain including an Fc region (subunit) as specified herein, comprised in an antibody according to the invention, comprises an additional C-terminal glycine-lysine dipeptide (G446 and K447, numbering according to Kabat EU index). In one aspect, a heavy chain including an Fc region (subunit) as specified herein, comprised in an antibody according to the invention, comprises an additional C-terminal glycine residue (G446, numbering according to Kabat EU index). Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, M D, 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

By "fused" is meant that the components (e.g. a Fab molecule and an Fc domain subunit) are linked by peptide bonds, either directly or via one or more peptide linkers.

The term "multispecific" means that the antibody is able to specifically bind to at least two distinct antigenic determinants. A multispecific antibody can be, for example, a bispecific antibody. Typically, a bispecific antibody comprises two antigen binding sites, each of which is specific for a different antigenic determinant. In certain aspects the multispecific (e.g. bispecific) antibody is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigenic determinant" or "antigen" refers to a site (e.g. a contiguous stretch of amino acids or a conformational configuration made up of different regions of non-contiguous amino acids) on a polypeptide macromolecule to which an antigen binding domain binds, forming an antigen binding domain-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). In a preferred aspect, the antigen is a human protein.

"NKG2D" refers to any native NKG2D from any vertebrate source, including mammals such as primates (e.g. humans), non-human primates (e.g. cynomolgus monkeys) and rodents (e.g. mice and rats), unless otherwise indicated. The term encompasses "full-length," unprocessed NKG2D as well as any form of NKG2D that results from processing in the cell. The term also encompasses naturally occurring variants of NKG2D, e.g., splice variants or allelic variants. In one aspect, NKG2D is human NKG2D, particularly the extracellular domain (ECD) of human NKG2D. The amino acid sequence of human NKG2D and its ECD are shown in SEQ ID NO: 87 and SEQ ID NO: 88, respectively. See also UniProt (www.uniprot.org) entry P26718 (version 176). In another aspect, NKG2D is cynomolgus (*Macaca fascicularis*) NKG2D, particularly the ECD of cynomolgus NKG2D. The amino acid sequence of cynomolgus NKG2D and its ECD are shown in SEQ ID NO: 89 and SEQ ID NO: 90, respectively. See also UniProt entry P61252 (version 71). In another aspect, NKG2D is murine (*Mus musculus*) NKG2D, particularly the ECD of murine NKG2D. The amino acid sequence of murine NKG2D and its ECD are shown in SEQ ID NO: 91 and SEQ ID NO: 92, respectively. See also UniProt entry O54709 (version 151). In certain aspects the antibody of the invention binds to an epitope of NKG2D that is conserved among the NKG2D antigens from different species, particularly human and cynomolgus NKG2D. In preferred aspects, the antibody binds to human NKG2D. In one aspect the first antigen binding domain is cross-reactive for (i.e. binds to) human and cynomolgus NKG2D.

A "target cell antigen" as used herein refers to an antigenic determinant presented on the surface of a target cell, for example a cell in a tumor such as a cancer cell or a cell of the tumor stroma (in that case a "tumor cell antigen"). Preferably, the target cell antigen is not NKG2D, and/or is expressed on a different cell than NKG2D. In one aspect, the target cell antigen is CEA.

"CEA" stands for carcinoembryonic antigen (also known as Carcinoembryonic antigen-related cell adhesion molecule 5 (CEACAM5)). The amino acid sequence of human CEA is shown in UniProt entry P06731 (version 188). "CEA" as used herein refers to any native CEA from any vertebrate source, including mammals such as primates (e.g. humans), non-human primates (e.g. cynomolgus monkeys) and rodents (e.g. mice and rats), unless otherwise indicated. The term encompasses "full-length," unprocessed CEA as well as any form of CEA that results from processing in the cell. The term also encompasses naturally occurring variants of CEA, e.g., splice variants or allelic variants. In one aspect, CEA is human CEA. In one aspect, CEA is cell membrane-bound CEA. In one aspect, CEA is CEA expressed on the surface of a cell, e.g. a cancer cell.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., an antibody and an antigen). The affinity of a molecule X for its partner Y can generally be represented by the dissociation constant ($K_D$). Affinity can be measured by well-established methods known in the art, including those described herein. A preferred method for measuring affinity is Surface Plasmon Resonance (SPR).

An "affinity matured" antibody refers to an antibody with one or more alterations in one or more complementary determining regions (CDRs), compared to a parent antibody which does not possess such alterations, such alterations resulting in an improvement in the affinity of the antibody for antigen.

"Reduced binding", for example reduced binding to an Fc receptor, refers to a decrease in affinity for the respective interaction, as measured for example by SPR. For clarity, the term includes also reduction of the affinity to zero (or below the detection limit of the analytic method), i.e. complete abolishment of the interaction. Conversely, "increased binding" refers to an increase in binding affinity for the respective interaction.

"T-cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art and described herein.

A "T-cell activating agent" as used herein refers to a molecule that is capable of inducing T cell activation, for example by binding to and activating (a component of) a T-cell receptor such as CD3. Accordingly, an exemplary T-cell activating agent may be an antibody that binds to CD3, particularly the epsilon subunit of CD3. A particular T-cell activating agent useful in the present invention is a bispecific antibody that binds to CD3 and a target cell antigen, such as a tumor cell antigen. Such T-cell activating bispecific antibody is also referred to herein as "T-cell bispecific antibody" or "TCB".

"CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one aspect, CD3 is human CD3, particularly the epsilon subunit of human CD3 (CD3ε). The amino acid sequence of human CD3ε is shown in UniProt (www.uniprot.org) entry P07766 (version 202). In another aspect, CD3 is cynomolgus (*Macaca fascicularis*) CD3, particularly cynomolgus CD3ε. The amino acid sequence of cynomolgus CD3ε is shown in NCBI GenBank no. BAB71849.1. In certain aspects a T-cell activating agent useful in the present invention binds to an epitope of CD3 that is conserved among the CD3 antigens from different species, particularly human and cynomolgus CD3. In preferred aspects, the T-cell activating agent binds to human CD3.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein preferably includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which may be non-identical in the sense that further components fused to each of the subunits (e.g. antigen binding domains) are not the same. In some aspects, the modification promoting the association of the first and the second subunit of the Fc domain comprises an amino acid mutation in the Fc domain, specifically an amino acid substitution. In a preferred aspect, the modification promoting the association of the first and the second subunit of the Fc domain comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89). In one aspect, the activating Fc receptor is FcγRIIIa (CD16a). Human FcγRIIIa (CD16a) including its sequence is described in UniProt entry P08637 (version 203).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example, the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Preferred amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, % amino acid sequence identity values are generated using the ggsearch program of the FASTA package version 36.3.8c or later with a BLOSUM50 comparison matrix. The FASTA program package was authored by W. R. Pearson and D. J. Lipman ("Improved Tools for Biological Sequence Analysis", PNAS 85 (1988) 2444-2448), W. R. Pearson ("Effective protein sequence comparison" Meth. Enzymol. 266 (1996) 227-258), and Pearson et. al. (Genomics 46 (1997) 24-36) and is publicly available from www.fasta.bioch.virginia.edu/fasta_www2/fasta_down.shtml or www.ebi.ac.uk/Tools/sss/fasta. Alternatively, a public server accessible at fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "polynucleotide" or "nucleic acid molecule" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al. (2017) Nature Medicine 23:815-817, or EP 2 101 823 B1).

An "isolated" nucleic acid molecule refers to a nucleic acid molecule that has been separated from a component of its natural environment. An isolated nucleic acid molecule includes a nucleic acid molecule contained in cells that ordinarily contain the nucleic acid molecule, but the nucleic acid molecule is present extrachromosomally or at a chromosomal location that is different from its natural chromosomal location.

"Isolated polynucleotide (or nucleic acid) encoding an antibody" refers to one or more polynucleotide molecules encoding antibody heavy and light chains (or fragments thereof), including such polynucleotide molecule(s) in a single vector or separate vectors, and such polynucleotide molecule(s) present at one or more locations in a host cell.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antibodies of the present invention. Host cells include cultured cells, e.g. mammalian cultured cells, such as HEK cells, CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. In one aspect, the host cell of the invention is a eukaryotic cell, particularly a mammalian cell. In one aspect, the host cell is not a cell within a human body.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, antibodies of the invention are used to delay development of a disease or to slow the progression of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). In certain aspects, the individual or subject is a human.

An "effective amount" of an agent, e.g., a pharmaceutical composition, refers to an amount effective, at dosages and for periods of time necessary, to achieve the desired therapeutic or prophylactic result.

The term "package insert" is used to refer to instructions customarily included in commercial packages of therapeutic products, that contain information about the indications, usage, dosage, administration, combination therapy, contraindications and/or warnings concerning the use of such therapeutic products.

II. Compositions and Methods

The invention provides antibodies that bind NKG2D, including multispecific antibodies that bind NKG2D and a second antigen. The antibodies show superior binding and agonistic activity on NKG2D, combined with other favorable properties for therapeutic application, e.g. with respect to efficacy and safety, pharmacokinetics, as well as produceability. Antibodies of the invention are useful, e.g., for the treatment of diseases such as cancer.

The antibodies of the invention are particularly useful for (co-)stimulation of cytotoxic T cells, e.g. in combination with a T-cell activating agent such as a T cell bispecific antibody (TCB). The antibodies of the invention can also efficiently activate other NKG2D-expressing immune cells, such as natural killer (NK) cells and γδ T cells, even without the need for simultaneous stimulation through an activating Fc receptor such as FcγRIIIa (CD16a). Through avoiding the need for Fc receptor binding and activation for their function, the antibodies of the present invention are believed to enable efficient immune cell activation, with a smaller risk of systemic side effects than an NKG2D antibody requiring Fc receptor binding and activation for its function. The antibodies of the present invention can also be used in multispecific format, binding to NKG2D and a target cell antigen (e.g. a tumor antigen) to achieve targeted immune cell activation, but without also binding to an activating Fc receptor (particularly FcγRIIIa (CD16a)) to reduce the risk of systemic side effects.

A. Anti-NKG2D Antibodies

The invention provides antibodies that bind to NKG2D.

In a first aspect the present invention provides an antibody that binds to NKG2D, wherein the antibody comprises a first antigen binding domain, comprising (i) a heavy chain variable region (VH) comprising a heavy chain complementarity determining region (HCDR) 1 of SEQ ID NO: 73, a HCDR 2 selected from the group consisting of SEQ ID NO: 74, SEQ ID NO: 102, SEQ ID NO: 103, SEQ ID NO: 104 and SEQ ID NO: 105, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78;

(ii) a VH comprising a HCDR 1 of SEQ ID NO: 65, a HCDR 2 of SEQ ID NO: 66, and a HCDR 3 of SEQ ID NO: 67, and a VL comprising a LCDR 1 of SEQ ID NO: 68, a LCDR 2 of SEQ ID NO: 69 and a LCDR 3 of SEQ ID NO: 70;

(iii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;

(iv) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;

(v) a VH comprising a HCDR 1 of SEQ ID NO: 49, a HCDR 2 of SEQ ID NO: 50, and a HCDR 3 of SEQ ID NO: 51, and a VL comprising a LCDR 1 of SEQ ID NO: 52, a LCDR 2 of SEQ ID NO: 53 and a LCDR 3 of SEQ ID NO: 54;

(vi) a VH comprising a HCDR 1 of SEQ ID NO: 57, a HCDR 2 of SEQ ID NO: 58, and a HCDR 3 of SEQ ID NO: 59, and a VL comprising a LCDR 1 of SEQ ID NO: 60, a LCDR 2 of SEQ ID NO: 61 and a LCDR 3 of SEQ ID NO: 62;

(vii) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;

(viii) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22;

(ix) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38; or (x) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46.

In one aspect, the present invention provides an antibody that binds to NKG2D, wherein the antibody comprises a first antigen binding domain, comprising (i) a VH comprising an amino acid sequence that is at least about 95%, 96%, 97%, 98%, 99% or 100% identical to an amino acid sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, and/or a VL comprising an amino acid sequence that is at least about 95%, 96%, 97%, 98%, 99% or 100% identical to the amino acid sequence of SEQ ID NO: 80;

(ii) a VH comprising an amino acid sequence that is at least about 95%, 96%, 97%, 98%, 99% or 100% identical to the amino acid sequence of SEQ ID NO: 71, and/or a VL comprising an amino acid sequence that is at least about 95%, 96%, 97%, 98%, 99% or 100% identical to the amino acid sequence of SEQ ID NO: 72;

(iii) a VH comprising an amino acid sequence that is at least about 95%, 96%, 97%, 98%, 99% or 100% identical to the amino acid sequence of SEQ ID NO: 7, and/or a VL comprising an amino acid sequence that is at least about 95%, 96%, 97%, 98%, 99% or 100% identical to the amino acid sequence of SEQ ID NO: 8;

(iv) a VH comprising an amino acid sequence that is at least about 95%, 96%, 97%, 98%, 99% or 100% identical to the amino acid sequence of SEQ ID NO: 31, and/or a VL comprising an amino acid sequence that is at least about 95%, 96%, 97%, 98%, 99% or 100% identical to the amino acid sequence of SEQ ID NO: 32;

(v) a VH comprising an amino acid sequence that is at least about 95%, 96%, 97%, 98%, 99% or 100% identical to the amino acid sequence of SEQ ID NO: 55, and/or a VL comprising an amino acid sequence that is at least about 95%, 96%, 97%, 98%, 99% or 100% identical to the amino acid sequence of SEQ ID NO: 56;

(vi) a VH comprising an amino acid sequence that is at least about 95%, 96%, 97%, 98%, 99% or 100% identical to the amino acid sequence of SEQ ID NO: 63, and/or a VL comprising an amino acid sequence that is at least about 95%, 96%, 97%, 98%, 99% or 100% identical to the amino acid sequence of SEQ ID NO: 64;

(vii) a VH comprising an amino acid sequence that is at least about 95%, 96%, 97%, 98%, 99% or 100% identical to the amino acid sequence of SEQ ID NO: 15, and/or a VL comprising an amino acid sequence that is at least about 95%, 96%, 97%, 98%, 99% or 100% identical to the amino acid sequence of SEQ ID NO: 16;

(viii) a VH comprising an amino acid sequence that is at least about 95%, 96%, 97%, 98%, 99% or 100% identical to the amino acid sequence of SEQ ID NO: 23, and/or a VL comprising an amino acid sequence that is at least about 95%, 96%, 97%, 98%, 99% or 100% identical to the amino acid sequence of SEQ ID NO: 24;

(ix) a VH comprising an amino acid sequence that is at least about 95%, 96%, 97%, 98%, 99% or 100% identical to the amino acid sequence of SEQ ID NO: 39, and/or a VL comprising an amino acid sequence that is at least about 95%, 96%, 97%, 98%, 99% or 100% identical to the amino acid sequence of SEQ ID NO: 40; or (x) a VH comprising an amino acid sequence that is at least about 95%, 96%, 97%, 98%, 99% or 100% identical to the amino acid sequence of SEQ ID NO: 47, and/or a VL comprising an amino acid sequence that is at least about 95%, 96%, 97%, 98%, 99% or 100% identical to the amino acid sequence of SEQ ID NO: 48.

In one aspect, the antibody comprises a first antigen binding domain, comprising
a heavy chain variable region (VH) comprising a heavy chain complementary determining region (HCDR) 1 of SEQ ID NO: 73, a HCDR 2 selected from the group consisting of SEQ ID NO: 74, SEQ ID NO: 102, SEQ ID NO: 103, SEQ ID NO: 104 and SEQ ID NO: 105, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78.

In one aspect, the antibody comprises a first antigen binding domain, comprising
a heavy chain variable region (VH) comprising a heavy chain complementary determining region (HCDR) 1 of SEQ ID NO: 73, a HCDR 2 of SEQ ID NO: 74, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78.

In one aspect, the antibody comprises a first antigen binding domain, comprising
a heavy chain variable region (VH) comprising a heavy chain complementary determining region (HCDR) 1 of SEQ ID NO: 73, a HCDR 2 of SEQ ID NO: 102, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78.

In a particular aspect, the antibody comprises a first antigen binding domain, comprising
a heavy chain variable region (VH) comprising a heavy chain complementary determining region (HCDR) 1 of SEQ ID NO: 73, a HCDR 2 of SEQ ID NO: 104, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78.

In one aspect, the antibody is a humanized antibody. In one aspect, the antigen binding domain is a humanized antigen binding domain (i.e. an antigen binding domain of a humanized antibody). In one aspect, the VH and/or the VL is a humanized variable region. In one aspect, the VH is a humanized variable region and the VL is a human variable region.

In one aspect, the VH and/or the VL comprises an acceptor human framework, e.g. a human immunoglobulin framework or a human consensus framework.

In one aspect, the VH comprises one or more heavy chain framework sequence (i.e. the FR1, FR2, FR3 and/or FR4 sequence) of a heavy chain variable region sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly a heavy chain variable region sequence selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the heavy chain variable region sequence of SEQ ID NO: 112. In one aspect, the VH comprises an amino acid sequence that is at least about 95%, 96%, 97%, 98%, or 99% identical to an amino acid sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly an amino acid sequence selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the amino acid sequence of SEQ ID NO: 112. In one aspect, the VH comprises an amino acid sequence that is at least about 95% identical to an amino acid sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly an amino acid sequence selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the amino acid sequence of SEQ ID NO: 112. In one aspect, the VH comprises an amino acid sequence that is at least about 98% identical to an amino acid sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly an amino acid sequence selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the amino acid sequence of SEQ ID NO: 112. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to NKG2D. In certain aspects, a total of 1 to 10 amino acids have been substituted, inserted and/or deleted in the amino acid sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly the amino acid sequence selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the amino acid sequence of SEQ ID NO: 112. In certain aspects, substitutions, insertions, or deletions occur in regions outside the CDRs (i.e., in the FRs). In one aspect, the VH comprises an amino acid sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly an amino acid sequence selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the amino acid sequence of SEQ ID NO: 112. Optionally, the VH comprises an amino acid sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly an amino acid sequence selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the amino acid sequence of SEQ ID NO: 112, including post-translational modifications of that sequence.

In one aspect, the VL comprises one or more light chain framework sequence (i.e. the FR1, FR2, FR3 and/or FR4 sequence) of the light chain variable region sequence of SEQ ID NO: 80. In one aspect, the VL comprises an amino acid sequence that is at least about 95%, 96%, 97%, 98%, or 99% identical to the amino acid sequence of SEQ ID NO: 80. In one aspect, the VL comprises an amino acid sequence that is at least about 95% identical to the amino acid sequence of SEQ ID NO: 80. In one aspect, the VL comprises an amino acid sequence that is at least about 98% identical to the amino acid sequence of SEQ ID NO: 80. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to NKG2D. In certain aspects, a total of 1 to 10 amino acids have been substituted, inserted and/or deleted in the amino acid sequence of SEQ ID NO: 80. In certain aspects, substitutions, insertions, or deletions occur in regions outside the CDRs (i.e., in the FRs). In one aspect, the VL comprises the amino acid sequence of SEQ ID NO: 80. Optionally, the VL comprises the amino acid sequence of SEQ ID NO: 80, including post-translational modifications of that sequence.

In one aspect, the VH comprises an amino acid sequence that is at least about 95%, 96%, 97%, 98%, or 99% identical to an amino acid sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly an amino acid sequence selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the amino acid sequence of SEQ ID NO: 112; and the VL comprises an amino acid sequence that is at least about 95%, 96%, 97%, 98%, or 99% identical to the amino acid sequence of SEQ ID NO: 80. In one aspect, the VH comprises an amino acid sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly an amino acid sequence selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the amino acid sequence of SEQ ID NO: 112; and the VL comprises the amino acid sequence of SEQ ID NO: 80.

In a further aspect, the invention provides an antibody that binds to NKG2D, wherein the antibody comprises a first antigen binding domain comprising a VH comprising an amino acid sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly an amino acid sequence selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the amino acid sequence of SEQ ID NO: 112; and a VL comprising the amino acid sequence of SEQ ID NO: 80.

In a further aspect, the invention provides an antibody that binds to NKG2D, wherein the antibody comprises a first antigen binding domain comprising a VH sequence selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly a VH sequence selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly a VH sequence of SEQ ID NO: 112; and a VL sequence of SEQ ID NO: 80.

In another aspect, the invention provides an antibody that binds to NKG2D, wherein the antibody comprises a first antigen binding domain comprising a VH comprising the heavy chain CDR sequences of a VH selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly a VH selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the VH of SEQ ID NO: 112; and a VL comprising the light chain CDR sequences of the VL of SEQ ID NO: 80.

In a further aspect, the first antigen binding domain comprises the HCDR1, HCDR2 and HCDR3 amino acid sequences of a VH selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly a VH selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the VH of SEQ ID NO: 112; and the LCDR1, LCDR2 and LCDR3 amino acid sequences of the VL of SEQ ID NO: 11.

In one aspect, the VH comprises the heavy chain CDR sequences of a VH selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly a VH selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the VH of SEQ ID NO: 112, and a framework of at least 95%, 96%, 97%, 98% or 99% sequence identity to the framework sequence of a VH selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly a VH selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the VH of SEQ ID NO: 112. In one aspect, the VH comprises the heavy chain CDR sequences of a VH selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly a VH selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the VH of SEQ ID NO: 112, and a framework of at least 95% sequence identity to the framework sequence of a VH selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly a VH selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the VH of SEQ ID NO: 112. In another aspect, the VH comprises the heavy chain CDR sequences of a VH selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly a VH selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the VH of SEQ ID NO: 112, and a framework of at least 98% sequence identity to the framework sequence of a VH selected from the group consisting of SEQ ID NO: 79, SEQ ID NO: 106, SEQ ID NO: 107, SEQ ID NO: 108, SEQ ID NO: 109, SEQ ID NO: 110, SEQ ID NO: 111, SEQ ID NO: 112 and SEQ ID NO: 113, more particularly a VH selected from the group consisting of SEQ ID NO: 107, SEQ ID NO: 108, SEQ ID NO: 109, SEQ ID NO: 110, SEQ ID NO: 111, SEQ ID NO: 112 and SEQ ID NO: 113, most particularly the VH of SEQ ID NO: 112.

In one aspect, the VL comprises the light chain CDR sequences of the VL of SEQ ID NO: 80 and a framework of at least 95%, 96%, 97%, 98% or 99% sequence identity to the framework sequence of the VL of SEQ ID NO: 80. In one aspect, the VL comprises the light chain CDR sequences of the VL of SEQ ID NO: 80 and a framework of at least 95% sequence identity to the framework sequence of the VL of SEQ ID NO: 80. In another aspect, the VL comprises the light chain CDR sequences of the VL of SEQ ID NO: 80 and a framework of at least 98% sequence identity to the framework sequence of the VL of SEQ ID NO: 80.

In one aspect, the antibody comprises a first antigen binding domain, comprising
a VH comprising a HCDR 1 of SEQ ID NO: 65, a HCDR 2 of SEQ ID NO: 66, and a HCDR 3 of SEQ ID NO: 67, and a VL comprising a LCDR 1 of SEQ ID NO: 68, a LCDR 2 of SEQ ID NO: 69 and a LCDR 3 of SEQ ID NO: 70.

In one aspect, the antibody is a human antibody. In one aspect, the antigen binding domain is a human antigen binding domain (i.e. an antigen binding domain of a human antibody). In one aspect, the VH and/or the VL is a human variable region.

In one aspect, the VH and/or VL comprises a human framework, e.g. a human immunoglobulin framework.

In one aspect, the VH comprises one or more heavy chain framework sequence (i.e. the FR1, FR2, FR3 and/or FR4 sequence) of the heavy chain variable region sequence of SEQ ID NO: 71. In one aspect, the VH comprises an amino acid sequence that is at least about 95%, 96%, 97%, 98%, or 99% identical to the amino acid sequence of SEQ ID NO: 71. In one aspect, the VH comprises an amino acid sequence that is at least about 95% identical to the amino acid sequence of SEQ ID NO: 71. In one aspect, the VH comprises an amino acid sequence that is at least about 98% identical to the amino acid sequence of SEQ ID NO: 71. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to NKG2D. In certain aspects, a total of 1 to 10 amino acids have been substituted, inserted and/or deleted in the amino acid sequence of SEQ ID NO: 71. In certain aspects, substitutions, insertions, or deletions occur in regions outside the CDRs (i.e., in the FRs). In one aspect, the VH comprises the amino acid sequence of SEQ ID NO: 71. Optionally, the VH comprises the amino acid sequence of SEQ ID NO: 71, including post-translational modifications of that sequence.

In one aspect, the VL comprises one or more light chain framework sequence (i.e. the FR1, FR2, FR3 and/or FR4 sequence) of the light chain variable region sequence of SEQ ID NO: 72. In one aspect, the VL comprises an amino acid sequence that is at least about 95%, 96%, 97%, 98%, or 99% identical to the amino acid sequence of SEQ ID NO: 72. In one aspect, the VL comprises an amino acid sequence that is at least about 95% identical to the amino acid sequence of SEQ ID NO: 72. In one aspect, the VL comprises an amino acid sequence that is at least about 98% identical to the amino acid sequence of SEQ ID NO: 72. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to NKG2D. In certain aspects, a total of 1 to 10 amino acids have been substituted, inserted and/or deleted in the amino acid sequence of SEQ ID NO: 72. In certain aspects, substitutions, insertions, or deletions occur in regions outside the CDRs (i.e., in the FRs). In one aspect, the VL comprises the amino acid sequence of SEQ ID NO: 72. Optionally, the VL comprises the amino acid sequence of SEQ ID NO: 72, including post-translational modifications of that sequence.

In one aspect, the VH comprises an amino acid sequence that is at least about 95%, 96%, 97%, 98%, or 99% identical to the amino acid sequence of SEQ ID NO: 71, and the VL comprises an amino acid sequence that is at least about 95%, 96%, 97%, 98%, or 99% identical to the amino acid sequence of SEQ ID NO: 72. In one aspect, the VH comprises the amino acid sequence of SEQ ID NO: 71 and the VL comprises the amino acid sequence of SEQ ID NO: 72.

In a further aspect, the invention provides an antibody that binds to NKG2D, wherein the antibody comprises a first antigen binding domain comprising a VH comprising the amino acid sequence of SEQ ID NO: 71 and a VL comprising the amino acid sequence of SEQ ID NO: 72.

In a further aspect, the invention provides an antibody that binds to NKG2D, wherein the antibody comprises a first antigen binding domain comprising a VH sequence of SEQ ID NO: 71 and a VL sequence of SEQ ID NO: 72.

In another aspect, the invention provides an antibody that binds to NKG2D, wherein the antibody comprises a first antigen binding domain comprising a VH comprising the heavy chain CDR sequences of the VH of SEQ ID NO: 71, and a VL comprising the light chain CDR sequences of the VL of SEQ ID NO: 72.

In a further aspect, the first antigen binding domain comprises the HCDR1, HCDR2 and HCDR3 amino acid sequences of the VH of SEQ ID NO: 71 and the LCDR1, LCDR2 and LCDR3 amino acid sequences of the VL of SEQ ID NO: 72.

In one aspect, the VH comprises the heavy chain CDR sequences of the VH of SEQ ID NO: 71 and a framework of at least 95%, 96%, 97%, 98% or 99% sequence identity to the framework sequence of the VH of SEQ ID NO: 71. In one aspect, the VH comprises the heavy chain CDR sequences of the VH of SEQ ID NO: 71 and a framework of at least 95% sequence identity to the framework sequence of the VH of SEQ ID NO: 71. In another aspect, the VH comprises the heavy chain CDR sequences of the VH of SEQ ID NO: 71 and a framework of at least 98% sequence identity to the framework sequence of the VH of SEQ ID NO: 71.

In one aspect, the VL comprises the light chain CDR sequences of the VL of SEQ ID NO: 72 and a framework of at least 95%, 96%, 97%, 98% or 99% sequence identity to the framework sequence of the VL of SEQ ID NO: 72. In one aspect, the VL comprises the light chain CDR sequences of the VL of SEQ ID NO: 72 and a framework of at least 95% sequence identity to the framework sequence of the VL of SEQ ID NO: 72. In another aspect, the VL comprises the light chain CDR sequences of the VL of SEQ ID NO: 72 and a framework of at least 98% sequence identity to the framework sequence of the VL of SEQ ID NO: 72.

In one aspect, the antibody comprises a first antigen binding domain, comprising
a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6.

In one aspect, the antibody is a human antibody. In one aspect, the antigen binding domain is a human antigen binding domain (i.e. an antigen binding domain of a human antibody). In one aspect, the VH and/or the VL is a human variable region.

In one aspect, the VH and/or VL comprises a human framework, e.g. a human immunoglobulin framework.

In one aspect, the VH comprises one or more heavy chain framework sequence (i.e. the FR1, FR2, FR3 and/or FR4 sequence) of the heavy chain variable region sequence of SEQ ID NO: 7. In one aspect, the VH comprises an amino acid sequence that is at least about 95%, 96%, 97%, 98%, or 99% identical to the amino acid sequence of SEQ ID NO: 7. In one aspect, the VH comprises an amino acid sequence that is at least about 95% identical to the amino acid sequence of SEQ ID NO: 7. In one aspect, the VH comprises an amino acid sequence that is at least about 98% identical to the amino acid sequence of SEQ ID NO: 7. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to NKG2D. In certain aspects, a total of 1 to 10 amino acids have been substituted, inserted and/or deleted in the amino acid sequence of SEQ ID NO: 7. In certain aspects, substitutions, insertions, or deletions occur in regions outside the CDRs (i.e., in the FRs). In one aspect, the VH comprises the amino acid sequence of SEQ ID NO: 7. Optionally, the VH comprises the amino acid sequence of SEQ ID NO: 7, including post-translational modifications of that sequence.

In one aspect, the VL comprises one or more light chain framework sequence (i.e. the FR1, FR2, FR3 and/or FR4 sequence) of the light chain variable region sequence of SEQ ID NO: 8. In one aspect, the VL comprises an amino acid sequence that is at least about 95%, 96%, 97%, 98%, or 99% identical to the amino acid sequence of SEQ ID NO: 8. In one aspect, the VL comprises an amino acid sequence that is at least about 95% identical to the amino acid sequence of SEQ ID NO: 8. In one aspect, the VL comprises an amino acid sequence that is at least about 98% identical to the amino acid sequence of SEQ ID NO: 8. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to NKG2D. In certain aspects, a total of 1 to 10 amino acids have been substituted, inserted and/or deleted in the amino acid sequence of SEQ ID NO: 8. In certain aspects, substitutions, insertions, or deletions occur in regions outside the CDRs (i.e., in the FRs). In one aspect, the VL comprises the amino acid sequence of SEQ ID NO: 8. Optionally, the VL comprises the amino acid sequence of SEQ ID NO: 8, including post-translational modifications of that sequence.

In one aspect, the VH comprises an amino acid sequence that is at least about 95%, 96%, 97%, 98%, or 99% identical to the amino acid sequence of SEQ ID NO: 7, and the VL comprises an amino acid sequence that is at least about 95%, 96%, 97%, 98%, or 99% identical to the amino acid sequence of SEQ ID NO: 8. In one aspect, the VH comprises the amino acid sequence of SEQ ID NO: 7 and the VL comprises the amino acid sequence of SEQ ID NO: 8.

In a further aspect, the invention provides an antibody that binds to NKG2D, wherein the antibody comprises a first antigen binding domain comprising a VH comprising the amino acid sequence of SEQ ID NO: 7 and a VL comprising the amino acid sequence of SEQ ID NO: 8.

In a further aspect, the invention provides an antibody that binds to NKG2D, wherein the antibody comprises a first antigen binding domain comprising a VH sequence of SEQ ID NO: 7 and a VL sequence of SEQ ID NO: 8.

In another aspect, the invention provides an antibody that binds to NKG2D, wherein the antibody comprises a first antigen binding domain comprising a VH comprising the heavy chain CDR sequences of the VH of SEQ ID NO: 7, and a VL comprising the light chain CDR sequences of the VL of SEQ ID NO: 8.

In a further aspect, the first antigen binding domain comprises the HCDR1, HCDR2 and HCDR3 amino acid sequences of the VH of SEQ ID NO: 7 and the LCDR1, LCDR2 and LCDR3 amino acid sequences of the VL of SEQ ID NO: 8.

In one aspect, the VH comprises the heavy chain CDR sequences of the VH of SEQ ID NO: 7 and a framework of at least 95%, 96%, 97%, 98% or 99% sequence identity to the framework sequence of the VH of SEQ ID NO: 7. In one aspect, the VH comprises the heavy chain CDR sequences of the VH of SEQ ID NO: 7 and a framework of at least 95% sequence identity to the framework sequence of the VH of SEQ ID NO: 7. In another aspect, the VH comprises the heavy chain CDR sequences of the VH of SEQ ID NO: 7 and a framework of at least 98% sequence identity to the framework sequence of the VH of SEQ ID NO: 7.

In one aspect, the VL comprises the light chain CDR sequences of the VL of SEQ ID NO: 8 and a framework of at least 95%, 96%, 97%, 98% or 99% sequence identity to the framework sequence of the VL of SEQ ID NO: 8. In one aspect, the VL comprises the light chain CDR sequences of the VL of SEQ ID NO: 8 and a framework of at least 95% sequence identity to the framework sequence of the VL of SEQ ID NO: 8. In another aspect, the VL comprises the light chain CDR sequences of the VL of SEQ ID NO: 8 and a framework of at least 98% sequence identity to the framework sequence of the VL of SEQ ID NO: 8.

In one aspect, the invention provides an antibody that binds to NKG2D, wherein the antibody comprises a first antigen binding domain comprising a VH sequence as in any of the aspects provided above, and a VL sequence as in any of the aspects provided above.

In one aspect, the antibody comprises a human constant region. In one aspect, the antibody is an immunoglobulin molecule comprising a human constant region, particularly an IgG class immunoglobulin molecule comprising a human CH1, CH2, CH3 and/or CL domain. Exemplary sequences of human constant domains are given in SEQ ID NOs 83 and 84 (human kappa and lambda CL domains, respectively) and SEQ ID NO: 85 (human IgG1 heavy chain constant domains CH1-CH2-CH3). In one aspect, the antibody comprises a light chain constant region comprising an amino acid sequence that is at least about 95%, 96%, 97%, 98%, 99% or 100% identical to the amino acid sequence of SEQ ID NO: 83 or SEQ ID NO: 84, particularly the amino acid sequence of SEQ ID NO: 83. In one aspect, the antibody comprises a heavy chain constant region comprising an amino acid sequence that is at least about 95%, 96%, 97%, 98%, 99% or 100% identical to the amino acid sequence of SEQ ID NO: 85. Particularly, the heavy chain constant region may comprise amino acid mutations in the Fc domain as described herein.

In one aspect, the first antigen binding domain comprises a human constant region. In one aspect, the first antigen binding moiety is a Fab molecule comprising a human constant region, particularly a human CH1 and/or CL domain. In one aspect, the first antigen binding domain comprises a light chain constant region comprising an amino acid sequence that is at least about 95%, 96%, 97%, 98%, 99% or 100% identical to the amino acid sequence of SEQ ID NO: 83 or SEQ ID NO: 84, particularly the amino acid sequence of SEQ ID NO: 83. Particularly, the light chain constant region may comprise amino acid mutations as described herein under "charge modifications" and/or may comprise deletion or substitutions of one or more (particularly two) N-terminal amino acids if in a crossover Fab molecule. In some aspects, the first antigen binding domain comprises a heavy chain constant region comprising an amino acid sequence that is at least about 95%, 96%, 97%, 98%, 99% or 100% identical to the CH1 domain sequence comprised in the amino acid sequence of SEQ ID NO: 85. Particularly, the heavy chain constant region (specifically CH1 domain) may comprise amino acid mutations as described herein under "charge modifications".

In one aspect, the antibody is a monoclonal antibody.

In one aspect, the antibody is an IgG, particularly an IgG$_1$, antibody. In one aspect, the antibody is a full-length antibody.

In another aspect, the antibody is an antibody fragment selected from the group of an Fv molecule, a scFv molecule, a Fab molecule, and a F(ab')$_2$ molecule; particularly a Fab molecule. In another aspect, the antibody fragment is a diabody, a triabody or a tetrabody.

The first antigen binding domain comprised in the antibody according to the present inventions binds to NKG2D.

In a preferred aspect, the antibody comprises not more than one antigen binding domain that binds to NKG2D. In one aspect the antibody provides monovalent binding to NKG2D. In other aspects, the antibody comprises more than one (e.g. two, three, or four) antigen binding domain that binds to NKG2D. In one aspect the antibody provides multivalent binding to NKG2D. In one aspect, the antibody comprises two antigen binding domains that bind to NKG2D. In one aspect the antibody provides bivalent binding to NKG2D. In another aspect, the antibody comprises four antigen binding domains that bind to NKG2D. In one aspect the antibody provides tetravalent binding to NKG2D.

In aspects wherein the antibody comprises more than one antigen binding domain that binds to NKG2D, preferably all of these antigen binding domains are identical, i.e. they have the same molecular format (e.g. conventional or crossover Fab molecule) and comprise the same amino acid sequences.

In another aspect, the first antigen binding domain is an antibody fragment selected from the group of an Fv molecule, a scFv molecule, a Fab molecule, and a F(ab')$_2$ molecule.

In one aspect, the first antigen binding domain is a Fab molecule. In a preferred aspect the first antigen binding domain is a Fab molecule wherein the variable domains VL and VH or the constant domains CL and CH1, particularly the variable domains VL and VH, of the Fab light chain and the Fab heavy chain are replaced by each other (i.e. the first antigen binding domain is a crossover Fab molecule).

In a further aspect, the antibody according to any of the above aspects may incorporate any of the features, singly or in combination, as described in sections II. A. 1.-10. below.

In a preferred aspect, the antibody comprises an Fc domain, particularly an IgG Fc domain, more particularly an IgG$_1$ Fc domain. In one aspect the Fc domain is a human Fc domain. In one aspect, the Fc domain is a human IgG$_1$ Fc domain. The Fc domain is composed of a first and a second subunit and may incorporate any of the features, singly or in combination, described hereinbelow in relation to Fc domain variants (section II. A. 10.).

In another preferred aspect, the antibody comprises a second antigen binding domain that binds to a second antigen (i.e. the antibody is a multispecific antibody, as further described hereinbelow (section II. A. 9.).

1. Antibody Fragments

In certain aspects, an antibody provided herein is an antibody fragment.

In one aspect, the antibody fragment is a Fab, Fab', Fab'-SH, or F(ab')$_2$ molecule, in particular a Fab molecule as described herein. "Fab' molecule" differ from Fab molecules by the addition of residues at the carboxy terminus of the CH1 domain including one or more cysteines from the antibody hinge region. Fab'-SH are Fab' molecules in which the cysteine residue(s) of the constant domains bear a free thiol group. Pepsin treatment yields an F(ab')$_2$ molecule that has two antigen-binding sites (two Fab molecules) and a part of the Fc region.

In another aspect, the antibody fragment is a diabody, a triabody or a tetrabody. "Diabodies" are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

In a further aspect, the antibody fragment is a single chain Fab molecule. A "single chain Fab molecule" or "scFab" is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL. In particular, said linker is a polypeptide of at least 30 amino acids, preferably between 32 and 50 amino acids. Said single chain Fab molecules are stabilized via the natural disulfide bond between the CL domain and the CH1 domain. In addition, these single chain Fab molecules might be further stabilized by generation of interchain disulfide bonds via insertion of cysteine residues (e.g., position 44 in the variable heavy chain and position 100 in the variable light chain according to Kabat numbering).

In another aspect, the antibody fragment is single-chain variable fragment (scFv). A "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

In another aspect, the antibody fragment is a single-domain antibody. "Single-domain antibodies" are antibody fragments comprising all or a portion of the heavy chain variable domain or all or a portion of the light chain variable domain of an antibody. In certain aspects, a single-domain antibody is a human single-domain antibody (Domantis, Inc., Waltham, M A; see, e.g., U.S. Pat. No. 6,248,516 B1).

Antibody fragments can be made by various techniques, including but not limited to proteolytic digestion of an intact antibody as well as recombinant production by recombinant host cells (e.g., E. coli), as described herein.

2. Chimeric and Humanized Antibodies

In certain aspects, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain aspects, an antibody provided herein is a humanized antibody. Typically, a non-human antibody is humanized to reduce immunogenicity to humans, while retaining the specificity and affinity of the parental non-human antibody. Generally, a humanized antibody comprises one or more variable domains in which the CDRs (or portions thereof) are derived from a non-human antibody, and FRs (or portions thereof) are derived from human antibody sequences. A humanized antibody optionally will also comprise at least a portion of a human constant region. In some aspects, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

3. Human Antibodies

In certain aspects, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described (see, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991)). Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating variable domain sequences selected from human-derived phage display libraries. Such variable domain sequences may then be combined with a desired human constant domain. Techniques for selecting human antibodies from antibody libraries are described below.

4. Library-Derived Antibodies

In certain aspects, an antibody provided herein is derived from a library. Antibodies of the invention may be isolated by screening combinatorial libraries for antibodies with the desired activity or activities. Methods for screening combinatorial libraries are reviewed, e.g., in Lerner et al. in *Nature Reviews* 16:498-508 (2016). For example, a variety of methods are known in the art for generating phage display libraries and screening such libraries for antibodies possessing the desired binding characteristics. Such methods are reviewed, e.g., in Frenzel et al. in *mAbs* 8:1177-1194 (2016); Bazan et al. in *Human Vaccines and Immunotherapeutics* 8:1817-1828 (2012) and Zhao et al. in *Critical Reviews in Biotechnology* 36:276-289 (2016) as well as in Hoogenboom et al. in *Methods in Molecular Biology* 178:1-37 (O'Brien et al., ed., Human Press, Totowa, N J, 2001) and in Marks and Bradbury in *Methods in Molecular Biology* 248:161-175 (Lo, ed., Human Press, Totowa, N J, 2003).

In certain phage display methods, repertoires of VH and VL genes are separately cloned by polymerase chain reaction (PCR) and recombined randomly in phage libraries, which can then be screened for antigen-binding phage as described in Winter et al. in *Annual Review of Immunology* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al. in *EMBO Journal* 12: 725-734 (1993). Furthermore, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in *Journal of Molecular Biology* 227: 381-388 (1992). Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764 and 2007/0292936.

Further examples of methods known in the art for screening combinatorial libraries for antibodies with a desired activity or activities include ribosome and mRNA display, as well as methods for antibody display and selection on bacteria, mammalian cells, insect cells or yeast cells. Methods for yeast surface display are reviewed, e.g., in Scholler et al. in *Methods in Molecular Biology* 503:135-56 (2012) and in Cherf et al. in *Methods in Molecular biology* 1319: 155-175 (2015) as well as in Zhao et al. in *Methods in Molecular Biology* 889:73-84 (2012). Methods for ribosome display are described, e.g., in He et al. in *Nucleic Acids Research* 25:5132-5134 (1997) and in Hanes et al. in *PNAS* 94:4937-4942 (1997).

Antibodies or antibody fragments isolated from human antibody libraries are considered human antibodies or human antibody fragments herein.

5. Glycosylation Variants

In certain aspects, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the invention may be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one aspect, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. *Arch. Biochem. Biophys.* 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87:614-622 (2004); Kanda, Y. et al., *Biotechnol. Bioeng.*, 94(4):680-688 (2006); and WO 2003/085107), or cells with reduced or abolished activity of a GDP-fucose synthesis or transporter protein (see, e.g., US2004259150, US2005031613, US2004132140, US2004110282).

In a further aspect, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

6. Cysteine Engineered Antibody Variants

In certain aspects, it may be desirable to create cysteine engineered antibodies, e.g., THIOMAB™ antibodies, in which one or more residues of an antibody are substituted with cysteine residues. In preferred aspects, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 8,30,930, 7,855,275, 9,000,130, or WO 2016040856.

7. Antibody Derivatives

In certain aspects, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

8. Immunoconjugates

The invention also provides immunoconjugates comprising an anti-NKG2D antibody herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one aspect, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in *Pharmacol Review* 68:3-19 (2016).

In another aspect, an immunoconjugate comprises an antibody of the invention conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another aspect, an immunoconjugate comprises an antibody of the invention conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, MRI), such as $I^{123}$, $I^{131}$, $In^{111}$, $F^{19}$, $C^{13}$, $N^{15}$, $O^{17}$, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

9. Multispecific Antibodies

In certain aspects, an antibody provided herein is a multispecific antibody, particularly a bispecific antibody. Multispecific antibodies are monoclonal antibodies that have binding specificities for at least two different antigenic determinants (e.g., two different proteins, or two different epitopes on the same protein). In certain aspects, the multispecific antibody has three or more binding specificities. In certain aspects, one of the binding specificities is for NKG2D and the other specificity is for any other antigen. In certain aspects, multispecific antibodies may bind to two (or more) different epitopes of NKG2D. Multispecific (e.g., bispecific) antibodies may also be used to localize cytotoxic agents or cells to cells which express NKG2D. Multispecific antibodies may be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)) and "knob-in-hole" engineering (see, e.g., U.S. Pat. No. 5,731,168, and Atwell et al., J. Mol. Biol. 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g., Gruber et al., J. Immunol., 152:5368 (1994)); and preparing trispecific antibodies as described, e.g., in Tutt et al. J. Immunol. 147: 60 (1991).

Engineered antibodies with three or more antigen binding sites, including for example, "Octopus antibodies", or DVD-Ig are also included herein (see, e.g., WO 2001/77342 and WO 2008/024715). Other examples of multispecific antibodies with three or more antigen binding sites can be found in WO 2010/115589, WO 2010/112193, WO 2010/136172, WO 2010/145792, and WO 2013/026831. The multispecific antibody or antigen binding fragment thereof also includes a "Dual Acting FAb" or "DAF" comprising an antigen binding site that binds to NKG2D as well as another different antigen, or two different epitopes of NKG2D (see, e.g., US 2008/0069820 and WO 2015/095539).

Multi-specific antibodies may also be provided in an asymmetric form with a domain crossover in one or more binding arms of the same antigen specificity (so called "CrossMab" technology), i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). Asymmetrical Fab arms can also be engineered by introducing charged or non-charged amino acid mutations into domain interfaces to direct correct Fab pairing. See e.g., WO 2016/172485.

Various further molecular formats for multispecific antibodies are known in the art and are included herein (see e.g., Spiess et al., Mol Immunol 67 (2015) 95-106).

Preferred aspects of the multispecific antibodies of the present invention are described in the following.

In one aspect, the invention provides an antibody that binds to NKG2D, comprising a first antigen binding domain that binds to NKG2D, as described herein, and comprising a second antigen binding domain that binds to a second antigen.

According to preferred aspects of the invention, the antigen binding domains comprised in the antibody are Fab molecules (i.e. antigen binding domains composed of a heavy and a light chain, each comprising a variable and a constant domain). In one aspect, the first and/or the second antigen binding domain is a Fab molecule. In one aspect, said Fab molecule is human. In another aspect, said Fab molecule is humanized. In yet another aspect, said Fab molecule comprises human heavy and light chain constant domains.

Preferably, at least one of the antigen binding domains is a crossover Fab molecule. Such modification reduces mispairing of heavy and light chains from different Fab molecules, thereby improving the yield and purity of the (multispecific) antibody of the invention in recombinant production. In a preferred crossover Fab molecule useful for the (multispecific) antibody of the invention, the variable domains of the Fab light chain and the Fab heavy chain (VL and VH, respectively) are exchanged. Even with this domain exchange, however, the preparation of the (multispecific) antibody may comprise certain side products due to a so-called Bence Jones-type interaction between mispaired heavy and light chains (see Schaefer et al, PNAS, 108 (2011) 11187-11191). To further reduce mispairing of heavy and light chains from different Fab molecules and thus increase the purity and yield of the desired (multispecific) antibody, charged amino acids with opposite charges may be introduced at specific amino acid positions in the CH1 and CL domains of either the Fab molecule(s) binding to the first antigen (NKG2D), or the Fab molecule(s) binding to the second antigen (e.g. a target cell antigen such as a tumor cell antigen), as further described herein. Charge modifications are made either in the conventional Fab molecule(s) comprised in the (multispecific) antibody (such as shown e.g. in FIG. 12), or in the VH/VL crossover Fab molecule(s) comprised in the (multispecific) antibody (but not in both). In preferred aspects, the charge modifications are made in the conventional Fab molecule(s) comprised in the (multispecific) antibody (which in preferred aspects bind(s) to the second antigen, e.g. a target cell antigen such as a tumor cell antigen).

In a preferred aspect according to the invention, the (multispecific) antibody is capable of simultaneous binding to the first antigen (i.e. NKG2D), and the second antigen (e.g. a target cell antigen such as a tumor cell antigen). In one aspect, the (multispecific) antibody is capable of cross-linking a NKG2D-expressing cells (such as a T cell or a NK cell) and a target cell (such as a tumor cell) by simultaneous binding to NKG2D and a target cell antigen. In one aspect, such simultaneous binding results in lysis of the target cell, particularly a target cell antigen-expressing tumor cell. In one aspect, such simultaneous binding results in activation of the NKG2D-expressing cell (such as a T cell or a NK cell). In other aspects, such simultaneous binding results in a cellular response of a NKG2D-expressing cell (such as a T cell or a NK cell) selected from the group of: proliferation, differentiation, cytokine secretion, cytotoxic effector molecule release, cytotoxic activity, and expression of activation markers. In one aspect, binding of the (multispecific) antibody to NKG2D without simultaneous binding to the target cell antigen does not result in activation of a NKG2D-expressing cell (such as a T cell or a NK cell).

In certain of these aspects, the (multispecific) antibody of the invention is combined with a T-cell activating agent, such as an antibody that binds to CD3, particularly a bispecific antibody that binds to CD3 and a target cell antigen, particularly a tumor cell antigen.

Preferably, a T cell according to any of the aspects of the invention is a cytotoxic T cell. In some aspects the T cell is a CD8$^+$ T cell. In other aspects the T cell is a γδ T cell.

a) First Antigen Binding Domain

The (multispecific) antibody of the invention comprises at least one antigen binding domain (the first antigen binding domain) that binds to NKG2D. In preferred aspects, NKG2D is human NKG2D or cynomolgus NKG2D, most particularly human NKG2D. In one aspect the first antigen binding domain is cross-reactive for (i.e. binds to) human and cynomolgus NKG2D. In some aspects, NKG2D is the extracellular domain of NKG2D.

In a preferred aspect, the (multispecific) antibody comprises not more than one antigen binding domain that binds to NKG2D. In one aspect the (multispecific) antibody provides monovalent binding to NKG2D. In other aspects, the (multispecific) antibody comprises more than one (e.g. two, three, or four) antigen binding domain that binds to NKG2D. In one aspect the (multispecific) antibody provides multivalent binding to NKG2D. In one aspect, the (multispecific) antibody comprises two antigen binding domains that bind to NKG2D. In one aspect the (multispecific) antibody provides bivalent binding to NKG2D. In another aspect, the (multispecific) antibody comprises four antigen binding domains that bind to NKG2D. In one aspect the (multispecific) antibody provides tetravalent binding to NKG2D.

In aspects wherein the (multispecific) antibody comprises more than one antigen binding domain that binds to NKG2D, preferably all of these antigen binding domains are identical, i.e. they have the same molecular format (e.g. conventional or crossover Fab molecule) and comprise the same amino acid sequences including the same amino acid substitutions in the CH1 and CL domain as described herein (if any).

In one aspect, the antigen binding domain(s) that binds to NKG2D is an antibody fragment selected from the group of an Fv molecule, a scFv molecule, a Fab molecule, and a F(ab')$_2$ molecule. In a preferred aspect, the antigen binding domain(s) that binds to NKG2D is a Fab molecule.

In some aspects, the antigen binding domain(s) that binds to NKG2D is a crossover Fab molecule as described herein, i.e. a Fab molecule wherein the variable domains VH and VL or the constant domains CH1 and CL of the Fab heavy and light chains are exchanged/replaced by each other. In such aspects, the antigen binding domain(s) that binds to the second antigen (e.g. a target cell antigen such as a tumor antigen) is preferably a conventional Fab molecule.

In alternative aspects, the antigen binding domain(s) that binds to NKG2D is a conventional Fab molecule. In such aspects, the antigen binding domain(s) that binds to the second antigen (e.g. a target cell antigen such as a tumor cell antigen) is a crossover Fab molecule as described herein, i.e. a Fab molecule wherein the variable domains VH and VL or the constant domains CH1 and CL of the Fab heavy and light chains are exchanged/replaced by each other.

In preferred aspects, the first antigen binding domain is a Fab molecule wherein the variable domains VL and VH or the constant domains CL and CH1, particularly the variable domains VL and VH, of the Fab light chain and the Fab heavy chain are replaced by each other (i.e. according to such aspect, the first antigen binding domain is a crossover Fab molecule wherein the variable or constant domains of the Fab light chain and the Fab heavy chain are exchanged). In one such aspect, the second antigen binding domain is a conventional Fab molecule.

b) Second Antigen Binding Domain

In certain aspects, the (multispecific) antibody of the invention comprises an antigen binding domain (the second antigen binding domain) that binds to a second antigen. The second antigen preferably is not NKG2D, i.e. different from NKG2D. In one aspect, the second antigen is an antigen expressed on a different cell than NKG2D (e.g. expressed on a cell other than a T cell or an NK cell). In one aspect, the second antigen is not an activating Fc receptor, particularly FcγRIIIa (CD16a). In one aspect, the antibody does not bind to an activating Fc receptor, particularly FcγRIIIa (CD16a). In one aspect, the second antigen is not CD3. In one aspect, the antibody does not bind to CD3.

In preferred aspects, the second antigen is a target cell antigen, particularly a tumor cell antigen. In a specific aspect, the second antigen is CEA. According to the invention, the second antigen binding domain is able to direct the (multispecific) antibody to a target site, for example to a specific type of tumor cell that expresses the second antigen.

In a preferred aspect, the (multispecific) antibody comprises not more than one antigen binding domain that binds to the second antigen. In one aspect the (multispecific) antibody provides monovalent binding to the second antigen. In other aspects, the (multispecific) antibody comprises more than one (e.g. two, three, or four) antigen binding domain that binds to the second antigen. In one aspect the (multispecific) antibody provides multivalent binding to the second antigen. In one aspect, the (multispecific) antibody comprises two antigen binding domains that bind to the second antigen. In one aspect the (multispecific) antibody provides bivalent binding to the second antigen.

In aspects wherein the (multispecific) antibody comprises more than one antigen binding domain, particularly Fab molecule, that binds to the second antigen, preferably each of these antigen binding domains binds to the same antigenic determinant. In an even more preferred aspect, all of these antigen binding domains are identical, i.e. they have the same molecular format (e.g. conventional or crossover Fab molecule) and comprise the same amino acid sequences including the same amino acid substitutions in the CH1 and CL domain as described herein (if any).

In one aspect, the antigen binding domain(s) that binds to the second antigen is an antibody fragment selected from the group of an Fv molecule, a scFv molecule, a Fab molecule, and a F(ab')$_2$ molecule. In a preferred aspect, the antigen binding domain(s) that binds to the second antigen is a Fab molecule. In another aspect, the antigen binding domain(s) that binds to the second antigen is an Fv molecule.

In some aspects, the antigen binding domain(s) that binds to the second antigen is conventional Fab molecule. In such aspects, the antigen binding domain(s) that binds to NKG2D is a crossover Fab molecule as described herein, i.e. a Fab molecule wherein the variable domains VH and VL or the constant domains CH1 and CL of the Fab heavy and light chains are exchanged/replaced by each other.

In alternative aspects, the antigen binding domain(s) that binds to the second antigen is a crossover Fab molecule as described herein, i.e. a Fab molecule wherein the variable domains VH and VL or the constant domains CH1 and CL of the Fab heavy and light chains are exchanged/replaced by each other. In such aspects, the antigen binding domain(s) that binds to NKG2D is a conventional Fab molecule.

In one aspect, the second antigen binding domain comprises a human constant region. In one aspect, the second antigen binding domain is a Fab molecule comprising a human constant region, particularly a human CH1 and/or CL domain. Exemplary sequences of human constant domains are given in SEQ ID NOs 83 and 84 (human kappa and lambda CL domains, respectively) and SEQ ID NO: 85 (human IgG1 heavy chain constant domains CH1-CH2-CH3). In one aspect, the second antigen binding domain comprises a light chain constant region comprising an amino acid sequence that is at least about 95%, 96%, 97%, 98%, 99% or 100% identical to the amino acid sequence of SEQ ID NO: 83 or SEQ ID NO: 84, particularly the amino acid sequence of SEQ ID NO: 83. Particularly, the light chain constant region may comprise amino acid mutations as described herein under "charge modifications" and/or may comprise deletion or substitutions of one or more (particularly two) N-terminal amino acids if in a crossover Fab molecule. In some aspects, the second antigen binding domain comprises a heavy chain constant region comprising an amino acid sequence that is at least about 95%, 96%, 97%, 98%, 99% or 100% identical to the CH1 domain sequence comprised in the amino acid sequence of SEQ ID NO: 85. Particularly, the heavy chain constant region (specifically CH1 domain) may comprise amino acid mutations as described herein under "charge modifications".

In some aspects, the second antigen is CEA, particularly human CEA.

In one aspect, the second antigen binding domain comprises a heavy chain variable region (VH) comprising a heavy chain complementary determining region (HCDR) 1 of SEQ ID NO: 114, a HCDR 2 of SEQ ID NO: 115, and a HCDR 3 of SEQ ID NO: 116, and a light chain variable region (VL) comprising a light chain complementarity determining region (LCDR) 1 of SEQ ID NO: 117, a LCDR 2 of SEQ ID NO: 118 and a LCDR 3 of SEQ ID NO: 119.

In one aspect, the second antigen binding domain comprises a VH comprising the heavy chain CDR sequences of the VH of SEQ ID NO: 120, and a VL comprising the light chain CDR sequences of the VL of SEQ ID NO: 121.

In one aspect, the VH of the second antigen binding domain comprises an amino acid sequence that is at least about 95%, 96%, 97%, 98%, or 99% identical to the amino acid sequence of SEQ ID NO: 120, and/or the VL of the second antigen binding domain comprises an amino acid sequence that is at least about 95%, 96%, 97%, 98%, or 99% identical to the amino acid sequence of SEQ ID NO: 121. In one aspect, the VH comprises the amino acid sequence of SEQ ID NO: 120 and/or the VL comprises the amino acid sequence of SEQ ID NO: 121.

In another aspect, the second antigen binding domain comprises a heavy chain variable region (VH) comprising a heavy chain complementary determining region (HCDR) 1 of SEQ ID NO: 122, a HCDR 2 of SEQ ID NO: 123, and a HCDR 3 of SEQ ID NO: 124, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 127.

In one aspect, the second antigen binding domain is (derived from) a humanized antibody. In one aspect, the second antigen binding domain is a humanized antigen binding domain (i.e. an antigen binding domain of a humanized antibody). In one aspect, the VH and/or the VL of the second antigen binding domain is a humanized variable region.

In one aspect, the VH of the second antigen binding domain comprises an acceptor human framework, e.g. a human immunoglobulin framework or a human consensus framework.

In one aspect, the VH of the second antigen binding domain comprises one or more heavy chain framework sequence (i.e. the FR1, FR2, FR3 and/or FR4 sequence) of the heavy chain variable region sequence of SEQ ID NO: 128. In one aspect, the VH comprises an amino acid sequence that is at least about 95%, 96%, 97%, 98%, or 99% identical to the amino acid sequence of SEQ ID NO: 128. In one aspect, the VH comprises an amino acid sequence that is at least about 95% identical to the amino acid sequence of SEQ ID NO: 128. In one aspect, the VH comprises an amino acid sequence that is at least about 98% identical to the amino acid sequence of SEQ ID NO: 128. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to the second antigen. In certain aspects, a total of 1 to 10 amino acids have been substituted, inserted and/or deleted in the amino acid sequence of SEQ ID NO: 128. In certain aspects, substitutions, insertions, or deletions occur in regions outside the CDRs (i.e., in the FRs). In one aspect, the VH comprises the amino acid sequence of SEQ ID NO: 128. Optionally, the VH comprises the amino acid sequence of SEQ ID NO: 128, including post-translational modifications of that sequence.

In one aspect, the VL of the second antigen binding domain comprises one or more light chain framework sequence (i.e. the FR1, FR2, FR3 and/or FR4 sequence) of the light chain variable region sequence of SEQ ID NO: 129. In one aspect, the VL comprises an amino acid sequence that is at least about 95%, 96%, 97%, 98%, or 99% identical to the amino acid sequence of SEQ ID NO: 129. In one aspect, the VL comprises an amino acid sequence that is at least about 95% identical to the amino acid sequence of SEQ ID NO: 129. In one aspect, the VL comprises an amino acid sequence that is at least about 98% identical to the amino acid sequence of SEQ ID NO: 129. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to the second antigen. In certain aspects, a total of 1 to 10 amino acids have been substituted, inserted and/or deleted in the amino acid sequence of SEQ ID NO: 129. In certain aspects, substitutions, insertions, or deletions occur in regions outside the CDRs (i.e., in the FRs). In one aspect, the VL comprises the amino acid sequence of SEQ ID NO: 129. Optionally, the VL comprises the amino acid sequence of SEQ ID NO: 129, including post-translational modifications of that sequence.

In one aspect, the VH of the second antigen binding domain comprises an amino acid sequence that is at least about 95%, 96%, 97%, 98%, or 99% identical to the amino acid sequence of SEQ ID NO: 128, and the VL of the second antigen binding domain comprises an amino acid sequence that is at least about 95%, 96%, 97%, 98%, or 99% identical to the amino acid sequence of SEQ ID NO: 129. In one aspect, the VH comprises the amino acid sequence of SEQ ID NO: 128 and the VL comprises the amino acid sequence of SEQ ID NO: 129.

In a further aspect, the second antigen binding domain comprises a VH comprising the amino acid sequence of SEQ ID NO: 128 and a VL comprising the amino acid sequence of SEQ ID NO: 129.

In a further aspect, the second antigen binding domain comprises a VH sequence of SEQ ID NO: 128 and a VL sequence of SEQ ID NO: 129.

In another aspect, the second antigen binding domain comprises a VH comprising the heavy chain CDR sequences of the VH of SEQ ID NO: 128, and a VL comprising the light chain CDR sequences of the VL of SEQ ID NO: 129.

In a further aspect, the second antigen binding domain comprises the HCDR1, HCDR2 and HCDR3 amino acid sequences of the VH of SEQ ID NO: 128 and the LCDR1, LCDR2 and LCDR3 amino acid sequences of the VL of SEQ ID NO: 129.

In one aspect, the VH of the second antigen binding domain comprises the heavy chain CDR sequences of the VH of SEQ ID NO: 128 and a framework of at least 95%, 96%, 97%, 98% or 99% sequence identity to the framework sequence of the VH of SEQ ID NO: 128. In one aspect, the VH comprises the heavy chain CDR sequences of the VH of SEQ ID NO: 128 and a framework of at least 95% sequence identity to the framework sequence of the VH of SEQ ID NO: 128. In another aspect, the VH comprises the heavy chain CDR sequences of the VH of SEQ ID NO: 128 and a framework of at least 98% sequence identity to the framework sequence of the VH of SEQ ID NO: 128.

In one aspect, the VL of the second antigen binding domain comprises the light chain CDR sequences of the VL of SEQ ID NO: 129 and a framework of at least 95%, 96%, 97%, 98% or 99% sequence identity to the framework sequence of the VL of SEQ ID NO: 129. In one aspect, the VL comprises the light chain CDR sequences of the VL of SEQ ID NO: 129 and a framework of at least 95% sequence identity to the framework sequence of the VL of SEQ ID NO: 129. In another aspect, the VL comprises the light chain CDR sequences of the VL of SEQ ID NO: 129 and a framework of at least 98% sequence identity to the framework sequence of the VL of SEQ ID NO: 129.

In another aspect, the second antigen binding domain comprises a heavy chain variable region (VH) comprising a heavy chain complementary determining region (HCDR) 1 of SEQ ID NO: 165, a HCDR 2 of SEQ ID NO: 168, and a HCDR 3 of SEQ ID NO: 171, and a light chain variable region (VL) comprising a light chain complementarity determining region (LCDR) 1 of SEQ ID NO: 177, a LCDR 2 of SEQ ID NO: 126 and a LCDR 3 of SEQ ID NO: 179.

In one aspect, the second antigen binding domain comprises
  (i) a heavy chain variable region (VH) comprising a heavy chain complementary determining region (HCDR) 1 of SEQ ID NO: 122, a HCDR 2 of SEQ ID NO: 123, and a HCDR 3 of SEQ ID NO: 172, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 180;
  (ii) a heavy chain variable region (VH) comprising a heavy chain complementary determining region (HCDR) 1 of SEQ ID NO: 122, a HCDR 2 of SEQ ID NO: 123, and a HCDR 3 of SEQ ID NO: 173, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 181;
  (iii) a heavy chain variable region (VH) comprising a heavy chain complementary determining region (HCDR) 1 of SEQ ID NO: 122, a HCDR 2 of SEQ ID NO: 123, and a HCDR 3 of SEQ ID NO: 174, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 182;
  (iv) a heavy chain variable region (VH) comprising a heavy chain complementary determining region (HCDR) 1 of SEQ ID NO: 166, a HCDR 2 of SEQ ID NO: 169, and a HCDR 3 of SEQ ID NO: 124, and a light chain variable region (VL) comprising a light chain complementarity determining region (LCDR) 1 of SEQ ID NO: 178, a LCDR 2 of SEQ ID NO: 126 and a LCDR 3 of SEQ ID NO: 127;
  (v) a heavy chain variable region (VH) comprising a heavy chain complementary determining region (HCDR) 1 of SEQ ID NO: 122, a HCDR 2 of SEQ ID NO: 170, and a HCDR 3 of SEQ ID NO: 124, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 127;
  (vi) a heavy chain variable region (VH) comprising a heavy chain complementary determining region (HCDR) 1 of SEQ ID NO: 122, a HCDR 2 of SEQ ID NO: 123, and a HCDR 3 of SEQ ID NO: 175, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 183;

(vii) a heavy chain variable region (VH) comprising a heavy chain complementary determining region (HCDR) 1 of SEQ ID NO: 122, a HCDR 2 of SEQ ID NO: 169, and a HCDR 3 of SEQ ID NO: 175, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 183;

(viii) a heavy chain variable region (VH) comprising a heavy chain complementary determining region (HCDR) 1 of SEQ ID NO: 122, a HCDR 2 of SEQ ID NO: 169, and a HCDR 3 of SEQ ID NO: 175, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 183;

(ix) a heavy chain variable region (VH) comprising a heavy chain complementary determining region (HCDR) 1 of SEQ ID NO: 122, a HCDR 2 of SEQ ID NO: 123, and a HCDR 3 of SEQ ID NO: 176, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 182;

(x) a heavy chain variable region (VH) comprising a heavy chain complementary determining region (HCDR) 1 of SEQ ID NO: 122, a HCDR 2 of SEQ ID NO: 169, and a HCDR 3 of SEQ ID NO: 176, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 182;

(xi) a heavy chain variable region (VH) comprising a heavy chain complementary determining region (HCDR) 1 of SEQ ID NO: 166, a HCDR 2 of SEQ ID NO: 169, and a HCDR 3 of SEQ ID NO: 172, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 180; or (xii) a heavy chain variable region (VH) comprising a heavy chain complementary determining region (HCDR) 1 of SEQ ID NO: 167, a HCDR 2 of SEQ ID NO: 170, and a HCDR 3 of SEQ ID NO: 172, and a light chain variable region (VL) comprising a light chain complementarity determining region (LCDR) 1 of SEQ ID NO: 125, a LCDR 2 of SEQ ID NO: 126 and a LCDR 3 of SEQ ID NO: 180.

In one aspect, the second antigen binding domain is (derived from) a humanized antibody. In one aspect, the second antigen binding domain is a humanized antigen binding domain (i.e. an antigen binding domain of a humanized antibody). In one aspect, the VH and/or the VL of the second antigen binding domain is a humanized variable region.

In one aspect, the VH of the second antigen binding domain comprises an acceptor human framework, e.g. a human immunoglobulin framework or a human consensus framework.

In one aspect, the VH of the second antigen binding domain comprises one or more heavy chain framework sequence (i.e. the FR1, FR2, FR3 and/or FR4 sequence) of a heavy chain variable region sequence selected from the group consisting of SEQ ID NO: 184, 186, 188, 190, 192, 194, 196, 198, 200, 202, 204 and 206. In one aspect, the VH comprises an amino acid sequence that is at least about 95%, 96%, 97%, 98%, or 99% identical to an amino acid sequence selected from the group consisting of SEQ ID NO: 184, 186, 188, 190, 192, 194, 196, 198, 200, 202, 204 and 206. In one aspect, the VH comprises an amino acid sequence that is at least about 95% identical to an amino acid sequence selected from the group consisting of SEQ ID NO: 184, 186, 188, 190, 192, 194, 196, 198, 200, 202, 204 and 206. In one aspect, the VH comprises an amino acid sequence that is at least about 98% identical to an amino acid sequence selected from the group consisting of SEQ ID NO: 184, 186, 188, 190, 192, 194, 196, 198, 200, 202, 204 and 206. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to the second antigen. In certain aspects, a total of 1 to 10 amino acids have been substituted, inserted and/or deleted in the amino acid sequence of SEQ ID NO: 184, 186, 188, 190, 192, 194, 196, 198, 200, 202, 204 or 206. In certain aspects, substitutions, insertions, or deletions occur in regions outside the CDRs (i.e., in the FRs). In one aspect, the VH comprises an amino acid sequence selected from the group consisting of SEQ ID NO: 184, 186, 188, 190, 192, 194, 196, 198, 200, 202, 204 and 206. Optionally, the VH comprises an amino acid sequence selected from the group consisting of SEQ ID NO: 184, 186, 188, 190, 192, 194, 196, 198, 200, 202, 204 and 206, including post-translational modifications of that sequence.

In one aspect, the VL of the second antigen binding domain comprises one or more light chain framework sequence (i.e. the FR1, FR2, FR3 and/or FR4 sequence) of a light chain variable region sequence selected from the group of SEQ ID NO: 185, 187, 189, 191, 193, 195, 197, 199, 201, 203, 205 and 207. In one aspect, the VL comprises an amino acid sequence that is at least about 95%, 96%, 97%, 98%, or 99% identical to an amino acid sequence selected from the group of SEQ ID NO: 185, 187, 189, 191, 193, 195, 197, 199, 201, 203, 205 and 207. In one aspect, the VL comprises an amino acid sequence that is at least about 95% identical to an amino acid sequence selected from the group of SEQ ID NO: 185, 187, 189, 191, 193, 195, 197, 199, 201, 203, 205 and 207. In one aspect, the VL comprises an amino acid sequence that is at least about 98% identical to an amino acid sequence selected from the group of SEQ ID NO: 185, 187, 189, 191, 193, 195, 197, 199, 201, 203, 205 and 207. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to the second antigen. In certain aspects, a total of 1 to 10 amino acids have been substituted, inserted and/or deleted in the amino acid sequence of SEQ ID NO: 185, 187, 189, 191, 193, 195, 197, 199, 201, 203, 205 or 207. In certain aspects, substitutions, insertions, or deletions occur in regions outside the CDRs (i.e., in the FRs). In one aspect, the VL comprises an amino acid sequence selected from the group of SEQ ID NO: 185, 187, 189, 191, 193, 195, 197, 199, 201, 203, 205 and 207. Optionally, the VL comprises an amino acid sequence selected from the group of SEQ ID NO: 185, 187, 189, 191, 193, 195, 197, 199, 201, 203, 205 and 207, including post-translational modifications of that sequence.

In one aspect, the VH of the second antigen binding domain comprises (i) an amino acid sequence that is at least about 95%, 96%, 97%, 98%, or 99% identical to the amino acid sequence of SEQ ID NO: 184, and the VL of the second antigen binding domain comprises an amino acid sequence that is at least about 95%, 96%, 97%, 98%, or 99% identical to the amino acid sequence of SEQ ID NO: 185;

(ii) an amino acid sequence that is at least about 95%, 96%, 97%, 98%, or 99% identical to the amino acid sequence of SEQ ID NO: 186, and the VL of the second antigen binding domain comprises an amino acid sequence that is at least about 95%, 96%, 97%, 98%, or 99% identical to the amino acid sequence of SEQ ID NO: 187;

(iii) an amino acid sequence that is at least about 95%, 96%, 97%, 98%, or 99% identical to the amino acid sequence of SEQ ID NO: 188, and the VL of the second antigen binding domain comprises an amino acid sequence that is at least about 95%, 96%, 97%, 98%, or 99% identical to the amino acid sequence of SEQ ID NO: 189;

(iv) an amino acid sequence that is at least about 95%, 96%, 97%, 98%, or 99% identical to the amino acid sequence of SEQ ID NO: 190, and the VL of the second antigen binding domain comprises an amino acid sequence that is at least about 95%, 96%, 97%, 98%, or 99% identical to the amino acid sequence of SEQ ID NO: 191;

(v) an amino acid sequence that is at least about 95%, 96%, 97%, 98%, or 99% identical to the amino acid sequence of SEQ ID NO: 192, and the VL of the second antigen binding domain comprises an amino acid sequence that is at least about 95%, 96%, 97%, 98%, or 99% identical to the amino acid sequence of SEQ ID NO: 193;

(vi) an amino acid sequence that is at least about 95%, 96%, 97%, 98%, or 99% identical to the amino acid sequence of SEQ ID NO: 194, and the VL of the second antigen binding domain comprises an amino acid sequence that is at least about 95%, 96%, 97%, 98%, or 99% identical to the amino acid sequence of SEQ ID NO: 195;

(vii) an amino acid sequence that is at least about 95%, 96%, 97%, 98%, or 99% identical to the amino acid sequence of SEQ ID NO: 196, and the VL of the second antigen binding domain comprises an amino acid sequence that is at least about 95%, 96%, 97%, 98%, or 99% identical to the amino acid sequence of SEQ ID NO: 197;

(viii) an amino acid sequence that is at least about 95%, 96%, 97%, 98%, or 99% identical to the amino acid sequence of SEQ ID NO: 198, and the VL of the second antigen binding domain comprises an amino acid sequence that is at least about 95%, 96%, 97%, 98%, or 99% identical to the amino acid sequence of SEQ ID NO: 199;

(ix) an amino acid sequence that is at least about 95%, 96%, 97%, 98%, or 99% identical to the amino acid sequence of SEQ ID NO: 200, and the VL of the second antigen binding domain comprises an amino acid sequence that is at least about 95%, 96%, 97%, 98%, or 99% identical to the amino acid sequence of SEQ ID NO: 201;

(x) an amino acid sequence that is at least about 95%, 96%, 97%, 98%, or 99% identical to the amino acid sequence of SEQ ID NO: 202, and the VL of the second antigen binding domain comprises an amino acid sequence that is at least about 95%, 96%, 97%, 98%, or 99% identical to the amino acid sequence of SEQ ID NO: 203;

(xi) an amino acid sequence that is at least about 95%, 96%, 97%, 98%, or 99% identical to the amino acid sequence of SEQ ID NO: 204, and the VL of the second antigen binding domain comprises an amino acid sequence that is at least about 95%, 96%, 97%, 98%, or 99% identical to the amino acid sequence of SEQ ID NO: 205; or (xii) an amino acid sequence that is at least about 95%, 96%, 97%, 98%, or 99% identical to the amino acid sequence of SEQ ID NO: 206, and the VL of the second antigen binding domain comprises an amino acid sequence that is at least about 95%, 96%, 97%, 98%, or 99% identical to the amino acid sequence of SEQ ID NO: 207.

In one aspect, the VH comprises (i) the amino acid sequence of SEQ ID NO: 184 and the VL comprises the amino acid sequence of SEQ ID NO: 185;

(ii) the amino acid sequence of SEQ ID NO: 186 and the VL comprises the amino acid sequence of SEQ ID NO: 187;

(iii) the amino acid sequence of SEQ ID NO: 188 and the VL comprises the amino acid sequence of SEQ ID NO: 189;

(iv) the amino acid sequence of SEQ ID NO: 190 and the VL comprises the amino acid sequence of SEQ ID NO: 191;

(v) the amino acid sequence of SEQ ID NO: 192 and the VL comprises the amino acid sequence of SEQ ID NO: 193;

(vi) the amino acid sequence of SEQ ID NO: 194 and the VL comprises the amino acid sequence of SEQ ID NO: 195;

(vii) the amino acid sequence of SEQ ID NO: 196 and the VL comprises the amino acid sequence of SEQ ID NO: 197;

(viii) the amino acid sequence of SEQ ID NO: 198 and the VL comprises the amino acid sequence of SEQ ID NO: 199;

(ix) the amino acid sequence of SEQ ID NO: 200 and the VL comprises the amino acid sequence of SEQ ID NO: 201;

(x) the amino acid sequence of SEQ ID NO: 202 and the VL comprises the amino acid sequence of SEQ ID NO: 203;

(xi) the amino acid sequence of SEQ ID NO: 204 and the VL comprises the amino acid sequence of SEQ ID NO: 205; or (xii) the amino acid sequence of SEQ ID NO: 206 and the VL comprises the amino acid sequence of SEQ ID NO: 207.

In a further aspect, the second antigen binding domain comprises (i) a VH comprising the amino acid sequence of SEQ ID NO: 184 and a VL comprising the amino acid sequence of SEQ ID NO: 185;

(ii) a VH comprising the amino acid sequence of SEQ ID NO: 186 and a VL comprising the amino acid sequence of SEQ ID NO: 187;

(iii) a VH comprising the amino acid sequence of SEQ ID NO: 188 and a VL comprising the amino acid sequence of SEQ ID NO: 189;

(iv) a VH comprising the amino acid sequence of SEQ ID NO: 190 and a VL comprising the amino acid sequence of SEQ ID NO: 191;

(v) a VH comprising the amino acid sequence of SEQ ID NO: 192 and a VL comprising the amino acid sequence of SEQ ID NO: 193;
(vi) a VH comprising the amino acid sequence of SEQ ID NO: 194 and a VL comprising the amino acid sequence of SEQ ID NO: 195;
(vii) a VH comprising the amino acid sequence of SEQ ID NO: 196 and a VL comprising the amino acid sequence of SEQ ID NO: 197;
(viii) a VH comprising the amino acid sequence of SEQ ID NO: 198 and a VL comprising the amino acid sequence of SEQ ID NO: 199;
(ix) a VH comprising the amino acid sequence of SEQ ID NO: 200 and a VL comprising the amino acid sequence of SEQ ID NO: 201;
(x) a VH comprising the amino acid sequence of SEQ ID NO: 202 and a VL comprising the amino acid sequence of SEQ ID NO: 203;
(xi) a VH comprising the amino acid sequence of SEQ ID NO: 204 and a VL comprising the amino acid sequence of SEQ ID NO: 205; or
(xii) a VH comprising the amino acid sequence of SEQ ID NO: 206 and a VL comprising the amino acid sequence of SEQ ID NO: 207.

In a further aspect, the second antigen binding domain comprises
(i) a VH sequence of SEQ ID NO: 184 and a VL sequence of SEQ ID NO: 185;
(ii) a VH sequence of SEQ ID NO: 186 and a VL sequence of SEQ ID NO: 187;
(iii) a VH sequence of SEQ ID NO: 188 and a VL sequence of SEQ ID NO: 189;
(iv) a VH sequence of SEQ ID NO: 190 and a VL sequence of SEQ ID NO: 191;
(v) a VH sequence of SEQ ID NO: 192 and a VL sequence of SEQ ID NO: 193;
(vi) a VH sequence of SEQ ID NO: 194 and a VL sequence of SEQ ID NO: 195;
(vii) a VH sequence of SEQ ID NO: 196 and a VL sequence of SEQ ID NO: 197;
(viii) a VH sequence of SEQ ID NO: 198 and a VL sequence of SEQ ID NO: 199;
(ix) a VH sequence of SEQ ID NO: 200 and a VL sequence of SEQ ID NO: 201;
(x) a VH sequence of SEQ ID NO: 202 and a VL sequence of SEQ ID NO: 203;
(xi) a VH sequence of SEQ ID NO: 204 and a VL sequence of SEQ ID NO: 205; or
(xii) a VH sequence of SEQ ID NO: 206 and a VL sequence of SEQ ID NO: 207.

In another aspect, the second antigen binding domain comprises
(i) a VH comprising the heavy chain CDR sequences of the VH of SEQ ID NO: 184, and a VL comprising the light chain CDR sequences of the VL of SEQ ID NO: 185;
(ii) a VH comprising the heavy chain CDR sequences of the VH of SEQ ID NO: 186, and a VL comprising the light chain CDR sequences of the VL of SEQ ID NO: 187;
(iii) a VH comprising the heavy chain CDR sequences of the VH of SEQ ID NO: 188, and a VL comprising the light chain CDR sequences of the VL of SEQ ID NO: 189;
(iv) a VH comprising the heavy chain CDR sequences of the VH of SEQ ID NO: 190, and a VL comprising the light chain CDR sequences of the VL of SEQ ID NO: 191;
(v) a VH comprising the heavy chain CDR sequences of the VH of SEQ ID NO: 192, and a VL comprising the light chain CDR sequences of the VL of SEQ ID NO: 193;
(vi) a VH comprising the heavy chain CDR sequences of the VH of SEQ ID NO: 194, and a VL comprising the light chain CDR sequences of the VL of SEQ ID NO: 195;
(vii) a VH comprising the heavy chain CDR sequences of the VH of SEQ ID NO: 196, and a VL comprising the light chain CDR sequences of the VL of SEQ ID NO: 197;
(viii) a VH comprising the heavy chain CDR sequences of the VH of SEQ ID NO: 198, and a VL comprising the light chain CDR sequences of the VL of SEQ ID NO: 199;
(ix) a VH comprising the heavy chain CDR sequences of the VH of SEQ ID NO: 200, and a VL comprising the light chain CDR sequences of the VL of SEQ ID NO: 201;
(x) a VH comprising the heavy chain CDR sequences of the VH of SEQ ID NO: 202, and a VL comprising the light chain CDR sequences of the VL of SEQ ID NO: 203;
(xi) a VH comprising the heavy chain CDR sequences of the VH of SEQ ID NO: 204, and a VL comprising the light chain CDR sequences of the VL of SEQ ID NO: 205; or
(xii) a VH comprising the heavy chain CDR sequences of the VH of SEQ ID NO: 206, and a VL comprising the light chain CDR sequences of the VL of SEQ ID NO: 207.

In a further aspect, the second antigen binding domain comprises
(i) the HCDR1, HCDR2 and HCDR3 amino acid sequences of the VH of SEQ ID NO: 184 and the LCDR1, LCDR2 and LCDR3 amino acid sequences of the VL of SEQ ID NO: 185;
(ii) the HCDR1, HCDR2 and HCDR3 amino acid sequences of the VH of SEQ ID NO: 186 and the LCDR1, LCDR2 and LCDR3 amino acid sequences of the VL of SEQ ID NO: 187;
(iii) the HCDR1, HCDR2 and HCDR3 amino acid sequences of the VH of SEQ ID NO: 188 and the LCDR1, LCDR2 and LCDR3 amino acid sequences of the VL of SEQ ID NO: 189;
(iv) the HCDR1, HCDR2 and HCDR3 amino acid sequences of the VH of SEQ ID NO: 190 and the LCDR1, LCDR2 and LCDR3 amino acid sequences of the VL of SEQ ID NO: 191;
(v) the HCDR1, HCDR2 and HCDR3 amino acid sequences of the VH of SEQ ID NO: 192 and the LCDR1, LCDR2 and LCDR3 amino acid sequences of the VL of SEQ ID NO: 193;
(vi) the HCDR1, HCDR2 and HCDR3 amino acid sequences of the VH of SEQ ID NO: 194 and the LCDR1, LCDR2 and LCDR3 amino acid sequences of the VL of SEQ ID NO: 195;
(vii) the HCDR1, HCDR2 and HCDR3 amino acid sequences of the VH of SEQ ID NO: 196 and the LCDR1, LCDR2 and LCDR3 amino acid sequences of the VL of SEQ ID NO: 197;

(viii) the HCDR1, HCDR2 and HCDR3 amino acid sequences of the VH of SEQ ID NO: 198 and the LCDR1, LCDR2 and LCDR3 amino acid sequences of the VL of SEQ ID NO: 199;

(ix) the HCDR1, HCDR2 and HCDR3 amino acid sequences of the VH of SEQ ID NO: 200 and the LCDR1, LCDR2 and LCDR3 amino acid sequences of the VL of SEQ ID NO: 201;

(x) the HCDR1, HCDR2 and HCDR3 amino acid sequences of the VH of SEQ ID NO: 202 and the LCDR1, LCDR2 and LCDR3 amino acid sequences of the VL of SEQ ID NO: 203;

(xi) the HCDR1, HCDR2 and HCDR3 amino acid sequences of the VH of SEQ ID NO: 204 and the LCDR1, LCDR2 and LCDR3 amino acid sequences of the VL of SEQ ID NO: 205; or (xii) the HCDR1, HCDR2 and HCDR3 amino acid sequences of the VH of SEQ ID NO: 206 and the LCDR1, LCDR2 and LCDR3 amino acid sequences of the VL of SEQ ID NO: 207.

In one aspect, the VH of the second antigen binding domain comprises the heavy chain CDR sequences of a VH selected from the group consisting of SEQ ID NO: 184, 186, 188, 190, 192, 194, 196, 198, 200, 202, 204 and 206 and a framework of at least 95%, 96%, 97%, 98% or 99% sequence identity to the framework sequence of a VH selected from the group consisting of SEQ ID NO: 184, 186, 188, 190, 192, 194, 196, 198, 200, 202, 204 and 206. In one aspect, the VH comprises the heavy chain CDR sequences of a VH selected from the group consisting of SEQ ID NO: 184, 186, 188, 190, 192, 194, 196, 198, 200, 202, 204 and 206 and a framework of at least 95% sequence identity to the framework sequence of a VH selected from the group consisting of SEQ ID NO: 184, 186, 188, 190, 192, 194, 196, 198, 200, 202, 204 and 206. In another aspect, the VH comprises the heavy chain CDR sequences of a VH selected from the group consisting of SEQ ID NO: 184, 186, 188, 190, 192, 194, 196, 198, 200, 202, 204 and 206 and a framework of at least 98% sequence identity to the framework sequence of a VH selected from the group consisting of SEQ ID NO: 184, 186, 188, 190, 192, 194, 196, 198, 200, 202, 204 and 206.

In one aspect, the VL of the second antigen binding domain comprises the light chain CDR sequences of a VL selected from the group of SEQ ID NO: 185, 187, 189, 191, 193, 195, 197, 199, 201, 203, 205 and 207 and a framework of at least 95%, 96%, 97%, 98% or 99% sequence identity to the framework sequence of a VL selected from the group of SEQ ID NO: 185, 187, 189, 191, 193, 195, 197, 199, 201, 203, 205 and 207. In one aspect, the VL comprises the light chain CDR sequences of a VL selected from the group of SEQ ID NO: 185, 187, 189, 191, 193, 195, 197, 199, 201, 203, 205 and 207 and a framework of at least 95% sequence identity to the framework sequence of a VL selected from the group of SEQ ID NO: 185, 187, 189, 191, 193, 195, 197, 199, 201, 203, 205 and 207. In another aspect, the VL comprises the light chain CDR sequences of a VL selected from the group of SEQ ID NO: 185, 187, 189, 191, 193, 195, 197, 199, 201, 203, 205 and 207 and a framework of at least 98% sequence identity to the framework sequence of a VL selected from the group of SEQ ID NO: 185, 187, 189, 191, 193, 195, 197, 199, 201, 203, 205 and 207.

In one aspect, the second antigen binding domain comprises a VH sequence as in any of the aspects provided in this section above, and a VL sequence as in any of the aspects provided in this section above.

c) Charge Modifications

The (multispecific) antibody of the invention may comprise amino acid substitutions in Fab molecules comprised therein which are particularly efficient in reducing mispairing of light chains with non-matching heavy chains (Bence-Jones-type side products), which can occur in the production of Fab-based multispecific antibodies with a VH/VL exchange in one (or more, in case of molecules comprising more than two antigen-binding Fab molecules) of their binding arms (see also PCT publication no. WO 2015/150447, particularly the examples therein, incorporated herein by reference in its entirety). The ratio of a desired (multispecific) antibody compared to undesired side products, in particular Bence Jones-type side products occurring in multispecific antibodies with a VH/VL domain exchange in one of their binding arms, can be improved by the introduction of charged amino acids with opposite charges at specific amino acid positions in the CH1 and CL domains (sometimes referred to herein as "charge modifications").

Accordingly, in some aspects wherein the first and the second antigen binding domain of the (multispecific) antibody are both Fab molecules, and in one of the antigen binding domains (particularly the first antigen binding domain) the variable domains VL and VH of the Fab light chain and the Fab heavy chain are replaced by each other, i) in the constant domain CL of the second antigen binding domain the amino acid at position 124 is substituted by a positively charged amino acid (numbering according to Kabat), and wherein in the constant domain CH1 of the second antigen binding domain the amino acid at position 147 or the amino acid at position 213 is substituted by a negatively charged amino acid (numbering according to Kabat EU index); or ii) in the constant domain CL of the first antigen binding domain the amino acid at position 124 is substituted by a positively charged amino acid (numbering according to Kabat), and wherein in the constant domain CH1 of the first antigen binding domain the amino acid at position 147 or the amino acid at position 213 is substituted by a negatively charged amino acid (numbering according to Kabat EU index).

The (multispecific) antibody does not comprise both modifications mentioned under i) and ii).

The constant domains CL and CH1 of the antigen binding domain having the VH/VL exchange are not replaced by each other (i.e. remain unexchanged).

In a more specific aspect, i) in the constant domain CL of the second antigen binding domain the amino acid at position 124 is substituted independently by lysine (K), arginine (R) or histidine (H) (numbering according to Kabat), and in the constant domain CH1 of the second antigen binding domain the amino acid at position 147 or the amino acid at position 213 is substituted independently by glutamic acid (E), or aspartic acid (D) (numbering according to Kabat EU index); or ii) in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 or the amino acid at position 213 is substituted independently by glutamic acid (E), or aspartic acid (D) (numbering according to Kabat EU index).

In one such aspect, in the constant domain CL of the second antigen binding domain the amino acid at position 124 is substituted independently by lysine (K), arginine (R)

or histidine (H) (numbering according to Kabat), and in the constant domain CH1 of the second antigen binding domain the amino acid at position 147 or the amino acid at position 213 is substituted independently by glutamic acid (E), or aspartic acid (D) (numbering according to Kabat EU index).

In a further aspect, in the constant domain CL of the second antigen binding domain the amino acid at position 124 is substituted independently by lysine (K), arginine (R) or histidine (H) (numbering according to Kabat), and in the constant domain CH1 of the second antigen binding domain the amino acid at position 147 is substituted independently by glutamic acid (E), or aspartic acid (D) (numbering according to Kabat EU index).

In a preferred aspect, in the constant domain CL of the second antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more preferred aspect, in the constant domain CL of the second antigen binding domain the amino acid at position 124 is substituted by lysine (K) (numbering according to Kabat) and the amino acid at position 123 is substituted by lysine (K) (numbering according to Kabat), and in the constant domain CH1 of the second antigen binding domain the amino acid at position 147 is substituted by glutamic acid (E) (numbering according to Kabat EU index) and the amino acid at position 213 is substituted by glutamic acid (E) (numbering according to Kabat EU index).

In an even more preferred aspect, in the constant domain CL of the second antigen binding domain the amino acid at position 124 is substituted by lysine (K) (numbering according to Kabat) and the amino acid at position 123 is substituted by arginine (R) (numbering according to Kabat), and in the constant domain CH1 of the second antigen binding domain the amino acid at position 147 is substituted by glutamic acid (E) (numbering according to Kabat EU index) and the amino acid at position 213 is substituted by glutamic acid (E) (numbering according to Kabat EU index).

In preferred aspects, if amino acid substitutions according to the above aspects are made in the constant domain CL and the constant domain CH1 of the second antigen binding domain, the constant domain CL of the second antigen binding domain is of kappa isotype.

Alternatively, the amino acid substitutions according to the above aspects may be made in the constant domain CL and the constant domain CH1 of the first antigen binding domain instead of in the constant domain CL and the constant domain CH1 of the second antigen binding domain. In preferred such aspects, the constant domain CL of the first antigen binding domain is of kappa isotype.

Accordingly, in one aspect, in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 or the amino acid at position 213 is substituted independently by glutamic acid (E), or aspartic acid (D) (numbering according to Kabat EU index).

In a further aspect, in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 is substituted independently by glutamic acid (E), or aspartic acid (D) (numbering according to Kabat EU index).

In still another aspect, in the constant domain CL of the first antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the first antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one aspect, in the constant domain CL of the first antigen binding domain the amino acid at position 124 is substituted by lysine (K) (numbering according to Kabat) and the amino acid at position 123 is substituted by lysine (K) (numbering according to Kabat), and in the constant domain CH1 of the first antigen binding domain the amino acid at position 147 is substituted by glutamic acid (E) (numbering according to Kabat EU index) and the amino acid at position 213 is substituted by glutamic acid (E) (numbering according to Kabat EU index).

In another aspect, in the constant domain CL of the first antigen binding domain the amino acid at position 124 is substituted by lysine (K) (numbering according to Kabat) and the amino acid at position 123 is substituted by arginine (R) (numbering according to Kabat), and in the constant domain CH1 of the first antigen binding domain the amino acid at position 147 is substituted by glutamic acid (E) (numbering according to Kabat EU index) and the amino acid at position 213 is substituted by glutamic acid (E) (numbering according to Kabat EU index).

In a preferred aspect, the (multispecific) antibody of the invention comprises
- (a) a first antigen binding domain that binds to NKG2D, wherein the first antigen binding domain is a Fab molecule wherein the variable domains VL and VH of the Fab light chain and the Fab heavy chain are replaced by each other, and comprises a heavy chain variable region (VH) and a light chain variable region (VL) as in any of the aspects provided in relation to the first antigen binding domain herein;
- (b) a second antigen binding domain that binds to a second antigen;
- wherein in the constant domain CL of the second (and, where present, third) antigen binding domain the amino acid at position 124 is substituted independently by lysine (K), arginine (R) or histidine (H) (numbering according to Kabat) (in a preferred aspect independently by lysine (K) or arginine (R)) and the amino acid at position 123 is substituted independently by lysine (K), arginine (R) or histidine (H) (numbering according to Kabat) (in a preferred aspect independently by lysine (K) or arginine (R)), and in the constant domain CH1 of the second (and, where present, third) antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

d) Multispecific Antibody Formats

Figure 12:
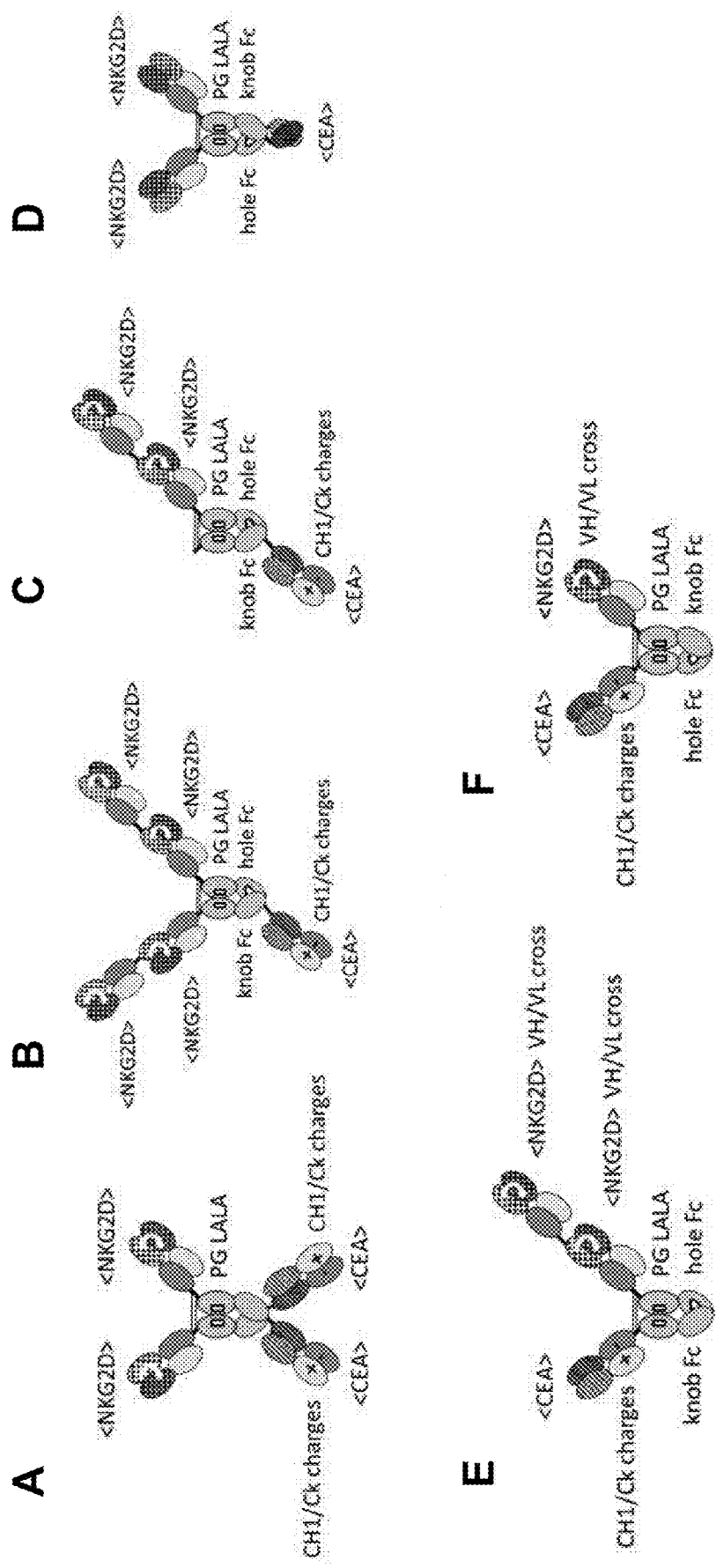
FIG. 12. Schematic illustration of NKG2D bispecific antibody formats (with CEA as exemplary second specificity). (A) D-format, (B) J-format, (C) K-format, (D) I-format, (E) L-format, (F) M-format.

The (multispecific) antibodies according to the present invention can have a variety of configurations. Exemplary configurations are depicted in FIG. 12.

In preferred aspects, the antigen binding domains comprised in the (multispecific) antibody are Fab molecules. In such aspects, the first, second etc. antigen binding domain may be referred to herein as first, second etc. Fab molecule, respectively.

In preferred aspects, the first and the second antigen binding domain are each a Fab molecule. In some aspects, the first and/or the second (particularly the second) antigen binding domain may be an Fv molecule.

In aspects wherein the first and the second antigen binding domain are each a Fab molecule, preferably the first antigen binding domain is a crossover Fab molecule as described herein (i.e. a Fab molecule wherein the variable domains VH and VL or the constant domains CH1 and CL of the Fab heavy and light chains are exchanged/replaced by each other), and the second antigen binding domain is a conventional Fab molecule—or vice versa.

In aspects wherein the (multispecific) antibody comprises more than one antigen binding domain that binds to NKG2D and/or more than one antigen binding domain that binds to a second antigen, preferably all the antigen binding domains that bind NKG2D are crossover Fab molecules as described herein, and all the antigen binding domains that bind the second antigen are conventional Fab molecules—or vice versa.

In preferred aspects, the (multispecific) antibody of the invention comprises an Fc domain composed of a first and a second subunit. The first and the second subunit of the Fc domain are capable of stable association.

The (multispecific) antibody according to the invention can have different configurations, i.e. the first, second and optionally further antigen binding domains may be fused to each other and to the Fc domain in different ways. The components may be fused to each other directly or, preferably, via one or more suitable peptide linkers. Where fusion of a Fab molecule is to the N-terminus of a subunit of the Fc domain, it is typically via an immunoglobulin hinge region.

In preferred aspects, the (multispecific) antibody of the invention comprises
(a) a first antigen binding domain that binds to NKG2D,
(b) a second antigen binding domain that binds to a second antigen, and
(c) an Fc domain composed of a first and a second subunit;
wherein the first and the second antigen binding domains are each a Fab molecule, and
wherein (i) the first antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the second subunit of the Fc domain and the first antigen binding domain is fused at the C-terminus of the Fab heavy chain to the N-terminus of the first subunit of the Fc domain.
An exemplary such configuration is depicted in FIG. 12F.

In one such aspect, the first antigen binding domain is a crossover Fab molecule as described herein, and the second antigen binding domain is a conventional Fab molecule. In a more specific such aspect, the first antigen binding domain is a crossover Fab molecule wherein the variable domains VH and VL are exchanged/replaced by each other, and the second antigen binding domain is a conventional Fab molecule comprising charge modifications as described herein.

In another such aspect, the first antigen binding domain is a conventional Fab molecule, and the second antigen binding domain is a crossover Fab molecule as described herein. In a more specific such aspect, the first antigen binding domain is a conventional Fab molecule comprising charge modifications as described herein, and the second antigen binding domain is a crossover Fab molecule wherein the variable domains VH and VL are exchanged/replaced by each other.

In a further such aspect, the Fc domain comprises a modification promoting the association of the first and the second subunit of the Fc domain, as described herein.

In still a further such aspect, the (multispecific) antibody essentially consists of the first and the second antigen binding domain and the Fc domain, and optionally one or more peptide linkers.

In other aspects, the (multispecific) antibody of the invention comprises
(a) a first antigen binding domain that binds to NKG2D,
(b) a second antigen binding domain that binds to a second antigen,
(c) a third antigen binding domain that binds to NKG2D, and
(d) an Fc domain composed of a first and a second subunit;
wherein the first, second and third antigen binding domains are each a Fab molecule, and
wherein (i) the first antigen binding domain is fused at the C-terminus of the Fab heavy chain to the N-terminus of the first subunit of the Fc domain, the second antigen binding domain is fused at the C-terminus of the Fab heavy chain to the N-terminus of the second subunit of the Fc domain, and the third antigen binding domain is fused at the C-terminus of the Fab heavy chain to the N-terminus of the Fab heavy chain of the first antigen binding domain, or (ii) the first antigen binding domain is fused at the C-terminus of the Fab heavy chain to the N-terminus of the second subunit of the Fc domain, the second antigen binding domain is fused at the C-terminus of the Fab heavy chain to the N-terminus of the first subunit of the Fc domain, and the third antigen binding domain is fused at the C-terminus of the Fab heavy chain to the N-terminus of the Fab heavy chain of the first antigen binding domain.
An exemplary such configuration is depicted in FIG. 12E.

In one such aspect, the first and the third antigen binding domains are each a crossover Fab molecule as described herein, and the second antigen binding domain is a conventional Fab molecule. In a more specific such aspect, the first and the third antigen binding domains are each a crossover Fab molecule wherein the variable domains VH and VL are exchanged/replaced by each other, and the second antigen binding domain is a conventional Fab molecule comprising charge modifications as described herein.

In another such aspect, the first and the third antigen binding domains are each a conventional Fab molecule, and the second antigen binding domain is a crossover Fab molecule as described herein. In a more specific such aspect, the first and the third antigen binding domains are each a conventional Fab molecule comprising charge modifications as described herein, and the second antigen binding domain is a crossover Fab molecule wherein the variable domains VH and VL are exchanged/replaced by each other.

In a further such aspect, the Fc domain comprises a modification promoting the association of the first and the second subunit of the Fc domain, as described herein.

In still a further such aspect, the (multispecific) antibody essentially consists of the first, the second and the third antigen binding domain and the Fc domain, and optionally one or more peptide linkers.

In other aspects, the (multispecific) antibody of the invention comprises
(a) a first antigen binding domain that binds to NKG2D,
(b) a second antigen binding domain that binds to a second antigen,
(c) a third antigen binding domain that binds to NKG2D, and
(d) an Fc domain composed of a first and a second subunit;
wherein the first, second and third antigen binding domains are each a Fab molecule, and
wherein (i) the first antigen binding domain is fused at the C-terminus of the Fab heavy chain to the N-terminus of the first subunit of the Fc domain, the second antigen binding domain is fused at the N-terminus of the Fab heavy chain to the C-terminus of the second subunit of the Fc domain, and the third antigen binding domain is fused at the C-terminus of the Fab heavy chain to the N-terminus of the Fab heavy chain of the first antigen binding domain, or (ii) the first antigen binding domain is fused at the C-terminus of the Fab heavy chain to the N-terminus of the second subunit of the Fc domain, the second antigen binding domain is fused at the N-terminus of the Fab heavy chain to the C-terminus of the first subunit of the Fc domain, and the third antigen binding domain is fused at the C-terminus of the Fab heavy chain to the N-terminus of the Fab heavy chain of the first antigen binding domain.

An exemplary such configuration is depicted in FIG. 12C.

In one such aspect, the first and the third antigen binding domains are each a crossover Fab molecule as described herein, and the second antigen binding domain is a conventional Fab molecule. In a more specific such aspect, the first and the third antigen binding domains are each a crossover Fab molecule wherein the variable domains VH and VL are exchanged/replaced by each other, and the second antigen binding domain is a conventional Fab molecule comprising charge modifications as described herein.

In another such aspect, the first and the third antigen binding domains are each a conventional Fab molecule, and the second antigen binding domain is a crossover Fab molecule as described herein. In a more specific such aspect, the first and the third antigen binding domains are each a conventional Fab molecule comprising charge modifications as described herein, and the second antigen binding domain is a crossover Fab molecule wherein the variable domains VH and VL are exchanged/replaced by each other.

In a further such aspect, the Fc domain comprises a modification promoting the association of the first and the second subunit of the Fc domain, as described herein.

In still a further such aspect, the (multispecific) antibody essentially consists of the first, the second and the third antigen binding domain and the Fc domain, and optionally one or more peptide linkers.

In other aspects, the (multispecific) antibody of the invention comprises
(a) a first antigen binding domain that binds to NKG2D,
(b) a second antigen binding domain that binds to a second antigen,
(c) a third antigen binding domain that binds to NKG2D,
(d) a fourth antigen binding domain that binds to NKG2D,
(e) a fifth antigen binding domain that binds to NKG2D, and
(f) an Fc domain composed of a first and a second subunit;
wherein the first, second, third, fourth and fifth antigen binding domains are each a Fab molecule, and
wherein (i) the first antigen binding domain is fused at the C-terminus of the Fab heavy chain to the N-terminus of the Fab heavy chain of the third antigen binding domain, and the third antigen binding domain is fused at the C-terminus of the Fab heavy chain to the N-terminus of the first subunit of the Fc domain, (ii) the fourth antigen binding domain is fused at the C-terminus of the Fab heavy chain to the N-terminus of the Fab heavy chain of the fifth antigen binding domain, and the fifth antigen binding domain is fused at the C-terminus of the Fab heavy chain to the N-terminus of the second subunit of the Fc domain, and (iii) the second antigen binding domain is fused at the N-terminus of the Fab heavy chain to the C-terminus of the first or the second subunit of the Fc domain.

An exemplary such configuration is depicted in FIG. 12B.

In one such aspect, the first, the third, the fourth and the fifth antigen binding domains are each a crossover Fab molecule as described herein, and the second antigen binding domain is a conventional Fab molecule. In a more specific such aspect, the first, the third, the fourth and the fifth antigen binding domains are each a crossover Fab molecule wherein the variable domains VH and VL are exchanged/replaced by each other, and the second antigen binding domain is a conventional Fab molecule comprising charge modifications as described herein.

In another such aspect, the first, the third, the fourth and the fifth antigen binding domains are each a conventional Fab molecule, and the second antigen binding domain is a crossover Fab molecule as described herein. In a more specific such aspect, the first, the third, the fourth and the fifth antigen binding domains are each a conventional Fab molecule comprising charge modifications as described herein, and the second antigen binding domain is a crossover Fab molecule wherein the variable domains VH and VL are exchanged/replaced by each other.

In a further such aspect, the Fc domain comprises a modification promoting the association of the first and the second subunit of the Fc domain, as described herein.

In still a further such aspect, the (multispecific) antibody essentially consists of the first, the second, the third, the fourth and the fifth antigen binding domain and the Fc domain, and optionally one or more peptide linkers.

In other aspects, the (multispecific) antibody of the invention comprises
(a) a first antigen binding domain that binds to NKG2D,
(b) a second antigen binding domain that binds to a second antigen,
(c) a third antigen binding domain that binds to NKG2D,
(d) a fourth antigen binding domain that binds to the second antigen,
(e) an Fc domain composed of a first and a second subunit;
wherein the first, second, third and fourth antigen binding domains are each a Fab molecule, and wherein the first antigen binding domain is fused at the C-terminus of the Fab heavy chain to the N-terminus of the first subunit of the Fc domain, the second antigen binding domain is fused at the N-terminus of the Fab heavy chain to the C-terminus of the first subunit of the Fc domain, the third antigen binding domain is fused at the C-terminus of the Fab heavy chain to the N-terminus of the second subunit of the Fc domain, and the fourth antigen binding domain is fused at the N-terminus of the Fab heavy chain to the C-terminus of the second subunit of the Fc domain.

An exemplary such configuration is depicted in FIG. 12A.

In one such aspect, the first and the third antigen binding domains are each a crossover Fab molecule as described herein, and the second and the fourth antigen binding domains are each a conventional Fab molecule. In a more specific such aspect, the first and the third antigen binding domains are each a crossover Fab molecule wherein the variable domains VH and VL are exchanged/replaced by each other, and the second and the fourth antigen binding domain are each a conventional Fab molecule comprising charge modifications as described herein.

In another such aspect, the first and the third antigen binding domains are each a conventional Fab molecule, and the second and the fourth antigen binding domains are each a crossover Fab molecule as described herein. In a more specific such aspect, the first and the third antigen binding domains are each a conventional Fab molecule comprising charge modifications as described herein, and the second and the fourth antigen binding domains are each a crossover Fab molecule wherein the variable domains VH and VL are exchanged/replaced by each other.

In a further such aspect, the (multispecific) antibody essentially consists of the first, the second, the third and the fourth antigen binding domain and the Fc domain, and optionally one or more peptide linkers.

In other aspects, the (multispecific) antibody of the invention comprises
 (a) a first antigen binding domain that binds to NKG2D,
 (b) a second antigen binding domain that binds to a second antigen,
 (c) a third antigen binding domain that binds to NKG2D, and
 (d) an Fc domain composed of a first and a second subunit;
 wherein the first and the third antigen binding domains are each a Fab molecule and the second antigen binding domain is an Fv molecule, and
 wherein the first antigen binding domain is fused at the C-terminus of the Fab heavy chain to the N-terminus of the first subunit of the Fc domain, the third antigen binding domain is fused at the C-terminus of the Fab heavy chain to the N-terminus of the second subunit of the Fc domain, and the second antigen binding domain is fused (i) at the N-terminus of the Fv heavy chain to the C-terminus of the first subunit of the Fc domain and at the N-terminus of the Fv light chain to the C-terminus of the second subunit of the Fc domain, or (ii) at the N-terminus of the Fv heavy chain to the C-terminus of the second subunit of the Fc domain and at the N-terminus of the Fv light chain to the C-terminus of the first subunit of the Fc domain.

An exemplary such configuration is depicted in FIG. 12D.

In one such aspect, the first and the third antigen binding domains are each a conventional Fab molecule.

In a further such aspect, the Fc domain comprises a modification promoting the association of the first and the second subunit of the Fc domain, as described herein.

In still a further such aspect, the (multispecific) antibody essentially consists of the first, the second and the third antigen binding domain and the Fc domain, and optionally one or more peptide linkers.

In configurations of the (multispecific) antibody wherein a Fab molecule is fused at the C-terminus of the Fab heavy chain to the N-terminus of each of the subunits of the Fc domain through an immunoglobulin hinge region, the two Fab molecules, the hinge regions and the Fc domain essentially form an immunoglobulin molecule. In a preferred aspect the immunoglobulin molecule is an IgG class immunoglobulin. In an even more preferred aspect the immunoglobulin is an IgG$_1$ subclass immunoglobulin. In another aspect the immunoglobulin is an IgG$_4$ subclass immunoglobulin. In a further preferred aspect the immunoglobulin is a human immunoglobulin. In other aspects the immunoglobulin is a chimeric immunoglobulin or a humanized immunoglobulin. In one aspect, the immunoglobulin comprises a human constant region, particularly a human Fc region.

The antigen binding domains may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally an integer from 1 to 10, typically from 2 to 4. In one aspect said peptide linker has a length of at least 5 amino acids, in one aspect a length of 5 to 100, in a further aspect of 10 to 50 amino acids. In one aspect said peptide linker is $(GxS)_n$ or $(GXS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3), in one aspect x=4 and n=2 or 4. In one aspect said peptide linker is $(G_4S)_2$ or $(G_4S)_4$. In particular aspects, the peptide linker for fusing the Fab heavy chains of a first and a second Fab molecule to each other in the multispecific antibody formats described hereinabove is $(G_4S)_2$. In further particular aspects, the peptide linker for fusing a Fab molecule or an Fv molecule to the C-terminus of the Fc domain in the multispecific antibody formats described hereinabove is $(G_4S)_4$. Suitable peptide linkers may also comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker. In particular aspects, the fusion of a Fab molecule to the N-terminus of an Fc domain subunit in the multispecific antibody formats described hereinabove is via an immunoglobulin hinge region, preferably via an immunoglobulin hinge region of the same subclass as the Fc domain (e.g. an IgG$_1$ hinge region where the Fc domain is of IgG$_1$ subclass).

In one aspect, the invention provides a (multispecific) antibody comprising
 (a) a first antigen binding domain that binds to NKG2D, wherein the first antigen binding domain comprises a heavy chain variable region (VH) comprising a heavy chain complementary determining region (HCDR) 1 of SEQ ID NO: 73, a HCDR 2 of SEQ ID NO: 104, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78, (b) a second antigen binding domain that binds to a second antigen, particularly a target cell antigen, more particularly a tumor cell antigen, and
(c) an Fc domain composed of a first and a second subunit;
wherein the first and the second antigen binding domains are each a Fab molecule, and
wherein (i) the first antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the second subunit of the Fc domain and the first antigen binding domain is fused at the C-terminus of the Fab heavy chain to the N-terminus of the first subunit of the Fc domain.

In one aspect, the invention provides a (multispecific) antibody comprising
(a) a first antigen binding domain that binds to NKG2D, wherein the first antigen binding domain comprises a heavy chain variable region (VH) comprising a heavy chain complementary determining region (HCDR) 1 of SEQ ID NO: 73, a HCDR 2 of SEQ ID NO: 104, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78,
(b) a second antigen binding domain that binds to a second antigen, particularly a target cell antigen, more particularly a tumor cell antigen, and
(c) an Fc domain composed of a first and a second subunit, comprising a modification promoting the association of the first and the second subunit of the Fc domain;
wherein the first and the second antigen binding domains are each a Fab molecule;
wherein (i) the first antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the second subunit of the Fc domain and the first antigen binding domain is fused at the C-terminus of the Fab heavy chain to the N-terminus of the first subunit of the Fc domain.

In one aspect, the invention provides a (multispecific) antibody comprising
(a) a first antigen binding domain that binds to NKG2D, wherein the first antigen binding domain comprises a heavy chain variable region (VH) comprising a heavy chain complementary determining region (HCDR) 1 of SEQ ID NO: 73, a HCDR 2 of SEQ ID NO: 104, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78,
(b) a second antigen binding domain that binds to a second antigen, particularly a target cell antigen, more particularly a tumor cell antigen, and
(c) an Fc domain composed of a first and a second subunit;
wherein the first and the second antigen binding domains are each a Fab molecule;
wherein (i) the first antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the second subunit of the Fc domain and the first antigen binding domain is fused at the C-terminus of the Fab heavy chain to the N-terminus of the first subunit of the Fc domain; and
wherein the Fc domain comprises one or more amino acid substitution that reduces binding to an Fc receptor and/or effector function, and/or wherein the antibody does not bind to FcγRIIIa (CD16a).

In one aspect, the invention provides a (multispecific) antibody comprising
a) a first antigen binding domain that binds to NKG2D, wherein the first antigen binding domain is a Fab molecule wherein the variable domains VL and VH or the constant domains CL and CH1 of the Fab light chain and the Fab heavy chain are replaced by each other, and comprises a heavy chain variable region (VH) comprising a heavy chain complementary determining region (HCDR) 1 of SEQ ID NO: 73, a HCDR 2 of SEQ ID NO: 104, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78;
b) a second antigen binding domain that binds to a second antigen, particularly a target cell antigen, more particularly a tumor cell antigen, wherein the second antigen binding domain is a (conventional) Fab molecule;
c) an Fc domain composed of a first and a second subunit;
wherein (i) the first antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the second subunit of the Fc domain and the first antigen binding domain is fused at the C-terminus of the Fab heavy chain to the N-terminus of the first subunit of the Fc domain.

In all of the different configurations of the (multispecific) antibody according to the invention, the amino acid substitutions ("charge modifications") described herein, if present, may either be in the CH1 and CL domains of the second antigen binding domain/Fab molecule, or in the CH1 and CL domains of the first antigen binding domain/Fab molecule. Preferably, they are in the CH1 and CL domains of the second antigen binding domain/Fab molecule. In accordance with the concept of the invention, if amino acid substitutions as described herein are made in the second antigen binding domain/Fab molecule, no such amino acid substitutions are made in the first antigen binding domain/Fab molecule. Conversely, if amino acid substitutions as described herein are made in the first antigen binding domain/Fab molecule, no such amino acid substitutions are made in the second antigen binding domain/Fab molecule. Amino acid substitutions are preferably made in (multispecific) antibodies comprising a Fab molecule wherein the variable domains VL and VH1 of the Fab light chain and the Fab heavy chain are replaced by each other.

In preferred aspects of the (multispecific) antibody according to the invention, particularly wherein amino acid substitutions as described herein are made in the second antigen binding domain/Fab molecule, the constant domain CL of the second Fab molecule is of kappa isotype. In other aspects of the (multispecific) antibody according to the invention, particularly wherein amino acid substitutions as described herein are made in the first antigen binding domain/Fab molecule, the constant domain CL of the first antigen binding domain/Fab molecule is of kappa isotype. In some aspects, the constant domain CL of the second antigen binding domain/Fab molecule and the constant domain CL of the first antigen binding domain/Fab molecule are of kappa isotype.

In one aspect, the invention provides a (multispecific) antibody comprising a) a first antigen binding domain that binds to NKG2D, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 73, a HCDR 2 of SEQ ID NO: 104, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78;

b) a second antigen binding domain that binds to a second antigen, particularly a target cell antigen, more particularly a tumor cell antigen, wherein the second antigen binding domain is a (conventional) Fab molecule;

c) an Fc domain composed of a first and a second subunit;

wherein in the constant domain CL of the second antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second antigen binding domain under b) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the second subunit of the Fc domain and the first antigen binding domain is fused at the C-terminus of the Fab heavy chain to the N-terminus of the first subunit of the Fc domain.

According to any of the above aspects, components of the (multispecific) antibody (e.g. Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$ or $G_4(SG_4)_n$ peptide linkers, wherein n is generally an integer from 1 to 10, typically from 2 to 4.

In one aspect according to these aspects of the inventions, the first antigen binding domain comprises a VH comprising an amino acid sequence that is at least about 95%, 96%, 97%, 98%, 99% or 100% identical to the amino acid sequence of SEQ ID NO: 112, and/or a VL comprising an amino acid sequence that is at least about 95%, 96%, 97%, 98%, 99% or 100% identical to the amino acid sequence of SEQ ID NO: 80.

In one aspect according to these aspects of the invention, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index).

In a further aspect according to these aspects of the invention, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index).

In still a further aspect according to these aspects of the invention, in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In still a further aspect according to these aspects of the invention, the Fc domain is a human $IgG_1$ Fc domain.

In one aspect the invention provides a (multispecific) antibody that binds to NKG2D and CEA, comprising a polypeptide comprising an amino acid sequence that is at least 95%, 96%, 97%, 98%, or 99% identical to the sequence of SEQ ID NO: 209, a polypeptide comprising an amino acid sequence that is at least 95%, 96%, 97%, 98%, or 99% identical to the sequence of SEQ ID NO: 210, a polypeptide comprising an amino acid sequence that is at least 95%, 96%, 97%, 98%, or 99% identical to the sequence of SEQ ID NO: 211, and a polypeptide comprising an amino acid sequence that is at least 95%, 96%, 97%, 98%, or 99% identical to the sequence of SEQ ID NO: 212. In one aspect the invention provides a (multispecific) antibody that binds to NKG2D and CEA, comprising a polypeptide comprising the amino acid sequence of SEQ ID NO: 209, a polypeptide comprising the amino acid sequence of SEQ ID NO: 210, a polypeptide comprising the amino acid sequence of SEQ ID NO: 211 and a polypeptide comprising the amino acid sequence of SEQ ID NO: 212.

In another aspect the invention provides a (multispecific) antibody that binds to NKG2D and CEA, comprising a polypeptide comprising an amino acid sequence that is at least 95%, 96%, 97%, 98%, or 99% identical to the sequence of SEQ ID NO: 213, a polypeptide comprising an amino acid sequence that is at least 95%, 96%, 97%, 98%, or 99% identical to the sequence of SEQ ID NO: 214, a polypeptide comprising an amino acid sequence that is at least 95%, 96%, 97%, 98%, or 99% identical to the sequence of SEQ ID NO: 215, and a polypeptide comprising an amino acid sequence that is at least 95%, 96%, 97%, 98%, or 99% identical to the sequence of SEQ ID NO: 216. In one aspect the invention provides a (multispecific) antibody that binds to NKG2D and CEA, comprising a polypeptide comprising the amino acid sequence of SEQ ID NO: 213, a polypeptide comprising the amino acid sequence of SEQ ID NO: 214, a polypeptide comprising the amino acid sequence of SEQ ID NO: 215 and a polypeptide comprising the amino acid sequence of SEQ ID NO: 216.

In further aspects the invention provides a (multispecific) antibody that binds to NKG2D and CEA, comprising a polypeptide comprising an amino acid sequence that is at least 95%, 96%, 97%, 98%, or 99% identical to the sequence of SEQ ID NO: 213, a polypeptide comprising an amino acid sequence that is at least 95%, 96%, 97%, 98%, or 99% identical to a sequence of SEQ ID NO: 214 in which the VL region sequence (SEQ ID NO: 193) is replaced by a VL region sequence selected from the group consisting of SEQ ID NO: 185, 187, 189, 191, 195, 197, 199, 201, 203, 205 and 207, a polypeptide comprising an amino acid sequence that is at least 95%, 96%, 97%, 98%, or 99% identical to the sequence of SEQ ID NO: 215, and a polypeptide comprising an amino acid sequence that is at least 95%, 96%, 97%, 98%, or 99% identical to a sequence of SEQ ID NO: 216 in which the VH region sequence (SEQ ID NO: 192) is replaced by a VH region sequence selected from the group consisting of SEQ ID NO: 184, 186, 188, 190, 194, 196, 198, 200, 202, 204 and 206. In one aspect the invention provides a (multispecific) antibody that binds to NKG2D and CEA, comprising a polypeptide comprising the amino acid sequence of SEQ ID NO: 213, a polypeptide comprising the amino acid sequence of SEQ ID NO: 214 in which the VL region sequence (SEQ ID NO: 193) is replaced by a VL region sequence selected from the group consisting of SEQ ID NO: 185, 187, 189, 191, 195, 197, 199, 201, 203, 205 and 207, a polypeptide comprising the amino acid sequence of SEQ ID NO: 215 and a polypeptide comprising the amino acid sequence of SEQ ID NO: 216 in which the VH region sequence (SEQ ID NO: 192) is replaced by a VH region sequence selected from the group consisting of SEQ ID NO: 184, 186, 188, 190, 194, 196, 198, 200, 202, 204 and 206. Preferably, in the above aspects, the VH and VL regions (SEQ ID NOs 192 and 193) are replaced by pairs of VH and VL regions corresponding to the binders identified in Table 16.

2. Fc Domain Variants

In preferred aspects, the (multispecific) antibody of the invention comprises an Fc domain composed of a first and a second subunit.

The Fc domain of the (multispecific) antibody consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one aspect, the (multispecific) antibody of the invention comprises not more than one Fc domain.

In one aspect, the Fc domain of the (multispecific) antibody is an IgG Fc domain. In a preferred aspect, the Fc domain is an $IgG_1$ Fc domain. In another aspect the Fc domain is an $IgG_4$ Fc domain. In a more specific aspect, the Fc domain is an $IgG_4$ Fc domain comprising an amino acid substitution at position S228 (Kabat EU index numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further preferred aspect, the Fc domain is a human Fc domain. In an even more preferred aspect, the Fc domain is a human $IgG_1$ Fc domain. An exemplary sequence of a human $IgG_1$ Fc region is given in SEQ ID NO: 86.

a) Fc Domain Modifications Promoting Heterodimerization (Multispecific) antibodies according to the invention comprise different antigen binding domains, which may be fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of (multispecific) antibodies in recombinant production, it will thus be advantageous to introduce in the Fc domain of the (multispecific) antibody a modification promoting the association of the desired polypeptides.

Accordingly, in preferred aspects, the Fc domain of the (multispecific) antibody according to the invention comprises a modification promoting the association of the first and the second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homodimers between the two first or the two second CH3 domains are formed). These different approaches for improved heavy chain heterodimerization are contemplated as different alternatives in combination with the heavy-light chain modifications (e.g. VH and VL exchange/replacement in one binding arm and the introduction of substitutions of charged amino acids with opposite charges in the CH1/CL interface) in the (multispecific) antibody which reduce heavy/light chain mispairing and Bence Jones-type side products.

In a specific aspect said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a preferred aspect, in the CH3 domain of the first subunit of the Fc domain of the (multispecific) antibody an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific aspect, in (the CH3 domain of) the first subunit of the Fc domain (the "knobs" subunit) the threonine residue at position 366 is replaced with a tryptophan residue (T366W), and in (the CH3 domain of) the second subunit of the Fc domain (the "hole" subunit) the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further aspect, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a preferred aspect, the first subunit of the Fc domain comprises the amino acid substitutions S354C and T366W, and the second subunit of the Fc domain comprises the amino acid substitutions Y349C, T366S, L368A and Y407V (numbering according to Kabat EU index).

In a preferred aspect the antigen binding domain that binds to CD3 is fused (optionally via the second antigen binding domain, that binds to a second antigen, and/or a peptide linker) to the first subunit of the Fc domain (comprising the "knob" modification). Without wishing to be bound by theory, fusion of the antigen binding domain that binds CD3 to the knob-containing subunit of the Fc domain will (further) minimize the generation of antibodies comprising two antigen binding domains that bind to CD3 (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one aspect, the heterodimerization approach described in EP 1870459, is used alternatively. This approach is based on the introduction of charged amino acids with opposite charges at specific amino acid positions in the CH3/CH3 domain interface between the two subunits of the Fc domain. A particular aspect for the (multispecific) antibody of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another aspect, the (multispecific) antibody of the invention comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another aspect, the (multispecific) antibody of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said (multispecific) antibody comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one aspect, the heterodimerization approach described in WO 2013/157953 is used alternatively. In one aspect, a first CH3 domain comprises amino acid mutation T366K and a second CH3 domain comprises amino acid mutation L351D (numberings according to Kabat EU index). In a further aspect, the first CH3 domain comprises further amino acid mutation L351K. In a further aspect, the second CH3 domain comprises further an amino acid mutation selected from Y349E, Y349D and L368E (particularly L368E) (numberings according to Kabat EU index).

In one aspect, the heterodimerization approach described in WO 2012/058768 is used alternatively. In one aspect a first CH3 domain comprises amino acid mutations L351Y, Y407A and a second CH3 domain comprises amino acid mutations T366A, K409F. In a further aspect the second CH3 domain comprises a further amino acid mutation at position T411, D399, S400, F405, N390, or K392, e.g. selected from a) T411N, T411R, T411Q, T411K, T411D, T411E or T411W, b) D399R, D399W, D399Y or D399K, c) S400E, S400D, S400R, or S400K, d) F405I, F405M, F405T, F405S, F405V or F405W, e) N390R, N390K or N390D, f) K392V, K392M, K392R, K392L, K392F or K392E (numberings according to Kabat EU index). In a further aspect a first CH3 domain comprises amino acid mutations L351Y, Y407A and a second CH3 domain comprises amino acid mutations T366V, K409F. In a further aspect, a first CH3 domain comprises amino acid mutation Y407A and a second CH3 domain comprises amino acid mutations T366A, K409F. In a further aspect, the second CH3 domain further comprises amino acid mutations K392E, T411E, D399R and S400R (numberings according to Kabat EU index).

In one aspect, the heterodimerization approach described in WO 2011/143545 is used alternatively, e.g. with the amino acid modification at a position selected from the group consisting of 368 and 409 (numbering according to Kabat EU index).

In one aspect, the heterodimerization approach described in WO 2011/090762, which also uses the knobs-into-holes technology described above, is used alternatively. In one aspect a first CH3 domain comprises amino acid mutation T366W and a second CH3 domain comprises amino acid mutation Y407A. In one aspect, a first CH3 domain comprises amino acid mutation T366Y and a second CH3 domain comprises amino acid mutation Y407T (numberings according to Kabat EU index).

In one aspect, the (multispecific) antibody or its Fc domain is of $IgG_2$ subclass and the heterodimerization approach described in WO 2010/129304 is used alternatively.

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such aspect, a first CH3 domain comprises amino acid substitution of K392 or N392 with a negatively charged amino acid (e.g. glutamic acid (E), or aspartic acid (D), particularly K392D or N392D) and a second CH3 domain comprises amino acid substitution of D399, E356, D356, or E357 with a positively charged amino acid (e.g. lysine (K) or arginine (R), particularly D399K, E356K, D356K, or E357K, and more particularly D399K and E356K). In a further aspect, the first CH3 domain further comprises amino acid substitution of K409 or R409 with a negatively charged amino acid (e.g. glutamic acid (E), or aspartic acid (D), particularly K409D or R409D). In a further aspect the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further aspect, the heterodimerization approach described in WO 2007/147901 is used alternatively. In one aspect, a first CH3 domain comprises amino acid mutations K253E, D282K, and K322D and a second CH3 domain comprises amino acid mutations D239K, E240K, and K292D (numberings according to Kabat EU index).

In still another aspect, the heterodimerization approach described in WO 2007/110205 can be used alternatively.

In one aspect, the first subunit of the Fc domain comprises amino acid substitutions K392D and K409D, and the second subunit of the Fc domain comprises amino acid substitutions D356K and D399K (numbering according to Kabat EU index).

b) Fc Domain Modifications Reducing Fc Receptor Binding and/or Effector Function The Fc domain confers to the (multispecific) antibody favorable pharmacokinetic properties, including a long serum half-life which contributes to good accumulation in the target tissue and a favorable tissue-blood distribution ratio. At the same time, binding of the (multispecific) antibody, via its Fc domain, to cells expressing Fc receptors may lead to cross-linking of Fc receptor-expressing cells (such as NK cells) with other NKG2D-expressing cells (such as CD8 T cells), and thereby to undesirable toxicity upon systemic administration. Moreover, the co-activation of Fc receptor signaling pathways may lead to cytokine release which, in combination with the T-cell activating properties and the long half-life of the (multispecific) antibody, results in excessive activation of cytokine receptors and severe side effects upon systemic administration. Activation of (Fc receptor-bearing) immune cells other than T cells may even reduce efficacy of the (multispecific) antibody due to the potential destruction of T cells e.g. by NK cells.

Accordingly, in preferred aspects, the Fc domain of the (multispecific) antibody according to the invention exhibits reduced binding affinity to an Fc receptor and/or reduced effector function, as compared to a native $IgG_1$ Fc domain. In one such aspect the Fc domain (or the (multispecific) antibody comprising said Fc domain) exhibits less than 50%, particularly less than 20%, more particularly less than 10% and most particularly less than 5% of the binding affinity to an Fc receptor, as compared to a native $IgG_1$ Fc domain (or a (multispecific) antibody comprising a native $IgG_1$ Fc domain), and/or less than 50%, particularly less than 20%, more particularly less than 10% and most particularly less than 5% of the effector function, as compared to a native $IgG_1$ Fc domain domain (or a (multispecific) antibody comprising a native $IgG_1$ Fc domain). In one aspect, the Fc domain (or the (multispecific) antibody comprising said Fc domain) does not substantially bind to an Fc receptor and/or induce effector function. In a preferred aspect the Fc receptor is an Fcγ receptor. In one aspect the Fc receptor is a human Fc receptor. In one aspect the Fc receptor is an activating Fc receptor. In a specific aspect the Fc receptor is an activating human Fcγ receptor, more specifically human FcγRIIIa, FcγRI or FcγRIIa, most specifically human FcγRIIIa (CD16a). In one aspect the effector function is one or more selected from the group of CDC, ADCC, ADCP, and cytokine secretion. In a preferred aspect, the effector function is ADCC. In one aspect, the Fc domain domain exhibits substantially similar binding affinity to neonatal Fc receptor (FcRn), as compared to a native $IgG_1$ Fc domain. Substantially similar binding to FcRn is achieved when the Fc domain (or the (multispecific) antibody comprising said Fc domain) exhibits greater than about 70%, particularly greater than about 80%, more particularly greater than about 90% of the binding affinity of a native $IgG_1$ Fc domain (or the (multispecific) antibody comprising a native $IgG_1$Fc domain) to FcRn.

In certain aspects the Fc domain is engineered to have reduced binding affinity to an Fc receptor and/or reduced effector function, as compared to a non-engineered Fc domain. In preferred aspects, the Fc domain of the (multispecific) antibody comprises one or more amino acid mutation that reduces the binding affinity of the Fc domain to an Fc receptor and/or effector function. Typically, the same one or more amino acid mutation is present in each of the two subunits of the Fc domain. In one aspect, the amino acid mutation reduces the binding affinity of the Fc domain to an Fc receptor. In one aspect, the amino acid mutation reduces the binding affinity of the Fc domain to an Fc receptor by at least 2-fold, at least 5-fold, or at least 10-fold. In aspects where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one aspect the (multispecific) antibody comprising an engineered Fc domain exhibits less than 20%, particularly less than 10%, more particularly less than 5% of the binding affinity to an Fc receptor as compared to a (multispecific) antibody comprising a non-engineered Fc domain. In a preferred aspect, the Fc receptor is an Fcγ receptor. In some aspects, the Fc receptor is a human Fc receptor. In some aspects, the Fc receptor is an activating Fc receptor. In a specific aspect, the Fc receptor is an activating human Fcγ receptor, more specifically human FcγRIIIa, FcγRI or FcγRIIa, most specifically human FcγRIIIa (CD16a). Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc domain to said receptor, is achieved when the Fc domain (or the (multispecific) antibody comprising said Fc domain) exhibits greater than about 70% of the binding affinity of a non-engineered form of the Fc domain (or the (multispecific) antibody comprising said non-engineered form of the Fc domain) to FcRn. The Fc domain, or (multispecific) antibodies of the invention comprising said Fc domain, may exhibit greater than about 80% and even greater than about 90% of such affinity. In certain aspects, the Fc domain of the (multispecific) antibody is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced cross-linking of target-bound antibodies, reduced dendritic cell maturation, or reduced T cell priming. In one aspect, the reduced effector function is one or more selected from the group of reduced CDC, reduced ADCC, reduced ADCP, and reduced cytokine secretion. In a preferred aspect, the reduced effector function is reduced ADCC. In one aspect the reduced ADCC is less than 20% of the ADCC induced by a non-engineered Fc domain (or a (multispecific) antibody comprising a non-engineered Fc domain).

In one aspect, the amino acid mutation that reduces the binding affinity of the Fc domain to an Fc receptor and/or effector function is an amino acid substitution. In one aspect, the Fc domain comprises an amino acid substitution at a position selected from the group of E233, L234, L235, N297, P331 and P329 (numberings according to Kabat EU index). In a more specific aspect, the Fc domain comprises an amino acid substitution at a position selected from the group of L234, L235 and P329 (numberings according to Kabat EU index). In some aspects, the Fc domain comprises the amino acid substitutions L234A and L235A (numberings according to Kabat EU index). In one such aspect, the Fc domain is an IgG$_1$ Fc domain, particularly a human IgG$_1$ Fc domain. In one aspect, the Fc domain comprises an amino acid substitution at position P329. In a more specific aspect, the amino acid substitution is P329A or P329G, particularly P329G (numberings according to Kabat EU index). In one aspect, the Fc domain comprises an amino acid substitution at position P329 and a further amino acid substitution at a position selected from E233, L234, L235, N297 and P331 (numberings according to Kabat EU index). In a more specific aspect, the further amino acid substitution is E233P, L234A, L235A, L235E, N297A, N297D or P331S. In preferred aspects, the Fc domain comprises amino acid substitutions at positions P329, L234 and L235 (numberings according to Kabat EU index). In more preferred aspects, the Fc domain comprises the amino acid mutations L234A, L235A and P329G ("P329G LALA", "PGLALA" or "LALAPG"). Specifically, in preferred aspects, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one such aspect, the Fc domain is an IgG$_1$ Fc domain, particularly a human IgG$_1$ Fc domain. The "P329G LALA" combination of amino acid substitutions almost completely abolishes Fcγ receptor (as well as complement) binding of a human IgG$_1$ Fc domain, as described in PCT publication no. WO 2012/130831, which is incorporated herein by reference in its entirety. WO 2012/130831 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some aspects, the Fc domain of the (multispecific) antibodies of the invention is an IgG$_4$ Fc domain, particularly a human IgG$_4$ Fc domain. In one aspect, the IgG$_4$ Fc domain comprises an amino acid substitution at position S228, specifically the amino acid substitution S228P (numberings according to Kabat EU index). To further reduce its binding affinity to an Fc receptor and/or its effector function, in one aspect, the IgG$_4$ Fc domain comprises an amino acid substitution at position L235, specifically the amino acid substitution L235E (numberings according to Kabat EU index). In another aspect, the IgG$_4$ Fc domain comprises an amino acid substitution at position P329, specifically the amino acid substitution P329G (numberings according to Kabat EU index). In a preferred aspect, the IgG$_4$ Fc domain comprises amino acid substitutions at positions S228, L235 and P329, specifically amino acid substitutions S228P, L235E and P329G (numberings according to Kabat EU index). Such IgG$_4$ Fc domain mutants and their Fcγ receptor binding properties are described in PCT publication no. WO 2012/130831, incorporated herein by reference in its entirety.

In a preferred aspect, the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G (numberings according to Kabat EU index).

In certain aspects, N-glycosylation of the Fc domain has been eliminated. In one such aspect, the Fc domain comprises an amino acid mutation at position N297, particularly an amino acid substitution replacing asparagine by alanine (N297A) or aspartic acid (N297D) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIACORE® instrument (GE Healthcare), and Fc receptors such as may be obtained by recombinant expression. Alternatively, binding affinity of Fc domains or (multispecific) antibodies comprising an Fc domain for Fc receptors may be evaluated using cell lines known to express particular Fc receptors, such as human NK cells expressing FcγIIIa receptor.

Effector function of an Fc domain, or a (multispecific) antibody comprising an Fc domain, can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes et al., Proc Natl Acad Sci USA 95, 652-656 (1998).

In some aspects, binding of the Fc domain to a complement component, specifically to C1q, is reduced. Accordingly, in some aspects wherein the Fc domain is engineered to have reduced effector function, said reduced effector function includes reduced CDC. C1q binding assays may be carried out to determine whether the Fc domain, or the (multispecific) antibody comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

FcRn binding and in vivo clearance/half-life determinations can also be performed using methods known in the art (see, e.g., Petkova, S. B. et al., *Int'l. Immunol.* 18(12):1759-1769 (2006); WO 2013/120929).

B. Polynucleotides

The invention further provides an isolated polynucleotide encoding an antibody of the invention. Such isolated polynucleotide may be a single polynucleotide or a plurality of polynucleotides.

The polynucleotides encoding (multispecific) antibodies of the invention may be expressed as a single polynucleotide that encodes the entire antibody or as multiple (e.g., two or more) polynucleotides that are co-expressed. Polypeptides encoded by polynucleotides that are co-expressed may associate through, e.g., disulfide bonds or other means to form a functional antibody. For example, the light chain portion of an antibody may be encoded by a separate polynucleotide from the portion of the antibody comprising the heavy chain of the antibody. When co-expressed, the heavy chain polypeptides will associate with the light chain polypeptides to form the antibody. In another example, the portion of the antibody comprising one of the two Fc domain subunits and optionally (part of) one or more Fab molecules could be encoded by a separate polynucleotide from the portion of the antibody comprising the other of the two Fc domain subunits and optionally (part of) a Fab molecule. When co-expressed, the Fc domain subunits will associate to form the Fc domain.

In some aspects, the isolated polynucleotide encodes the entire antibody molecule according to the invention as described herein. In other aspects, the isolated polynucleotide encodes a polypeptide comprised in the antibody according to the invention as described herein.

In certain aspects the polynucleotide or nucleic acid is DNA. In other aspects, a polynucleotide of the present invention is RNA, for example, in the form of messenger RNA (mRNA). RNA of the present invention may be single stranded or double stranded.

C. Recombinant Methods

Antibodies of the invention may be obtained, for example, by solid-state peptide synthesis (e.g. Merrifield solid phase synthesis) or recombinant production. For recombinant production one or more polynucleotide encoding the antibody, e.g., as described above, is isolated and inserted into one or more vectors for further cloning and/or expression in a host cell. Such polynucleotide may be readily isolated and sequenced using conventional procedures. In one aspect a vector, particularly an expression vector, comprising the polynucleotide (i.a. a single polynucleotide or a plurality of polynucleotides) of the invention is provided. Methods which are well known to those skilled in the art can be used to construct expression vectors containing the coding sequence of an antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the antibody (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as inducible promoters (e.g. promoters inducible by tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody is desired, DNA encoding a signal sequence may be placed upstream of the nucleic acid encoding an antibody of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain aspects, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the antibody may be included within or at the ends of the antibody (fragment) encoding polynucleotide.

In a further aspect, a host cell comprising a polynucleotide (i.e. a single polynucleotide or a plurality of polynucleotides) of the invention is provided. In certain aspects a host cell comprising a vector of the invention is provided. The polynucleotides and vectors may incorporate any of the features, singly or in combination, described herein in relation to polynucleotides and vectors, respectively. In one such aspect a host cell comprises (e.g. has been transformed or transfected with) one or more vector comprising one or more polynucleotide that encodes (part of) an antibody of the invention. As used herein, the term "host cell" refers to any kind of cellular system which can be engineered to generate the antibody of the invention or fragments thereof. Host cells suitable for replicating and for supporting expression of antibodies are well known in the art. Such cells may be transfected or transduced as appropriate with the particular expression vector and large quantities of vector containing cells can be grown for seeding large scale fermenters to obtain sufficient quantities of the antibody for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gemgross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr CHO cells (Urlaub et al., Proc Natl Acad Sci USA 77, 4216 (1980)); and myeloma cell lines such as Y0, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one aspect, the host cell is a eukaryotic cell, particularly a mammalian cell, such as a Chinese Hamster Ovary (CHO) cell, a human embryonic kidney (HEK) cell or a lymphoid cell (e.g., Y0, NS0, Sp20 cell). In one aspect, the host cell is not a cell within a human body.

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one aspect, a method of producing an antibody according to the invention is provided, wherein the method comprises culturing a host cell comprising a polynucleotide encoding the antibody, as provided herein, under conditions suitable for expression of the antibody, and optionally recovering the antibody from the host cell (or host cell culture medium).

The components of the (multispecific) antibody of the invention may be genetically fused to each other. The (multispecific) antibody can be designed such that its components are fused directly to each other or indirectly through a linker sequence. The composition and length of the linker may be determined in accordance with methods well known in the art and may be tested for efficacy. Examples of linker sequences between different components of (multispecific) antibodies are provided herein. Additional sequences may also be included to incorporate a cleavage site to separate the individual components of the fusion if desired, for example an endopeptidase recognition sequence.

Antibodies prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification, an antibody, ligand, receptor or antigen can be used to which the antibody binds. For example, for affinity chromatography purification of antibodies of the invention, a matrix with protein A or protein G may be used. Sequential Protein A or G affinity chromatography and size exclusion chromatography can be used to isolate an antibody essentially as described in the Examples. The purity of the antibody can be determined by any of a variety of well-known analytical methods including gel electrophoresis, high pressure liquid chromatography, and the like.

D. Assays

Antibodies provided herein may be identified, screened for, or characterized for their physical/chemical properties and/or biological activities by various assays known in the art.

1. Binding Assays

The binding (affinity) of the antibody to a target antigen or an Fc receptor can be determined for example by surface plasmon resonance (SPR), using standard instrumentation such as a BIACORE® instrument (GE Healthcare), and receptors or target proteins such as may be obtained by recombinant expression. Alternatively, binding of antibodies to different receptors or target antigens may be evaluated using cell lines expressing the particular receptor or target antigen, for example by flow cytometry (FACS). A specific illustrative and exemplary aspect for measuring binding activity to human or cynomolgus NKG2D is described in the following.

In one aspect, the binding activity to NKG2D is determined by SPR as follows:

SPR is performed on a BIACORE® B4000 instrument (GE Healthcare). Anti-Fab capturing antibody (GE Healthcare, #28958325) is immobilized on a Series S Sensor Chip CM5 (GE Healthcare) using standard amine coupling chemistry, at a surface density of about 1500 resonance units (RU). As running and dilution buffer, PBS-T (10 mM phosphate buffered saline including 0.05% TWEEN® (polysorbate) 20, pH 7.4) is used. The flow cells are set to 25° C. and primed twice with running buffer.

Antibody is captured by injecting a ~10 µg/ml solution for 60 sec at a flow rate of 10 µl/min. Association is measured by injection of di huNKG2D ECD Fc avi (SEQ ID NO: 96) or di cyNKG2D ECD Fc avi (SEQ ID NO: 97) in various concentrations in solution for 180 s at a flow rate of 30 µl/min starting with 600 nM, 300 nM, 150 nM following 1:3 dilutions. The dissociation phase is monitored for up to 450 s and triggered by switching from the sample solution to running buffer. The surface is regenerated by washing for 2×90 s with 10 mM glycine pH 2.1 at a flow rate of 30 µl/min and an additional stabilization period of 180 s. Bulk refractive index differences are corrected by subtracting the response obtained from the surface with the capturing antibody alone. Blank injections are also subtracted (=double referencing). For calculation of $K_D$, $k_a$ and $k_d$, the Langmuir 1:1 model in the BIACORE® 4000 Evaluation software 1.1 (GE Healthcare) or TraceDrawer 1.6.1 (Ridgeview Instruments AB) is used.

2. Activity Assays

Biological activity of the (multispecific) antibodies of the invention can be measured by various assays as described in the Examples. Biological activities may for example include the induction of proliferation of NKG2D-expressing cells, the induction of signaling in NKG2D-expressing cells, the induction of expression of activation markers in NKG2D-expressing cells, the induction of cytokine secretion by NKG2D-expressing cells, the induction of lysis of target cells such as tumor cells, and the induction of tumor regression and/or the improvement of survival.

E. Compositions, Formulations, and Routes of Administration

In a further aspect, the invention provides pharmaceutical compositions comprising any of the antibodies provided herein, e.g., for use in any of the below therapeutic methods. In one aspect, a pharmaceutical composition comprises an antibody according to the invention and a pharmaceutically acceptable carrier. In another aspect, a pharmaceutical composition comprises an antibody according to the invention and at least one additional therapeutic agent, e.g., as described below.

Further provided is a method of producing an antibody of the invention in a form suitable for administration in vivo, the method comprising (a) obtaining an antibody according to the invention, and (b) formulating the antibody with at least one pharmaceutically acceptable carrier, whereby a preparation of antibody is formulated for administration in vivo.

Pharmaceutical compositions of the present invention comprise an effective amount of antibody dissolved or dispersed in a pharmaceutically acceptable carrier. The phrase "pharmaceutically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains an antibody and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic.

Parenteral compositions include those designed for administration by injection, e.g. subcutaneous, intradermal, intralesional, intravenous, intraarterial intramuscular, intrathecal or intraperitoneal injection. For injection, the antibodies of the invention may be formulated in aqueous solutions, particularly in physiologically compatible buffers such as Hanks' solution, Ringer's solution, or physiological saline buffer. The solution may contain formulatory agents such as suspending, stabilizing and/or dispersing agents. Alternatively, the antibodies may be in powder form for constitution with a suitable vehicle, e.g., sterile pyrogen-free water, before use. Sterile injectable solutions are prepared by incorporating the antibodies of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular aspects, prolonged absorption of an injectable composition can be brought about by the use in the compositions of agents delaying absorption, such as, for example, aluminum monostearate, gelatin or combinations thereof.

In addition to the compositions described previously, the antibodies may also be formulated as a depot preparation. Such long acting formulations may be administered by implantation (for example subcutaneously or intramuscularly) or by intramuscular injection. Thus, for example, the antibodies may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the antibodies of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The antibodies may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

F. Therapeutic Methods and Compositions

Any of the antibodies provided herein may be used in therapeutic methods. Antibodies of the invention may be used as immunotherapeutic agents, for example in the treatment of cancers.

For use in therapeutic methods, antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, antibodies of the invention for use as a medicament are provided. In further aspects, antibodies of the invention for use in treating a disease are provided. In certain aspects, antibodies of the invention for use in a method of treatment are provided. In one aspect, the invention provides an antibody of the invention for use in the treatment of a disease in an individual in need thereof. In certain aspects, the invention provides an antibody for use in a method of treating an individual having a disease comprising administering to the individual an effective amount of the antibody. In certain aspects the disease to be treated is a proliferative disorder. In a preferred aspect the disease is cancer. In certain aspects the method further comprises administering to the individual an effective amount of at least one additional therapeutic agent, e.g., an anti-cancer agent if the disease to be treated is cancer. In further aspects, the invention provides an antibody of the invention for use in inducing lysis of a target cell, particularly a tumor cell. In certain aspects, the invention provides an antibody of the invention for use in a method of inducing lysis of a target cell, particularly a tumor cell, in an individual comprising administering to the individual an effective amount of the antibody to induce lysis of a target cell. In certain aspects, the method further comprises administering a T-cell activating agent, such as an antibody that binds to CD3, particularly a bispecific antibody that binds to CD3 and a target cell antigen, particularly a tumor cell antigen. In certain aspects, the use is in combination with a T-cell activating agent, such as an antibody that binds to CD3, particularly a bispecific antibody that binds to CD3 and a target cell antigen, particularly a tumor cell antigen. An "individual" according to any of the above aspects is a mammal, preferably a human.

In a further aspect, the invention provides for the use of an antibody of the invention in the manufacture or preparation of a medicament. In one aspect the medicament is for the treatment of a disease in an individual in need thereof. In a further aspect, the medicament is for use in a method of treating a disease comprising administering to an individual having the disease an effective amount of the medicament. In certain aspects the disease to be treated is a proliferative disorder. In a preferred aspect the disease is cancer. In one aspect, the method further comprises administering to the individual an effective amount of at least one additional therapeutic agent, e.g., an anti-cancer agent if the disease to be treated is cancer. In a further aspect, the medicament is for inducing lysis of a target cell, particularly a tumor cell. In still a further aspect, the medicament is for use in a method of inducing lysis of a target cell, particularly a tumor cell, in an individual comprising administering to the individual an effective amount of the medicament to induce lysis of a target cell. In certain aspects, the method further comprises administering a T-cell activating agent, such as an antibody that binds to CD3, particularly a bispecific antibody that binds to CD3 and a target cell antigen, particularly a tumor cell antigen. In certain aspects, the treatment is in combination with a T-cell activating agent, such as an antibody that binds to CD3, particularly a bispecific antibody that binds to CD3 and a target cell antigen, particularly a tumor cell antigen. An "individual" according to any of the above aspects may be a mammal, preferably a human.

In a further aspect, the invention provides a method for treating a disease. In one aspect, the method comprises administering to an individual having such disease an effective amount of an antibody of the invention. In one aspect a composition is administered to said individual, comprising the antibody of the invention in a pharmaceutically acceptable form. In certain aspects the disease to be treated is a proliferative disorder. In a preferred aspect the disease is cancer. In certain aspects the method further comprises administering to the individual an effective amount of at least one additional therapeutic agent, e.g., an anti-cancer agent if the disease to be treated is cancer. In certain aspects, the method further comprises administering a T-cell activating agent, such as an antibody that binds to CD3, particularly a bispecific antibody that binds to CD3 and a target cell antigen, particularly a tumor cell antigen. An "individual" according to any of the above aspects may be a mammal, preferably a human.

In a further aspect, the invention provides a method for inducing lysis of a target cell, particularly a tumor cell. In one aspect the method comprises contacting a target cell with an antibody of the invention in the presence of a T cell, particularly a cytotoxic T cell. In a further aspect, a method for inducing lysis of a target cell, particularly a tumor cell, in an individual is provided. In one such aspect, the method comprises administering to the individual an effective amount of an antibody of the invention to induce lysis of a target cell. In certain aspects, the method further comprises administering a T-cell activating agent, such as an antibody that binds to CD3, particularly a bispecific antibody that binds to CD3 and a target cell antigen, particularly a tumor cell antigen. In one aspect, an "individual" is a human.

In certain aspects, the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that may be treated using an antibody of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain aspects, the cancer is selected from the group consisting of kidney cancer, bladder cancer, skin cancer, lung cancer, colorectal cancer, breast cancer, brain cancer, head and neck cancer and prostate cancer. In one aspect, the cancer in a cancer expressing the second antigen. A skilled artisan readily recognizes that in many cases the antibody may not provide a cure but may only provide partial benefit. In some aspects, a physiological change having some benefit is also considered therapeutically beneficial. Thus, in some aspects, an amount of antibody that provides a physiological change is considered an "effective amount". The subject, patient, or individual in need of treatment is typically a mammal, more specifically a human.

In some aspects, an effective amount of an antibody of the invention is administered to an individual for the treatment of disease.

For the prevention or treatment of disease, the appropriate dosage of an antibody of the invention (when used alone or in combination with one or more other additional therapeutic agents) will depend on the type of disease to be treated, the route of administration, the body weight of the patient, the type of antibody, the severity and course of the disease, whether the antibody is administered for preventive or therapeutic purposes, previous or concurrent therapeutic interventions, the patient's clinical history and response to the antibody, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various timepoints, bolus administration, and pulse infusion are contemplated herein.

The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

The antibodies of the invention will generally be used in an amount effective to achieve the intended purpose. For use to treat or prevent a disease condition, the antibodies of the invention, or pharmaceutical compositions thereof, are administered or applied in an effective amount.

For systemic administration, an effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art.

Dosage amount and interval may be adjusted individually to provide plasma levels of the antibodies which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

An effective dose of the antibodies of the invention will generally provide therapeutic benefit without causing substantial toxicity. Toxicity and therapeutic efficacy of an antibody can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Antibodies that exhibit large therapeutic indices are preferred. In one aspect, the antibody according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with antibodies of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

The antibodies of the invention may be administered in combination with one or more other agents in therapy. For instance, an antibody of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular disease being treated, preferably those with complementary activities that do not adversely affect each other. In certain aspects, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In one aspect, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent. In preferred aspects, the additional therapeutic agent is a T-cell activating agent. In one such aspect, the additional therapeutic agent is an antibody that binds to CD3, particularly a bispecific antibody that binds to CD3 and a target cell antigen, particularly a tumor cell antigen. In one aspect, the target cell antigen to which the additional therapeutic agent binds is the same as the second antigen, and/or is co-expressed (e.g. on the same target cell) like the second antigen.

In one aspect, the additional therapeutic agent is a CD3×CEA bispecific antibody. Further aspects of the CD3×CEA bispecific antibodies that may be used in combination with the anti-NKG2D (multispecific) antibodies of the invention are described hereinbelow. In a specific aspect, the additional therapeutic agent is CEA-TCB (CDR sequences of SEQ ID NOs 130-135 (CD3) and 138-143 (CEA), variable region sequences of SEQ ID NOs 136 and 137 (CD3) and 144 and 145 (CEA), full sequences of SEQ ID NOs 154-157) or CEA-TCB (2) (CDR sequences of SEQ ID NOs 130-135 (CD3) and 146-151 (CEA), variable region sequences of SEQ ID NOs 136 and 137 (CD3) and 152 and 153 (CEA), full sequences of SEQ ID NOs 158-161).

Such other agents are suitably present in combination in amounts that are effective for the purpose intended. The effective amount of such other agents depends on the amount of antibody used, the type of disorder or treatment, and other factors discussed above. The antibodies are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the antibody of the invention can occur prior to, simultaneously, and/or following, administration of the additional therapeutic agent and/or adjuvant. Antibodies of the invention may also be used in combination with radiation therapy.

CD3×CEA Bispecific Antibodies for Combination with Antibodies of the Invention

The CD3×CEA bispecific antibody comprises a first antigen binding moiety that specifically binds to CD3, and a second antigen binding moiety that specifically binds to CEA.

In one aspect, the first antigen binding moiety comprises a heavy chain variable region comprising the heavy chain CDR (HCDR) 1 of SEQ ID NO: 130, the HCDR2 of SEQ ID NO: 131, and the HCDR3 of SEQ ID NO: 132; and a light chain variable region comprising the light chain CDR (LCDR) 1 of SEQ ID NO: 133, the LCDR2 of SEQ ID NO: 134 and the LCDR3 of SEQ ID NO: 135.

In one aspect, the second antigen binding moiety comprises a heavy chain variable region comprising the heavy chain CDR (HCDR) 1 of SEQ ID NO: 138, the HCDR2 of SEQ ID NO: 139, and the HCDR3 of SEQ ID NO: 140; and a light chain variable region comprising the light chain CDR (LCDR) 1 of SEQ ID NO: 141, the LCDR2 of SEQ ID NO: 142 and the LCDR3 of SEQ ID NO: 143; or (ii) a heavy chain variable region comprising the heavy chain CDR (HCDR) 1 of SEQ ID NO: 146, the HCDR2 of SEQ ID NO: 147, and the HCDR3 of SEQ ID NO: 148; and a light chain variable region comprising the light chain CDR (LCDR) 1 of SEQ ID NO: 149, the LCDR2 of SEQ ID NO: 150 and the LCDR3 of SEQ ID NO: 151.

In a particular aspect, the CD3×CEA bispecific antibody comprises
(i) a first antigen binding moiety that specifically binds to CD3 and comprises a heavy chain variable region comprising the heavy chain CDR (HCDR) 1 of SEQ ID NO: 130, the HCDR2 of SEQ ID NO: 131, and the HCDR3 of SEQ ID NO: 132; and a light chain variable region comprising the light chain CDR (LCDR) 1 of SEQ ID NO: 133, the LCDR2 of SEQ ID NO: 134 and the LCDR3 of SEQ ID NO: 135; and (ii) a second antigen binding moiety that specifically binds to CEA and comprises a heavy chain variable region comprising the heavy chain CDR (HCDR) 1 of SEQ ID NO: 138, the HCDR2 of SEQ ID NO: 139, and the HCDR3 of SEQ ID NO: 140; and a light chain variable region comprising the light chain CDR (LCDR) 1 of SEQ ID NO: 141, the LCDR2 of SEQ ID NO: 142 and the LCDR3 of SEQ ID NO: 143; or (ii) a heavy chain variable region comprising the heavy chain CDR (HCDR) 1 of SEQ ID NO: 146, the HCDR2 of SEQ ID NO: 147, and the HCDR3 of SEQ ID NO: 148; and a light chain variable region comprising the light chain CDR (LCDR) 1 of SEQ ID NO: 149, the LCDR2 of SEQ ID NO: 150 and the LCDR3 of SEQ ID NO: 151.

In one aspect, the first antigen binding moiety comprises a heavy chain variable region sequence that is at least about 95%, 96%, 97%, 98%, 99% or 100% identical to the amino acid sequence of SEQ ID NO: 136 and a light chain variable region sequence that is at least about 95%, 96%, 97%, 98%, 99% or 100% identical to the amino acid sequence of SEQ ID NO: 137.

In one aspect, the first antigen binding moiety comprises the heavy chain variable region sequence of SEQ ID NO: 136 and the light chain variable region sequence of SEQ ID NO: 137.

In one aspect, the second antigen binding moiety comprises a heavy chain variable region sequence that is at least about 95%, 96%, 97%, 98%, 99% or 100% identical to the amino acid sequence of SEQ ID NO: 144 and a light chain variable region sequence that is at least about 95%, 96%, 97%, 98%, 99% or 100% identical to the amino acid sequence of SEQ ID NO: 145; or (ii) a heavy chain variable region sequence that is at least about 95%, 96%, 97%, 98%, 99% or 100% identical to the amino acid sequence of SEQ ID NO: 152 and a light chain variable region sequence that is at least about 95%, 96%, 97%, 98%, 99% or 100% identical to the amino acid sequence of SEQ ID NO: 153.

In one aspect, the second antigen binding moiety comprises the heavy chain variable region sequence of SEQ ID NO: 144 and the light chain variable region sequence of SEQ ID NO: 145; or (ii) the heavy chain variable region sequence of SEQ ID NO: 152 and the light chain variable region sequence of SEQ ID NO: 153.

In some aspects, the first and/or the second antigen binding moiety is a Fab molecule. In some aspects, the first antigen binding moiety is a crossover Fab molecule wherein either the variable or the constant regions of the Fab light chain and the Fab heavy chain are exchanged. In such aspects, the second antigen binding moiety preferably is a conventional Fab molecule.

In some aspects wherein the first and the second antigen binding moiety of the bispecific antibody are both Fab molecules, and in one of the antigen binding moieties (particularly the first antigen binding moiety) the variable domains VL and VH of the Fab light chain and the Fab heavy chain are replaced by each other, i) in the constant domain CL of the first antigen binding moiety the amino acid at position 124 is substituted by a positively charged amino acid (numbering according to Kabat), and wherein in the constant domain CH1 of the first antigen binding moiety the amino acid at position 147 or the amino acid at position 213 is substituted by a negatively charged amino acid (numbering according to Kabat EU index); or ii) in the constant domain CL of the second antigen binding moiety the amino acid at position 124 is substituted by a positively charged amino acid (numbering according to Kabat), and wherein in the constant domain CH1 of the second antigen binding moiety the amino acid at position 147 or the amino acid at position 213 is substituted by a negatively charged amino acid (numbering according to Kabat EU index).

The bispecific antibody does not comprise both modifications mentioned under i) and ii). The constant domains CL and CH1 of the antigen binding moiety having the VH/VL exchange are not replaced by each other (i.e. remain unexchanged).

In a more specific aspect,
i) in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 or the amino acid at position 213 is substituted independently by glutamic acid (E), or aspartic acid (D) (numbering according to Kabat EU index); or ii) in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D) (numbering according to Kabat EU index).

In one such aspect, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D) (numbering according to Kabat EU index).

In a further aspect, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index).

In a particular aspect, in the constant domain CL of the second antigen binding moiety the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular aspect, in the constant domain CL of the second antigen binding moiety the amino acid at position 124 is substituted by lysine (K) (numbering according to Kabat) and the amino acid at position 123 is substituted by lysine (K) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index).

In an even more particular aspect, in the constant domain CL of the second antigen binding moiety the amino acid at position 124 is substituted by lysine (K) (numbering according to Kabat) and the amino acid at position 123 is substituted by arginine (R) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index).

In particular aspects, if amino acid substitutions according to the above aspects are made in the constant domain CL and the constant domain CH1 of the second antigen binding moiety, the constant domain CL of the second antigen binding moiety is of kappa isotype.

In some aspects, the first and the second antigen binding moiety are fused to each other, optionally via a peptide linker.

In some aspects, the first and the second antigen binding moiety are each a Fab molecule and either (i) the second antigen binding moiety is fused at the C-terminus of the Fab heavy chain to the N-terminus of the Fab heavy chain of the first antigen binding moiety, or (ii) the first antigen binding moiety is fused at the C-terminus of the Fab heavy chain to the N-terminus of the Fab heavy chain of the second antigen binding moiety.

In some aspects, the CD3×CEA bispecific antibody provides monovalent binding to CD3.

In particular aspects, the CD3×CEA bispecific antibody comprises a single antigen binding moiety that specifically binds to CD3, and two antigen binding moieties that specifically bind to CEA. Thus, in some aspects, the CD3×CEA bispecific antibody comprises a third antigen binding moiety that specifically binds to CEA. In some aspects, the third antigen moiety is identical to the first antigen binding moiety (e.g. is also a Fab molecule and comprises the same amino acid sequences).

In particular aspects, the CD3×CEA bispecific antibody further comprises an Fc domain composed of a first and a second subunit. In one aspect, the Fc domain is an IgG Fc domain. In a particular aspect, the Fc domain is an $IgG_1$ Fc domain. In another aspect the Fc domain is an $IgG_4$ Fc domain. In a more specific aspect, the Fc domain is an $IgG_4$ Fc domain comprising an amino acid substitution at position S228 (Kabat EU index numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further particular aspect, the Fc domain is a human Fc domain. In a particularly preferred aspect, the Fc domain is a human $IgG_1$ Fc domain. An exemplary sequence of a human $IgG_1$ Fc region is given in SEQ ID NO. 86.

In some aspects wherein the first, the second and, where present, the third antigen binding moiety are each a Fab molecule, (a) either (i) the second antigen binding moiety is fused at the C-terminus of the Fab heavy chain to the N-terminus of the Fab heavy chain of the first antigen binding moiety and the first antigen binding moiety is fused at the C-terminus of the Fab heavy chain to the N-terminus of the first subunit of the Fc domain, or (ii) the first antigen binding moiety is fused at the C-terminus of the Fab heavy chain to the N-terminus of the Fab heavy chain of the second antigen binding moiety and the second antigen binding moiety is fused at the C-terminus of the Fab heavy chain to the N-terminus of the first subunit of the Fc domain; and (b) the third antigen binding moiety, where present, is fused at the C-terminus of the Fab heavy chain to the N-terminus of the second subunit of the Fc domain.

In particular aspects, the Fc domain comprises a modification promoting the association of the first and the second subunit of the Fc domain. The site of most extensive protein-protein interaction between the two subunits of a human IgG Fc domain is in the CH3 domain. Thus, in one aspect said modification is in the CH3 domain of the Fc domain.

In a specific aspect said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain. The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in some aspects, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. Preferably said amino acid residue having a larger side chain volume is selected from the group consisting of arginine (R), phenylalanine (F), tyrosine (Y), and tryptophan (W). Preferably said amino acid residue having a smaller side chain volume is selected from the group consisting of alanine (A), serine (S), threonine (T), and valine (V). The protuberance and cavity can be made by altering the nucleic acid encoding the polypeptides, e.g. by site-specific mutagenesis, or by peptide synthesis.

In a specific such aspect, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numbering according to Kabat EU index). In a further aspect, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numbering according to Kabat EU index). In a preferred aspect, the first subunit of the Fc domain comprises the amino acid substitutions S354C and T366W, and the second subunit of the Fc domain comprises the amino acid substitutions Y349C, T366S, L368A and Y407V (numbering according to Kabat EU index).

In some aspects, the Fc domain comprises one or more amino acid substitution that reduces binding to an Fc receptor and/or effector function.

In a particular aspect the Fc receptor is an Fcγ receptor. In one aspect the Fc receptor is a human Fc receptor. In one aspect the Fc receptor is an activating Fc receptor. In a specific aspect the Fc receptor is an activating human Fcγ receptor, more specifically human FcγRIIIa, FcγRI or FcγRIIa, most specifically human FcγRIIIa (CD16a). In one aspect the effector function is one or more selected from the group of complement dependent cytotoxicity (CDC), antibody-dependent cell-mediated cytotoxicity (ADCC), antibody-dependent cellular phagocytosis (ADCP), and cytokine secretion. In a particular aspect, the effector function is ADCC.

Typically, the same one or more amino acid substitution is present in each of the two subunits of the Fc domain. In one aspect, the one or more amino acid substitution reduces the binding affinity of the Fc domain to an Fc receptor. In one aspect, the one or more amino acid substitution reduces the binding affinity of the Fc domain to an Fc receptor by at least 2-fold, at least 5-fold, or at least 10-fold.

In one aspect, the Fc domain comprises an amino acid substitution at a position selected from the group of E233, L234, L235, N297, P331 and P329 (numberings according to Kabat EU index). In a more specific aspect, the Fc domain comprises an amino acid substitution at a position selected from the group of L234, L235 and P329 (numberings according to Kabat EU index). In some aspects, the Fc domain comprises the amino acid substitutions L234A and L235A (numberings according to Kabat EU index). In one such aspect, the Fc domain is an IgG$_1$ Fc domain, particularly a human IgG$_1$ Fc domain. In one aspect, the Fc domain comprises an amino acid substitution at position P329. In a more specific aspect, the amino acid substitution is P329A or P329G, particularly P329G (numberings according to Kabat EU index). In one aspect, the Fc domain comprises an amino acid substitution at position P329 and a further amino acid substitution at a position selected from E233, L234, L235, N297 and P331 (numberings according to Kabat EU index). In a more specific aspect, the further amino acid substitution is E233P, L234A, L235A, L235E, N297A, N297D or P331S. In particular aspects, the Fc domain comprises amino acid substitutions at positions P329, L234 and L235 (numberings according to Kabat EU index). In more particular aspects, the Fc domain comprises the amino acid mutations L234A, L235A and P329G ("P329G LALA", "PGLALA" or "LALAPG"). Specifically, in preferred aspects, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index). In one such aspect, the Fc domain is an IgG$_1$ Fc domain, particularly a human IgG$_1$ Fc domain.

In a preferred aspect, the CD3×CEA bispecific antibody comprises (i) a first antigen binding moiety that specifically binds to CD3, comprising a heavy chain variable region comprising the heavy chain CDR (HCDR) 1 of SEQ ID NO: 130, the HCDR2 of SEQ ID NO: 131, and the HCDR3 of SEQ ID NO: 132; and a light chain variable region comprising the light chain CDR (LCDR) 1 of SEQ ID NO: 133, the LCDR2 of SEQ ID NO: 134 and the LCDR3 of SEQ ID NO: 135, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety that specifically bind to CEA, comprising a heavy chain variable region comprising the heavy chain CDR (HCDR) 1 of SEQ ID NO: 138, the HCDR2 of SEQ ID NO: 139, and the HCDR3 of SEQ ID NO: 140; and a light chain variable region comprising the light chain CDR (LCDR) 1 of SEQ ID NO: 141, the LCDR2 of SEQ ID NO: 142 and the LCDR3 of SEQ ID NO: 143, wherein the second and third antigen binding moiety are each a Fab molecule, particularly a conventional Fab molecule;

(iii) an Fc domain composed of a first and a second subunit, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

In one aspect, the first antigen binding moiety comprises a heavy chain variable region sequence that is at least about 95%, 96%, 97%, 98%, 99% or 100% identical to the amino acid sequence of SEQ ID NO: 136 and a light chain variable region sequence that is at least about 95%, 96%, 97%, 98%, 99% or 100% identical to the amino acid sequence of SEQ ID NO: 137.

In one aspect, the first antigen binding moiety comprises the heavy chain variable region sequence of SEQ ID NO: 136 and the light chain variable region sequence of SEQ ID NO: 137.

In one aspect, the second and third antigen binding moiety comprise a heavy chain variable region sequence that is at least about 95%, 96%, 97%, 98%, 99% or 100% identical to the amino acid sequence of SEQ ID NO: 144 and a light chain variable region sequence that is at least about 95%, 96%, 97%, 98%, 99% or 100% identical to the amino acid sequence of SEQ ID NO: 145.

In one aspect, the second and third antigen binding moieties comprise the heavy chain variable region of SEQ ID NO: 144 and the light chain variable region of SEQ ID NO: 145.

The Fc domain according to the above aspects may incorporate, singly or in combination, all of the features described hereinabove in relation to Fc domains.

In one aspect, the antigen binding moieties and the Fc region are fused to each other by peptide linkers, particularly by peptide linkers as in SEQ ID NO: 154 and SEQ ID NO: 155.

In one aspect, the CD3×CEA bispecific antibody comprises a polypeptide comprising a sequence that is at least 80%, 85%, 90%, 95%, 96%, 97%, 98%, or 99% identical to the sequence of SEQ ID NO: 154, a polypeptide comprising a sequence that is at least 80%, 85%, 90%, 95%, 96%, 97%, 98%, or 99% identical to the sequence of SEQ ID NO: 155, a polypeptide comprising a sequence that is at least 80%, 85%, 90%, 95%, 96%, 97%, 98%, or 99% identical to the sequence of SEQ ID NO: 156, and a polypeptide (particularly two polypeptides) comprising a sequence that is at least 80%, 85%, 90%, 95%, 96%, 97%, 98%, or 99% identical to the sequence of SEQ ID NO: 157.

In one aspect, the CD3×CEA bispecific antibody comprises a polypeptide comprising the sequence of SEQ ID NO: 154, a polypeptide comprising the sequence of SEQ ID NO: 155, a polypeptide comprising the sequence of SEQ ID NO: 156, and a polypeptide (particularly two polypeptides) comprising the sequence of SEQ ID NO: 157.

In a particular aspect, the CD3×CEA bispecific antibody is cibisatamab (WHO Drug Information (International Nonproprietary Names for Pharmaceutical Substances), Recommended INN: List 80, 2018, vol. 32, no. 3, p. 438).

In one aspect, the CD3×CEA bispecific antibody comprises (i) a first antigen binding moiety that specifically binds to CD3, comprising a heavy chain variable region comprising the heavy chain CDR (HCDR) 1 of SEQ ID NO: 130, the HCDR2 of SEQ ID NO: 131, and the HCDR3 of SEQ ID NO: 132; and a light chain variable region comprising the light chain CDR (LCDR) 1 of SEQ ID NO: 133, the LCDR2 of SEQ ID NO: 134 and the LCDR3 of SEQ ID NO: 135, wherein the first antigen binding moiety is a crossover Fab molecule wherein either the variable or the constant regions, particularly the variable regions, of the Fab light chain and the Fab heavy chain are exchanged;

(ii) a second and a third antigen binding moiety that specifically bind to CEA, comprising a heavy chain variable region comprising the heavy chain CDR (HCDR) 1 of SEQ ID NO: 146, the HCDR2 of SEQ ID NO: 147, and the HCDR3 of SEQ ID NO: 148; and a light chain variable region comprising the light chain CDR (LCDR) 1 of SEQ ID NO: 149, the LCDR2 of SEQ ID NO: 150 and the LCDR3 of SEQ ID NO: 151, wherein the second and third antigen binding moiety are each a Fab molecule, particularly a conventional Fab molecule;

(iii) an Fc domain composed of a first and a second subunit capable of stable association, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

In one aspect, the first antigen binding moiety comprises a heavy chain variable region sequence that is at least about 95%, 96%, 97%, 98%, 99% or 100% identical to the amino acid sequence of SEQ ID NO: 136 and a light chain variable region sequence that is at least about 95%, 96%, 97%, 98%, 99% or 100% identical to the amino acid sequence of SEQ ID NO: 137.

In one aspect, the first antigen binding moiety comprises the heavy chain variable region sequence of SEQ ID NO: 136 and the light chain variable region sequence of SEQ ID NO: 137. In one aspect, the second and third antigen binding moiety comprise a heavy chain variable region sequence that is at least about 95%, 96%, 97%, 98%, 99% or 100% identical to the amino acid sequence of SEQ ID NO: 152 and a light chain variable region sequence that is at least about 95%, 96%, 97%, 98%, 99% or 100% identical to the amino acid sequence of SEQ ID NO: 153. In one aspect, the second and third antigen binding moieties comprise the heavy chain variable region of SEQ ID NO: 152 and the light chain variable region of SEQ ID NO: 153.

The Fc domain according to the above aspects may incorporate, singly or in combination, all of the features described hereinabove in relation to Fc domains.

In one aspect, the antigen binding moieties and the Fc region are fused to each other by peptide linkers, particularly by peptide linkers as in SEQ ID NO: 158 and SEQ ID NO: 159.

In one aspect, in the constant domain CL of the second and the third Fab molecule under (ii) the amino acid at position 124 is substituted by lysine (K) (numbering according to Kabat) and the amino acid at position 123 is substituted by lysine (K) or arginine (R), particularly by arginine (R) (numbering according to Kabat), and in the constant domain CH1 of the second and the third Fab molecule under (ii) the amino acid at position 147 is substituted by glutamic acid (E) (numbering according to Kabat EU index) and the amino acid at position 213 is substituted by glutamic acid (E) (numbering according to Kabat EU index).

In one aspect, the bispecific antibody comprises a polypeptide comprising a sequence that is at least 80%, 85%, 90%, 95%, 96%, 97%, 98%, or 99% identical to the sequence of SEQ ID NO: 158, a polypeptide comprising a sequence that is at least 80%, 85%, 90%, 95%, 96%, 97%, 98%, or 99% identical to the sequence of SEQ ID NO: 159, a polypeptide comprising a sequence that is at least 80%, 85%, 90%, 95%, 96%, 97%, 98%, or 99% identical to the sequence of SEQ ID NO: 160, and a polypeptide (particularly two polypeptides) comprising a sequence that is at least 80%, 85%, 90%, 95%, 96%, 97%, 98%, or 99% identical to the sequence of SEQ ID NO: 161.

In one aspect, the bispecific antibody comprises a polypeptide comprising the sequence of SEQ ID NO: 158, a polypeptide comprising the sequence of SEQ ID NO: 159, a polypeptide comprising the sequence of SEQ ID NO: 160, and a polypeptide (particularly two polypeptides) comprising the sequence of SEQ ID NO: 161.

Other CD3×CEA bispecific antibodies as will be known to the skilled practitioner are also contemplated for use in the present invention.

In one aspect, the CD3×CEA bispecific antibody is MEDI565 (AMG211, MT 111).

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this aspect of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

H. Methods and Compositions for Diagnostics and Detection

In certain aspects, any of the antibodies provided herein is useful for detecting the presence of its target (e.g. NKG2D) in a biological sample. The term "detecting" as used herein encompasses quantitative or qualitative detection. In certain aspects, a biological sample comprises a cell or tissue, such as prostate tissue.

In one aspect, an antibody according to the invention for use in a method of diagnosis or detection is provided. In a further aspect, a method of detecting the presence of NKG2D in a biological sample is provided. In certain aspects, the method comprises contacting the biological sample with an antibody of the present invention under conditions permissive for binding of the antibody to NKG2D, and detecting whether a complex is formed between the antibody and NKG2D. Such method may be an in vitro or in vivo method. In one aspect, an antibody of the invention is used to select subjects eligible for therapy with an antibody that binds to NKG2D, e.g. where NKG2D is a biomarker for selection of patients.

Exemplary disorders that may be diagnosed using an antibody of the invention include cancer.

In certain aspects, an antibody according to the present invention is provided, wherein the antibody is labelled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

III. Sequences

|  | Amino Acid Sequence | SEQ ID NO |
|---|---|---|
| HCDR1 5C5 | SYAMS | 1 |
| HCDR2 5C5 | AISGSGGSTYYADSVKG | 2 |
| HCDR3 5C5 | ELYREYMDY | 3 |
| LCDR1 5C5 | QGDSLRSYYAS | 4 |
| LCDR2 5C5 | GKNNRPS | 5 |
| LCDR3 5C5 | NSRDSFSIHQNV | 6 |
| VH 5C5 | EVQLLESGGGLVQPGGSLRLSCAASGFTFSSYAMSWVRQA PGKGLEWVSAISGSGGSTYYADSVKGRFTISRDNSKNTLYL QMNSLRAEDTAVYYCAKELYREYMDYWGQGTLVTVSS | 7 |
| VL 5C5 | SSELTQDPAVSVALGQTVRITCQGDSLRSYYASWYQQKPG QAPVLVIYGKNNRPSGIPDRFSGSSSGNTASLTITGAQAEDE ADYYCNSRDSFSIHQNVFGGGTKLTVL | 8 |
| HCDR1 13C6 | SYWIG | 9 |
| HCDR2 13C6 | IIYPGDSDTRYSPSFQG | 10 |
| HCDR3 13C6 | LYPVGVYFDY | 11 |

-continued

|  | Amino Acid Sequence | SEQ ID NO |
|---|---|---|
| LCDR1 13C6 | RASQSISSWLA | 12 |
| LCDR2 13C6 | DASSLES | 13 |
| LCDR3 13C6 | QQYWSYWM | 14 |
| VH 13C6 | EVQLVQSGAEVKKPGESLKISCKGSYSFTSYWIGWVRQM PGKGLEWMGIIYPGDSDTRYSPSFQGQVTISADKSISTAYLQ WSSLKASDTAMYYCARLYPVGVYFDYWGQGTLVTVSS | 15 |
| VL 13C6 | DIQMTQSPSTLSASVGDRVTITCRASQSISSWLAWYQQKPG KAPKLLIYDASSLESGVPSRFSGSGSGTEFTLTISSLQPDDFA TYYCQQYWSYWMFGQGTKVEIK | 16 |
| HCDR1 001 | YWMT | 17 |
| HCDR2 001 | CIHGGSSGSTYYASWVNG | 18 |
| HCDR3 001 | PGYRSWSKTFDL | 19 |
| LCDR1 001 | RASQDISESLN | 20 |
| LCDR2 001 | AASSLQS | 21 |
| LCDR3 001 | QQANSFPLT | 22 |
| VH 001 | QQLEQSGGGLVTPGGSLKLCCIGSGFDFNTYWMTWVRQAP GKGLEWIGCIHGGSSGSTYYASWVNGRFTLSRDIDQSTGCL QVNSLTAADTAMYYCARPGYRSWSKTFDLWGQGTMVTV SS | 23 |
| VL 001 | DIQMTQSPSSLSASVGDRVTITCRASQDISESLNWYQQKPG KAPKLLIYAASSLQSGVPSRFSGSGSGTDYTLTISSLQPEDFA TYYCQQANSFPLTFGGGTKVEIK | 24 |
| HCDR1 013 | IYWMS | 25 |
| HCDR2 013 | RIYGGSSDYTAYASWVNG | 26 |
| HCDR3 013 | LNPSFSRSFDY | 27 |
| LCDR1 013 | RASQGIFSWLV | 28 |
| LCDR2 013 | GASTLQS | 29 |
| LCDR3 013 | QQGYSTPYT | 30 |
| VH 013 | EQSGGGAGGGLVKPGGSLELCCKASGFDFSIYWMSWVRQS PGKGLEWIGRIYGGSSDYTAYASWVNGRFTLSRDIDQSTGC LQLNSLTAADTAMYYCVRLNPSFSRSFDYWGQGTLVTVSS | 31 |
| VL 013 | DIQMTQSPSSVSASVGDRVTITCRASQGIFSWLVWYQQKPG KAPELLMYGASTLQSGVPSRFSGSGSGTDFTLTISSLQPEDF ATYYCQQGYSTPYTFGQGTKVEIK | 32 |
| HCDR1 014 | SYAMS | 33 |
| HCDR2 014 | RISDGGGTIYYTDSVKG | 34 |
| HCDR3 014 | HRLYDSIGAYAMDV | 35 |
| LCDR1 014 | RASQSISSYLN | 36 |
| LCDR2 014 | DASNLET | 37 |

| | Amino Acid Sequence | SEQ ID NO |
|---|---|---|
| LCDR3 014 | QQANSFPLT | 38 |
| VH 014 | EVQLLESGGGLVQPGGSLRLSCAASGFTFSSYAMSWVRQA PGKGLEWVSRISDGGGTIYYTDSVKGRFTIARDNSKNTLYL EMKSLRAEDTAVYYCAKHRLYDSIGAYAMDVWGQGTTV AVSS | 39 |
| VL 014 | DIQMTQSPSSLSASVGDRVTITCRASQSISSYLNWYQQKPG KAPKLLIYDASNLETGVPSRFSGSGSGTDFTLTISSLQPEDFA TYYCQQANSFPLTFGPGTKVDIK | 40 |
| HCDR1 018 | YWMT | 41 |
| HCDR2 018 | CIHGGDSGATYYANWVNG | 42 |
| HCDR3 018 | PGYPSWSKTFDL | 43 |
| LCDR1 018 | QASQDISNALN | 44 |
| LCDR2 018 | AASTLQS | 45 |
| LCDR3 018 | QHSNSFPLT | 46 |
| VH 018 | QQLEQSGGGLVTPGGSLKVCCKASGFDFTTYWMTWVRQA PEKGLEWIGCIHGGDSGATYYANWVNGRFTLSRDIDQSTG CLQLNSLTAADTAMYYCARPGYPSWSKTFDLWGQGTMVT VSS | 47 |
| VL 018 | DIQMTQSPSSLSASVGDRVTITCQASQDISNALNWYQQKPG KAPKLLIYAASTLQSGVPSRFSGSGSGTDFTLTISSLQPEDFA TYYCQHSNSFPLTFGGGTKVEIK | 48 |
| HCDR1 230 | YWMT | 49 |
| HCDR2 230 | CIHGGGSGTTSYASWVNG | 50 |
| HCDR3 230 | PGYRSWSKTFDL | 51 |
| LCDR1 230 | QANQDISNALN | 52 |
| LCDR2 230 | AASSLQS | 53 |
| LCDR3 230 | QQAASFPLT | 54 |
| VH 230 | QQLEQSGGGLVKPGGSLELCCIASGFDFSTYWMTWVRQAP GKGLEWIGCIHGGGSGTTSYASWVNGRFTLSRDIDQSTGCL QLTSLTAADTAMYYCARPGYRSWSKTFDLWGQGTMVTVS S | 55 |
| VL 230 | DIQMTQSPSSLSASVGDRVTITCQANQDISNALNWYQQKPG KAPKLLIYAASSLQSGVPSRFSGSGSGTDFTLTISSLQPEDFA AYYCQQAASFPLTFGGGTKVEIK | 56 |
| HCDR1 296 | SYAMS | 57 |
| HCDR2 296 | AIGIGGGGTYYADSVKG | 58 |
| HCDR3 296 | GASFDFINFFPY | 59 |
| LCDR1 296 | RASQGISNDLA | 60 |
| LCDR2 296 | AASSLQS | 61 |
| LCDR3 296 | QQTYSTPLT | 62 |

| | Amino Acid Sequence | SEQ ID NO |
|---|---|---|
| VH 296 | EVQLLESGGGLVQPGGSLRLSCAASGFTFSSYAMSWVRQA PGKGLEWVSAIGIGGGGTYYADSVKGRFTISRDNSKNTLYL QMNSLRAEDTAVYHCAKGASFDFINFFPYWGQGTLVTVSS | 63 |
| VL 296 | DIQMTQSPSSLSASVGDRVTITCRASQGISNDLAWYQQKPG KAPKLLIYAASSLQSGVPSRFSGSGSGTDFTLTISSLQPEDFA TYYCQQTYSTPLTFGGGTKVEIK | 64 |
| HCDR1 320 | DYAMS | 65 |
| HCDR2 320 | YNSFSVGSTDYADSVKG | 66 |
| HCDR3 320 | HSGNYYTGPFHY | 67 |
| LCDR1 320 | RASQGISSYLA | 68 |
| LCDR2 320 | AASSLES | 69 |
| LCDR3 320 | QQSYSTPIT | 70 |
| VH 320 | EVQLLESGGGLVQPGGSLRLSCATSGFTFSDYAMSWVRQA PGKGLEWVSYNSFSVGSTDYADSVKGRFTISRDNSKNTLYL QMNSLRAEDTAVYYCSKHSGNYYTGPFHYWGQGTLVTVS S | 71 |
| VL 320 | DIQLTQSPSFLSASVGDRVTITCRASQGISSYLAWYQQKPGK APKLLIYAASSLESGVPSRFSGSGSGTDFTLTISSLQPEDFAT YYCQQSYSTPITFGQGTRLEIK | 72 |
| HCDR1 395 | TFWMT | 73 |
| HCDR2 395 | CIHGGSGSRDYASWVNG | 74 |
| HCDR3 395 | PGYRSWSKTFDL | 75 |
| LCDR1 395 | RASQDISGALN | 76 |
| LCDR2 395 | AASSLQS | 77 |
| LCDR3 395 | QQANSFPLT | 78 |
| VH 395 | QEQLEQSGGGLVTPGGSLKLCCTASGFDNTFWMTWVRQ APGKGLEWIGCIHGGSGSRDYASWVNGRFTLSRDIDQSTAC LQVNSLTAADTAMYYCARPGYRSWSKTFDLWGQGTMVT VSS | 79 |
| VL 395 | DIQMTQSPSSLSASVGDRVTITCRASQDISGALNWYQQKPG KAPNLLIYAASSLQSGVPSRFSGSGSGTDYTLTISSLQPEDFA TYYCQQANSFPLTFGGGTKVEIK | 80 |
| Untargeted VH | EVQLLESGGGLVQPGGSLRLSCAASGFTFSSYAMSWVRQA PGKGLEWVSAISGSGGSTYYADSVKGRFTISRDNSKNTLYL QMNSLRAEDTAVYYCAKGSGFDYWGQGTLVTVSS | 81 |
| Untargeted VL | EIVLTQSPGTLSLSPGERATLSCRASQSVSSSYLAWYQQKPG QAPRLLIYGASSRATGIPDRFSGSGSGTDFTLTISRLEPEDFA VYYCQQYGSSPLTFGQGTKVEIK | 82 |
| Human kappa CL domain | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC | 83 |
| Human lambda CL domain | QPKAAPSVTLFPPSSEELQANKATLVCLISDFYPGAVTVAW KADSSPVKAGVETTTPSKQSNNKYAASSYLSLTPEQWKSH RSYSCQVTHEGSTVEKTVAPTECS | 84 |

-continued

| | Amino Acid Sequence | SEQ ID NO |
|---|---|---|
| Human IgG1 heavy chain constant region (CH1-CH2-CH3) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPSRDELTKNQ VSLTCLVKGFYPSDIAVEWESNGQPENNYKTTPPVLDSDGS FFLYSKLTVDKSRWQQGNVFSCSVMHEALHNHYTQKSLSL SP | 85 |
| hIgG1 Fc region | DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVYTLPPSRDELTKNQVSLTCLVKGFYPSDIAVEWE SNGQPENNYKTTPPVLDSDGSFFLYSKLTVDKSRWQQGNV FSCSVMHEALHNHYTQKSLSLSP | 86 |
| huNKG2D | MGWIRGRRSRHSWEMSEFHNYNLDLKKSDFSTRWQKQRC PVVKSKCRENASPFFFCCFIAVAMGIRFIIMVAIWSAVFLNS LFNQEVQIPLTESYCGPCPKNWICYKNNCYQFFDESKNWYE SQASCMSQNASLLKVYSKEDQDLLKLVKSYHWMGLVHIPT NGSWQWEDGSILSPNLLTIIEMQKGDCALYASSFKGYIENC STPNTYICMQRTV | 87 |
| huNKG2D ECD | NSLFNQEVQIPLTESYCGPCPKNWICYKNNCYQFFDESKNW YESQASCMSQNASLLKVYSKEDQDLLKLVKSYHWMGLVH IPTNGSWQWEDGSILSPNLLTIIEMQKGDCALYASSFKGYIE NCSTPNTYICMQRTV | 88 |
| cyNKG2D | MGWIRGRRPRHNLEMSEFHNYKLGLAKSDFSTRCQKQRCP VIKSKCRENASPLFFCCFIAVAMGIRFIIMVTIWSAVFLNSLF NQEVQIPLTESYCGPCPKNWICYKNNCYQFFNESKNWYES QASCMSQNASLLKVYSKEDQDLLKLVKSYHWMGLVHIPT NGSWQWEDGSILSPNLLTIIEMQKGDCALYASSFKGYIENC SIPNTYICMQRTV | 89 |
| cyNKG2D ECD | NSLFNQEVQIPLTESYCGPCPKNWICYKNNCYQFFNESKNW YESQASCMSQNASLLKVYSKEDQDLLKLVKSYHWMGLVH IPTNGSWQWEDGSILSPNLLTIIEMQKGDCALYASSFKGYIE NCSIPNTYICMQRTV | 90 |
| muNKG2D | MALIRDRKSHHSEMSKCHNYDLKPAKWDTSQEQQKQRLA LTTSQPGENGIIRGRYPIEKLKISPMFVVRVLAIALAIRFTLN TLMWLAIFKETFQPVLCNKEVPVSSREGYCGPCPNNWICHR NNCYQFFNEEKTWNQSQASCLSQNSSLLKIYSKEEQDFLKL VKSYHWMGLVQIPANGSWQWEDGSSLSYNQLTLVEIPKGS CAVYGSSFKAYTEDCANLNTYICMKRAV | 91 |
| muNKG2D ECD | NKEVPVSSREGYCGPCPNNWICHRNNCYQFFNEEKTWNQS QASCLSQNSSLLKIYSKEEQDFLKLVKSYHWMGLVQIPANG SWQWEDGSSLSYNQLTLVEIPKGSCAVYGSSFKAYTEDCA NLNTYICMKRAV | 92 |
| his avi huNKG2D ECD | HHHHHHGSGLNDIFEAQKIEWHEGGGGSNSLFNQEVQIPLT ESYCGPCPKNWICYKNNCYQFFDESKNWYESQASCMSQN ASLLKVYSKEDQDLLKLVKSYHWMGLVHIPTNGSWQWED GSILSPNLLTIIEMQKGDCALYASSFKGYIENCSTPNTYICMQ RTV | 93 |
| mono huNKG2D ECD Fc kh avi (knob) | GLNDIFEAQKIEWHEDKTHTCPPCPAPELLGGPSVFLFPPKP KDTLMISRTPEVTCVVVDVSHEDPEVKFNWYVDGVEVHN AKTKPREEQYNSTYRVVSVLTVLHQDWLNGKEYKCKVSN KALPAPIEKTISKAKGQPREPQVYTLPPCRDELTKNQVSLW CLVKGFYPSDIAVEWESNGQPENNYKTTPPVLDSDGSFFLY SKLTVDKSRWQQGNVFSCSVMHEALHNHYTQKSLSLSPGG GGGSGGGGSNSLFNQEVQIPLTESYCGPCPKNWICYKNNCY QFFDESKNVVYESQASCMSQNASLLKVYSKEDQDLLKLVKS YHWMGLVHIPTNGSWQWEDGSILSPNLLTIIEMQKGDCAL YASSFKGYIENCSTPNTYICMQRTV | 94 |

-continued

| | Amino Acid Sequence | SEQ ID NO |
|---|---|---|
| mono huNKG2D ECD Fc kh avi (hole) | DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVCTLPPSRDELTKNQVSLSCAVKGFYPSDIAVEWE SNGQPENNYKTTPPVLDSDGSFFLVSKLTVDKSRWQQGNV FSCSVMHEALHNRFTQKSLSLSPGK | 95 |
| di huNKG2D ECD Fc avi | GLNDIFEAQKIEWHEDKTHTCPPCPAPELLGGPSVFLFPPKP KDTLMISRTPEVTCVVVDVSHEDPEVKFNWYVDGVEVHN AKTKPREEQYNSTYRVVSVLTVLHQDWLNGKEYKCKVSN KALGAPIEKTISKAKGQPREPQVYTLPPSRDELTKNQVSLTC LVKGFYPSDIAVEWESNGQPENNYKTTPPVLDSDGSFFLYS KLTVDKSRWQQGNVFSCSVMHEALHNHYTQKSLSLSPGG GGGSGGGGSNSLFNQEVQIPLTESYCGPCPKNWICYKNNCY QFFDESKNVVYESQASCMSQNASLLKVYSKEDQDLLKLVKS YHWMGLVHIPTNGSWQWEDGSILSPNLLTIIEMQKGDCAL YASSFKGYIENCSTPNTYICMQRTV | 96 |
| di cyNKG2D ECD Fc avi | GLNDIFEAQKIEWHEDKTHTCPPCPAPELLGGPSVFLFPPKP KDTLMISRTPEVTCVVVDVSHEDPEVKFNWYVDGVEVHN AKTKPREEQYNSTYRVVSVLTVLHQDWLNGKEYKCKVSN KALGAPIEKTISKAKGQPREPQVYTLPPSRDELTKNQVSLTC LVKGFYPSDIAVEWESNGQPENNYKTTPPVLDSDGSFFLYS KLTVDKSRWQQGNVFSCSVMHEALHNHYTQKSLSLSPGG GGGSGGGGSNSLFNQEVQIPLTESYCGPCPKNWICYKNNCY QFFNESKNWYESQASCMSQNASLLKVYSKEDQDLLKLVKS YHWMGLVHIPTNGSWQWEDGSILSPNLLTIIEMQKGDCAL YASSFKGYIENCSIPNTYICMQRTV | 97 |
| di muNKG2D ECD Fc avi | GLNDIFEAQKIEWHEDKTHTCPPCPAPELLGGPSVFLFPPKP KDTLMISRTPEVTCVVVDVSHEDPEVKFNWYVDGVEVHN AKTKPREEQYNSTYRVVSVLTVLHQDWLNGKEYKCKVSN KALGAPIEKTISKAKGQPREPQVYTLPPSRDELTKNQVSLTC LVKGFYPSDIAVEWESNGQPENNYKTTPPVLDSDGSFFLYS KLTVDKSRWQQGNVFSCSVMHEALHNHYTQKSLSLSPGG GGGSGGGGSNKEVPVSSREGYCGPCPNNWICHRNNCYQFF NEEKTWNQSQASCLSQNSSLLKIYSKEEQDFLKLVKSYHW MGLVQIPANGSWQWEDGSSLSYNQLTLVEIPKGSCAVYGS SFKAYTEDCANLNTYICMKRAV | 98 |
| di huNKG2D ECD mu IgG1 Fc | DGCKPCICTVPEVSSVFIFPPKPKDVLTITLTPKVTCVVVDIS KDAPEVQFSWFVDDVEVHTAQTQPREEQFNSTFRSVSELPI MHQDWLNGKEFKCRVNSAAFGAPIEKTISKTKGRPKAPQV YTIPPPKEQMAKDKVSLTCMITDFFPEDITVEWQWNGQPAE NYKNTQPIMDTDGSYFVYSKLNVQKSNWEAGNTFTCSVLH EGLHNHHTEKSLSHSPGGGGGSGGGGSGGGGSNSLFNQEV QIPLTESYCGPCPKNWICYKNNCYQFFDESKNWYESQASC MSQNASLLKVYSKEDQDLLKLVKSYHWMGLVHIPTNGSW QWEDGSILSPNLLTIIEMQKGDCALYASSFKGYIENCSTPNT YICMQRTV | 99 |
| ECD FL MICB Fc avi (knob) | AEPHSLRYNLMVLSQDESVQSGFLAEGHLDGQPFLRYDRQ KRRAKPQGQWAEDVLGAKTWDTETEDLTENGQDLRRTLT HIKDQKGGLHSLQEIRVCEIHEDSSTRGSRHFYYDGELFLSQ NLETQESTVPQSSRAQTLAMNVTNFWKEDAMKTKTHYRA MQADCLQKLQRYLKSGVAIRRTVPPMVNVTSSEVSEGNIT VTCRASSFYPRNITLTWRQDGVSLSHNTQQWGDVLPDGNG TYQTWVATRIRQGEEQRFTCYMEHSGNHGTHPVPSGKVLV LQSQRTVDASGGSPTPPTPGGGSADKTHTCPPCPAPEAAGG PSVFLFPPKPKDTLMISRTPEVTCVVVDVSHEDPEVKFNWY VDGVEVHNAKTKPREEQYNSTYRVVSVLTVLHQDWLNGK EYKCKVSNKALGAPIEKTISKAKGQPREPQVYTLPPCRDEL TKNQVSLWCLVKGFYPSDIAVEWESNGQPENNYKTTPPVL DSDGSFFLYSKLTVDKSRWQQGNVFSCSVMHEALHNHYT QKSLSLSPGKSGGLNDIFEAQKIEWHE | 100 |
| ECD FL MICB Fc avi (hole) | DKTHTCPPCPAPEAAGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALGAPIEKTISKAKG QPREPQVCTLPPSRDELTKNQVSLSCAVKGFYPSDIAVEWE SNGQPENNYKTTPPVLDSDGSFFLVSKLTVDKSRWQQGNV FSCSVMHEALHNRFTQKSLSLSPGK | 101 |

-continued

| | Amino Acid Sequence | SEQ ID NO |
|---|---|---|
| HCDR1 (395, P1AE4972, P1AE4973, P1AE4975, P1AE4977, P1AE4978, P1AE4979, P1AE4980, P1AE4981) | TFWMT | 73 |
| HCDR2 (P1AE4972) | SIHGGSGSRDYASWVNG | 102 |
| HCDR2 (P1AE4973, P1AE4975, P1AE4977, P1AE4978, P1AE4979) | SIHGGSGSRDYADSVKG | 103 |
| HCDR2 (P1AE4980) | SIHGGSGSRDYSPSFQG | 104 |
| HCDR2 (P1AE4981) | SIHGGSGSRDYNPSLKS | 105 |
| HCDR3 (395, P1AE4972, P1AE4973, P1AE4975, P1AE4977, P1AE4978, P1AE4979, P1AE4980, P1AE4981) | PGYRSWSKTFDL | 75 |
| VH 395(C50S) = P1AE4972 | QEQLEQSGGGLVTPGGSLKLCCTASGFDFNTFWMTWVRQ APGKGLEWIGSIHGGSGSRDYASWVNGRFTLSRDIDQSTAC LQVNSLTAADTAMYYCARPGYRSWSKTFDLWGQGTMVT VSS | 106 |
| Hu395 P1AE4973 | EVQLLESGGGLVQPGGSLRLSCAASGFDFNTFWMTWVRQ APGKGLEWVGSIHGGSGSRDYADSVKGRFTISRDNSKNTL VHYLQMNSLRAEDTAVYYCARPGYRSWSKTFDLWGQGTTVT VSS | 107 |
| Hu395 P1AE4975 VH | EVQLLESGGGLVQPGGSLRLSCAASGFDFNTFWMTWVRQ APGKGLEWVGSIHGGSGSRDYADSVKGRFTISRDNSKNTA YLQMNSLRAEDTAVYYCARPGYRSWSKTFDLWGQGTTVT VSS | 108 |
| Hu395 P1AE4977 VH | EVQLLESGGGLVQPGGSLRLSCAASGFDFNTFWMTWVRQ APGKGLEWVGSIHGGSGSRDYADSVKGRFTISRDIDQSTAY LQMNSLRAEDTAVYYCARPGYRSWSKTFDLWGQGTTVTV SS | 109 |
| Hu395 P1AE4978 VH | EVQLVESGGGLVQPGGSLRLSCAASGFDFNTFWMTWVRQ APGKGLEWVGSIHGGSGSRDYADSVKGRFTISADIDQSTAY LQMNSLRAEDTAVYYCARPGYRSWSKTFDLWGQGTTVTV SS | 110 |
| Hu395 P1AE4979 VH | QEQLLESGGGLVQPGGSLRLSCAASGFDFNTFWMTWVRQ APGKGLEWVGSIHGGSGSRDYADSVKGRFTISRDIDQSTAY LQMNSLRAEDTAVYYCARPGYRSWSKTFDLWGQGTTVTV SS | 111 |
| Hu395 P1AE4980 VH | QEQLVQSGAEVKKPGESLKISCKGSGFDFNTFWMTWVRQ MPGKGLEWMGSIHGGSGSRDYSPSFQGQVTISADIDQSTAY LQWSSLKASDTAMYYCARPGYRSWSKTFDLWGQGTTVTV SS | 112 |

| | Amino Acid Sequence | SEQ ID NO |
|---|---|---|
| Hu395 P1AE4981 VH | QEQLQESGPGLVKPSETLSLTCTVSGFDFNTFWMTWIRQPP GKGLEWIGSIHGGSGSRDYNPSLKSRVTISVDIDQNQFSLKL SSVTAADTAVYYCARPGYRSWSKTFDLWGQGTTVTVSS | 113 |
| B9 HCDR1 | SYWMH | 114 |
| B9 HCDR2 | FIRNKANGGTTEYAASVKG | 115 |
| B9 HCDR3 | DRGLRFYFDY | 116 |
| B9 LCDR1 | TLRRGINVGAYSIY | 117 |
| B9 LCDR2 | YKSDSDKQQGS | 118 |
| B9 LCDR3 | MIWHSGASAV | 119 |
| B9 VH | VQLVESGGGLVQPGRSLRLSCAASGFTVSSYWMHWVRQA PGKGLEWVGFIRNKANGGTTEYAASVKGRFTISRDDSKNT LYLQMNSLRAEDTAVYYCARDRGLRFYFDYWGQGTTVTV SS | 120 |
| B9 VL | QAVLTQPASLSASPGASASLTCTLRRGINVGAYSIYWYQQK PGSPPQYLLRYKSDSDKQQGSGVSSRFSASKDASANAGILLI SGLQSEDEADYYCMIWHSGASAVFGGGTKLTVL | 121 |
| huA5B7 HCDR1 | DYYMN | 122 |
| huA5B7 HCDR2 | FIGNKANAYTTEYSASVKG | 123 |
| huA5B7 HCDR3 | DRGLRFYFDY | 124 |
| huA5B7 LCDR1 | RASSSVTYIH | 125 |
| huA5B7 LCDR2 | ATSNLAS | 126 |
| huA5B7 LCDR3 | QHWSSKPPT | 127 |
| huA5B7 VH | EVQLLESGGGLVQPGGSLRLSCAASGFTFTDYYMNWVRQA PGKGLEWLGFIGNKANAYTTEYSASVKGRFTISRDKSKNTL YLQMNSLRAEDTATYYCTRDRGLRFYFDYWGQGTTVTVS S | 128 |
| huA5B7 VL | EIVLTQSPATLSLSPGERATLSCRASSSVTYIHWYQQKPGQA PRSWIYATSNLASGIPARFSGSGSGTDFTLTISSLEPEDFAVY YCQHWSSKPPTFGQGTKLEIK | 129 |
| CD3 HCDR1 | TYAMN | 130 |
| CD3 HCDR2 | RIRSKYNNYATYYADSVKG | 131 |
| CD3 HCDR3 | HGNFGNSYVSWFAY | 132 |
| CD3 LCDR1 | GSSTGAVTTSNYAN | 133 |
| CD3 LCDR2 | GTNKRAP | 134 |
| CD3 LCDR3 | ALWYSNLWV | 135 |
| CD3 VH | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSS | 136 |

| | Amino Acid Sequence | SEQ ID NO |
|---|---|---|
| CD3 VL | QAVVTQEPSLTVSPGGTVTLTCGSSTGAVTTSNYANWVQE KPGQAFRGLIGGTNKRAPGTPARFSGSLLGGKAALTLSGAQ PEDEAEYYCALWYSNLWVFGGGTKLTVL | 137 |
| CEA HCDR1 | EFGMN | 138 |
| CEA HCDR2 | WINTKTGEATYVEEFKG | 139 |
| CEA HCDR3 | WDFAYYVEAMDY | 140 |
| CEA LCDR1 | KASAAVGTYVA | 141 |
| CEA LCDR2 | SASYRKR | 142 |
| CEA LCDR3 | HQYYTYPLFT | 143 |
| CEA VH | QVQLVQSGAEVKKPGASVKVSCKASGYTFTEFGMNWVRQ APGQGLEWMGWINTKTGEATYVEEFKGRVTFTTDTSTSTA YMELRSLRSDDTAVYYCARWDFAYYVEAMDYWGQGTTV TVSS | 144 |
| CEA VL | DIQMTQSPSSLSASVGDRVTITCKASAAVGTYVAWYQQKP GKAPKLLIYSASYRKRGVPSRFSGSGSGTDFTLTISSLQPEDF ATYYCHQYYTYPLFTFGQGTKLEIK | 145 |
| CEA (2) HCDR1 | DTYMH | 146 |
| CEA (2) HCDR2 | RIDPANGNSKYVPKFQG | 147 |
| CEA (2) HCDR3 | FGYYVSDYAMAY | 148 |
| CEA (2) LCDR1 | RAGESVDIFGVGFLH | 149 |
| CEA (2) LCDR2 | RASNRAT | 150 |
| CEA (2) LCDR3 | QQTNEDPYT | 151 |
| CEA (2) VH | QVQLVQSGAEVKKPGSSVKVSCKASGFNIKDTYMHWVRQ APGQGLEWMGRIDPANGNSKYVPKFQGRVTITADTSTSTA YMELSSLRSEDTAVYYCAPFGYYVSDYAMAYWGQGTLVT VSS | 152 |
| CEA (2) VL | EIVLTQSPATLSLSPGERATLSCRAGESVDIFGVGFLHWYQQ KPGQAPRLLIYRASNRATGIPARFSGSGSGTDFTLTISSLEPE DFAVYYCQQTNEDPYTFGQGTKLEIK | 153 |
| CEA-TCB HC1 | QVQLVQSGAEVKKPGASVKVSCKASGYTFTEFGMNWVRQ APGQGLEWMGWINTKTGEATYVEEFKGRVTFTTDTSTSTA YMELRSLRSDDTAVYYCARWDFAYYVEAMDYWGQGTTV TVSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDGGGGSGGGGSEVQLL ESGGGLVQPGGSLRLSCAASGFTFSTYAMNWVRQAPGKGL EWVSRIRSKYNNYATYYADSVKGRFTISRDDSKNTLYLQM NSLRAEDTAVYYCVRHGNFGNSYVSWFAYWGQGTLVTVS SASVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGECDKTHTCPPCPAPEA AGGPSVFLFPPKPKDTLMISRTPEVTCVVVDVSHEDPEVKF NWYVDGVEVHNAKTKPREEQYNSTYRVVSVLTVLHQDW LNGKEYKCKVSNKALGAPIEKTISKAKGQPREPQVYTLPPC RDELTKNQVSLWCLVKGFYPSDIAVEWESNGQPENNYKTT PPVLDSDGSFFLYSKLTVDKSRWQQGNVFSCSVMHEALHN HYTQKSLSLSPGK | 154 |

-continued

| | Amino Acid Sequence | SEQ ID NO |
|---|---|---|
| CEA-TCB HC2 | QVQLVQSGAEVKKPGASVKVSCKASGYTFTEFGMNWVRQ APGQGLEWMGWINTKTGEATYVEEFKGRVTFTTDTSTSTA YMELRSLRSDDTAVYYCARWDFAYYVEAMDYWGQGTTV TVSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPEAAG GPSVFLFPPKPKDTLMISRTPEVTCVVVDVSHEDPEVKFNW YVDGVEVHNAKTKPREEQYNSTYRVVSVLTVLHQDWLNG KEYKCKVSNKALGAPIEKTISKAKGQPREPQVCTLPPSRDE LTKNQVSLSCAVKGFYPSDIAVEWESNGQPENNYKTTPPVL DSDGSFFLVSKLTVDKSRWQQGNVFSCSVMHEALHNHYT QKSLSLSPGK | 155 |
| CEA-TCB LC1 | QAVVTQEPSLTVSPGGTVTLTCGSSTGAVTTSNYANWVQE KPGQAFRGLIGGTNKRAPGTPARFSGSLLGGKAALTLSGAQ PEDEAEYYCALWYSNLWVFGGGTKLTVLSSASTKGPSVFP LAPSSKSTSGGTAALGCLVKDYFPEPVTVSWNSGALTSGVH TFPAVLQSSGLYSLSSVVTVPSSSLGTQTYICNVNHKPSNTK VDKKVEPKSC | 156 |
| CEA-TCB LC2 | DIQMTQSPSSLSASVGDRVTITCKASAAVGTYVAWYQQKP GKAPKLLIYSASYRKRGVPSRFSGSGSGTDFTLTISSLQPEDF ATYYCHQYYTYPLFTFGQGTKLEIKRTVAAPSVFIFPPSDEQ LKSGTASVVCLLNNFYPREAKVQWKVDNALQSGNSQESVT EQDSKDSTYSLSSTLTLSKADYEKHKVYACEVTHQGLSSPV TKSFNRGEC | 157 |
| CEA-TCB (2) HC1 | QVQLVQSGAEVKKPGSSVKVSCKASGFNIKDTYMHWVRQ APGQGLEWMGRIDPANGNSKYVPKFQGRVTITADTSTSTA YMELSSLRSEDTAVYYCAPFGYYVSDYAMAYWGQGTLVT VSSASTKGPSVFPLAPSSKSTSGGTAALGCLVEDYFPEPVTV SWNSGALTSGVHTFPAVLQSSGLYSLSSVVTVPSSSLGTQT YICNVNHKPSNTKVDEKVEPKSCDGGGGSGGGGSQAVVTQ EPSLTVSPGGTVTLTCGSSTGAVTTSNYANWVQEKPGQAF RGLIGGTNKRAPGTPARFSGSLLGGKAALTLSGAQPEDEAE YYCALWYSNLWVFGGGTKLTVLSSASTKGPSVFPLAPSSKS TSGGTAALGCLVKDYFPEPVTVSWNSGALTSGVHTFPAVL QSSGLYSLSSVVTVPSSSLGTQTYICNVNHKPSNTKVDKKV EPKSCDKTHTCPPCPAPEAAGGPSVFLFPPKPKDTLMISRTP EVTCVVVDVSHEDPEVKFNWYVDGVEVHNAKTKPREEQY NSTYRVVSVLTVLHQDWLNGKEYKCKVSNKALGAPIEKTI SKAKGQPREPQVYTLPPCRDELTKNQVSLWCLVKGFYPSDI AVEWESNGQPENNYKTTPPVLDSDGSFFLYSKLTVDKSRW QQGNVFSCSVMHEALHNHYTQKSLSLSP | 158 |
| CEA-TCB (2) HC2 | QVQLVQSGAEVKKPGSSVKVSCKASGFNIKDTYMHWVRQ APGQGLEWMGRIDPANGNSKYVPKFQGRVTITADTSTSTA YMELSSLRSEDTAVYYCAPFGYYVSDYAMAYWGQGTLVT VSSASTKGPSVFPLAPSSKSTSGGTAALGCLVEDYFPEPVTV SWNSGALTSGVHTFPAVLQSSGLYSLSSVVTVPSSSLGTQT YICNVNHKPSNTKVDEKVEPKSCDKTHTCPPCPAPEAAGGP SVFLFPPKPKDTLMISRTPEVTCVVVDVSHEDPEVKFNWYV DGVEVHNAKTKPREEQYNSTYRVVSVLTVLHQDWLNGKE YKCKVSNKALGAPIEKTISKAKGQPREPQVCTLPPSRDELT KNQVSLSCAVKGFYPSDIAVEWESNGQPENNYKTTPPVLDS DGSFFLVSKLTVDKSRWQQGNVFSCSVMHEALHNHYTQK SLSLSP | 159 |
| CEA-TCB (2) LC1 | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSSASVAAPSVFIFPPSDEQLKSGTASVVCLLNNFYPR EAKVQWKVDNALQSGNSQESVTEQDSKDSTYSLSSTLTLS KADYEKHKVYACEVTHQGLSSPVTKSFNRGEC | 160 |
| CEA-TCB (2) LC2 | EIVLTQSPATLSLSPGERATLSCRAGESVDIFGVGFLHWYQQ KPGQAPRLLIYRASNRATGIPARFSGSGSGTDFTLTISSLEPE DFAVYYCQQTNEDPYTFGQGTKLEIKRTVAAPSVFIFPPSDR KLKSGTASVVCLLNNFYPREAKVQWKVDNALQSGNSQES VTEQDSKDSTYSLSSTLTLSKADYEKHKVYACEVTHQGLSS PVTKSFNRGEC | 161 |
| A5B7 HCDR2 | FIGNKANGYTTEYSASVKG | 162 |

| | Amino Acid Sequence | SEQ ID NO |
|---|---|---|
| A5B7 VH | EVKLVESGGGLVQPGGSLRLSCATSGFTFTDYYMNWVRQP PGKALEWLGFIGNKANGYTTEYSASVKGRFTISRDKSQSIL YLQMNTLRAEDSATYYCTRDRGLRFYFDYWGQGTTLTVSS | 163 |
| A5B7 VL | QTVLSQSPAILSASPGEKVTMTCRASSSVTYIHWYQQKPGS SPKSWIYATSNLASGVPARFSGSGSGTSYSLTISRVEAEDAA TYYCQHWSSKPPTFGGGTKLEIK | 164 |
| HCDR1 consensus | DYXMN, wherein X is Y or A or E | 165 |
| HCDR1 | DYAMN | 166 |
| HCDR1 | DYEMN | 167 |
| HCDR2 consensus | $X_1IX_2$NKANAYTTEYSASVKG, wherein $X_1$ is F or V, $X_2$ is G or S | 168 |
| HCDR2 | VISNKANAYTTEYSASVKG | 169 |
| HCDR2 | FISNKANAYTTEYSASVKG | 170 |
| HCDR3 consensus | DRG$X_1$RF$X_2$FDY, wherein $X_1$ is L or I, $X_2$ is Y or G or Q or S | 171 |
| HCDR3 | DRGIRFGFDY | 172 |
| HCDR3 | DRGLRFSFDY | 173 |
| HCDR3 | DRGIRFYFDY | 174 |
| HCDR3 | DRGIRFYFDY | 175 |
| HCDR3 | DRGIRFSFDY | 176 |
| LCDR1 consensus | XASSSVTYIH, wherein X is R or H | 177 |
| LCDR1 | HASSSVTYIH | 178 |
| LCDR3 consensus | QHWSS$X_1X_2$PT, wherein $X_1$ is K or V or Q or I, $X_2$ is P or S | 179 |
| LCDR3 | QHWSSVPPT | 180 |
| LCDR3 | QHWSSQPPT | 181 |
| LCDR3 | QHWSSISPT | 182 |
| LCDR3 | QHWSSKSPT | 183 |
| P006.038 VH | EVQLLESGGGLVQPGGSLRLSCAASGFTFTDYYMNWVRQA PGKGLEWLGFIGNKANAYTTEYSASVKGRFTISRDKSKNTL YLQMNSLRAEDTATYYCTRDRGIRFGFDYWGQGTTVTVSS | 184 |
| P006.038 VL | EIVLTQSPATLSLSPGERATLSCRASSSVTYIHWYQQKPGQA PRSWIYATSNLASGIPARFSGSGSGTDFTLTISSLEPEDFAVY YCQHWSSVPPTFGQGTKLEIK | 185 |
| P005.097 VH | EVQLLESGGGLVQPGGSLRLSCAASGFTFTDYYMNWVRQA PGKGLEWLGFIGNKANAYTTEYSASVKGRFTISRDKSKNTL YLQMNSLRAEDTATYYCTRDRGLRFSFDYWGQGTTVTVSS | 186 |
| P005.097 VL | EIVLTQSPATLSLSPGERATLSCRASSSVTYIHWYQQKPGQA PRSWIYATSNLASGIPARFSGSGSGTDFTLTISSLEPEDFAVY YCQHWSSQPPTFGQGTKLEIK | 187 |
| P005.103 VH | EVQLLESGGGLVQPGGSLRLSCAASGFTFTDYYMNWVRQA PGKGLEWLGFIGNKANAYTTEYSASVKGRFTISRDKSKNTL YLQMNSLRAEDTATYYCTRDRGIRFYFDYWGQGTTVTVSS | 188 |

-continued

| | Amino Acid Sequence | SEQ ID NO |
|---|---|---|
| P005.103 VL | EIVLTQSPATLSLSPGERATLSCRASSSVTYIHWYQQKPGQA PRSWIYATSNLASGIPARFSGSGSGTDFTLTISSLEPEDFAVY YCQHWSSISPTFGQGTKLEIK | 189 |
| P002.139 VH | EVQLLESGGGLVQPGGSLRLSCAASGFYFTDYAMNWVRQ APGKGLEWLGVISNKANAYTTEYSASVKGRFTISRDKSKNT LYLQMNSLRAEDTATYYCTRDRGLRFYFDYWGQGTTVTV SS | 190 |
| P002.139 VL | EIVLTQSPATLSLSPGERATLSCHASSSVTYIHWYQQKPGQA PRSWIYATSNLASGIPARFSGSGSGTDFTLTISSLEPEDFAVY YCQHWSSKPPTFGQGTKLEIK | 191 |
| P001.177 VH | EVQLLESGGGLVQPGGSLRLSCAASGFYFTDYYMNWVRQ APGKGLEWLGFISNKANAYTTEYSASVKGRFTISRDKSKNT LYLQMNSLRAEDTATYYCTRDRGLRFYFDYWGQGTTVTV SS | 192 |
| P001.177 VL | EIVLTQSPATLSLSPGERATLSCRASSSVTYIHWYQQKPGQA PRSWIYATSNLASGIPARFSGSGSGTDFTLTISSLEPEDFAVY YCQHWSSKPPTFGQGTKLEIK | 193 |
| P005.102 VH | EVQLLESGGGLVQPGGSLRLSCAASGFTFTDYYMNWVRQA PGKGLEWLGFIGNKANAYTTEYSASVKGRFTISRDKSKNTL YLQMNSLRAEDTATYYCTRDRGIRFQFDYWGQGTTVTVSS | 194 |
| P005.102 VL | EIVLTQSPATLSLSPGERATLSCRASSSVTYIHWYQQKPGQA PRSWIYATSNLASGIPARFSGSGSGTDFTLTISSLEPEDFAVY YCQHWSSKSPTFGQGTKLEIK | 195 |
| P005.102-combo1 VH | EVQLLESGGGLVQPGGSLRLSCAASGFYFTDYYMNWVRQ APGKGLEWLGVISNKANAYTTEYSASVKGRFTISRDKSKNT LYLQMNSLRAEDTATYYCTRDRGIRFQFDYWGQGTTVTVS S | 196 |
| P005.102-combo1 VL | EIVLTQSPATLSLSPGERATLSCRASSSVTYIHWYQQKPGQA PRSWIYATSNLASGIPARFSGSGSGTDFTLTISSLEPEDFAVY YCQHWSSKSPTFGQGTKLEIK | 197 |
| P005.102-combo2 VH | EVQLLESGGGLVQPGGSLRLSCAASGFYFSDYYMNWVRQ APGKGLEWLGVISNKANAYTTEYSASVKGRFTISRDKSKNT LYLQMNSLRAEDTATYYCTRDRGIRFQFDYWGQGTTVTVS S | 198 |
| P005.102-combo2 VL | EIVLTQSPATLSLSPGERATLSCRASSSVTYIHWYQQKPGQA PRSWIYATSNLASGIPARFSGSGSGTDFTLTISSLEPEDFAVY YCQHWSSKSPTFGQGTKLEIK | 199 |
| P005.103-combo1 VH | EVQLLESGGGLVQPGGSLRLSCAASGFTFTDYYMNWVRQA PGKGLEWLGFIGNKANAYTTEYSASVKGRFTISRDKSKNTL YLQMNSLRAEDTATYYCTRDRGIRFSFDYWGQGTTVTVSS | 200 |
| P005.103-combo1 VL | EIVLTQSPATLSLSPGERATLSCRASSSVTYIHWYQQKPGQA PRSWIYATSNLASGIPARFSGSGSGTDFTLTISSLEPEDFAVY YCQHWSSISPTFGQGTKLEIK | 201 |
| P005.103-combo2 VH | EVQLLESGGGLVQPGGSLRLSCAASGFYFTDYYMNWVRQ APGKGLEWLGVISNKANAYTTEYSASVKGRFTISRDKSKNT LYLQMNSLRAEDTATYYCTRDRGIRFSFDYWGQGTTVTVS S | 202 |
| P005.103-combo2 VL | EIVLTQSPATLSLSPGERATLSCRASSSVTYIHWYQQKPGQA PRSWIYATSNLASGIPARFSGSGSGTDFTLTISSLEPEDFAVY YCQHWSSISPTFGQGTKLEIK | 203 |
| P006.038-combo1 VH | EVQLLESGGGLVQPGGSLRLSCAASGFYFTDYAMNWVRQ APGKGLEWLGVISNKANAYTTEYSASVKGRFTISRDKSKNT LYLQMNSLRAEDTATYYCTRDRGIRFGFDYWGQGTTVTVS S | 204 |
| P006.038-combo1 VL | EIVLTQSPATLSLSPGERATLSCRASSSVTYIHWYQQKPGQA PRSWIYATSNLASGIPARFSGSGSGTDFTLTISSLEPEDFAVY YCQHWSSVPPTFGQGTKLEIK | 205 |

-continued

| | Amino Acid Sequence | SEQ ID NO |
|---|---|---|
| P006.038-combo2 VH | EVQLLESGGGLVQPGGSLRLSCAASGFTFSDYEMNWVRQA PGKGLEWLGFISNKANAYTTEYSASVKGRFTISRDKSKNTL YLQMNSLRAEDTATYYCTRDRGIRFGFDYWGQGTTVTVSS | 206 |
| P006.038-combo2 VL | EIVLTQSPATLSLSPGERATLSCRASSSVTYIHWYQQKPGQA PRSWIYATSNLASGIPARFSGSGSGTDFTLTISSLEPEDFAVY YCQHWSSVPPTFGQGTKLEIK | 207 |
| hu N(A2B2)A-avi-His | QLTTESMPFNVAEGKEVLLLVHNLPQQLFGYSWYKGERVD GNRQIVGYAIGTQQATPGPANSGRETIYPNASLLIQNVTQN DTGFYTLQVIKSDLVNEEATGQFHVYPELPKPFITSNNSNPV EDEDAVALTCEPEIQNTTYLWWVNNQSLPVSPRLQLSNDN RTLTLLSVTRNDVGPYECGIQNKLSVDHSDPVILNVLYGPD DPTISPSYTYYRPGVNLSLSCHAASNPPAQYSWLIDGNIQQH TQELFISNITEKNSGLYTCQANNSASGHSRTTVKTITVSALSP VVAKPQIKASKTTVTGDKDSVNLTCSTNDTGISIRWFFKNQ SLPSSERMKLSQGNITLSINPVKREDAGTYWCEVFNPISKNQ SDPIMLNVNYNALPQENLINVDGSGLNDIFEAQKIEWHEAR AHHHHHH | 208 |
| NKG2D (P1AE4980) VL - CH1 - Fc (knob, PGLALA) | DIQMTQSPSSLSASVGDRTITCRASQDISGALNWYQQKPG KAPNLLIYAASSLQSGVPSRFSGSGSGTDYTLTISSLQPEDFA TYYCQQANSFPLTFGGGTKVEIKASTKGPSVFPLAPSSKSTS GGTAALGCLVKDYFPEPVTVSWNSGALTSGVHTFPAVLQS SGLYSLSSVVTVPSSSLGTQTYICNVNHKPSNTKVDKKVEP KSDKTHTCPPCPAPEAAGGPSVFLFPPKPKDTLMISRTPEV TCVVVDVSHEDPEVKFNWYVDGVEVHNAKTKPREEQYNS TYRVVSVLTVLHQDWLNGKEYKCKVSNKALGAPIEKTISK AKGQPREPQVYTLPPCRDELTKNQVSLWCLVKGFYPSDIA VEWESNGQPENNYKTTPPVLDSDGSFFLYSKLTVDKSRWQ QGNVFSCSVMHEALHNHYTQKSLSLSP | 209 |
| CEA (huA5B7) VH - CH1 - Fc (hole, PGLALA) | EVQLLESGGGLVQPGGSLRLSCAASGFTFIDYYMNWVRQA PGKGLEWLGFIGNKANAYTTEYSASVKGRFTISRDKSKNTL YLQMNSLRAEDTATYYCTRDRGLRFYFDYWGQGTTVTVS SASTKGPSVFPLAPSSKSTSGGTAALGCLVEDYFPEPVTVS WNSGALTSGVHTFPAVLQSSGLYSLSSVVTVPSSSLGTQTYI CNVNHKPSNTKVDEKVEPKSCDKTHTCPPCPAPEAAGGPS VFLFPPKPKDTLMISRTPEVTCVVVDVSHEDPEVKFNWYVD GVEVHNAKTKPREEQYNSTYRVVSVLTVLHQDWLNGKEY KCKVSNKALGAPIEKTISKAKGQPREPQVCTLPPSRDELTK NQVSLSCAVKGFYPSDIAVEWESNGQPENNYKTTPPVLSD GSFFLVSKLTVDKSRWQQGNVFSCSVMHEALHNHYTQKSL SLSP | 210 |
| NKG2D (P1AE4980) VH - CL | QEQLVQSGAEVKKPGESLKISCKGSGFDFNTFWMTWVRQ MPGKGLEWMGSIHGGSGSRDYSPSFQGQVTISADIDQSTAY LQWSSLKASDTAMYYCARPGYRSWSKTFDLWGQGTTVTV SSASVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 211 |
| CEA (huA5B7) VL - CL | EIVLTQSPATLSLSPGERATLSCRASSSVTYIHWYQQKPGQA PRSWIYATSNLASGIPARFSGSGSGTDFTLTISSLEPEDFAVY YCQHWSSKPPTFGQGTKLEIKRTVAAPSVFIFPPSDRKLKSG TASVVCLLNNFYPREAKVQWKVDNALQSGNSQESVTEQDS KDSTYSLSSTLTLSKADYEKHKVYACEVTHQGLSSPVTKSF NRGEC | 212 |
| NKG2D (P1AE4980) VH - CH1 - Fc (knob, PGLALA) | QEQLVQSGAEVKKPGESLKISCKGSGFDFNTFWMTWVRQ MPGKGLEWMGSIHGGSGSRDYSPSFQGQVTISADIDQSTAY LQWSSLKASDTAMYYCARPGYRSWSKTFDLWGQGTTVTV SSASTKGPSVFPLAPSSKSTSGGTAALGCLVEDYFPEPVTVS WNSGALTSGVHTFPAVLQSSGLYSLSSVVTVPSSSLGTQTYI CNVNHKPSNTKVDEKVEPKSCDKTHTCPPCPAPEAAGGPS VFLFPPKPKDTLMISRTPEVTCVVVDVSHEDPEVKFNWYVD GVEVHNAKTKPREEQYNSTYRVVSVLTVLHQDWLNGKEY KCKVSNKALGAPIEKTISKAKGQPREPQVYTLPPCRDELTK NQVSLWCLVKGFYPSDIAVEWESNGQPENNYKTTPPVLDS DGSFFLYSKLTVDKSRWQQGNVFSCSVMHEALHNHYTQK SLSLSP | 213 |

| | Amino Acid Sequence | SEQ ID NO |
|---|---|---|
| CEA (P001.177) VL - CH1 - Fc (hole, PGLALA) | EIVLTQSPATLSLSPGERATLSCRASSSVTYIHWYQQKPGQA PRSWIYATSNLASGIPARFSGSGSGTDFTLTISSLEPEDFAV YCQHWSSKPPTFGQGTKLEIKSSASTKGPSVFPLAPSSKSTS GGTAALGCLVKDYFPEPVTVSWNSGALTSGVHTFPAVLQS SGLYSLSSVVTVPSSSLGTQTYICNVNHKPSNTKVDKKVEP KSCDKTHTCPPCPAPEAAGGPSVFLFPPKPKDTLMISRTPEV TCVVVDVSHEDPEVKFNWYVDGVEVHNAKTKPREEQYNS TYRVVSVLTVLHQDWLNGKEYKCKVSNKALGAPIEKTISK AKGQPREPQVCTLPPSRDELTKNQVSLSCAVKGFYPSDIAV EWESNGQPENNYKTTPPVLDSDGSFFLVSKLTVDKSRWQQ GNVFSCSVMHEALHNHYTQKSLSLSP | 214 |
| NKG2D (P1AE4980) VL - CL | DIQMTQSPSSLSASVGDRVTITCRASQDISGALNWYQQKPG KAPNLLIYAASSLQSGVPSRFSGSGSGTDYTLTISSLQPEDFA TYYCQQANSFPLTFGGGTKVEIKRTVAAPSVFIFPPSDRKLK SGTASVVCLLNNFYPREAKVQWKVDNALQSGNSQESVTEQ DSKDSTYSLSSTLTLSKADYEKHKVYACEVTHQGLSSPVTK SFNRGEC | 215 |
| CEA (P001.177) VH - CL | EVQLLESGGGLVQPGGSLRLSCAASGFYFTDYYMNWVRQ APGKGLEWLGFISNKANAYTTEYSASVKGRFTISRDKSKNT LYLQMNSLRAEDTATYYCTRDRGLRFYFDYWGQGTTVTV SSASVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 216 |
| C26 VH | QVQLQQWGAGLLKPSETLSLTCAVYGGSFSGYYWSWIRQP PGKGLEWIGEIDHSGSTNYNPSLKSRVTISVDTSKNQFSLKL SSVTAADTAVYYCARARGPWSFDPWGQGTLVTVSS | 217 |
| C26 VL | DIQMTQSPSTLSASVGDRVTITCRASQSISSWLAWYQQKPG KAPKLLIYKASSLESGVPSRFSGSGSGTEFTLTISSLQPDDFA TYYCQQYGSFPITFGGGTKVEIK | 218 |
| ADI27743 VH | QVQLQQWGAGLLKPSETLSLTCAVYGGSFSGYYWSWIRQP PGKGLEWIGEIDHSGSTNYNPSLKSRVTISVDTSKNQFSLKL SSVTAADTAVYYCARARGPWSFDPWGQGTLVTVSS | 219 |
| ADI27743 VL | DIQMTQSPSTLSASVGDRVTITCRASQSISSWLAWYQQKPG KAPKLLIYKASSLESGVPSRFSGSGSGTEFTLTISSLQPDDFA TYYCQQYNSYPTFGGGTKVEIK | 220 |
| C26 IgG (PG LALA) HC | QVQLQQWGAGLLKPSETLSLTCAVYGGSFSGYYWSWIRQP PGKGLEWIGEIDHSGSTNYNPSLKSRVTISVDTSKNQFSLKL SSVTAADTAVYYCARARGPWSFDPWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKKVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALGAPIEKTISKAKGQPREPQVYTLPPSRDELTKNQVSLT CLVKGFYPSDIAVEWESNGQPENNYKTTPPVLDSDGSFFLY SKLTVDKSRWQQGNVFSCSVMHEALHNHYTQKSLSLSPGK | 221 |
| C26 IgG (PG LALA) LC | DIQMTQSPSTLSASVGDRVTITCRASQSISSWLAWYQQKPG KAPKLLIYKASSLESGVPSRFSGSGSGTEFTLTISSLQPDDFA TYYCQQYGSFPITFGGGTKVEIKRTVAAPSVFIFPPSDEQLK SGTASVVCLLNNFYPREAKVQWKVDNALQSGNSQESVTEQ DSKDSTYSLSSTLTLSKADYEKHKVYACEVTHQGLSSPVTK SFNRGEC | 222 |
| ADI27743 IgG (PG LALA) HC | QVQLQQWGAGLLKPSETLSLTCAVYGGSFSGYYWSWIRQP PGKGLEWIGEIDHSGSTNYNPSLKSRVTISVDTSKNQFSLKL SSVTAADTAVYYCARARGPWSFDPWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKKVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALGAPIEKTISKAKGQPREPQVYTLPPSRDELTKNQVSLT CLVKGFYPSDIAVEWESNGQPENNYKTTPPVLDSDGSFFLY SKLTVDKSRWQQGNVFSCSVMHEALHNHYTQKSLSLSPGK | 223 |

-continued

| | Amino Acid Sequence | SEQ ID NO |
|---|---|---|
| ADI27743 IgG (PG LALA) LC | DIQMTQSPSTLSASVGDRVTITCRASQSISSWLAWYQQKPG KAPKLLIYKASSLESGVPSRFSGSGSGTEFTLTISSLQPDDFA TYYCQQYNSYPTFGGGTKVEIKRTVAAPSVFIFPPSDEQLKS GTASVVCLLNNFYPREAKVQWKVDNALQSGNSQESVTEQ DSKDSTYSLSSTLTLSKADYEKHKVYACEVTHQGLSSPVTK SFNRGEC | 224 |
| NKG2D (C26) VL - CH1 - Fc (hole, PGLALA) | DIQMTQSPSTLSASVGDRVTITCRASQSISSWLAWYQQKPG KAPKLLIYKASSLESGVPSRFSGSGSGTEFTLTISSLQPDDFA TYYCQQYGSFPITFGGGTKVEIKSSASTKGPSVFPLAPSSKST SGGTAALGCLVKDYFPEPVTVSWNSGALTSGVHTFPAVLQ SSGLYSLSSVVTVPSSSLGTQTYICNVNHKPSNTKVDKKVE PKSCDKTHTCPPCPAPEAAGGPSVFLFPPKPKDTLMISRTPE VTCVVVDVSHEDPEVKFNWYVDGVEVHNAKTKPREEQYN STYRVVSVLTVLHQDWLNGKEYKCKVSNKALGAPIEKTIS KAKGQPREPQVCTLPPSRDELTKNQVSLSCAVKGFYPSDIA VEWESNGQPENNYKTTPPVLDSDGSFFLVSKLTVDKSRWQ QGNVFSCSVMHEALHNHYTQKSLSLSPGK | 225 |
| NKG2D (C26) VH - CL | QVQLQQWGAGLLKPSETLSLTCAVYGGSFSGYYWSWIRQP PGKGLEWIGEIDHSGSTNYNPSLKSRVTISVDTSKNQFSLKL SSVTAADTAVYYCARARGPWSFDPWGQGTLVTVSSASVA APSVFIFPPSDEQLKSGTASVVCLLNNFYPREAKVQWKVDN ALQSGNSQESVTEQDSKDSTYSLSSTLTLSKADYEKHKVYA CEVTHQGLSSPVTKSFNRGEC | 226 |
| NKG2D (ADI27743) VL - CH1 - Fc (hole, PGLALA) | DIQMTQSPSTLSASVGDRVTITCRASQSISSWLAWYQQKPG KAPKLLIYKASSLESGVPSRFSGSGSGTEFTLTISSLQPDDFA TYYCQQYNSYPTFGGGTKVEIKSSASTKGPSVFPLAPSSKST SGGTAALGCLVKDYFPEPVTVSWNSGALTSGVHTFPAVLQ SSGLYSLSSVVTVPSSSLGTQTYICNVNHKPSNTKVDKKVE PKSCDKTHTCPPCPAPEAAGGPSVFLFPPKPKDTLMISRTPE VTCVVVDVSHEDPEVKFNWYVDGVEVHNAKTKPREEQYN STYRVVSVLTVLHQDWLNGKEYKCKVSNKALGAPIEKTIS KAKGQPREPQVCTLPPSRDELTKNQVSLSCAVKGFYPSDIA VEWESNGQPENNYKTTPPVLDSDGSFFLVSKLTVDKSRWQ QGNVFSCSVMHEALHNHYTQKSLSLSPGK | 227 |
| NKG2D (ADI27743) VH - CL | QVQLQQWGAGLLKPSETLSLTCAVYGGSFSGYYWSWIRQP PGKGLEWIGEIDHSGSTNYNPSLKSRVTISVDTSKNQFSLKL SSVTAADTAVYYCARARGPWSFDPWGQGTLVTVSSASVA APSVFIFPPSDEQLKSGTASVVCLLNNFYPREAKVQWKVDN ALQSGNSQESVTEQDSKDSTYSLSSTLTLSKADYEKHKVYA CEVTHQGLSSPVTKSFNRGEC | 228 |
| CEA (huA5B7) VH - CHI - Fc (knob, PGLALA) | EVQLLESGGGLVQPGGSLRLSCAASGFTFTDYYMNWVRQA PGKGLEWLGFIGNKANAYTTEYSASVKGRFTISRDKSKNTL YLQMNSLRAEDTATYYCTRDRGLRFYFDYWGQGTTVTVS SASTKGPSVFPLAPSSKSTSGGTAALGCLVEDYFPEPVTVS WNSGALTSGVHTFPAVLQSSGLYSLSSVVTVPSSSLGTQTYI CNVNHKPSNTKVDEKVEPKSCDKTHTCPPCPAPEAAGGPS VFLFPPKPKDTLMISRTPEVTCVVVDVSHEDPEVKFNWYVD GVEVHNAKTKPREEQYNSTYRVVSVLTVLHQDWLNGKEY KCKVSNKALGAPIEKTISKAKGQPREPQVYTLPPCRDELTK NQVSLWCLVKGFYPSDIAVEWESNGQPENNYKTTPPVLDS DGSFFLYSKLTVDKSRWQQGNVFSCSVMHEALHNHYTQK SLSLSPGK | 229 |
| CEA (huA5B7) VL - CL | EIVLTQSPATLSLSPGERATLSCRASSSVTYIHWYQQKPGQA PRSWIYATSNLASGIPARFSGSGSGTDFTLTISSLEPEDFAVY YCQHWSSKPPTFGQGTKLEIKRTVAAPSVFIFPPSDRKLKSG TASVVCLLNNFYPREAKVQWKVDNALQSGNSQESVTEQDS KDSTYSLSSTLTLSKADYEKHKVYACEVTHQGLSSPVTKSF NRGEC | 230 |

IV. Examples

The following are examples of methods and compositions of the invention. It is understood that various other aspects may be practiced, given the general description provided above.

Example 1. General Methods and Tools

Recombinant DNA Techniques

Standard methods were used to manipulate DNA as described in Sambrook, J. et al, Molecular cloning: A laboratory manual; Cold Spring Harbor Laboratory press, Cold spring Harbor, New York, 1989. The molecular biological reagents were used according to the manufacturer's instructions. General information regarding the nucleotide sequences of human immunoglobulin light and heavy chains is given in: Kabat, E. A. et al. (1991) Sequences of Proteins of Immunological Interest, Fifth Ed., NIH Publication No 91-3242.

DNA Sequencing

DNA sequences were determined by double strand sequencing.

Gene Synthesis

Desired gene segments, where required, were either generated by PCR using appropriate templates or were synthesized at Geneart AG (Regensburg, Germany) from synthetic oligonucleotides and PCR products by automated gene synthesis. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow subcloning into the respective expression vectors. All constructs were designed with a 5'-end DNA sequence coding for a leader peptide which targets proteins for secretion in eukaryotic cells.

Generation of NKG2D Receptors and MIC-B Ligand

Several constructs of NKG2D receptors as well as an MIC-B ligand were generated to be used as antigens for phage display, immunogen for protein immunization of transgenic rabbits, and as screening and characterization tools. The extracellular domain (ECD) of human NKG2D was cloned as 4 different constructs: 1. with N-terminal H6-avi-tags to form non-covalent dimers (his avi huNKG2D ECD) (SEQ ID NO: 93), 2. as a monovalent Fc-fusion to the C-terminus of an avi-tagged human IgG1 Fc-knob chain paired with an 'empty' human IgG1 Fc-hole chain (mono huNKG2D ECD Fc kh avi) (SEQ ID NO: 94 and 95), 3. as a dimeric Fc-fusion to the C-terminus of an avi-tagged human IgG1 Fc dimerized by an intact hinge-region (di huNKG2D ECD Fc avi) (SEQ ID NO: 96), and 4. as a dimeric Fc-fusion to the C-terminus of a murine IgG1 Fc dimerized by an intact hinge-region (di huNKG2D ECD mu IgG1 Fc) (SEQ ID NO: 99). This murine Fc-fusion was used for increased immunogenicity in the transgenic rabbits. The ECDs of cynomolgus and murine NKG2D (di cyNKG2D ECD Fc avi and di muNKG2D ECD Fc avi respectively) were cloned in a similar fashion as the human dimeric Fc-fusion to the C-terminus of an avi-tagged human IgG1 Fc as outlined above (SEQ ID NOs 97 and 98, respectively). Moreover, the ECD of the NKG2D ligand MIC-B (ECD FL MIC-B Fc avi) was cloned as monovalent N-terminal fusion to a human IgG1 Fc-knob chain carrying a C-terminal avi-tag and paired with an 'empty' human IgG1 Fc-hole chain (SEQ ID NOs 100 and 101). Above receptors and the MIC-B ligand are depicted in FIG. 1. Except for di huNKG2D ECD mu IgG1 Fc, they comprise an N-terminal avi-tag allowing site-specific biotinylation upon co-expression of Bir A biotin ligase. In addition to the expression cassette, each vector contains an EBV oriP sequence for autonomous replication in EBV-EBNA expressing cell lines. They were transiently transfected into HEK 293 cells, stably expressing the EBV-derived protein EBNA. A simultaneously co-transfected plasmid encoding biotin ligase Bir A allowed avi tag-specific biotinylation in vivo. The Fc-tagged proteins were then purified using a protein A MABSELECT SURE™ column followed by gel filtration whereas the H6-tagged NKG2D construct was purified by Ni-NTA affinity chromatography followed by gel filtration.

Generation of NKG2D/DAP10 Expressing Cell Lines

Full-length cDNAs encoding human NKG2D and DAP10 were subcloned into mammalian expression vector. The plasmid was transfected into CHO-KIM (Roche) and 293T (ATCC® (American Type Culture Collection), CRL-3216) cells using LIPOFECTAMINE™ LTX Reagent (Invitrogen, #15338100) according to the manufacturer's protocol. Stably transfected NKG2D/DAP10-positive CHO cells were maintained in CDM2 Opt. 1.1 medium (GIBCO, #08-0059) supplemented with 10 nM L-Glutamine (Gibco, #25030081). 293T cells were maintained in DMEM (Gibco, #11965092) supplemented with 10% fetal bovine serum (Gibco, #16140063) and 1% GLUTAMAX™ Supplement (Gibco; #31331-028). Two days after transfection, puromycin (Invivogen; #ant-pr-1) was added to 6 μg/mL for CHO cells and to 1 μg/mL for 293T cells. After initial selection, the cells with the highest cell surface expression of NKG2D were sorted by BD FACSARIA™ III cell sorter (BD Biosciences) and cultured to establish stable cell clones. The expression level and stability was confirmed by FACS analysis using anti-NKG2D antibody KYK-2.0 (Kwong et al. (2008) J Mol Biol 384, 1143-1156) and PerCP-conjugated Fc gamma-specific goat anti-human IgG (Jackson ImmunoResearch, #109-126-097) as secondary antibody over a period of 4 weeks.

Example 2. Generation of Anti-NKG2D Antibodies by Phage Display

Generation of Generic Fab-Libraries

Two generic phage display antibody libraries in the Fab-format were generated on the basis of human germline genes. The libraries were randomized in CDR3 of the light chain (L3) and CDR3 of the heavy chain (H3) using randomized primers of different lengths spanning these CDRs and were assembled from 3 fragments by "splicing by overlapping extension" (SOE) PCR. After assembly of sufficient amounts of full length randomized Fab fragments, they were digested with NcoI/NheI alongside with similarly treated acceptor phagemid vector. Fab library inserts were ligated with phagemid vector and purified ligations were used for transformations into *E. coli* TGT. Phagemid particles displaying the Fab library were rescued using helper phage VCSM13 and purified by PEG/NaCl purification to be used for selections.

Selection of Anti-NKG2D Binders from Generic Fab Libraries by Phage Display

NKG2D binders were selected from the libraries against di muNKG2D ECD Fc avi (SEQ ID NO: 98) and di huNKG2D ECD Fc avi (SEQ ID NO: 96), or di huNKG2D ECD Fc avi (SEQ ID NO: 96) and his avi huNKG2D ECD (SEQ ID NO: 93), in an alternating fashion over 4 panning rounds.

Specific binders were identified by ELISA as follows: 100 µl of 50 nM biotinylated di huNKG2D ECD Fc avi (SEQ ID NO: 96) or his avi huNKG2D ECD (SEQ ID NO: 93) were coated on neutravidin plates. Fab-containing bacterial supernatants were added and binding Fabs were detected via their Flag-tags by using an anti-Flag/HRP secondary antibody. Clones exhibiting significant signals over background, like clone 5C5 and clone 13C6, were short-listed for sequencing and further analyses.

Purification of Fabs

Fabs from bacterial cultures were purified for the determination of the kinetic parameters. For each clone, a 500 ml culture was inoculated with bacteria harboring the corresponding phagemid and induced with 1 mM IPTG at an $OD_{600}$ 0.9. Afterwards, the cultures were incubated at 25° C. overnight and harvested by centrifugation. After the incubation of the resuspended pellet for 20 min in 25 ml PPB buffer (30 mM TRIS™ (tris(hydroxymethyl)aminomethane)-HCl pH8, 1 mM EDTA, 20% sucrose), bacteria were centrifuged again and the supernatant was harvested. This incubation step was repeated once with 25 ml of a 5 mM $MgSO_4$ solution. The supernatants of both incubation steps were pooled, filtered and loaded on an IMAC column (HisGRAVITRAP™, GE Healthcare). Subsequently, the column was washed with 40 ml washing buffer (500 mM NaCl, 20 mM imidazole, 20 mM $NaH_2PO_4$ pH 7.4). After the elution (500 mM NaCl, 500 mM imidazole, 20 mM $NaH_2PO_4$ pH 7.4) the eluate was re-buffered using PD10 columns (GE Healthcare). The kinetic parameters of the purified Fabs were then studied by SPR-analysis (PROTEON™ XPR36, Biorad) in a dilution series that ranged from 100 nM to 6.25 nM for clone 5C5 (SEQ ID NO: 7 (VH) and SEQ ID NO: 8 (VL)) and 200 nM to 12.5 nM for clone 13C6 (SEQ ID NO: 15 (VH) and SEQ ID NO: 16 (VL)).

Affinity-Determination by Surface Plasmon Resonance (SPR)

Affinity ($K_D$) of selected Fab clones was measured by surface plasmon resonance using a PROTEON™ XPR36 instrument (Biorad) at 25° C. with biotinylated mono huNKG2D ECD Fc kh avi (SEQ ID NO: 94 and SEQ ID NO: 95) and di huNKG2D ECD Fc avi (SEQ ID NO: 96) immobilized on NLC chips by neutravidin capture. Immobilization of recombinant antigens (ligand): Antigens were diluted with PBST (10 mM phosphate, 150 mM sodium chloride pH 7.4, 0.005% TWEEN® (polysorbate) 20) to 10 µg/ml, then injected at 30 µl/minute at varying contact times in vertical orientation for immobilization. Injection of analytes: For one-shot kinetics measurements, injection direction was changed to horizontal orientation, two-fold dilution series of purified Fab (varying concentration ranges between 200 and 6.25 nM) were injected simultaneously at 60 µl/min along separate channels 1-5, with association times of 200 s or 300 s, respectively, and dissociation times of 360 s. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in PROTEON™ Manager v3.1 software by simultaneously fitting the association and dissociation sensorgrams. The equilibrium dissociation constant ($K_D$) was calculated as the ratio $k_{off}/k_{on}$. The kinetic and thermodynamic data of all measurements are summarized in Table 1. Cross-reactivity of clones 5C5 and 13C6 to cynomolgus NKG2D, i.e. binding to di cyNKG2D ECD Fc avi, was assessed on IgG level (see Example 9).

TABLE 1

Affinities of anti-NKG2D Fabs to human NKG2D as determined by SPR.

| antibody | mono huNKG2D ECD Fc kh | | | di huNKG2D ECD Fc avi | | |
| --- | --- | --- | --- | --- | --- | --- |
| | ka (1/Ms) | kd (1/s) | KD (M) | ka (1/Ms) | kd (1/s) | KD (M) |
| 5C5 | 3.6E+05 | 5.5E−03 | 1.5E−08 | 2.5E+05 | 5.6E−03 | 2.2E−08 |
| 13C6 | 1.2E+04 | 9.6E−04 | 7.9E−08 | 9.5E+03 | 7.0E−04 | 7.4E−08 |

Cloning of Variable Antibody Domains into IgG Expression Vectors (IgG Conversion)

Fabs of phage display derived antibodies 5C5 and 13C6 were converted into an IgG1/lambda or kappa antibody, respectively. For this, the PCR-amplified DNA fragments of heavy and light chain V-domains were inserted in frame into either a human IgG1 constant heavy chain or the human constant lambda or constant kappa light chain containing respective recipient mammalian expression vector. The antibody expression was driven by an MPSV promoter and transcription terminated by a synthetic polyA signal sequence located downstream of the CDS. In addition to the expression cassette, each vector contained an EBV oriP sequence for autonomous replication in EBV-EBNA expressing cell lines.

Example 3. Generation of Anti-NKG2D Antibodies by Immunization of Transgenic Rabbits Animal Care, Immunization of Rabbits and Organ Removal In addition to the antibodies generated by phage display described above, further antibodies were derived from transgenic rabbits expressing a humanized antibody repertoire (see, e.g. WO 2000/46251, WO 2002/12437, WO 2005/007696, WO 2006/047367, WO 2007/019223, and WO 2008/027986, all incorporated herein by reference in their entirety), upon immunization with NKG2D antigens. The animals were housed according to the Appendix A "Guidelines for accommodation and care of animals" in an AAALAC-accredited animal facility. All animal immunization protocols and experiments were approved by the Government of Upper Bavaria (permit number 55.2-1-54-2532-90-14) and performed according to the German Animal Welfare Act and the Directive 2010/63 of the European Parliament and Council.

Rabbits were immunized with recombinant human NKG2D ECD protein (his avi huNKG2D ECD (SEQ ID NO: 93)) or recombinant human NKG2D ECD fused to the C-terminus of a murine IgG1 Fc (di huNKG2D ECD mu IgG1 Fc (SEQ ID NO: 99)), or immunized genetically, using a plasmid expression vector coding for full-length human NKG2D and DAP10, alternating with CHO cells recombinantly expressing full-length human NKG2D and DAP10.

Antigen-specific titer was determined by ELISA in serum from immunized animals (see below).

B Cell Cloning

Rabbit peripheral blood mononuclear cells (PBMC) were isolated for B cell cloning. Macrophages and monocytes were depleted through unspecific adhesion to a layer of HEK293 cells. The cells in the supernatant (peripheral blood lymphocytes (PBLs)) were used for the antigen panning step. Antigen-specific B cells were enriched through binding to antigen-coated plates (his avi huNKG2D ECD (SEQ ID NO: 93) or HEK293T cells recombinantly expressing full-length human NKG2D and DAP10). Enriched cells were subjected to single cell sorting by flow cytometry.

The rabbit B cells were cultivated as described by Seeber et al. (Seeber et al. (2014) PLoS One 4; 9(2)), and supernatants used for Level 1 screening by ELISA (see below).

PCR Amplification and Subcloning of V-Domains for Recombinant Expression of IgG Antibodies Total RNA was prepared from B cells lysate and used to generate cDNA by reverse transcriptase reaction. cDNA was used to amplify the immunoglobulin heavy and light chain variable regions (VH and VL) by PCR using appropriate primers.

For recombinant expression of rabbit monoclonal bivalent antibodies, PCR-products coding for VH or VL were cloned as cDNA into expression vectors by the overhang cloning method (Haun et al. (1992) Biotechniques 13, 515-518; Li et al. (2007) Nature Methods 4, 251-256). The expression vectors contained an expression cassette consisting of a 5' CMV promoter including intron A, and a 3' BGH poly adenylation sequence. In addition to the expression cassette, the plasmids contained a pUC18-derived origin of replication and a beta-lactamase gene conferring ampicillin resistance for plasmid amplification in E. coli. Three variants of the basic plasmid were used: one plasmid containing the rabbit IgG constant region designed to accept the VH regions, and two additional plasmids containing either rabbit or human kappa LC constant region to accept the VL regions. Linearized expression plasmids coding for the kappa or gamma constant region and VL NH inserts were amplified by PCR using overlapping primers. Purified PCR products were incubated with T4 DNA-polymerase which generated single-strand overhangs. The reaction was stopped by dCTP addition. In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing. For Level 2 screening by ELISA (see below), the isolated heavy chain (HC) and light chain (LC) plasmids were transiently co-transfected into HEK293 cells and the supernatants were harvested after 1 week to be subsequently subjected to micro-purification.

Example 4. Screening of Anti-NKG2D Antibodies for NKG2D Binding by ELISA

For screening of the clones derived from immunization of transgenic rabbits, either supernatants of the B-cell cultivation (Level 1 screening, see above) or subcloned and micro-purified IgGs (Level 2 screening, see above) were used.

Protein Binding ELISA for Human NKG2D

Nunc streptavidin coated plates (MicroCoat, #11974998001) were coated with 25 μl/well biotinylated his avi huNKG2D ECD (SEQ ID NO: 93) at a concentration of 0.5 μg/ml and incubated at room temperature (RT) for 1 hour. After washing with 3×90 μl/well PBST-buffer (10× PBS, Roche #11666789001+0.1% TWEEN® (polysorbate) 20), 25 μl anti-NKG2D antibodies were added in 1:3 dilutions starting at a concentration of 3 μg/ml or alternatively with a 1:30 dilution of the original sample and incubated 1 h at RT. After washing (3×90 μl/well PBST-buffer), 25 μl/well anti hu kappa chain HRP (horseradish peroxidase)-conjugate (Millipore, #AP502P, 1:2000) was added and incubated at RT for 1 h. After washing (3×90 μl/well PBST-buffer) 25 μl/well TMB (3,3',5,5'-tetramethylbenzidine) substrate (Roche, #11835033001) was added. Measurements were performed at OD 370/492 nm and results are summarized in Table 2 below.

All antibodies bound specifically and in a dose-dependent manner to the immobilized his avi huNKG2D ECD.

TABLE 2

Binding of anti-NKG2D antibodies to recombinant human NKG2D determined by ELISA. $EC_{50}$ and OD max.

| Molecule | $EC_{50}$ [nM] | OD max |
|---|---|---|
| clone 001 | 0.8 | 2.5 |
| clone 013 | 2 | 2.5 |
| clone 014 | 1 | 1.7 |
| clone 018 | 1.1 | 2.3 |
| clone 230 | n.d. | 2.4 |
| clone 296 | n.d. | 2.1 |
| clone 320 | 1.4 | 2.4 |
| clone 395 | n.d. | 2.4 |

(n.d. = not determined)

Protein Binding ELISA for Cynomolgous NKG2D

Nunc streptavidin coated plates (MicroCoat, #11974998001) were coated with 25 μl/well biotinylated di cyNKG2D ECD Fc avi (SEQ ID NO: 97) at a concentration of 0.25 μg/ml and incubated at room temperature (RT) for 1 hour. The assay was performed as described above for human NKG2D.

The results are summarized in Table 3. All antibodies are cross-reactive to cynomolgus NKG2D and this has also been confirmed by surface plasmon resonance (see Example 9).

TABLE 3

Binding of anti-NKG2D antibodies to recombinant cynomolgus NKG2D determined by ELISA. $EC_{50}$ and OD max.

| antibody | $EC_{50}$ [nM] | OD max |
|---|---|---|
| clone 001 | 0.3 | 1.7 |
| clone 013 | 0.4 | 1.5 |
| clone 014 | n.d. | 0.4 |
| clone 018 | 0.4 | 1.3 |
| clone 230 | 1.3 | 1.6 |
| clone 296 | 0.7 | 0.9 |
| clone 320 | 0.4 | 0.9 |
| clone 395 | 0.6 | 1.4 |

(n.d. = not determined)

Protein Binding ELISA for Murine NKG2D

Nunc streptavidin coated plates (MicroCoat, #11974998001) were coated with 25 μl/well biotinylated di muNKG2D ECD Fc avi (SEQ ID NO: 98) at a concentration of 1 μg/ml and incubated at room temperature (RT) for 1 hour. The assay was performed as described above for human NKG2D.

The results are summarized in Table 4. The antibodies are not or only very weakly cross-reactive to murine NKG2D.

TABLE 4

Binding of anti-NKG2D antibodies to recombinant murine NKG2D determined by ELISA. $EC_{50}$ and OD max.

| antibody | $EC_{50}$ [nM] | OD max |
|---|---|---|
| clone 001 | n.d. | 0.2 |
| clone 013 | n.d. | 0.4 |
| clone 014 | n.d. | 0.1 |
| clone 018 | n.d. | 0.1 |

TABLE 4-continued

Binding of anti-NKG2D antibodies to recombinant
murine NKG2D determined by ELISA. $EC_{50}$ and OD max.

| antibody | $EC_{50}$ [nM] | OD max |
|---|---|---|
| clone 230 | n.d. | 0.3 |
| clone 296 | n.d. | 0.3 |
| clone 320 | n.d. | 0.1 |
| clone 395 | n.d. | 0.3 |

(n.d. = not determined)

Human NKG2D Cell-Surface Binding ELISA

25 µl/well of HEK293T cells recombinantly expressing full-length human NKG2D and DAP10 (15000 cells/well) or unmodified HEK293T were seeded into 384-well poly-D-lysine plates (Corning, #356662) and incubated overnight at 37° C. in cell culture medium (Gibco, #42430-25+10% FCS (PAN, #P30-2006)+1 µg/ml puromycin+1× penicillin/streptomycin (Roche, #11074440001, 500×)). The next day after removal of medium, 25 µl anti-NKG2D antibodies were added in 1:3 dilutions starting at a concentration of 3 µg/ml or alternatively with a 1:20 dilution of the original sample and incubated for 2 h at 4° C. After washing (1×90 µl in PBST) cells were fixed by addition of 30 µl/well glutaraldehyde to a final concentration of 0.05% (Sigma, #G5882), 10 min at room temperature. After washing (2×90 µl/well PBST-buffer), 25 µl/well anti hu kappa POD (Millipore, #AP502P, 1:2000) was added and incubated at RT for 1 h. After washing (3×90 µl/well with PBST-buffer) 25 µl/well TMB substrate (Roche, #11835033001) was added and incubated for 6-10 min. Measurement were performed on a Tecan Safire 2 instrument at OD 370/492 nm.

The results are summarized in Table 5. All antibodies bound specifically and in a dose-dependent manner to HEK293T cells that recombinantly expressed full-length human NKG2D and DAP10, except for the weak binders clone 013 and 014 for which binding could not be detected in this assay. None of these antibodies bound to non-transfected HEK293T reference cells.

TABLE 5

Cell binding of anti-NKG2D antibodies
determined by cell ELISA. $EC_{50}$ and OD max.

| | HEK293T human NKG2D | | HEK293T | |
|---|---|---|---|---|
| antibody | $EC_{50}$ [nM] | OD max | $EC_{50}$ [nM] | OD max |
| clone 001 | 2.2 | 1.0 | n.d. | 0.2 |
| clone 013 | n.d. | n.d. | n.d. | 0.2 |
| clone 014 | n.d. | n.d. | n.d. | 0.2 |
| clone 018 | 1.9 | 0.8 | n.d. | 0.1 |
| clone 230 | n.d. | 0.7 | n.d. | 0.2 |
| clone 296 | n.d. | 0.5 | n.d. | 0.2 |
| clone 320 | n.d. | 1.0 | n.d. | 0.2 |
| clone 395 | n.d. | 0.8 | n.d. | 0.2 |

(n.d. = not determined)

Example 5. Screening of Anti-NKG2D Antibodies for MIC-B Competition by ELISA 384-well Maxisorp plates (Nunc, #464718) were coated with 25 µl/well recombinant human MIC-B (ECD FL MIC-B Fc avi, SEQ ID NOs 100 and 101)) at a concentration of 2 µg/ml and incubated at room temperature (RT) for 1 hour. After washing with 3×90 µl/well PBST-buffer (10× PBS (Roche, #11666789001)+0.1% TWEEN® (polysorbate) 20), each well was incubated with 90 µl blocking buffer (10×PBS (Roche, #11666789001)+2% Bovine Serum Albumin Fraction V, fatty acid free (Roche, #10735086001)+0.05% TWEEN® (polysorbate) 20) for 1 h at RT. In parallel, recombinant biotinylated human NKG2D was incubated with anti-NKG2D antibodies (2 µg/ml NKG2D with 1:3 dilutions of antibody starting at a concentration of 3 µg/ml) on a polypropylene plate (Weidman, #23490-101) for 1 h at RT. After washing (3×90 µl/well PBST-buffer), 25 µl/well of the NKG2D-antibody mixtures were transferred to the assay plate and incubated for 1 h at RT. After washing (3×90 µl/well PBST-buffer), 25 µl/well Poly-HRP40-Streptavidin (Fitzgerald, #65R-S104PHRPx) was added in a 1:2000 dilution and incubated for 1 h at RT. After an additional washing step (3×90 µl/well PBST-buffer), 25 µl TMB substrate (Roche, #11835033001) was added to each well. Measurements were performed at OD 370/492 nm.

Figure 2:
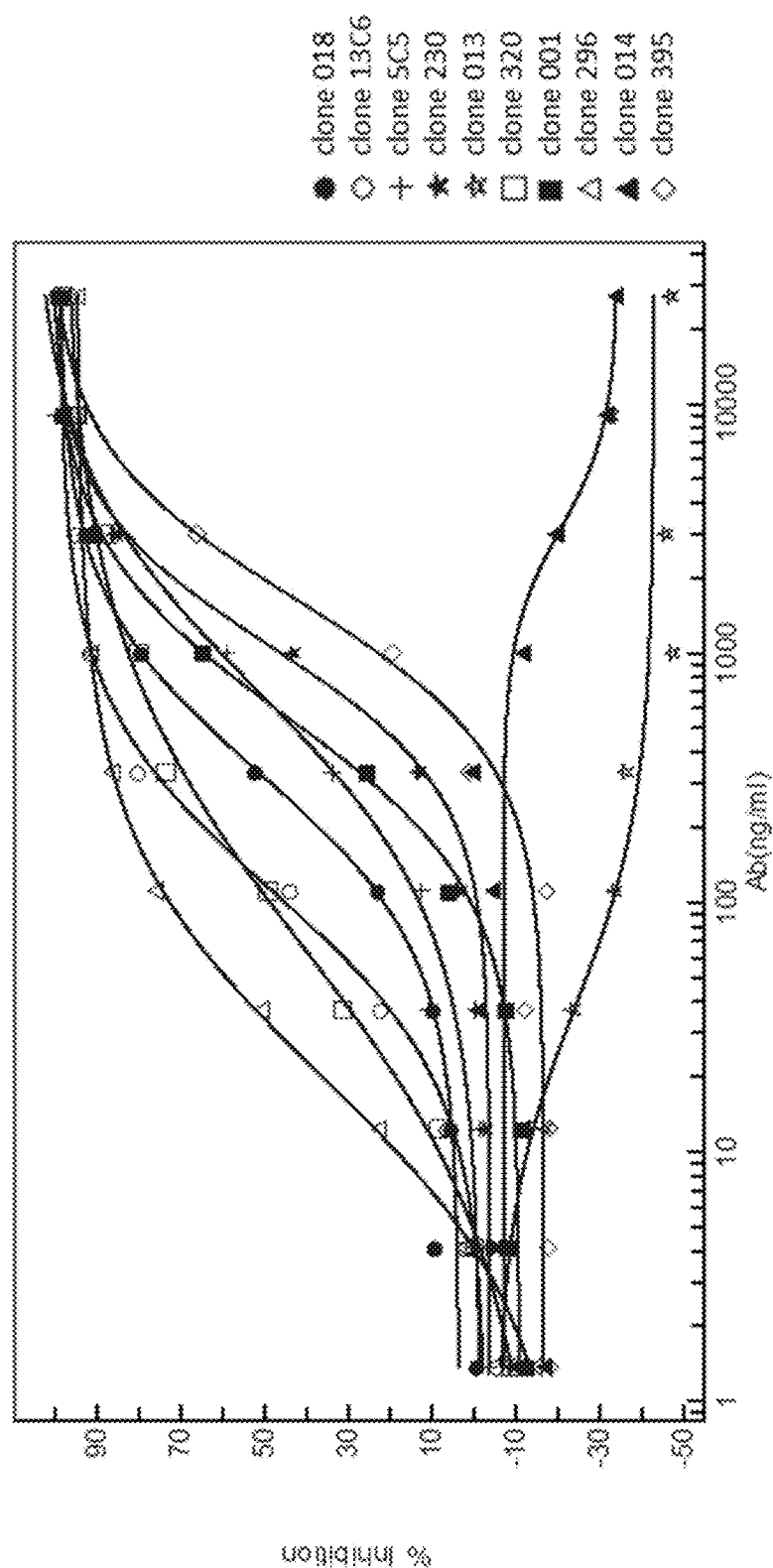
FIG. 2. Screening of anti-NKG2D antibodies for MIC-B competition by ELISA. Percent inhibition of binding of NKG2D to MIC-B, relative to binding of recombinant biotinylated human NKG2D to plate-immobilized MIC-B without anti-NKG2D antibody, is shown.

The results are shown in FIG. 2 and Table 6. "Negative" inhibition curves of clones 013 and 014 can be explained by a stronger re-binding of NKG2D, cross-linked by the antibody, to immobilized MIC-B on the plate (the zero value is the binding of recombinant biotinylated human NKG2D to plate-immobilized MIC-B, without anti-NKG2D antibody). Thus, antibodies with such a profile are non-inhibitory regarding the NKG2D: MIC-B interaction. The other 8 antibodies inhibit the binding of NKG2D to its ligand MIC-B with differing potencies.

TABLE 6

$EC_{50}$ of NKG2D:MIC-B inhibition by anti-NKG2D antibodies.

| antibody | $EC_{50}$ [ng/ml]* |
|---|---|
| clone 13C6 | 111 |
| clone 5C5 | 717 |
| clone 001 | 560 |
| clone 013 | no inhibition |
| clone 014 | no inhibition |
| clone 018 | 332 |
| clone 230 | 1065 |
| clone 296 | 20 |
| clone 320 | 67 |
| clone 395 | 1636 |

(*estimated when no full upper or lower plateau was reached)

Example 6. Upscaled Expression, Purification and Analysis of IgGs

The antibody molecules were generated in transiently transfected HEK293 cells (human embryonic kidney cell line 293-derived) cultivated in F17 Medium (Invitrogen). For transfection "293-Free" Transfection Reagent (Novagen) was used. The respective antibody heavy- and light chain molecules as described above were expressed from individual expression plasmids. Transfections were performed as specified in the manufacturer's instructions. Immunoglobulin-containing cell culture supernatants were harvested 3-7 days after transfection and frozen at −80° C. until purification. General information regarding the recombinant expression of human immunoglobulins in e.g. HEK293 cells is given in: Meissner et al. (2001) Biotechnol Bioeng 75, 197-203 (incorporated herein by reference).

The recombinant antibodies were purified from the supernatant in two steps by affinity chromatography using protein A-Sepharose™ affinity chromatography (GE Healthcare) and SUPERDEX® 200 (GE Healthcare) size exclusion chromatography. Briefly, the antibody-containing clarified culture supernatants were loaded onto a MABSELECT SURE™ Protein A (5-50 ml) column equilibrated with PBS buffer (10 mM Na$_2$HPO$_4$, 1 mM KH$_2$PO$_4$, 137 mM NaCl and 2.7 mM KCl, pH 7.4). Unbound proteins were washed out with equilibration buffer. The antibodies were eluted with 100 mM citrate buffer, pH 2.8. The protein-containing fractions were neutralized with 1/10 eluate volume of 2 M TRIS™ (tris(hydroxymethyl)aminomethane) buffer, pH 9.0. In a subsequent step, the eluted protein fractions were pooled and processed according to one of the three options: a) concentrated with an AMICON® Ultra centrifugal filter device (MWCO: 30 K, Millipore) and loaded on a SUPERDEX®200 HILOAD® 16/60 gel filtration column (GE Healthcare) equilibrated with 20 mM histidine, 140 mM NaCl, at pH 6.0, or b) loaded onto a SUPERDEX®200 HILOAD® 16/60 gel filtration column (GE Healthcare) equilibrated with 20 mM histidine, 140 mM NaCl, at pH 6.0, or c) dialysed with 10K SLIDE-A-LYZER™ (Thermo Fisher Scientific). Monomeric antibody fractions were pooled. The protein concentration of purified antibodies and derivatives was determined by determining the optical density (OD) at 280 nm with the OD at 320 nm as background correction, using the molar extinction coefficient calculated on the basis of the amino acid sequence according to Pace et. al. (1995) Protein Science 4, 2411-2423 (incorporated by reference). Antibody samples were snap-frozen and stored at −80° C.

The homogeneity of the antibodies was confirmed by CE-SDS LABCHIP® GX (PerkinElmer) in the presence or absence of a reducing agent. Under reducing conditions, light and heavy chain polypeptide chains of the IgGs were identified after CE-SDS at apparent molecular sizes analogous to the calculated molecular weights.

The quality of the antibodies was confirmed by analytical SEC (size-exclusion chromatography) using a BioSuite High Resolution SEC, 250 Å, 5 μm run on an ULTIMATE™ 3000 HPLC system (Thermo Fisher Scientific). Elution from the chromatography material was performed by applying 200 mM K$_2$HPO$_4$/KH$_2$PO$_4$, 250 mM KCl, pH 6.2. Main peak of analytical SEC resulted in >91% for all analyzed samples.

Example 7. Screening of Anti-NKG2D Antibodies (IgGs) for NKG2D Binding by FACS For the EC$_{50}$ determination of binding to NK-92 cells, the antibodies were pre-labeled with a ZENON™ Human IgG Labeling Kit (Thermo Fisher Scientific). The IgGs were stained with a 5-fold excess of ZENON™ reagent A and unbound staining reagent was blocked with an equal amount of ZENON™ reagent B. After the preparation of a dilution series in steps of 1:3, 5.0×10$^4$ NK-92 cells per well in a 96-well plate were incubated with 50 μL pre-labeled antibody solution for 1 h at 4° C. Cells were washed twice with FACS buffer (2.5% FCS in PBS) and resuspended in 70 μL buffer. Fluorescence was measured using a BD FACS Canto device and EC$_{50}$ was determined (Table 7).

The antibodies exhibited specific and dose-dependent binding to NK92 cells with EC50 values ranging from 0.988 to 0.031 μg/mL. For clones 013, 014, and 5C5, being weak cell binders, no EC$_{50}$ values could be determined.

TABLE 7

EC$_{50}$ of NK92 cell binding of NKG2D antibodies as determined by FACS

| antibody | EC$_{50}$ [μg/mL] |
| --- | --- |
| clone 018 | 0.758 |
| clone 13C6 | 0.058 |
| clone 5C5 | n.d. |
| clone 230 | 0.988 |
| clone 013 | n.d. |
| clone 320 | 0.734 |
| clone 001 | 0.729 |
| clone 395 | 0.203 |
| clone 296 | 0.031 |
| clone 014 | n.d. |

(n.d. = not determined).

Example 8. Re-Directed Lysis of Target Cells by Anti-NKG2D Antibodies (IgGs)

Calcein Labeling of Target Cells

P815 cells (a murine FcγR expressing mast cell line) were harvested by centrifugation in a 50 mL Falcon tube (300×g, 5 min) and subsequently re-suspended to 1.0×10$^6$ cells/mL in P815 growth medium. 50 μL calcein-AM per 5.0×10$^6$ cells were added and labeling reaction was incubated for 30 min at 37° C. The cells were washed 3× with AIM-V assay medium and re-suspended to 6.0×10$^5$ cells/mL Antibody Treatment The antibodies were adjusted to 80 μg/mL in assay medium. Subsequently, 1:3 dilutions were prepared in AIM-V medium in a V-bottom plate according to the plate scheme by mixing 40 μL pre-dilution with 80 μL AIM-V medium. P815 cells were adjusted to 6.0×10$^5$ cells/mL and 50 μL/well cell suspension was added to the antibody dilutions resulting in 3.0×10$^4$ cells/well and incubated for 30 min at 37° C. to allow binding of the antibodies to the Fc-receptors of the cells.

Afterwards, the plate was centrifuged for 3 min at 400×g and the supernatants were discarded. NK-92 cells were resuspended to 7.5×10$^5$ cells/mL in assay medium. P815 cells were resuspended in 200 μL NK-92 cell suspension (=1.5×10$^5$ cells/well=E:T ratio 1:5). The plates were incubated for 4 h at 37° C.

Calcein Release

After centrifugation of the plates for 4 min at 420×g, the supernatants were discarded and the cells were washed once with 200 μL PBS (final centrifugation 420×g, 4 min). The cells were then resuspended in 200 μL/well 1% TRITON™ (polyethylene glycol tert-octylphenyl ether) X-100 PBS and 180 μL of the lysed cells were transferred into a Costar®Assay PLate, 96 well, black with clear bottom, and the fluorescence was measured (excitation filter 485 nm, band-pass filter 530 nm). The "% cell killing" was determined as quotient of the measured values against maximal release where the cells were re-suspended in 200 μL 1% TRITON™ (polyethylene glycol tert-octylphenyl ether) X-100 in assay medium.

Figure 3:
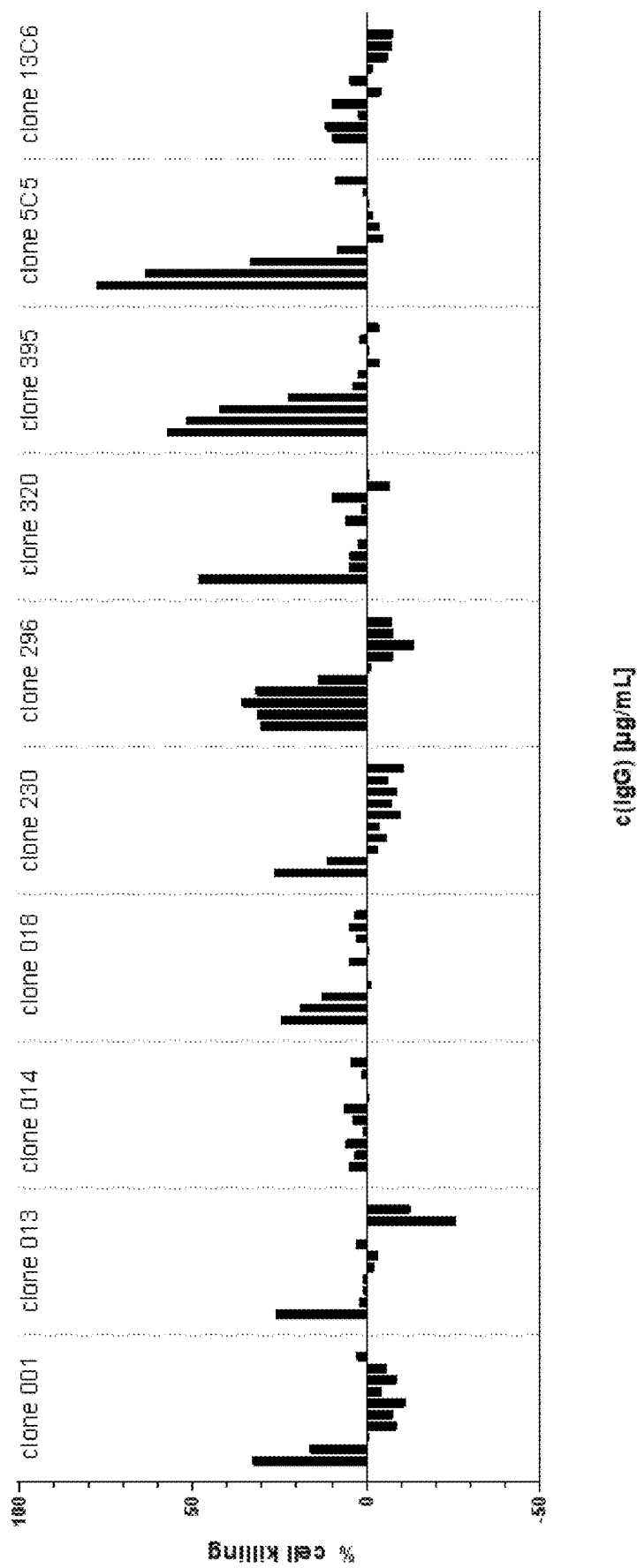
FIG. 3. Re-directed lysis of target cells by anti-NKG2D antibodies. Percent cell killing by anti-NKG2D antibodies as determined by calcein release from labeled P815 target cells. Antibody concentrations for each clone are (from left to right) 40.0, 13.33, 4.44, 1.48, 0.49, 0.165, 0.055, 0.018, 0.006, 0.002 µg/ml.

The result is shown in FIG. 3. The tested antibodies exhibited different degrees of cell killing. In particular for clones 395 and 5C5, dose-dependent cell killing by activated NK92 cells could be observed.

Example 9. Determination of Kinetic Rate Constants and Affinities of Anti-NKG2D Antibodies (IgGs) to Human and Cynomolgus NKG2D by Surface Plasmon Resonance (SPR)

Around 1500 resonance units (RU) of the capture antibody (10 μg/ml human Fab Capture Kit, GE Healthcare Life Sciences, #28958325) were coupled onto a CM5 chip (GE Healthcare, #BR-1005-30) using a BIACORE® B4000 instrument (GE Healthcare) at pH 5.0 by using an amine coupling kit supplied by GE Healthcare. The sample and system buffer was PBS-T (10 mM phosphate buffered saline including 0.05% TWEEN® (polysorbate) 20) pH 7.4. The flow cells were set to 25° C.—and the sample block set to 12° C.—and primed twice with running buffer. The antibody was captured by injecting a ~10 μg/ml solution for 60 sec at a flow rate of 10 μl/min. Association was measured by injection of di huNKG2D ECD Fc avi (SEQ ID NO: 96) or di cyNKG2D ECD Fc avi (SEQ ID NO: 97) in various concentrations in solution for 180 s at a flow rate of 30 μl/min starting with 600 nM, 300 nM, 150 nM following 1:3 dilutions. The dissociation phase was monitored for up to 450 s and triggered by switching from the sample solution to running buffer. The surface was regenerated by 2×90 s washing with a glycine pH 2.1 solution at a flow rate of 30 μl/min and an additional stabilization period of 180 s. Bulk refractive index differences were corrected by subtracting the response obtained from an anti-human Fab surface. Blank injections were also subtracted (=double referencing). For calculation of $K_D$, $k_a$ and $k_d$ (see Table 8), the Langmuir 1:1 model in the BIACORE® 4000 Evaluation software 1.1 (GE Healthcare) or TraceDrawer 1.6.1 (Ridgeview Instruments AB) were used.

Affinities of these agonistic anti-NKG2D antibodies range from subnanomolar (clone 395) to micromolar (clone 014) affinities. All of them cross-react with cynomolgus NKG2D whereas for clone 296 there is a 187-fold difference between binding to human NKG2D (3.8 nM) vs. cynomolgus NKG2D (710 nM). Clone 395 exhibits the highest affinity to human and cynomolgus NKG2D of all antibodies, in the 3-digit picomolar range.

Example 10. Epitope Binning of Anti-NKG2D Antibodies (IgGs) on Human NKG2D by SPR The sensor surface of an SA chip (GE Healthcare, #BR-1005-31) was conditioned with three 1-minute injections of 1 M NaCl in 50 mM NaOH before the ligand was immobilized. Around 200-300 resonance units (RU) of mono huNKG2D ECD Fc kh avi (SEQ ID NOs 94 and 95) were coupled onto the sensorchip surface using a BIACORE® T200 instrument (GE Healthcare). An extra wash using 50% isopropanol in 1 M NaCl and 50 mM NaOH was performed after ligand injection. The sample and system buffer was PBS-T (10 mM phosphate buffered saline including 0.05% TWEEN® (polysorbate) 20) pH 7.4. The flow cells were set to 25° C., the sample block set to 12° C., and the sensorchip surface was primed with running buffer twice. The first and second antibody were injected by "dual" injection, each at a concentration of 200 nM for 180 s at a flow rate of 30 μl/min. Saturation of the immobilized antigen with the first antibody was essential. The dissociation phase was monitored for up to 120 s and triggered by switching from the sample solution to running buffer. The surface was regenerated by washing with a glycine pH 2.1 solution at a flow rate of 30 μl/min for 40 s and an additional stabilization period of 180 s. Bulk refractive index differences were corrected by subtracting the response obtained from the blank surface. Blank injections were also subtracted (=double referencing). Binding responses were analyzed by BIACORE® T200 Evaluation software 3.0 (GE Healthcare).

Figure 4:
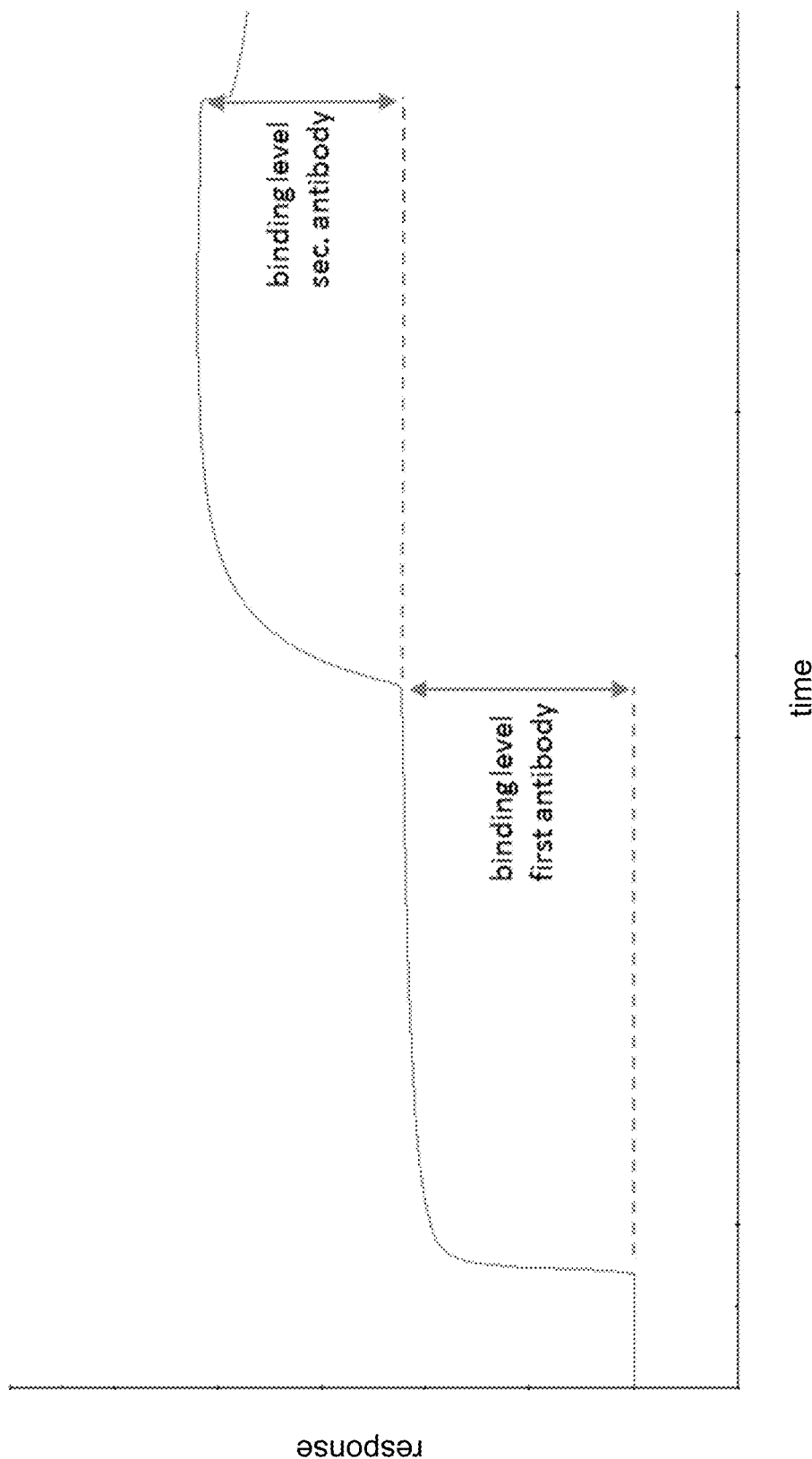
FIG. 4. Example of a SPR sensorgram showing two injections of antibodies binding to different epitopes.

The second antibody can only bind the antigen saturated by the first antibody if its epitope is not the same or does not overlap with that of the first antibody. An exemplary sensorgram is shown in FIG. 4. If the epitopes of both antibodies are identical or overlapping, complete or partial blocking will occur. Blocking was calculated as % binding of second antibody (Table 9) in relation to the binding level of the first antibody (value of binding level of first antibody was set to 100%).

TABLE 8

Kinetic rate constants and affinities to human and cynomolgus NKG2D.

| | di huNKG2D ECD Fc avi | | | di cyNKG2D ECD Fc avi | | |
|---|---|---|---|---|---|---|
| antibody | ka (1/Ms) | kd (1/s) | KD (M) | ka (1/Ms) | kd (1/s) | KD (M) |
| clone 13C6 | 3.4E+04 | 2.8E−04 | 8.2E−09 | 2.0E+04 | 9.2E−04 | 4.7E−08 |
| clone 018 | 4.3E+04 | 1.3E−03 | 2.9E−08 | 3.9E+04 | 8.0E−04 | 2.1E−08 |
| clone 001 | 5.2E+04 | 4.5E−04 | 8.5E−09 | 4.8E+04 | 2.1E−04 | 4.5E−09 |
| clone 5C5 | 2.2E+05* | 1.4E−02* | 6.3E−08* | 1.1E+05 | 9.1E−04 | 8.4E−09 |
| clone 230 | 4.3E+04 | 1.6E−04 | 3.6E−09 | 4.0E+04 | 1.0E−04 | 2.6E−09 |
| clone 395 | 5.7E+04 | 3.2E−05 | 5.5E−10 | 4.7E+04 | 3.6E−05 | 7.8E−10 |
| clone 013 | 8.4E+04 | 1.3E−03 | 1.6E−08 | 8.1E+04 | 6.4E−04 | 7.9E−09 |
| clone 296 | 2.1E+05 | 7.9E−04 | 3.8E−09 | 1.3E+05* | 9.0E−02* | 7.1E−07* |
| clone 320 | 8.3E+04 | 9.1E−03 | 1.1E−07 | 7.8E+04 | 4.7E−03 | 6.1E−08 |
| clone 014 | 1.1E+05* | 2.1E−01* | 2.0E−06* | 4.7E+04* | 6.1E−02* | 1.3E−06* |

*has been calculated by TraceDrawer 1.6.1 (Ridgeview Instruments AB)

TABLE 9

Different panels of antibodies tested against each other including respective self-blocking controls. Values represent percentage of binding of second antibody in relation to the binding response of the first antibody. Numbers in bold indicate simultaneous binding, underlined numbers indicate mutual blocking. Cut-off between simultaneous binding and blocking was defined at 30%.

| first antibody | second antibody | | | | | | | |
|---|---|---|---|---|---|---|---|---|
| | clone 018 | clone 13C6 | clone 5C5 | clone 230 | clone 013 | clone 320 | clone 001 | clone 296 |
| clone 018 | 0 | 0 | −5 | 3 | 81 | −3 | 4 | 2 |
| clone 13C6 | 2 | 0 | −4 | 4 | 57 | 0 | 5 | 3 |
| clone 5C5 | 50 | 101 | 0 | 56 | 121 | 75 | 56 | 32 |
| clone 230 | −1 | −1 | −5 | 0 | 83 | −4 | −1 | 0 |
| clone 013 | 79 | 70 | 49 | 89 | 0 | 3 | 83 | 66 |
| clone 320 | 6 | 9 | 16 | 8 | 7 | 0 | 8 | 8 |
| clone 001 | −1 | −2 | −6 | 3 | 80 | −1 | 0 | −2 |
| clone 296 | 15 | 13 | 8 | 21 | 97 | 14 | 20 | 0 |

| first antibody | second antibody | | | | | | | |
|---|---|---|---|---|---|---|---|---|
| | clone 13C6 | clone 5C5 | clone 013 | clone 320 | clone 306 | clone 002 | clone 132 | clone 366 |
| clone 13C6 | 0 | −7 | 46 | −5 | 3 | 0 | 25 | 66 |
| clone 5C5 | 92 | 0 | 106 | 62 | 48 | 43 | −13 | 123 |
| clone 013 | 74 | 53 | 0 | 4 | 85 | 54 | 33 | 10 |
| clone 320 | 13 | 11 | 4 | 0 | 10 | 6 | −27 | 51 |
| clone 306 | −1 | −3 | 77 | −5 | 0 | −2 | −12 | 90 |
| clone 002 | 4 | 1 | 33 | −3 | 5 | 0 | −8 | 15 |
| clone 132 | 178 | 36 | 113 | 56 | 72 | 62 | 0 | 141 |
| clone 366 | 71 | 46 | −5 | 24 | 89 | 5 | 25 | 0 |

| first antibody | second antibody | | | | | | | |
|---|---|---|---|---|---|---|---|---|
| | clone 13C6 | clone 5C5 | clone 013 | clone 320 | clone 001 | clone 296 | clone 014 | clone 395 |
| clone 13C6 | 0 | −9 | 48 | −6 | −1 | −4 | −15 | 3 |
| clone 5C5 | 90 | 0 | 100 | 58 | 44 | 24 | 77 | 52 |
| clone 013 | 72 | 51 | 0 | 4 | 79 | 59 | 63 | 83 |
| clone 320 | 21 | 16 | 10 | 0 | 14 | 8 | 46 | 20 |
| clone 001 | 3 | −1 | 78 | −2 | 0 | 1 | 52 | 8 |
| clone 296 | 20 | 10 | 93 | 13 | 20 | 0 | 49 | 28 |
| clone 014 | 85 | 14 | 79 | 71 | 63 | 62 | 0 | 72 |
| clone 395 | −5 | −12 | 66 | −4 | −5 | −3 | 53 | 0 |

TABLE 9C

| first antibody | second antibody | | | | | | | |
|---|---|---|---|---|---|---|---|---|
| | clone 13C6 | clone 5C5 | clone 013 | clone 320 | clone 001 | clone 296 | clone 014 | clone 395 |
| clone 13C6 | 0 | −9 | 48 | −6 | −1 | −4 | −15 | 3 |
| clone 5C5 | 90 | 0 | 100 | 58 | 44 | 24 | 77 | 52 |
| clone 013 | 72 | 51 | 0 | 4 | 79 | 59 | 63 | 83 |
| clone 320 | 21 | 16 | 10 | 0 | 14 | 8 | 46 | 20 |
| clone 001 | 3 | −1 | 78 | −2 | 0 | 1 | 52 | 8 |
| clone 296 | 20 | 10 | 93 | 13 | 20 | 0 | 49 | 28 |
| clone 014 | 85 | 14 | 79 | 71 | 63 | 62 | 0 | 72 |
| clone 395 | −5 | −12 | 66 | −4 | −5 | −3 | 53 | 0 |

Three different epitope bins could be established by this SPR-based competition assay (Table 10). The majority of antibodies fall into epitope bin 1 with two antibodies representing epitope bin 2 (clones 5C5 and 132) and three antibodies representing epitope bin 3 (clones 013, 014, and 366).

TABLE 10

Epitope bins of anti-NKG2D antibodies.

| bin 1 | bin 2 | bin 3 |
|---|---|---|
| clone 13C6 | clone 5C5 | clone 013 |
| clone 018 | clone 132 | clone 014 |
| clone 230 | | clone 366 |
| clone 296 | | |
| clone 001 | | |
| clone 306 | | |
| clone 395 | | |
| clone 002 | | |
| clone 320 | | |

The anti-NKG2D antibody clones 5C5, 320, 230, 013, 296 and 395 were selected for further analysis.

Example 11. Specific Binding of Anti-NKG2D Antibodies (IgGs) to Human NKG2D on Immune Cells Binding to human NKG2D was confirmed for selected antibody clones using NKG2D positive immune cells, namely NK cells, γδ T cells and CD8 T cells. Binding of the antibodies to the human NKG2D positive NK cell line NK92, to human CD8 T cells, expanded human NK cells and expanded human γδ T cells was assessed by flow cytometry. A non-binding control was included in the experiment (untargeted IgG (VH and VL sequences of SEQ ID NOs 81 and 82) with L234A L235A P329G ("PGLALA") mutation in Fc region).

Methods

Binding to the Human NK Cell Line NK92

Viability of NK92 cells was checked and cells were re-suspended and adjusted to a density of 1 mio cells/ml. 100 µl of this cell suspension (containing 0.1 mio cells) were seeded into a 96 well round bottom plate. The plate was centrifuged for 4 min at 400×g and the supernatant was removed. Then 40 µl of the diluted antibodies or FACS buffer were added to the cells and incubated for 30 min at 4° C. After the incubation the cells were washed twice with 150 µl FACS buffer per well. Then 20 µl of the diluted APC anti-human Fc specific secondary antibody (Jackson ImmunoResearch, #109-116-170) was added to the cells. The cells were incubated for an additional 30 min at 4° C. To remove unbound antibody, the cells were washed again twice with 150 µl per well FACS buffer. To fix the cells 100 µl of FACS buffer containing 1% PFA were added to the wells. Before measuring the cells were re-suspended in 150 µl FACS buffer. The fluorescence was measured using a BD CantoII flow cytometer.

Binding to CD8 T Cells

Viability of freshly isolated PBMCs was checked and cells were adjusted to a density of 1 mio cells/ml in FACS buffer. 100 µl of the PBMCs (containing 0.1 mio cells) were seeded into a 96 well round bottom plate. The plate was centrifuged for 4 min at 400×g and the supernatant was removed. Then 0.5 µl FC BLOCK™ (BD Bioscience) in 20 µl total volume per well were added and the plate was incubated for 30 min at 4° C. Supernatant was removed and then 40 µl of the diluted NKG2D antibodies were added to the cells and incubated for additional 30 min at 4° C. After the incubation the cells were washed twice with 150 µl FACS buffer per well. Then 20 µl of the diluted FITC anti-human Fc specific secondary antibody (Jackson ImmunoResearch, #109-096-098) together with CD8 APC (Clone SK1, BioLegend) and CD3 PE/Cy7 (clone UCHT1, BioLegend) was added to the cells to detect the NKG2D antibodies and identify CD8 T cells as CD8 and CD3 positive cells within PBMCs. The cells were incubated for an additional 30 min at 4° C. To remove unbound antibody, the cells were washed again twice with 150 µl per well FACS buffer. To fix the cells 100 µl of FACS buffer containing 1% PFA were added to the wells. Before measuring the cells were re-suspended in 150 µl FACS buffer. The fluorescence was measured using a BD CantoII flow cytometer.

Binding to Expanded NK Cells

Viability of expanded NK cells was checked and cells were adjusted to a density of 1 mio cells/ml in FACS buffer. 100 µl of these cell suspensions (containing 0.1 mio cells) were seeded into a 96 well round bottom plate. The plate was centrifuged for 4 min at 400×g and the supernatant was removed. Then 0.5 µl FC BLOCK™ (BD Bioscience) in 20 µl total volume per well were added and the plate was incubated for 30 min at 4° C. Supernatant was removed and then 40 µl of the diluted NKG2D antibodies were added to the cells and incubated for additional 30 min at 4° C. After the incubation the cells were washed twice with 150 µl FACS buffer per well. Then 20 µl of the diluted FITC anti-human Fc specific secondary antibody (Jackson ImmunoResearch, #109-096-098) was added to the cells. The cells were incubated for an additional 30 min at 4° C. To remove unbound antibody the cells were washed again twice with 150 µl per well FACS buffer. To fix the cells 100 µl of FACS buffer containing 1% PFA were added to the wells. Before measuring the cells were re-suspended in 150 µl FACS buffer. The fluorescence was measured using a BD CantoII flow cytometer.

Binding to Expanded γδ T Cells

Viability of expanded γδ T cells was checked and cells were adjusted to a density of 1 mio cells/ml in FACS buffer. 100 µl of these cell suspensions (containing 0.1 mio cells) were seeded into a 96 well round bottom plate. The plate was centrifuged for 4 min at 400×g and the supernatant was removed. Then 40 µl of the diluted NKG2D antibodies were added to the cells and incubated for additional 30 min at 4° C. After the incubation the cells were washed twice with 150 µl FACS buffer per well. Then 20 µl of the diluted secondary FITC anti-human Fc specific secondary antibody (Jackson ImmunoResearch, #109-096-098) was added to the cells. The cells were incubated for an additional 30 min at 4° C. To remove unbound antibody, the cells were washed again twice with 150 µl per well FACS buffer. To fix the cells 100 µl of FACS buffer containing 1% PFA were added to the wells. Before measuring the cells were re-suspended in 150 µl FACS buffer. The fluorescence was measured using a BD CantoII flow cytometer.

Generation of Expanded Human NK Cells

NK cells were isolated from PBMCs using the NK Cell Isolation Kit (Miltenyi Biotec, #130-092-657). For this, non-NK cells were indirectly magnetically labeled followed by magnetic separation using a MACS Separator. Unlabeled NK cells were then passing through a MACS column, while non-NK cells were retained in the column.

After cell isolation, NK cells were then cultivated using the NK Cell Activation/Expansion Kit (Miltenyi Biotec, #130-094-483). When starting with the NK expansion culture, anti-Biotin Bead Particles were loaded with biotinylated antibodies against CD335 and CD2. These particles were then added once to the cell culture in a bead-to-cell ratio of 1:2. Cells were put in a 24-well cell culture plate at a cell density of 1 million cells per ml. NK cells were incubated for 6 days and inspected daily. Fresh culture medium was added if necessary. At day 6, cells were re-suspended and counted. NK cells were then kept at 1-1.5 million cells per ml for further culture. The expansion medium for NK cells contained NK MACS medium (NK MACS Basal medium (Miltenyi Biote, #130-107-879,) with 2% NK MACS supplement (#130-107-210), 5% human AB serum and 500 IU/ml IL2 (PROLEUKIN® (aldesleukin), Novartis).

Generation of Expanded Human γδ T Cells

The protocol used to generate expanded human γδ T cells was adapted from Rincon-Orozco et al. (2005) J Immunol 175, 2144-2151 (incorporated herein by reference). Briefly, freshly isolated PBMCs were re-suspended at 1 mio cells/ml in γδ T cell expansion medium (RPMI 1640, 10% FBS, 1% GLUTAMAX™, 100 mM sodium pyruvate, 10 mM MEM NEAA, 100 µM β-mercaptoethanol, 1 µg/ml IPP (Sigma-Aldrich) and 100 U/ml IL-2 (PROLEUKIN® (aldesleukin), Novartis) and plated in a 24-well cell culture plate. Half of the medium was exchanged at day 3 and 7. At day 10 after isolation, γδ T cells were isolated using the human TCRγδ T cell isolation kit (Miltenyi Biotec, #130-092-892). γδ T cells were kept in 24 well cell culture plates at 1-2 mio cells/ml in γδ T cell expansion medium to further expand them.

Results

Figure 5:
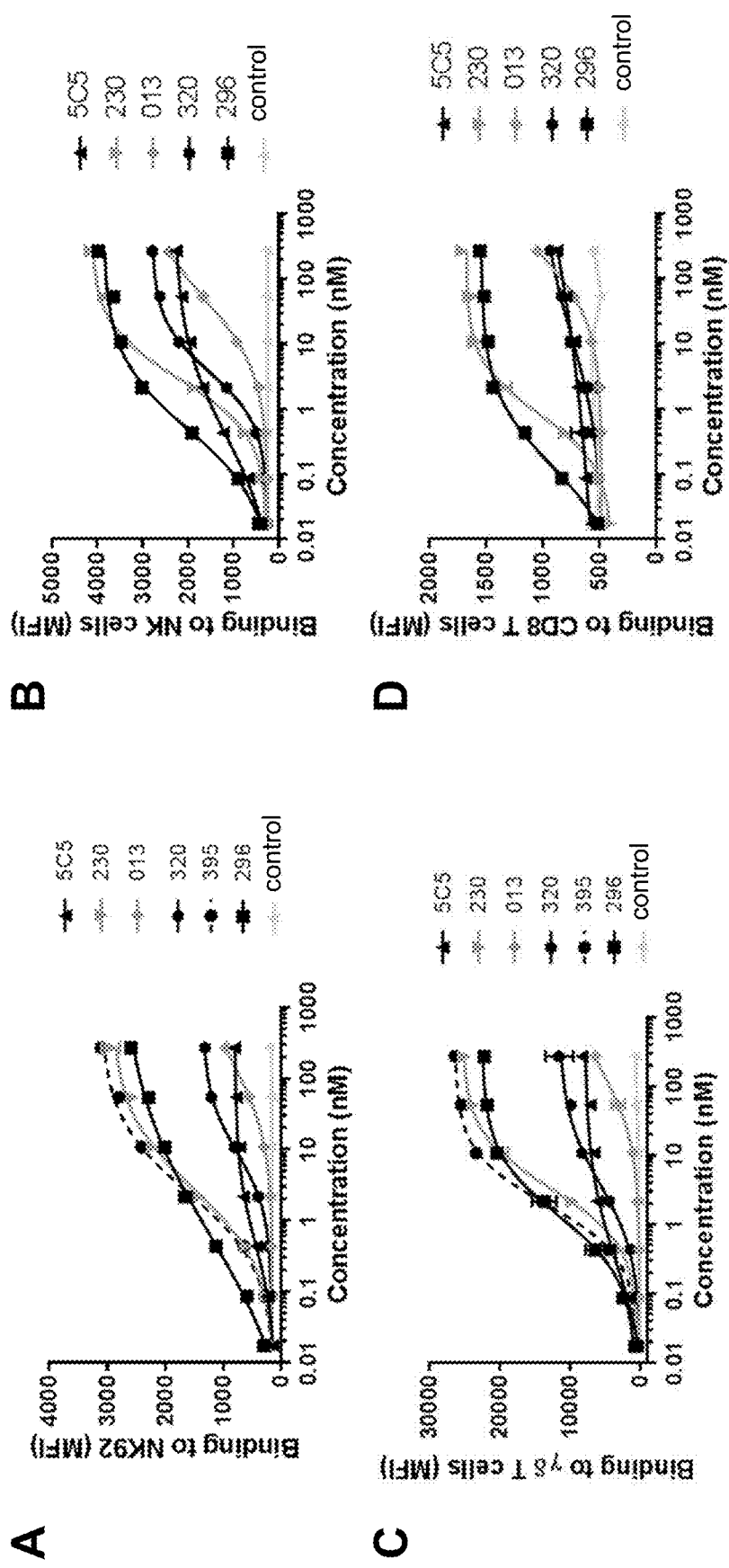
FIG. 5. Binding of anti-NKG2D antibodies compared to the non-binding control antibody to (A) the human NK cell line NK92, (B) expanded human NK cells, (C) expanded human γδ T cells, and (D) freshly isolated human CD8 T cells as measured by flow cytometry.

The selected antibodies, 5C5, 320, 230, 013, 296 and 395, bound in a concentration dependent manner to the tested immune cells (FIG. 5). The expression level of NKG2D is different on each immune cell subset but the binding strength indicated by $EC_{50}$ values (Table 11) was comparable for each clone on all NKG2D positive immune cells. Interestingly the NKG2D antibodies clustered into two groups regarding their binding behavior; group A had a higher overall binding and group B had a lower (about half compared to A) binding to NKG2D (FIG. 5). This pattern was observed on all tested NKG2D positive immune cells (NK cells, CD8 T cells and γδ T cells) and indicated differences in the binding mode between the two groups of agonistic NKG2D antibodies.

TABLE 11

$EC_{50}$ values binding of NKG2D antibodies to NKG2D positive immune cells

| EC50 (nM) | NK92 | NK cells | γδ T cells | CD8 T cells |
|---|---|---|---|---|
| 5C5 | 0.47 | 0.40 | 0.28 | |
| | (0.30 to 0.73) | (0.27 to 0.59) | (0.11 to 0.73) | |
| 230 | 2.72 | 2.87 | 3.31 | 0.83 |
| | (2.15 to 3.43) | (2.65 to 3.11) | (2.97 to 3.69) | (0.67 to 1.04) |
| 013 | 122.2 | 48.8 | 132.9 | 264 |
| | (66.47 to 224.6) | (41.17 to 57.85) | (20.30 to 869.9) | (8.42 to 8276) |
| 320 | 8.97 | 3.68 | 3.84 | 13.05 |
| | (7.95 to 10.11) | (3.49 to 3.88) | (2.36 to 6.26) | (2.38 to 71.53) |
| 296 | 0.63 | 0.48 | 1.32 | 0.13 |
| | (0.34 to 1.15) | (0.39 to 0.61) | (1.03 to 1.69) | (0.058 to 0.31) |
| 395 | 2.49 | Not measured | 1.94 | Not measured |
| | (2.16 to 2.86) | | (1.81 to 2.08) | |

The anti-NKG2D antibodies bind specifically to immune cells that are described to express NKG2D. Most antibodies have low $EC_{50}$ values (0.28-13.5 nM) indicating a high affinity binding to NKG2D which is comparable for the different tested immune cell subsets being NK cells, γδ T cells and CD8 T cells.

Example 12. Activation of NKG2D-Positive Immune Cells with Crosslinked Anti-NKG2D Antibodies (IgGs)

Next, the agonistic activity of the human NKG2D $IgG_1$ antibodies was confirmed.

Activity of Anti-NKG2D Antibodies on NK92 Cells

We tested the activation of NKG2D on the human NK cell line NK92 upon crosslinking by coating the antibodies at the indicated concentrations to protein A beads. Protein A beads presenting the anti-NKG2D antibodies were co-incubated with NK92 cells for 24 h. Subsequently IFNγ release of NK92 cells into the supernatant was determined by cytometric bead array (CBA), as a marker for activation of NK92 cells induced by NKG2D activation.

All anti-NKG2D antibodies were tested for their agonistic activity and subsequently the best agonistic clones were selected for further characterization.

Figure 6:
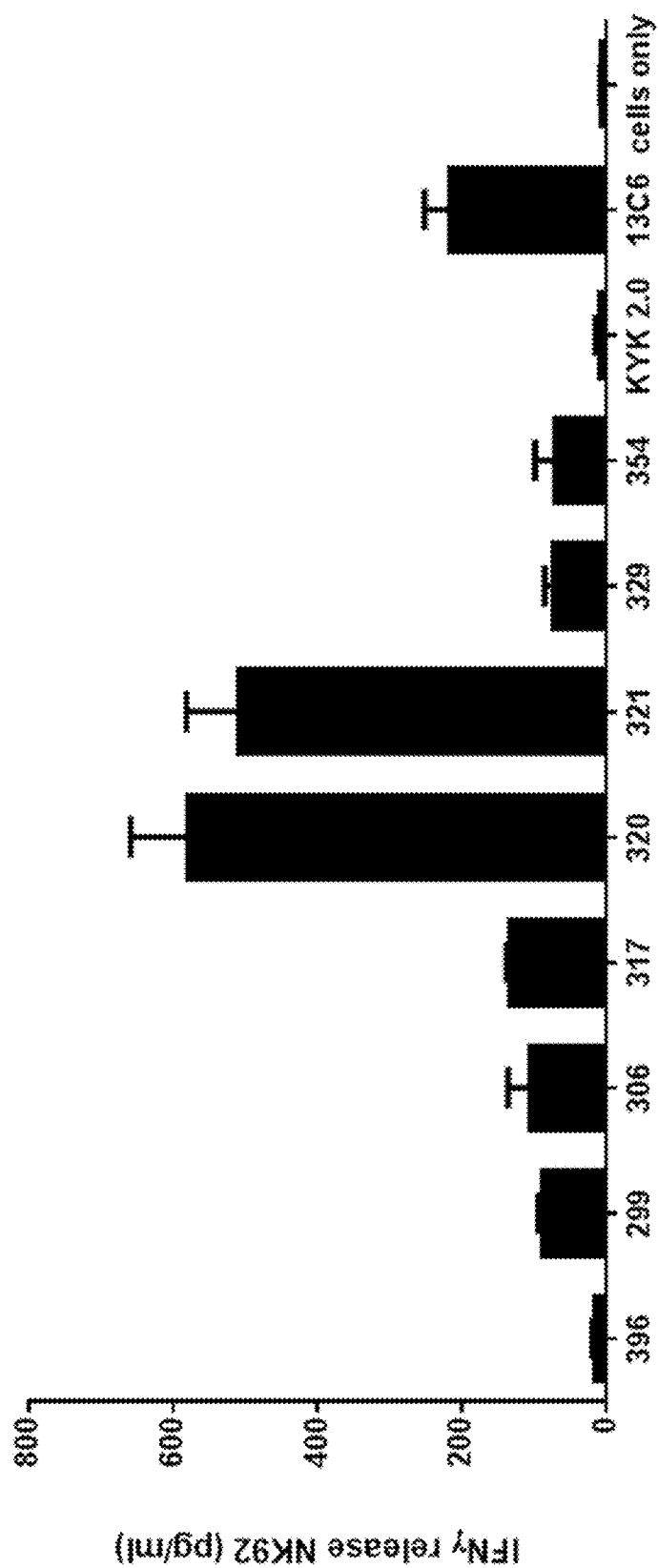
FIG. 6. Activation of NKG2D-positive immune cells with anti-NKG2D antibodies. The human NK cell line NK92 was co-cultured with anti-NKG2D antibodies (IgG1) captured on protein A beads. Activation of NK cells was determined by measuring INFγ release into the supernatant using CBA technology.

In FIG. 6 an example of a series of anti-NKG2D antibodies was tested for IFNγ release and their activity was compared to the benchmark agonistic anti-NKG2D antibody KYK-2.0 (Kwong et al. (2008) J Mol Biol 384, 1143-1156) which had only minor activity to induce IFNγ release of NK92 cells.

The best agonistic anti-NKG2D antibodies were selected for retesting of their functional activity in more detail.

Figure 7:
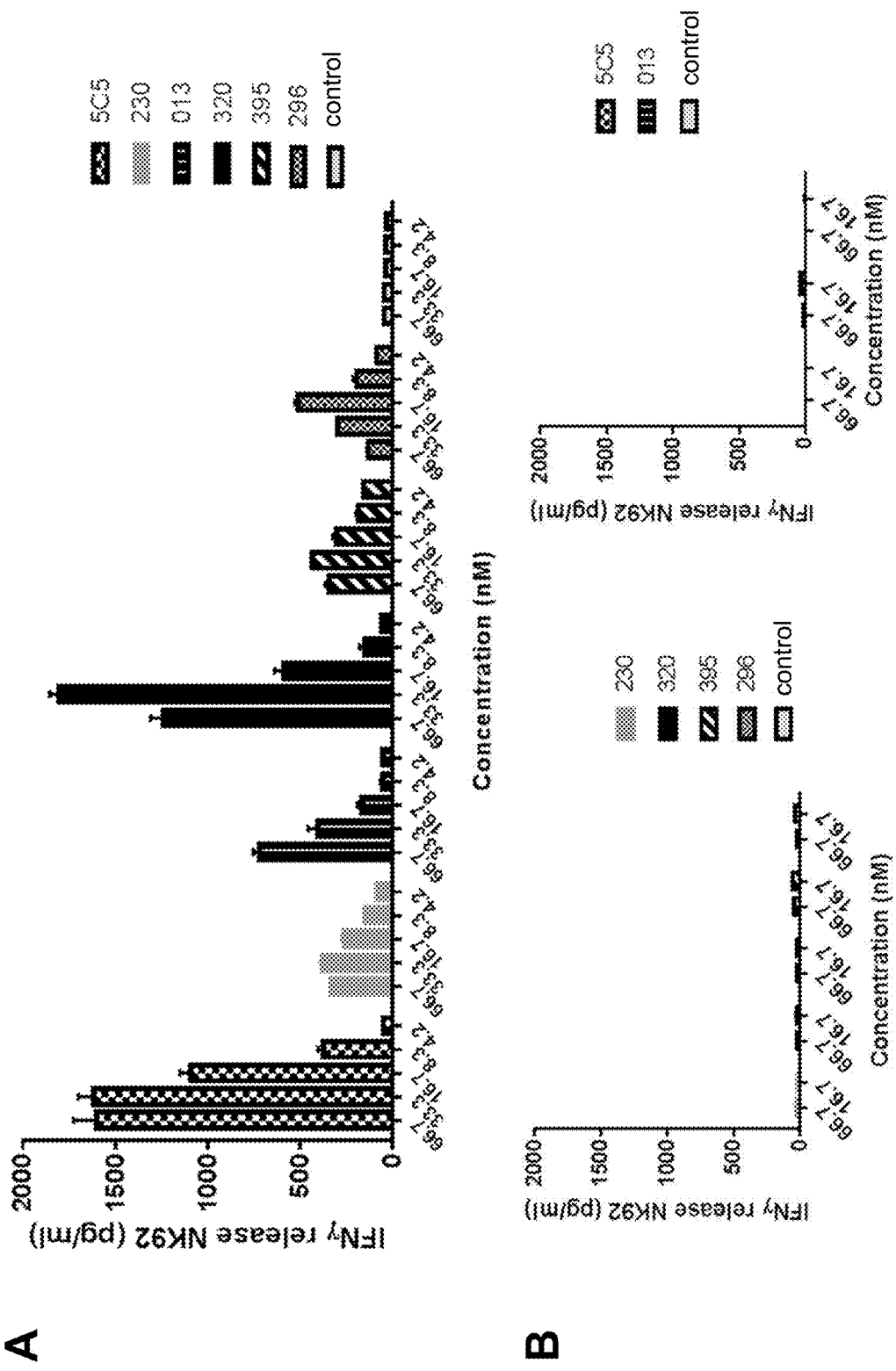
FIG. 7. Activation of NKG2D-positive immune cells with anti-NKG2D antibodies. The human NK cell line NK92 was co-cultured with anti-NKG2D antibodies (IgG1) captured on protein A beads (A) or in solution (B). Activation of NK cells was determined by measuring INFγ release into the supernatant using CBA technology.

The selected anti-NKG2D antibodies induced IFNγ release of NK92 cells in a concentration dependent manner upon crosslinking with differences in potency (FIG. 7A). Activation of NKG2D by the agonistic anti-NKG2D antibodies could only be induced by the crosslinked antibodies; anti-NKG2D antibodies in solution had no agonistic potential to induce IFNγ release in this setting (FIG. 7B). This indicates that our agonistic anti-NKG2D antibodies will not induce immune cell activation in the absence of any crosslinker and therefore no systemic activation is to be expected with these antibodies.

Activity of Anti-NKG2D Antibodies on Primary Human NK Cells

Figure 8:
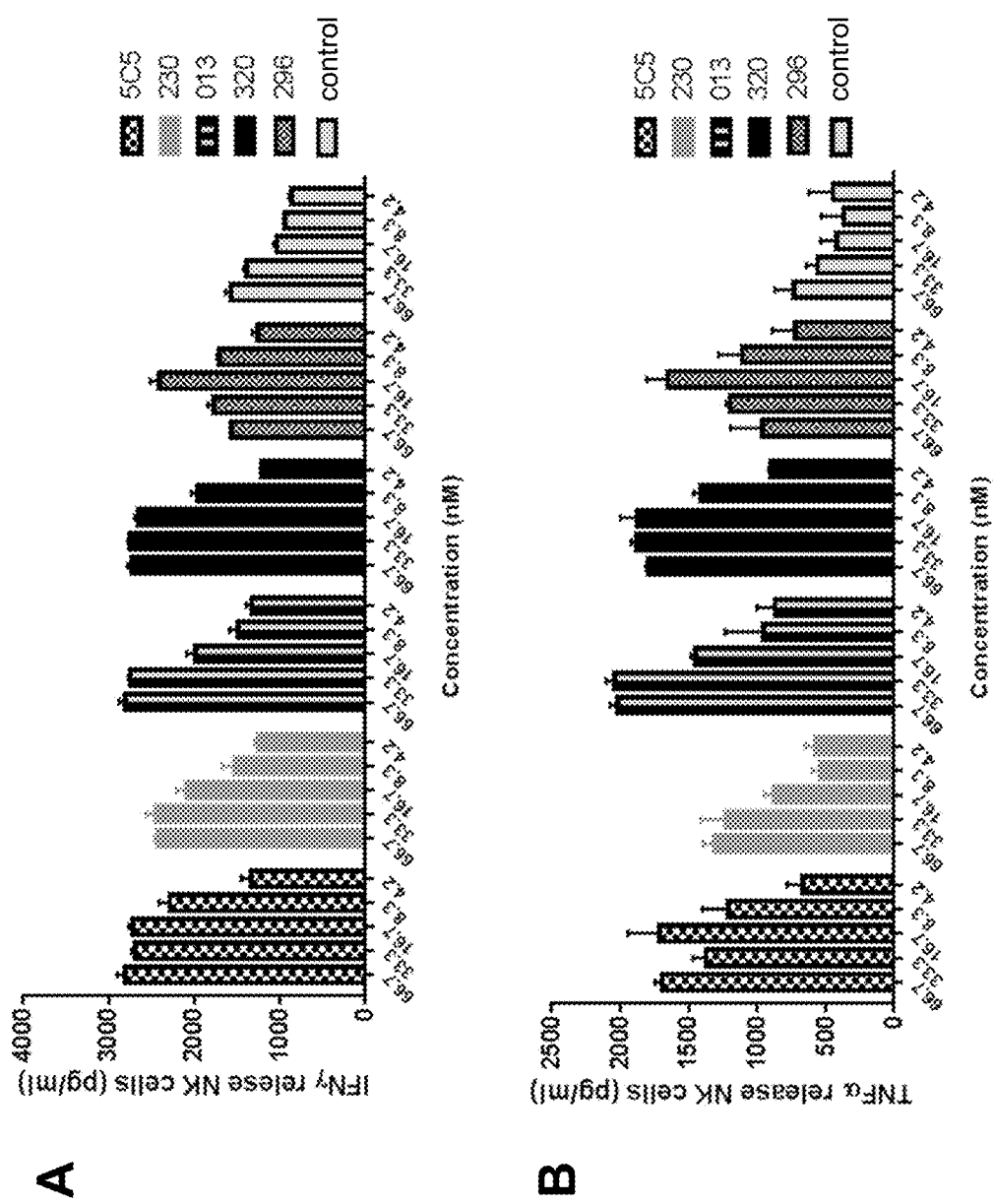
FIG. 8. Activation of NKG2D-positive immune cells with anti-NKG2D antibodies. Human primary expanded NK cells were co-cultured with anti-NKG2D antibodies (IgG1) captured on protein A beads. Activation of NK cells was determined by measuring INFγ and TNFα release into the supernatant by CBA technology.

Anti-NKG2D antibodies that showed agonistic activity on the human NK92 cell line were subsequently tested on expanded primary human NK cells as a more physiological cell population. The same setup was used to assess functional activity of the antibodies on this cell type. As seen on NK92 cells, all tested anti-NKG2D antibodies induced activation of human NK cells compared to the non-binding isotype control $IgG_1$ indicated by IFNγ and TNFα release into the supernatant (FIG. 8). The non-binding isotype control $IgG_1$ (see above) induced some background activity due to the ability of the $IgG_1$ antibodies to bind to and crosslink Fc receptors on NK cells. This means that the measured effect of the agonistic NKG2D antibodies in this setup was a combination of activating Fc receptors and NKG2D which was superior compared to activation of Fc receptors alone (seen with the control).

Activity of Anti-NKG2D Antibodies on Human γδ T Cells

Figure 9:
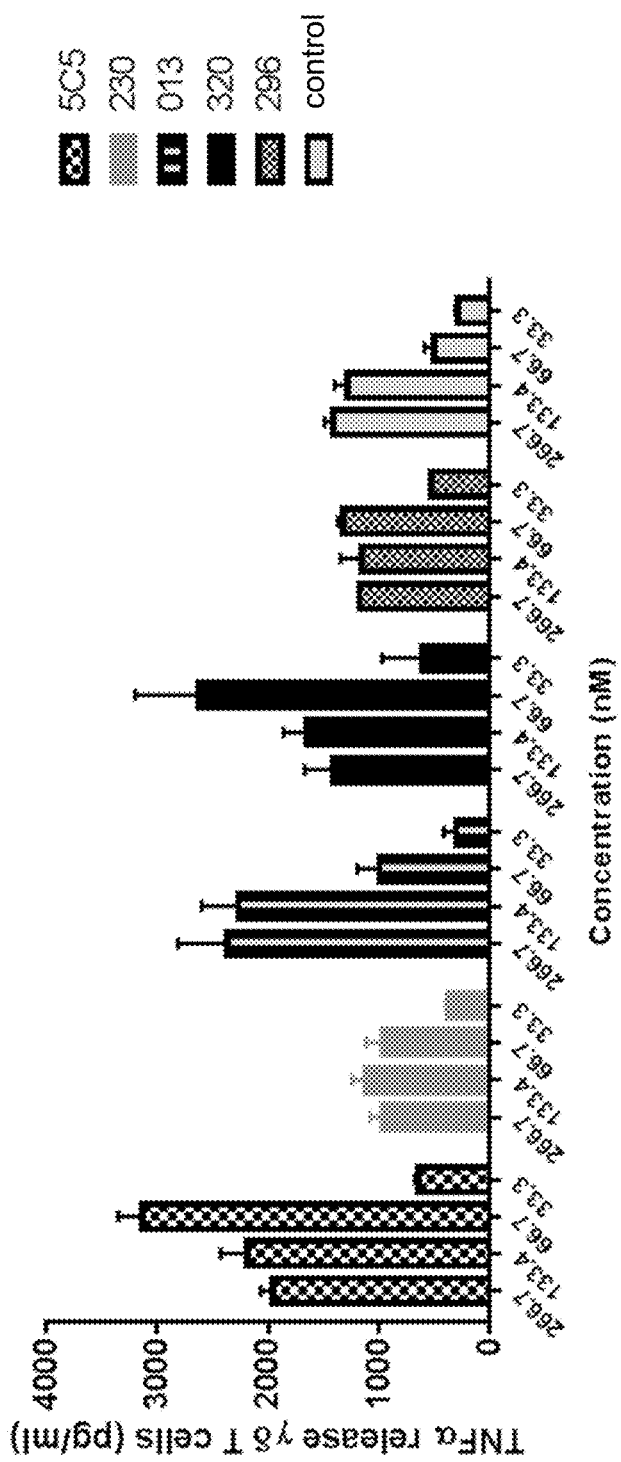
FIG. 9. Activation of NKG2D-positive immune cells with anti-NKG2D antibodies. Human primary expanded γδ T cells were co-cultured with anti-NKG2D antibodies (IgG$_1$) captured on protein A beads. Activation of NK cells was determined by measuring TNFα release into the supernatant by CBA technology.

After having tested the agonistic anti-NKG2D antibodies on NK cells, it was also tested if they could activate γδ T cells. γδ T cells are the second cell population that is reported to directly respond upon NKG2D triggering. To get sufficient amounts of γδ T cells, freshly isolated PBMCs were activated with IPP (isopentenyl pyrophosphate) and IL-2 to preferentially expand γδ T cells. Expanded γδ T cells were isolated and subsequently co-cultured with the agonistic NKG2D IgG1 antibodies bound to protein A beads. Again, the non-binding isotype control (see above) was included in the experiment. After 24 h the supernatant was collected and release of TNFα into the supernatant was determined by CBA. The tested NKG2D antibodies induced TNFα release of γδ T cells into the supernatant indicating activation of NKG2D by the antibodies (FIG. 9) as seen for the other tested cell subsets.

Methods

Protein A Dynabeads (Invitrogen, #10001D) were resuspended and 10 µl of the bead solution was diluted within 5 ml PBS. Subsequently, 50 µl of the diluted bead solution was transferred into each well of a 96 well round bottom plate which corresponded to about 200'000 beads per well. Calculation was done by assuming that 1 µl of the stock bead solution contains about 2 million beads. The plate was centrifuged at 400×g for 3 min and the supernatant was removed. Then 50 µl of the anti-NKG2D antibodies diluted in PBS were added to the beads and incubated for 1 h in the fridge to allow binding of the antibodies to the beads.

After incubation the plate was centrifuged again at 400×g for 3 min and washed twice with 150 µl PBS per well to remove antibodies that were not captured by the protein A beads. Effector cells which could be NK92, expanded human NK cells or expanded human γδ T cells were counted and viability was checked. NK92 and expanded NK cells were re-suspended in RPMI 1640 containing 10% FCS, 1% glutamine and 10 ng/ml PROLEUKIN® (aldesleukin), and γδ T cells were re-suspended in RPMI 1640 containing 10% FBS, 1% GLUTAMAX™ and 100 U/ml IL-2 (PRO-LEUKIN® (aldesleukin), Novartis). 100 µl of the cell suspension with a concentration of 1 mio cells per ml were seeded in each well of a 96 well round bottom plate containing the protein A beads and incubated for 24 h at 37° C.

After 24 h of incubation the supernatant containing released cytokines was harvested and either stored at −20° C. or directly used for CBA (BD Bioscience) analysis. Depending of the effector cells different cytokines were analyzed. CBA analysis was performed according to manufacturer's instructions but instead of 50 µl bead and sample volume only 25 µl bead and sample volume were used and all other reagent amounts were adapted accordingly. The analysis was performed using a BD FACS CantoII flow cytometer.

Example 13. Co-Stimulation of CD8 T Cell Clones with Crosslinked Anti-NKG2D Antibodies NLV-specific CD8 T cell clones and MART1-specific CD8 T cell clones were used to assess the co-stimulatory potential of the anti-NKG2D antibodies. The used CD8 T cell clones are NKG2D positive. To address the co-stimulatory potential of the anti-NKG2D antibodies (with a CD3 antibody providing the primary stimulation ("signal 1"), 96 well plates were coated with anti-human antibody to immobilize the anti-NKG2D antibodies and with anti-mouse antibody to capture the CD3 antibody. Subsequently, the CD8 T cell were added to the plates and incubated for 24 h. After stimulation, the CD8 T cell clones were harvested and analyzed by measuring CD25 upregulation for activation. In addition, the same experiment was performed with NLV-specific CD8 T cell clones in the absence of CD3 antibody to assess the potential of the anti-NKG2D antibodies to directly activate CD8 T cell in the absence of signal 1. Again, the non-binding isotype control (see above) was included in the experiments.

In more detail, to test co-stimulation of the CD8 T cell clones with the anti-NKG2D antibodies, a 96 well round bottom plate was coated with 2 µg/ml anti-human IgG (Jackson ImmunoResearch, #109-006-098) and 2 µg/ml anti-mouse IgG (Jackson ImmunoResearch, #115-005-071) in 50 µl PBS per well overnight at 4° C. On the next day, the plate was washed three times with 200 µl PBS containing 1% BSA. Then 200 µl of PBS containing 1% BSA was added to each well and incubated for 90 min at 37° C. to block free plastic surface with BSA. After removing the supernatant, 0.25 µg/ml in 50 µl per well of the CD3 antibody (BioLegend, #317304) and the respective anti-NKG2D human IgG1 antibodies or the control were added to each well. The plate was incubated for 90 min at 37° C. Afterwards the plate was washed three times with 200 µl per well of PBS containing 1% BSA and stored in the fridge until 100'000 cells of the CD8 T cell clones were added in the evening. The cells were incubated overnight at 37° C. On the next day the CD8 T cell clones were harvested, washed twice with FACS buffer and stained with CD8 FITC (clone SK-1, BioLegend), CD25 PE (clone M-A251, BioLegend) and CD69 BV421 or CD69 APC (clone FN50, BioLegend) for 30 min at 4° C. To remove unbound antibody, the cells were washed again twice with 150 µl per well FACS buffer. To fix the cells, 100 µl of FACS buffer containing 1% PFA were added to the wells. Before measuring, the cells were re-suspended in 150 µl FACS buffer. The fluorescence was measured using a BD CantoII or FORTESSA™ flow cytometer.

Figure 10:
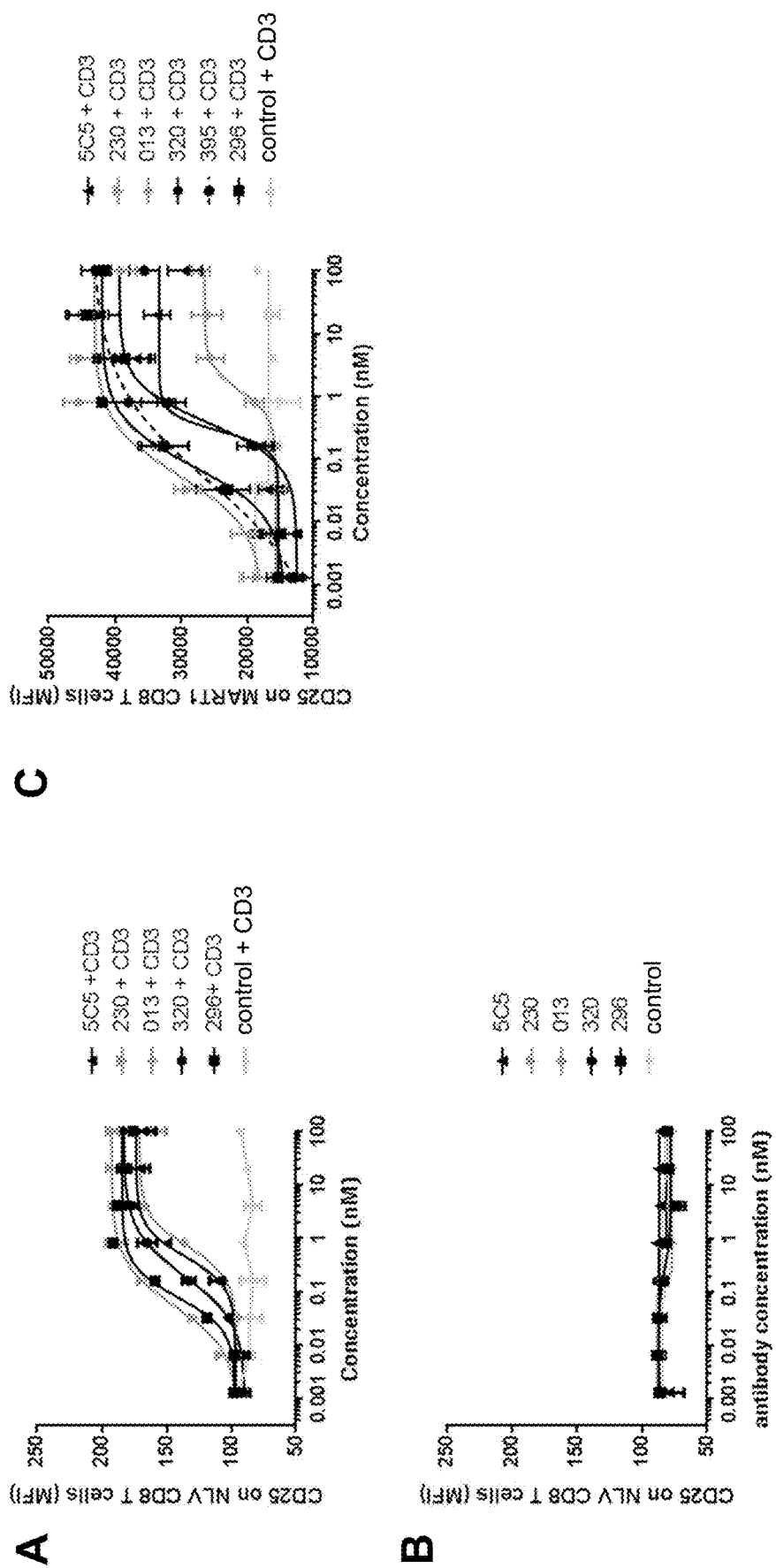
FIG. 10. Co-stimulation of CD8 T cell clones with anti-NKG2D antibodies. NLV-specific (A and B) and MART1-specific (C) CD8 T cell clones were cultured in plates with coated anti-NKG2D antibodies (IgG$_1$) in combination with a fixed concentration of CD3 antibody (A and C) or in the absence of CD3 antibody (B). Upregulation of CD25 as determined by flow cytometry was used as marker for activation of the CD8 T cell clones.

The results are shown in FIG. 10. We could confirm that our agonistic NKG2D antibodies have exclusively co-stimulatory potential on CD8 T cells and depend on "signal 1", here delivered by a CD3 antibody that induced activation of CD8 T cells.

Example 14. Humanization of Agonistic Anti-NKG2D Antibody 395

The agonistic anti-NKG2D antibody 395 was obtained by immunization of transgenic rabbits. While the VL domain was already human, the VH domain was of rabbit sequence and had to be humanized. More precisely, the VL domain is a human germline IGKV1D-39 #01 with 3 amino acids matured in CDRL1 (S28D, S31G, and Y32A) and 3 in CDRL3 (S91A, Y92N, and T94F). No change was made in CDRL2. In addition, two somatic mutations are observed in FR2L and FR3L: K45N and F71Y, respectively. This human variable domain was not modified. The variable heavy chain of antibody 395 is a rabbit VH matured from the germline RABBIT_IGHV1S7 #01 with several somatic mutations in the framework regions and the CDRs: 8 in FR H1, 4 in HCDR1, none in FR H2, 4 in HCDR2, and 6 in FR H3. In addition, the immunoglobulin VH domain of clone 395 contains 3 additional cysteines at Kabat position 21, 50, and 79. According to its germline, positions 21 and 79 form a disulfide bridge. The cysteine in position 50 has no partner as the partner C35 of the germline has been matured to a threonine.

The humanization eliminated the additional disulfide bridge as no human germline presents such a feature. For developability reasons, C50 was mutated to its close analog, a serine, to avoid influencing too much the binding of clone 395 to its target NKG2D. None of the human germlines selected as acceptor frameworks has a serine in Kabat position 50.

hVH5_51, hVH3_23, and hVH4_59 were selected as acceptor frameworks. They represent frequently used human germlines with a high degree of sequence similarity to the VH-domain of antibody 395 and no or only small predicted Abangle deviations (representing the change in orientation of the respective humanized variable heavy chain domains compared to the original rabbit variable heavy chain both paired with the unmodified human light chain variable domain). In addition, the CDRs of the VH-domain of antibody 395 were grafted onto the VH framework of trastuzumab, a framework based on VH3_23 and well characterized as a stable antibody.

Figure 11:
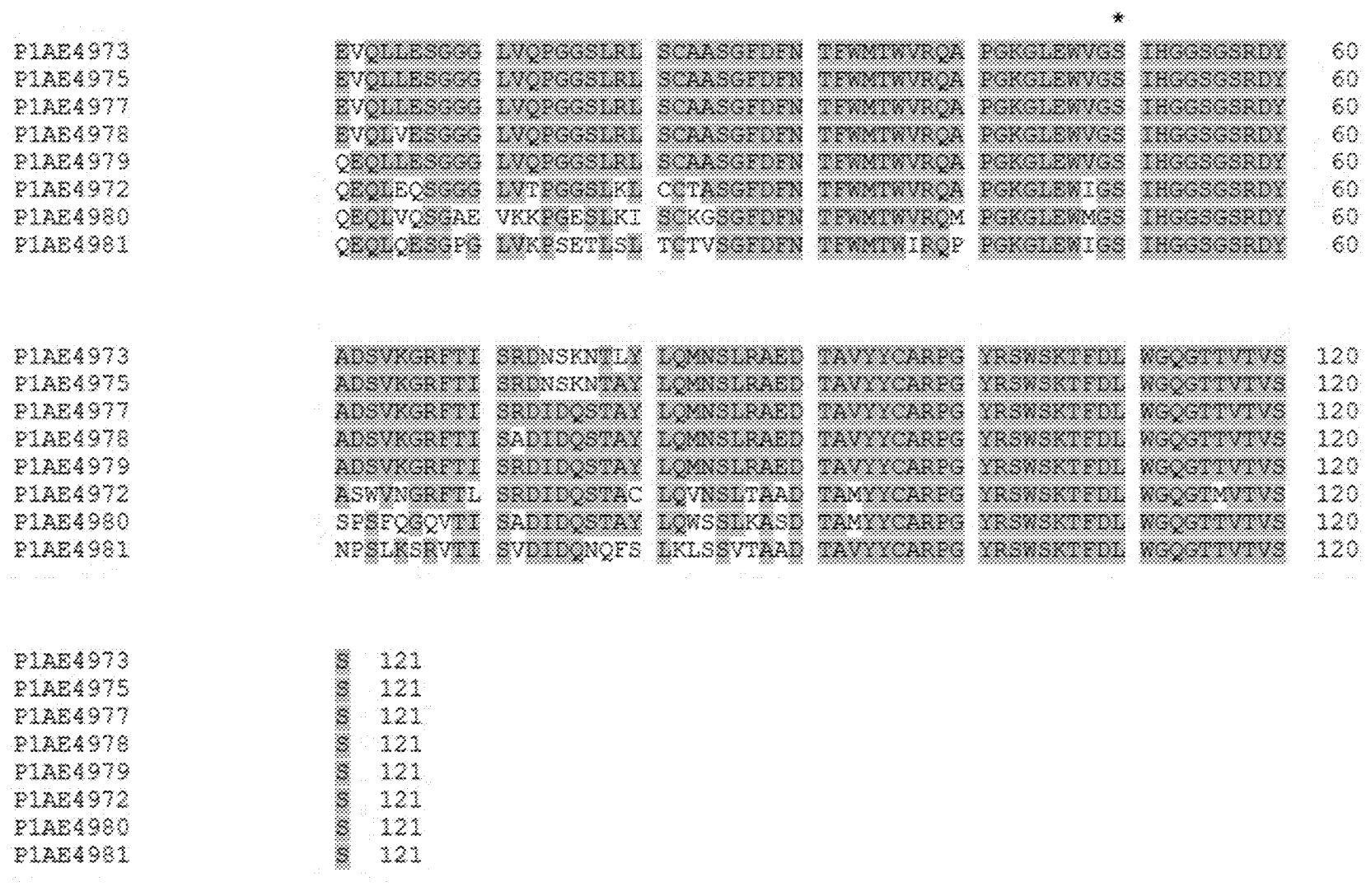

The humanized sequences shown in FIG. 11 were selected to be expressed and tested for their binding and function. The sequences are also given in SEQ ID NOs 107, 108, 109, 110, 111, 112 and 113 (sequences P1AE4973, P1AE4975, P1AE4977, P1AE4978, P1AE4979, P1AE4980 and P1AE4981, respectively). Sequence P1AE4972 (SEQ ID NO: 106) corresponds to the parental VH sequence of antibody 395 (SEQ ID NO: 79) with a C50S mutation.

Some forward-mutations were considered at the end of HCDR2 as these residues are supposed to be far away from the binding site to the antigen NKG2D. On the other hand, some back-mutations were also considered in order to stick more closely to the original amino acids of clone 395. A prominent example is the S49G back-mutation on hVH3_23. In some variants, the N-terminal QE motif is also considered as those amino acids are located in the back of the HCDR3. The "CDR4" loop is characterized by the sequence IDQS that has been reintroduced in some variants as this loop is sometimes in contact with the antigen as the fourth CDR of the variable heavy domain.

The humanized VH-domain variants of antibody 395 and its original human VL-domain have been used to generate bispecific NKG2D×CEA antibodies which were then tested for binding and functionality (see Examples 17 and 18).

Example 15. Generation of Bispecific NKG2D Antibodies

Bispecific NKG2D antibody in several formats were generated and tested, using CEA as exemplary second specificity. The bispecific antibody formats were termed D, J, K, I, L, and M, and are schematically depicted in FIG. 12. The D format is bivalent for NKG2D and CEA, the J format is tetravalent for NKG2D and monovalent for CEA, the K, I, and L formats are bivalent for NKG2D and monovalent for CEA, whereas the M format is monovalent for NKG2D and CEA. In the case of different heavy chains, heterodimerization was achieved by application of knobs-into-holes technology. In order to avoid light chain mispairing, CrossMab (Fab domain crossover) technology was applied, except for the I format, where this is not required. In the crossed (in these examples NKG2D binding) Fab portion(s) of the bispecific antibody, the VH and VL domains were exchanged by each other, while specific charge mutations (in these examples 147E/213E (Kabat EU index) and 123R/124K (Kabat), respectively) were introduced in the constant domains CH1 and CL of the non-crossed (in these examples CEA binding) Fab(s).

The agonistic anti-NKG2D antibodies 5C5, 013, 230, 320 and 395, which showed good agonistic activity as IgGs, were chosen for functional assessment in the different bispecific antibody formats. In the antibody 395, comprising a rabbit VH-domain, an unpaired cysteine C50 in CDRH2 was replaced by a serine without affecting binding or function. Antibodies B9 (CDR and VH and VL sequences SEQ ID NOs 114-119, 120 and 121; see also WO 2007/071422 (SEQ ID NOs 27-29, 32-34, 22 and 26); incorporated herein by reference in its entirety) and huA5B7 (CDR and VH and VL sequences SEQ ID NOs 122-127, 128 and 129; see also EP application no. 19182505.8 and the PCT application claiming priority thereof, incorporated herein by reference in its entirety) used as exemplary anti-CEA antibodies for the second specificity.

TABLE 13

Overview of bispecific NKG2D × CEA antibody formats.

| clone | D format | J format | K format | I format | L format | M format |
|-------|----------|----------|----------|----------|----------|----------|
| 5C5   | B9       | B9       | B9       | B9       | —        | —        |
| 013   | B9       | —        | B9       | B9       | —        | —        |
| 230   | —        | —        | —        | B9       | —        | —        |
| 320   | B9       | B9       | B9       | B9       | B9       | —        |
| 395   | —        | —        | —        | B9       | —        | B9       |

Production of Bi-Specific Antibodies

Bispecific antibodies were generated by transient transfection of HEK293 EBNA cells. Cells were centrifuged and, medium was replaced by pre-warmed CD CHO medium (Thermo Fisher, #10743029). Expression vectors were mixed in CD CHO medium, polyethylenimine (PEI; Polysciences, #23966-1) was added, the solution vortexed and incubated for 10 minutes at room temperature. Afterwards, cells (2 mio/ml) were mixed with the vector/PEI solution, transferred to a flask and incubated for 3 hours at 37° C. in a shaking incubator with a 5% $CO_2$ atmosphere. After the incubation, Excell medium with supplements (80% of total volume) was added (Mammalian Cell Cultures for Biologics Manufacturing, Eds. W. Zhou and A. Kantardjieff, Springer Verlag 2014). One day after transfection, supplements (Feed, 12% of total volume) were added. Cell supernatants were harvested after 7 days by centrifugation and subsequent filtration (0.2 μm filter), and proteins were purified from the harvested supernatant by standard methods as indicated below.

Purification and Analytics of Bi-Specific Antibodies

Proteins were purified from filtered cell culture supernatants referring to standard protocols. In brief, Fc containing proteins were purified from cell culture supernatants by Protein A-affinity chromatography (equilibration buffer: 20 mM sodium citrate, 20 mM sodium phosphate, pH 7.5; elution buffer: 20 mM sodium citrate, pH 3.0). Elution was achieved at pH 3.0 followed by immediate pH neutralization of the sample. The protein was concentrated by centrifugation (Millipore AMICON® ULTRA-15, #UFC903096), and aggregated protein was separated from monomeric protein by size exclusion chromatography in 20 mM histidine, 140 mM sodium chloride, pH 6.0.

The concentrations of purified proteins were determined by measuring the absorption at 280 nm using the mass extinction coefficient calculated on the basis of the amino acid sequence according to Pace et al. (Protein Science, 4, 2411-2423 (1995). Purity and molecular weight of the proteins were analyzed by CE-SDS in the presence and absence of a reducing agent using a LABCHIP® GXII (Perkin Elmer). Determination of the aggregate content was performed by HPLC chromatography at 25° C. using analytical size-exclusion column (TSKGEL® G3000 SW XL or UP-SW3000) equilibrated in running buffer (25 mM $K_2HPO_4$, 125 mM NaCl, 200 mM L-arginine monohydrochloride, pH 6.7 or 200 mM $KH_2PO_4$, 250 mM KCl pH 6.2, respectively).

Example 16. Comparison of Different Bispecific Antibody Formats with Different Agonistic Anti-NKG2D Antibodies Selected anti-NKG2D antibodies with good agonistic activity (5C5, 013, 230 and 320) were converted into bispecific antibodies in the I format, using the anti-CEA antibody B9 as exemplary second specificity. The bispecific antibodies should induce activation of NKG2D on immune cells by crosslinking via CEA on tumor cells.

The bispecific antibodies were tested for their functional activity in combination with a suboptimal fixed concentration of a CEA×CD3 bispecific antibody (CEA-T cell bispecific antibody (TCB), SEQ ID NOs 130-137 (CD3 CDRs and VH/VL), 138-145 (CEA CDRs and VH/VL), and 154-157; to provide "signal 1") in the Jurkat NFAT NKG2D reporter cell assay. In this assay, engagement of NKG2D in the presence of signal 1 delivered by CEA-TCB via CD3 activation led to an increased activation of NFAT. This activation resulted in an increase of luminescence upon addition of the luciferase substrate.

Figure 13:
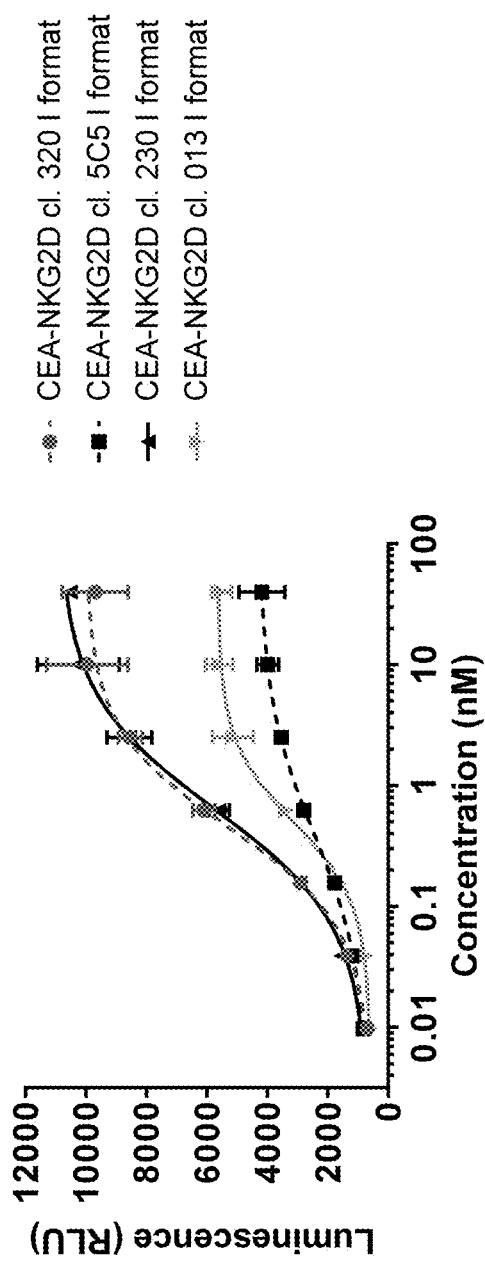
FIG. 13. Several anti-NKG2D antibodies were tested for their functional activity as bispecific constructs targeted to CEA in the Jurkat NFAT NKG2D reporter cell assay on MKN-45 cells in combination with 5 nM CEA-TCB. Activation of Jurkat NFAT NKG2D reporter cells was determined by measuring luminescence after 5 hours upon treatment.

As shown in FIG. 13, all four tested CEA-NKG2D constructs were able to induce activation on top of a fixed concentration of CEA-TCB in a concentration dependent manner. The constructs containing anti-NKG2D clones 320 and 230 had the highest activity followed by the constructs containing anti-NKG2D clones 013 and 5C5. These results proved that our selected agonistic anti-NKG2D antibodies were able to increase T cell activation upon crosslinking via CEA on tumor cells in the presence of "signal 1" delivered in this example through CD3 engagement by CEA-TCB.

Figure 14:
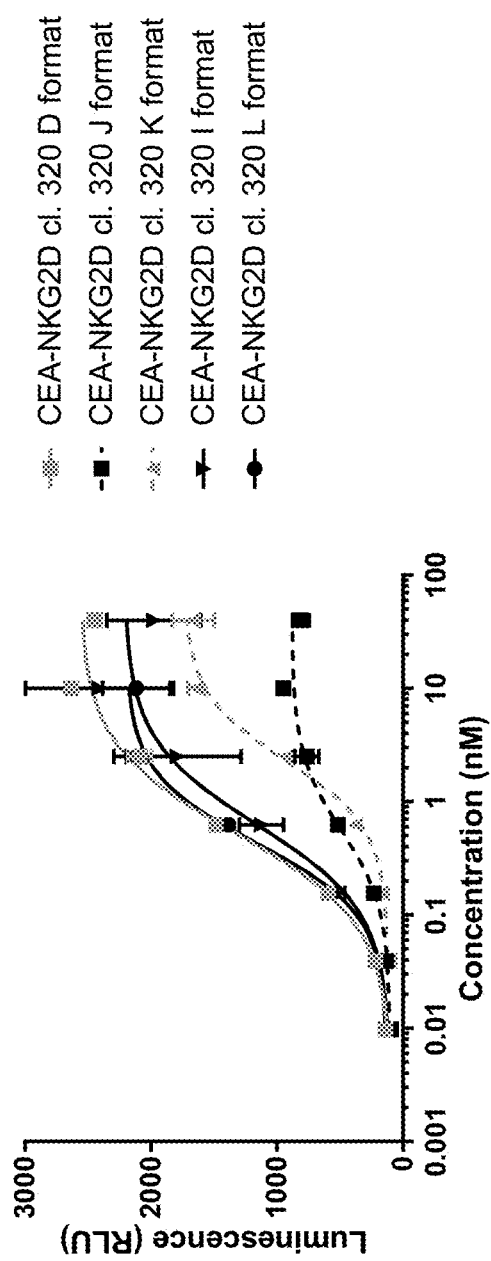
FIG. 14. The anti-NKG2D antibody 320 was tested in different bispecific formats (with CEA as second specificity) for its functional activity in a Jurkat NFAT NKG2D reporter cell assay on MKN-45 cells in combination with 5 nM CEA-TCB. Activation of Jurkat NFAT NKG2D reporter cells was determined by measuring luminescence after 5 hours upon treatment.

Anti-NKG2D antibody 320 was chosen for further evaluation of different bispecific antibody formats. It was among the most potent ones in the tested I format and was therefore considered to be a good candidate for further evaluation of different bispecific formats. Four additional bispecific formats were designed with different valences for NKG2D and CEA, to be able to identify a format with ideal properties for agonizing NKG2D. The bispecific formats D, J, K and L were produced, again using the anti-CEA antibody B9 as exemplary second specificity, and their functional activity was tested in the Jurkat NFAT NKG2D reporter cell assay in combination with CEA-TCB. The activity of the new formats was compared to the previously tested I format and subsequently the format with the highest potency to induce NKG2D activation was selected. The formats D and L had the highest potency, similar to the activity of the previously tested I format. The format K and J had a much weaker activity compared to the other tested formats and were therefore not considered for further characterization (FIG. 14).

Antibody 320 in the bispecific antibody formats D, J, K, L and I was further tested for binding to NK92 cells expressing NKG2D and LS180 cells expressing CEA, measured by flow cytometry.

Figure 15:
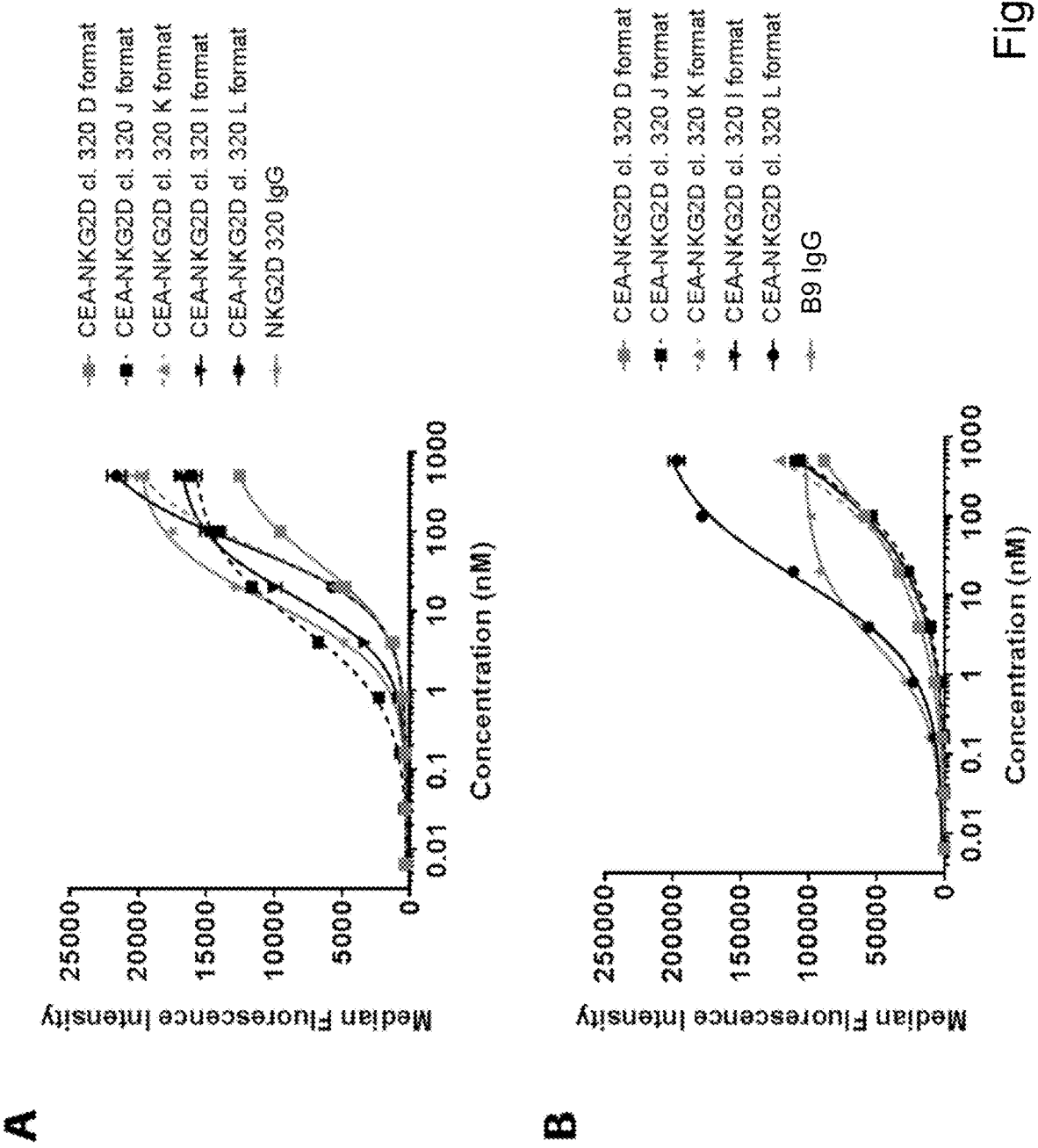
FIG. 15. Binding of NKG2D×CEA bispecific antibodies with the anti-NKG2D antibody 320 to NKG2D positive NK92 cells (A) and CEA positive LS180 cells (B), as measured by flow cytometry and compared to the respective IgGs.

On NK92 cells, the tetravalent construct J had the lowest EC50 values followed by the 320 IgG and the I format which bind similar and format K, L and D have the weakest binding (FIG. 15A). On CEA-expressing LS180 cells, the formats D, J, K and I had reduced binding to CEA compared to format L. Format L had a comparable EC50 as the respective B9 IgG but a higher overall binding (FIG. 15B).

Figure 16:
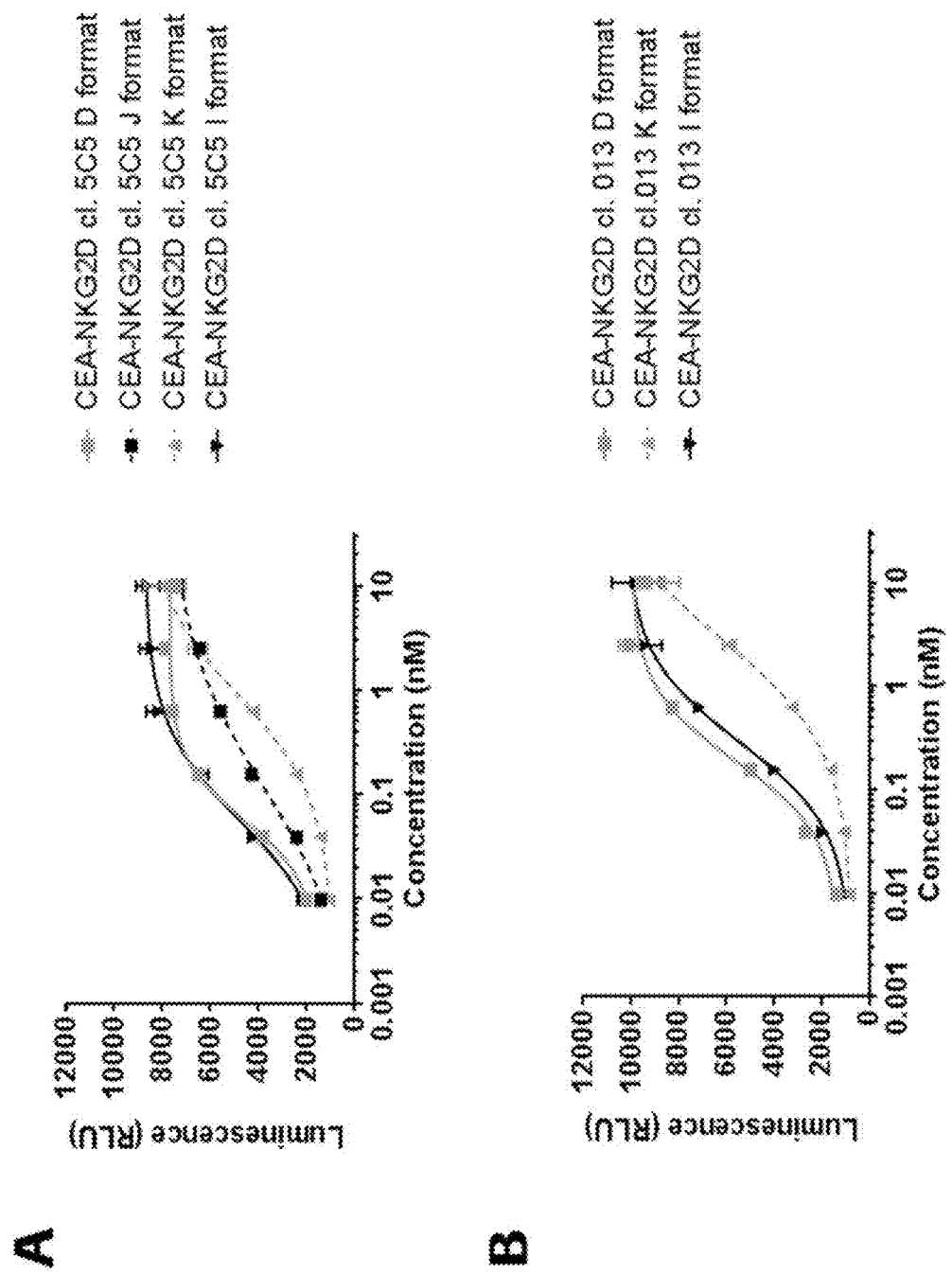
FIG. 16. The anti-NKG2D antibodies 5C5 (A) and 013 (B) were tested in different bispecific formats (with CEA as second specificity) for their functional activity in a Jurkat NFAT NKG2D reporter cell assay on MKN45 cells in combination with 5 nM CEA-TCB. Activation of Jurkat NFAT NKG2D reporter cells was determined by measuring luminescence after 5 hours upon addition of treatment.

In a next step, selected formats were tested for two additional potent agonistic anti-NKG2D antibodies, 5C5 and 013. Anti-NKG2D antibody 5C5 was converted into formats D, J and K and antibody 013 was converted into formats D and K. Functional activity was tested in the Jurkat NFAT NKG2D reporter cell assay in combination with CEA-TCB and compared to the activity of the respective I formats. As seen with antibody 320, also with antibody 5C5 (FIG. 16A) and antibody 013 (FIG. 16B) the previously tested format I was one of the most potent formats and the bivalent format K had the lowest activity.

Figure 17:
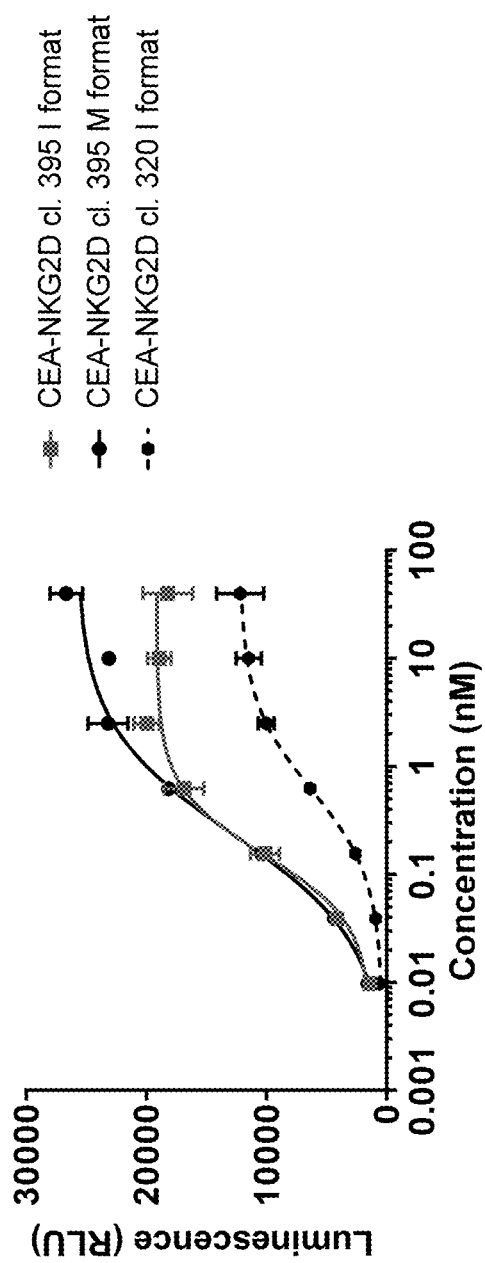
FIG. 17. The functional activity of two bispecific formats (M and I) of the anti-NKG2D antibody 395 was compared to the functional activity of the I format of the anti-NKG2D antibody 320 in the Jurkat NFAT NKG2D reporter cell assay on MKN45 cells in combination with 5 nM CEA-TCB. Activation of Jurkat NFAT NKG2D reporter cells was determined by measuring luminescence after 5 hours upon addition of treatment.

An additional potent agonistic anti-NKG2D antibody, antibody 395, was then converted into the bispecific I format being the most potent bispecific format so far. In addition, an IgG like 1+1 format (M format) was generated with antibody 395. The functional activity of these constructs was tested in the Jurkat NFAT NKG2D reporter cell assay in combination with CEA-TCB and compared to the functional activity of the I format with antibody 320 which was one of the most potent ones tested so far. As seen in FIG. 17, both bispecific formats with anti-NKG2D antibody 395 were significantly more potent than the ones with antibody 320. Comparing the two formats with antibody 395, the M format had a higher overall activity than the I format and was therefore selected for further characterization (FIG. 17).

Figure 18:
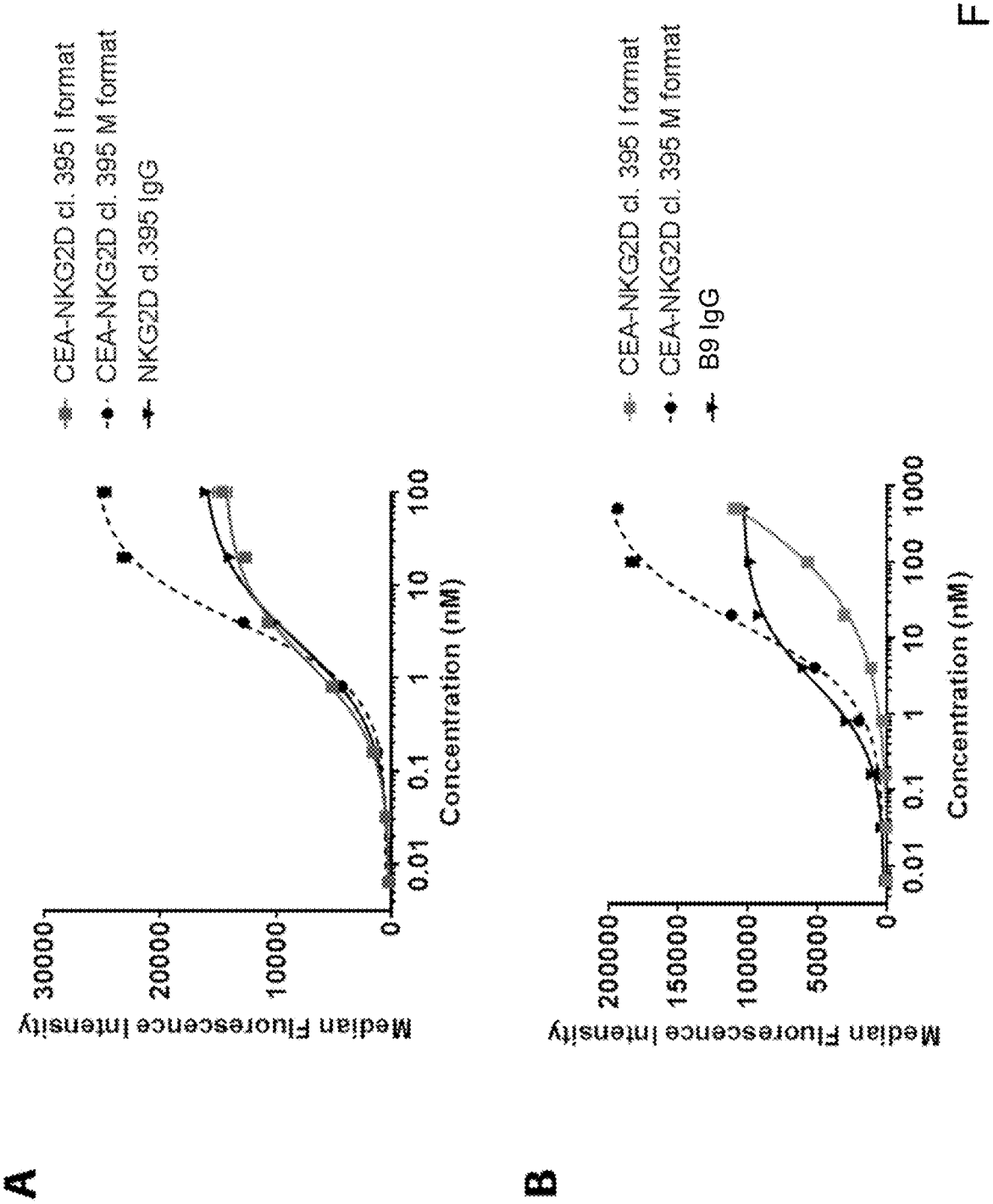
FIG. 18. Binding of NKG2D×CEA bispecific antibodies with the anti-NKG2D antibody 395 to NKG2D positive NK92 cells (A) and CEA positive LS180 cells (B), as measured by flow cytometry and compared to the respective IgGs.

Binding of the two bispecific formats I and M of the anti-NKG2D antibody 395 to NKG2D on NK92 (FIG. 18A) and to CEA on L180 cells (FIG. 18B) was assessed by flow cytometry. The bivalent I format bound comparably well to NKG2D as the corresponding 395 IgG. The monovalent format M had a higher overall binding (i.e. more molecules bound) due to the monovalent binding, but the EC50 values were still similar to what was seen with the respective 395 IgG. On the CEA-positive LS180 cells, the M format had a higher overall binding and also a higher EC50 value compared to the respective B9 IgG. The I format had only a weak binding to CEA, indicating that the C-terminal fusion of the CEA binder B9 had a negative impact on the binding to CEA.

Figure 19:
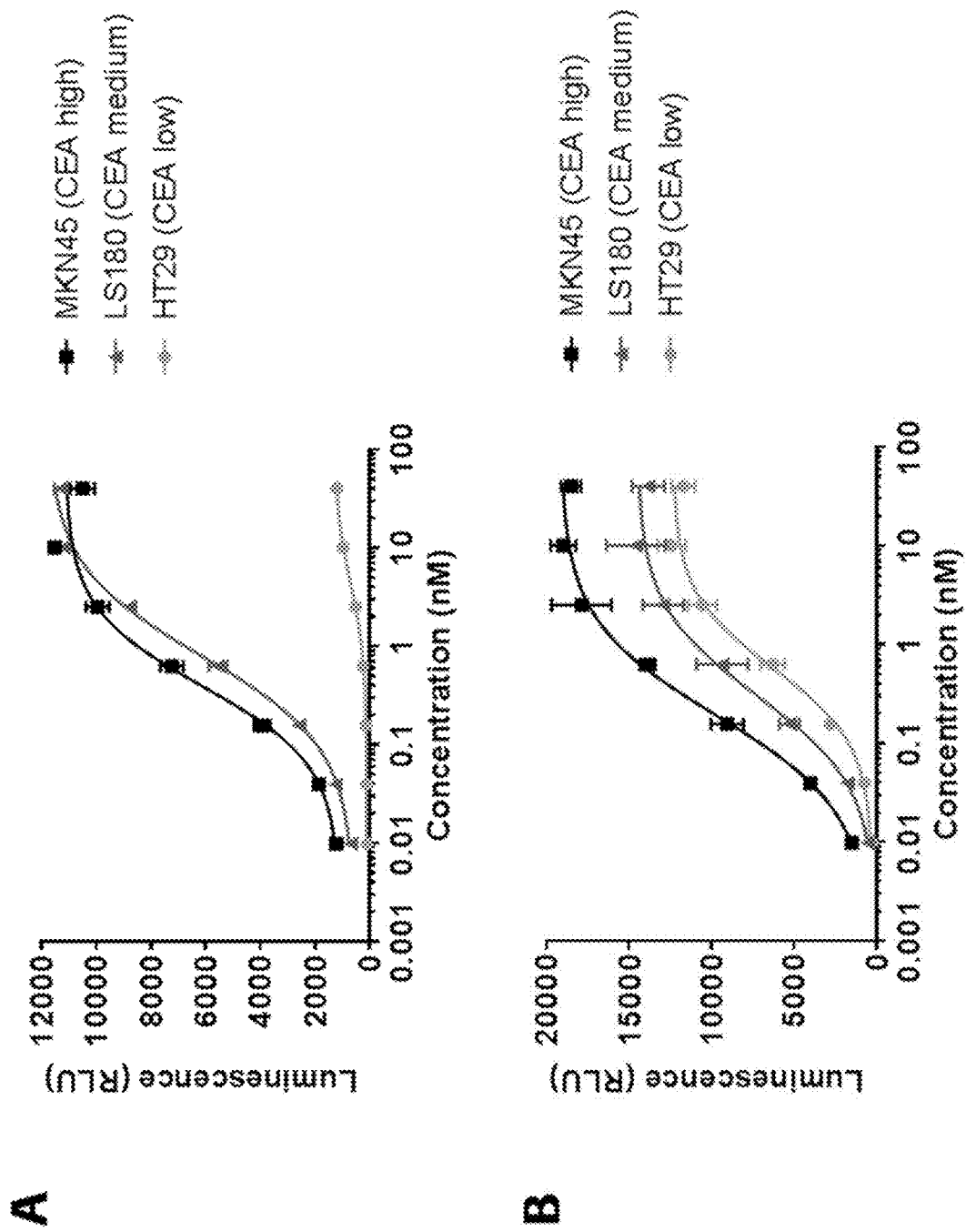
FIG. 19. The functional activity of two different NKG2D× CEA bispecific antibodies was tested in the Jurkat NFAT NKG2D reporter cell assay in the presence of tumor cell lines with different expression levels of CEA. Activation of Jurkat NFAT NKG2D reporter cells was determined by measuring luminescence after 5 hours upon treatment. (A) Bispecific antibody with anti-NKG2D antibody 320 in the I format, (B) Bispecific antibody with anti-NKG2D antibody 395 in the M format.

To further characterize the bispecific M format with antibody 395 and the I format with antibody 320, both constructs were tested in the Jurkat NFAT NKG2D reporter cell assay on CEA high MKN-45 cells, CEA medium LS-180 cells and CEA low HT-29 cells. The I format with antibody 320 had good activity on CEA high MKN-45 cells and CEA medium LS-180 but only very weak activity on CEA low HT-29 cells (FIG. 19A), whereas the M format with antibody 395 had good activity on all three tested CEA cell lines (FIG. 19B) and the activity was only slightly reduced on the CEA low cell line.

Figure 20:
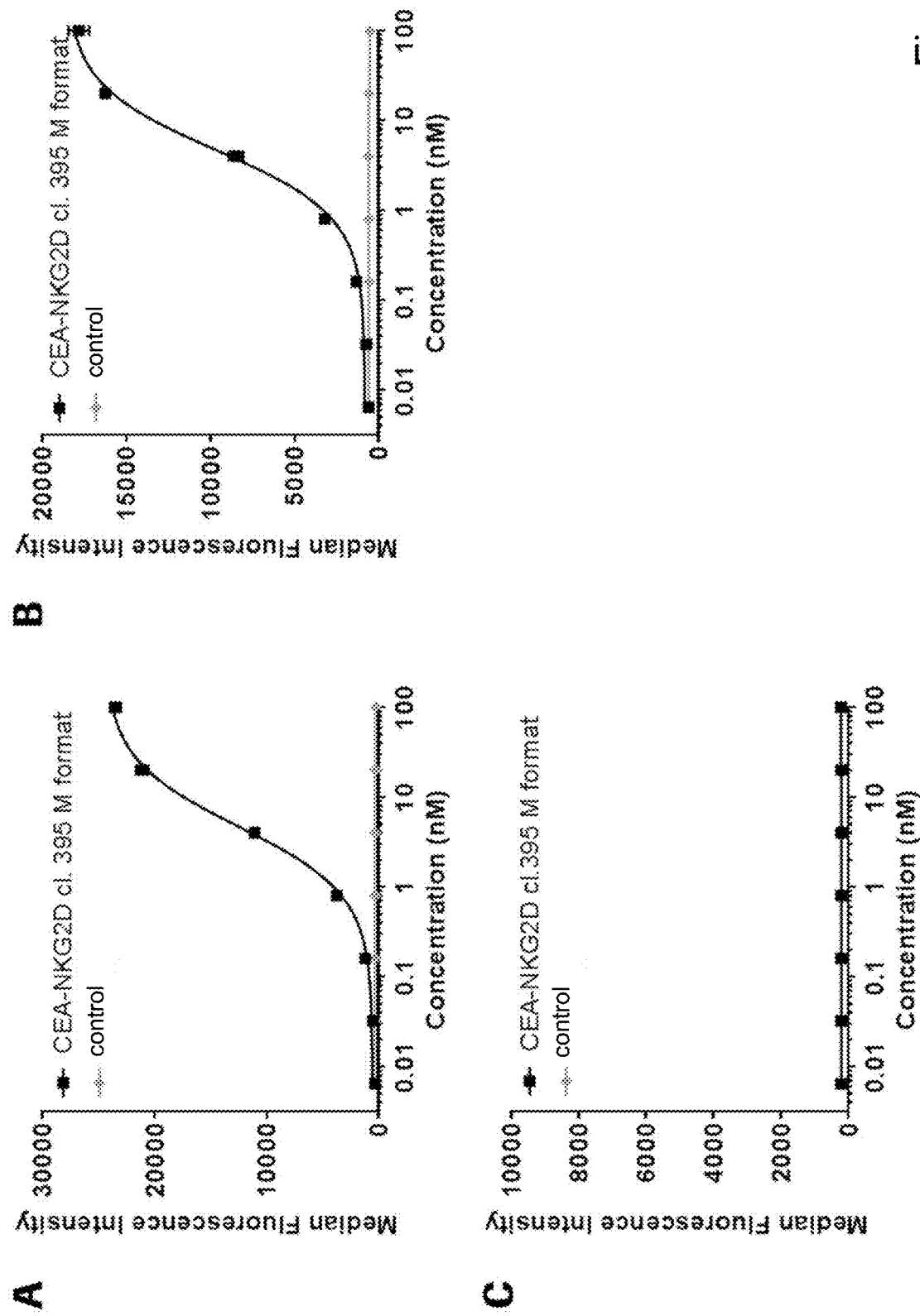
FIG. 20. Binding of the bispecific antibody with the anti-NKG2D antibody 395 in the M format to CD8 T cells (A), NK cells (B) and CD4 T cells (C) within freshly isolated PBMCs as measured by flow cytometry.

Format M was subsequently chosen for further characterization as the agonistic anti-NKG2D antibody 395 in the M format had the highest potency compared to all other tested bispecific constructs. As a next step, binding of the bispecific format M to NKG2D expressed on CD8 T cells and NK cells was tested by flow cytometry using freshly isolated PBMCs from a healthy donor. As negative control, binding to NKG2D negative CD4 T cells was tested and the non-binding control was included in the experiment (untargeted IgG (VH and VL sequences of SEQ ID NOs 81 and 82) with L234A L235A P329G ("PGLALA") mutation in Fc region—see also above). As expected, the bispecific construct showed strong binding to CD8 T cells (FIG. 20A) and NK cells (FIG. 20B) but no binding to CD4 T cells (FIG. 20C), while the non-binding control showed no binding to any of the tested cell types.

Functional activity of the selected bispecific antibody (antibody 395 in the M format) was then tested in a co-culture assay of CEA expressing tumor cells with freshly isolated PBMCs to assess activation of CD8 T cells upon NKG2D engagement in combination with a TCB. Upregulation of the early activation marker CD69 and the late activation marker CD25 was measured as a marker for CD8 T cell activation. NKG2D×CEA bispecific antibody treatment in combination with a CD3×CEA bispecific antibody (CEA-TCB (2), SEQ ID NOs 130-137 (CD3 CDRs and VH/VL), 146-153 (CEA CDRs and VH/VL), and 158-161) induced increased upregulation of CD25 and CD69 on CD8

Figure 21:
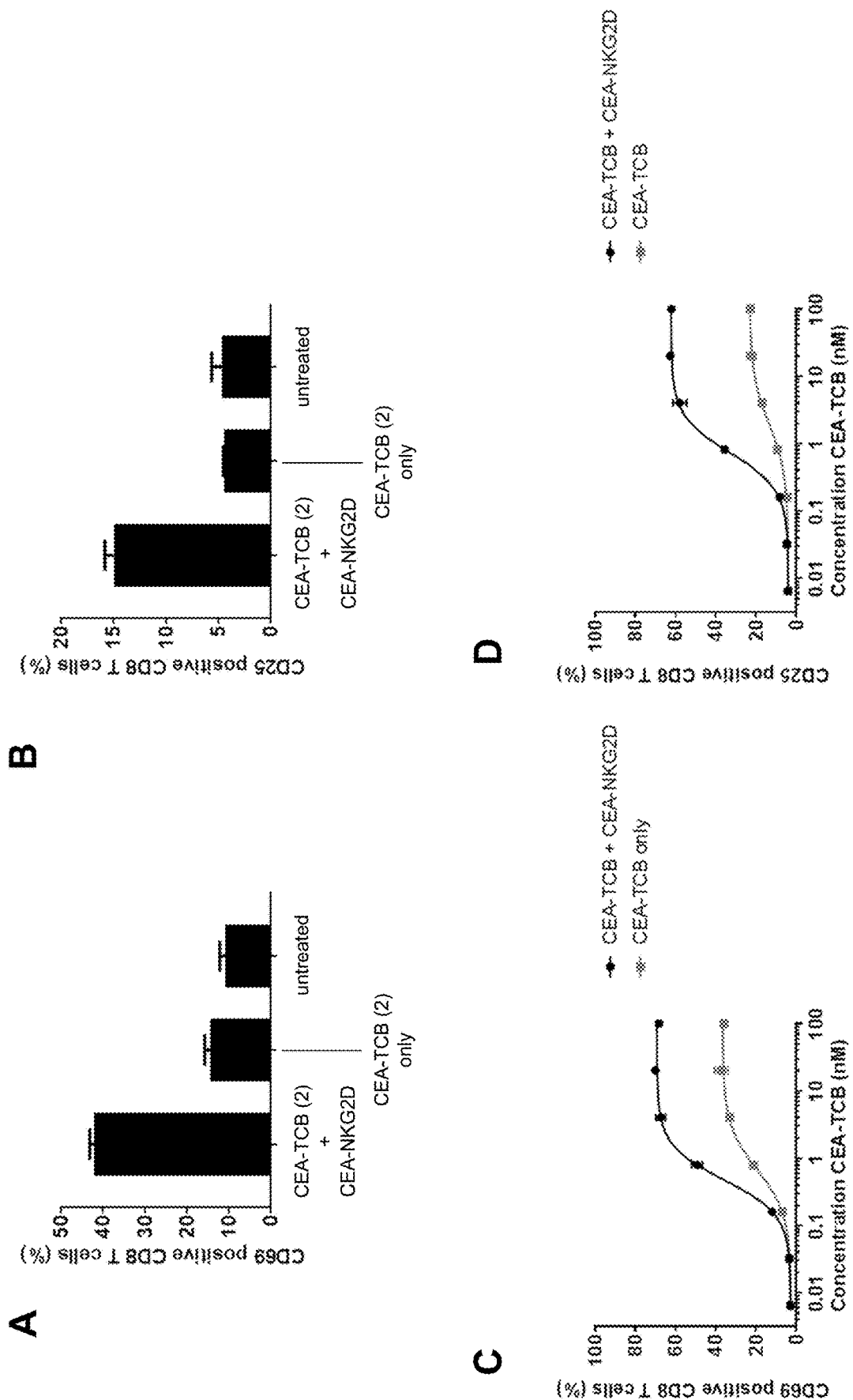
FIG. 21. Activation of CD8 T cells with the combination of a T-cell bispecific antibody (TCB) and the NKG2D×CEA bispecific antibody with anti-NKG2D antibody 395 in the M format as measured by flow cytometry. (A, B) Upregulation of CD69 (A) and CD25 (B) on CD8 T cells within PBMCs upon treatment with 0.1 nM CEA-TCB (2) alone or in combination with 0.4 nM NKG2D×CEA bispecific antibody on LS180 tumor cells for 48 h. (C, D) Upregulation of CD69 (C) and CD25 (D) on CD8 T cells within PBMCs upon treatment with CEA-TCB alone or in combination with 2 nM of NKG2D×CEA bispecific antibody on MKN-45 cells for 48 h.

T cells in the presence of the colorectal adenocarcinoma cell line LS-180 compared to treatment with CEA-TCB (2) alone (FIGS. 21 A and B). The NKG2D×CEA bispecific antibody also boosted the activation of CD8 T cells mediated by CEA-TCB in the presence of MKN-45 cells, which could be seen by increased upregulation of CD25 and CD69 on CD8 T cells with the combination of the NKG2D×CEA bispecific antibody with CEA-TCB compared to CEA-TCB alone (FIGS. 21 C and D).

Methods

Jurkat NFAT NKG2D Reporter Cell Assay

NKG2D-expressing Jurkat NFAT cells (Jurkat NFAT NKG2D) were generated by stable transfection of Jurkat NFAT Fluc cells (Promega). The cells were cultured in advanced RPMI 1640 (Gibco) medium containing 2% FBS, 1% GLUTAMAX™ (Gibco) and 200 µg/ml hygromycin. Jurkat NFAT NKG2D reporter cells were co-cultured with the tumor cell lines MKN45 (DSMZ ACC 409), LS180 (ATCC® (American Type Culture Collection) CL-187), HT-29 (ATCC® (American Type Culture Collection) HTB-38) or HeLa (ATCC® (American Type Culture Collection) CRM-CCL-2). The assay was performed in assay medium (advanced RPMI 1640 (Gibco) containing 2% FCS and 1% GLUTAMAX™ (Gibco)).

Tumor cells were detached using trypsin. The cells were counted and viability was checked. The target cells were re-suspended in assay medium and 60 000 cells were seeded per well in a white flat bottom 96 well plate. Then the T-cell bispecific antibody (TCB), the NKG2D bispecific antibodies were added at the indicated concentrations. Jurkat NFAT NKG2D reporter cells were counted, viability was checked and 0.1 mio cells were seeded per well, corresponding to an effector-to-target (E:T) ratio of 1.6:1. Also, 2% end-volume of GloSensor cAMP Reagent (E1291, Promega) was added to each well. After the indicated incubation time, luminescence was measured using a Tecan Spark10M device.

Binding to NK92 and Tumor Cell Lines

Viability of NK92 cells or tumor cells (MKN-45, LS180) was checked and cells were re-suspended and adjusted to a density of 1 mio cells/ml. 100 µl per well of this cell suspension (containing 0.1 mio cells) were seeded into a 96 well round bottom plate. The plate was centrifuged for 4 min at 400×g and the supernatant was removed. Then 40 µl of the diluted antibodies or FACS buffer were added to the cells and incubated for 30 min at 4° C. After the incubation the cells were washed twice with 150 µl FACS buffer per well. Then 20 µl of the diluted APC anti-human Fc specific secondary antibody (Jackson ImmunoResearch, #109-116-170), was added to the cells. The cells were incubated for an additional 30 min at 4° C. To remove unbound antibody, the cells were washed again twice with 150 µl per well FACS buffer. To fix the cells, 100 µl of FACS buffer containing 1% PFA were added to the wells. Before measuring, the cells were re-suspended in 150 µl FACS buffer. The fluorescence was measured using a BD flow cytometer.

Binding to PBMCs

Viability of freshly isolated peripheral blood mononuclear cells (PBMCs) was checked and cells were adjusted to a density of 1 mio cells/ml in FACS buffer. 100 µl per well of the PBMCs (containing 0.1 mio cells) were seeded into a 96 well round bottom plate. The plate was centrifuged for 4 min at 400×g and the supernatant was removed. Then 0.5 µl FC BLOCK™ (BD Bioscience) in 20 µl total volume per well were added and the plate was incubated for 30 min at 4° C. Supernatant was removed and then 40 µl of the diluted anti-NKG2D antibodies were added to the cells and incubated for additional 30 min at 4° C. After the incubation, the cells were washed twice with 150 µl FACS buffer per well. Then 20 µl of the diluted PE anti-human Fc specific secondary antibody (Jackson ImmunoResearch, #109-116-170) together with CD3 FITC (clone UCHT1, BioLegend), CD8 APC/Cy7 (Clone SK1, BioLegend), CD4 APC (clone RPA-T4, BioLegend) and CD56 BV421 (clone HCD56, BioLegend) was added to the cells to detect the anti-NKG2D antibodies and identify CD8 T cells as CD8 and CD3 double positive cells, CD4 T cells as CD4 and CD3 double positive cells, and NK cells as CD3 negative and CD56 positive cells within PBMCs. The cells were incubated for an additional 30 min at 4° C. To remove unbound antibody, the cells were washed again twice with 150 µl per well FACS buffer. To fix the cells, 100 µl of FACS buffer containing 1% PFA were added to the wells. Before measuring the cells were re-suspended in 150 µl FACS buffer. The fluorescence was measured using a BD flow cytometer.

Activation of CD8 T Cells in Combination with T-Cell Bispecific Antibody (TCB)

PBMCs were isolated from blood of healthy donors and viability was checked before the start of the assay. Target cells (MKN-45 or LS180) were detached using Trypsin (Gibco) and viability was checked. The target cells were re-suspended in assay medium (advanced RPMI 1640 (Gibco) containing 2% FBS and 1% GLUTAMAX™ (Gibco)) at a density of 0.6 mio cells/ml. The cells were seeded into a 96 well plate at 30 000 cells/well. Antibodies were diluted in assay medium and the indicated concentrations of the diluted anti-NKG2D antibodies or the TCB were added to the target cells. Then the isolated PBMCs at a cell density of 6 mio cells/ml (E:T 10:1) were added, resulting in 300 000 cells/well and a final volume of 200 µl per well. The assay was incubated for 48 h at 37° C. in the incubator. Afterwards PBMCs were harvested and analyzed by flow cytometry. The cells were centrifuged for 4 min at 400×g and washed once with PBS. Aqua Live stain (L34957, Thermo Fisher Scientific) was added in 50 µl PBS (diluted 1:1000 in PBS) and incubated for 20 min at room temperature. Afterwards 100 µl FACS buffer was added and the plate was centrifuged for 4 min at 400×g. Supernatant was removed and cells were washed again with 150 µl FACS Buffer. Then 30 µl per well of the antibody mix containing CD3 FITC (clone UCHT1, BioLegend), CD8 APC/Cy7 (clone SK1, BioLegend), CD56 BV421 (clone HCD56, BioLegend), CD25 PE (clone M-A251, BioLegend), CD69 APC (clone FN50, BioLegend) and CD44 AF700 (clone IM7, BioLegend) was added to the cells. The cells were incubated for 30 min in the fridge. Afterwards the cells were washed twice with FACS buffer and re-suspended in 100 µl FACS buffer containing 1% PFA per well. Before the measurement, cells were resuspended in 150 µl FACS buffer. The analysis was performed using a BD LSR FORTESSA™ device.

Example 17. Determination of Affinities of Bispecific NKG2D×CEA Antibodies in M Format Comprising Humanized Variants of Antibody 395 to Human NKG2D and Human CEA Using Surface Plasmon Resonance (BIACORE®)

The affinities of the bispecific NKG2D×CEA antibodies in M format comprising the humanized variants of antibody 395 were assessed by surface plasmon resonance using a BIACORE® T200 instrument. On a CM5 chip, an anti-penta-His capture antibody (Qiagen Penta·His Antibody, BSA-free; #34660) was immobilized by standard amine coupling on flow cells 2 and 3 at approximately 12'000 RU.

As respective ligands, his avi huNKG2D ECD (SEQ ID NO: 93) was captured on flow cell 2 and hu N(A2B2)A-avi-His (SEQ ID NO: 208), containing the A2 domain of human CEA, was captured on flow cell 3 at approximately 20 RU. The bispecific NKG2D×CEA antibodies in M format comprising the humanized variants of antibody 395 were subsequently injected as analytes in 3-fold dilutions ranging from 800 to 0.366 nM for a contact time of 120 s, a dissociation time of 250 or 1000 s and at a flow rate of 30 µl/min. Regeneration at the level of the anti-H6 tag capture antibody was achieved by 2 pulses of 10 mM glycine/HCl pH 2.0 for 60 s. Data were double-referenced against the unimmobilized flow cell 1 and a zero concentration of the analyte. The sensorgrams of the analytes were fitted to a simple 1:1 Langmuir interaction model. Affinity constants [$K_D$] for both targets are summarized in Table 14.

TABLE 14

Affinity constants of bispecific NKG2D × CEA antibodies in M format binding to human NKG2D and human CEA (A2 domain). These bispecific antibodies comprise different humanized VH-domain variants of agonistic anti-NKG2D antibody 395.

| humanized variant | affinity to hu NKG2D ECD [M] | affinity to hu N(A2B2)A [M] |
|---|---|---|
| P1AE4972 (non-humanized comparator) | 1.05E−08 | 3.34E−09 |
| P1AE4973 | 1.45E−08 | 2.55E−09 |
| P1AE4975 | 1.86E−08 | 3.66E−09 |
| P1AE4977 | 2.29E−08 | 3.77E−09 |
| P1AE4978 | 3.74E−08 | 3.84E−09 |
| P1AE4979 | 1.72E−08 | 5.13E−09 |
| P1AE4980 | 1.26E−08 | 3.45E−09 |
| P1AE4981 | 4.63E−08 | 3.23E−09 |

The bispecific NKG2D×CEA antibodies comprising humanized VH-domain variants of agonistic anti-NKG2D antibody 395 are of slightly lower affinities than the construct with the non-humanized parental rabbit VH-domain (P1AE4972). However, P1AE4980 has a very comparable affinity to human NKG2D as P1AE4972 (13 nM vs. 11 nM). Affinities of these bispecific antibodies to human CEA (A2 domain) do not differ significantly as they all comprise the same CEA binder (huA5B7).

The humanized variant P1AE4980 (M format, in combination with CEA binder huA5B7) was chosen for further detailed functional characterization. Moreover, this bispecific molecule is thermally stable as determined by dynamic light scattering (DLS) ($T_{agg}$ 63° C.) and suited for cell-line development.

In order to further increase the potency of this preferred molecule P1AE4980 (M format, in combination with CEA binder huA5B7), the CEA binder huA5B7 was replaced by an affinity matured binder (see Example 19).

Figure 22:
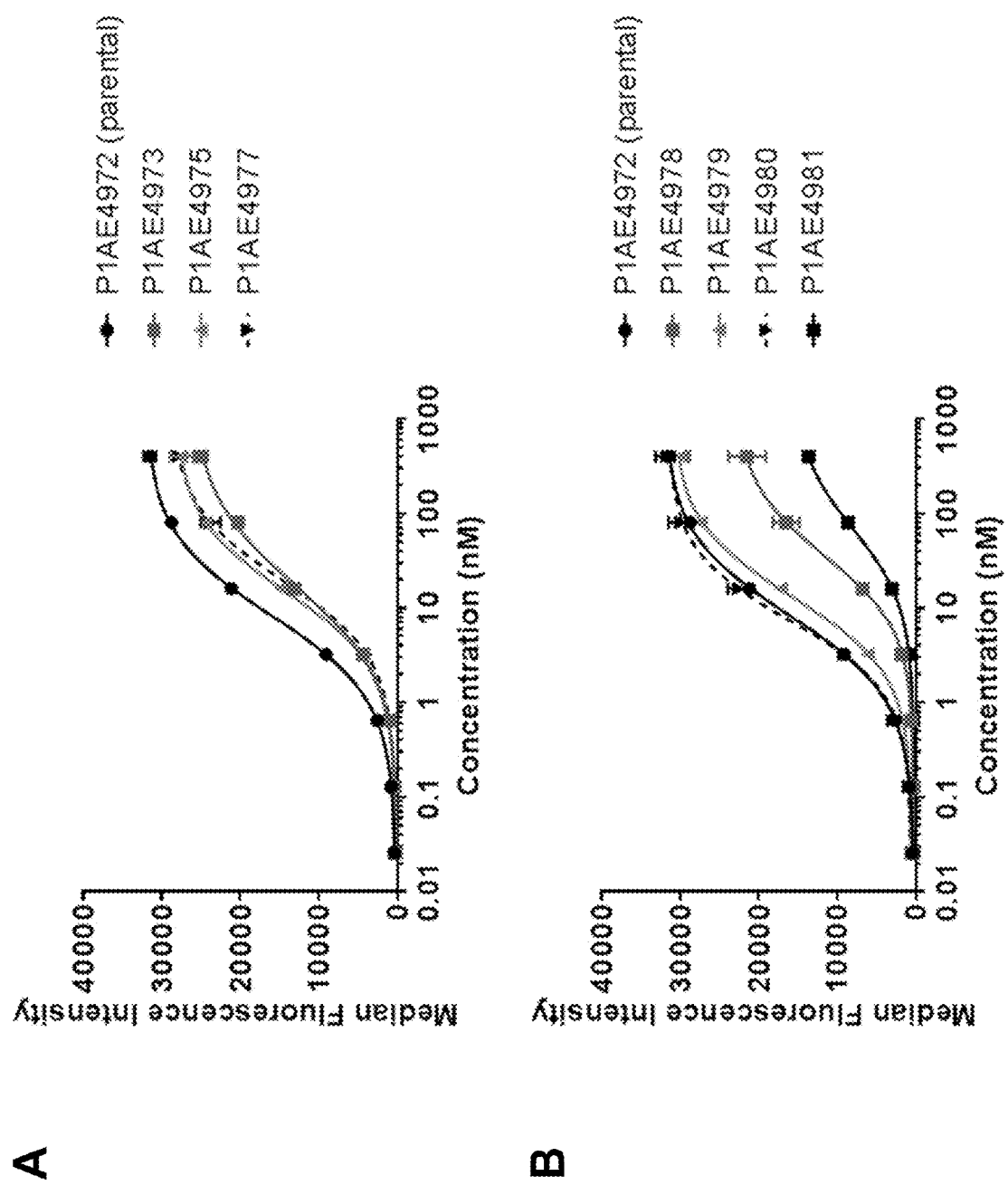
FIG. 22. Binding of humanized variants of anti-NKG2D antibody 395 in the bispecific M format to NKG2D expressed on NK92 cells was measured by flow cytometry and compared to the parental anti-NKG2D antibody (P1AE4972). (A) P1AE4973, P1AE4975, P1AE4977. (B) P1AE4978, P1AE4979, P1AE4980, P1AE4981.

Example 18. Functional Characterization of Humanization Variants of Anti-NKG2D Antibody 395 in the Bispecific M Format The parental (with the C50S mutation) and seven humanized variants of the agonistic anti-NKG2D antibody 395 were converted into NKG2D×CEA bispecific antibodies in the M format, using CEA binder huA5B7 as second specificity. Binding of the humanized variants in the bispecific format to NKG2D on NK92 was compared to the binding of the parental antibody 395 (P1AE4972, including the C50S mutation). The variant P1AE4980 showed comparable binding to NKG2D as the parental antibody, binding of variants P1AE4973, P1AE4975, P1AE4977 and P1AE4979 was slightly reduced, binding of variant P1AE4978 was stronger reduced and variant P1AE4981 bound only weakly to NKG2D (FIG. 22, Table 15).

TABLE 15

EC50 values of binding of humanized variants of anti-NKG2D antibody 395 in bispecific M format to NK92 cells.

| Humanization variant | EC50 (nM) | 95% confidence interval |
|---|---|---|
| P1AE4972 | 8.471 | 7.768 to 9.256 |
| P1AE4973 | 17.59 | 14.73 to 21.54 |
| P1AE4975 | 14.92 | 13.28 to 16.88 |
| P1AE4977 | 19.61 | 17.45 to 22.24 |
| P1AE4978 | 35.52 | 27.02 to 50.19 |
| P1AE4979 | 13.14 | 11.78 to 14.71 |
| P1AE4980 | 7.376 | 6.208 to 8.783 |
| P1AE4981 | 68.25 | 62.51 to 75.51 |

Figure 23:
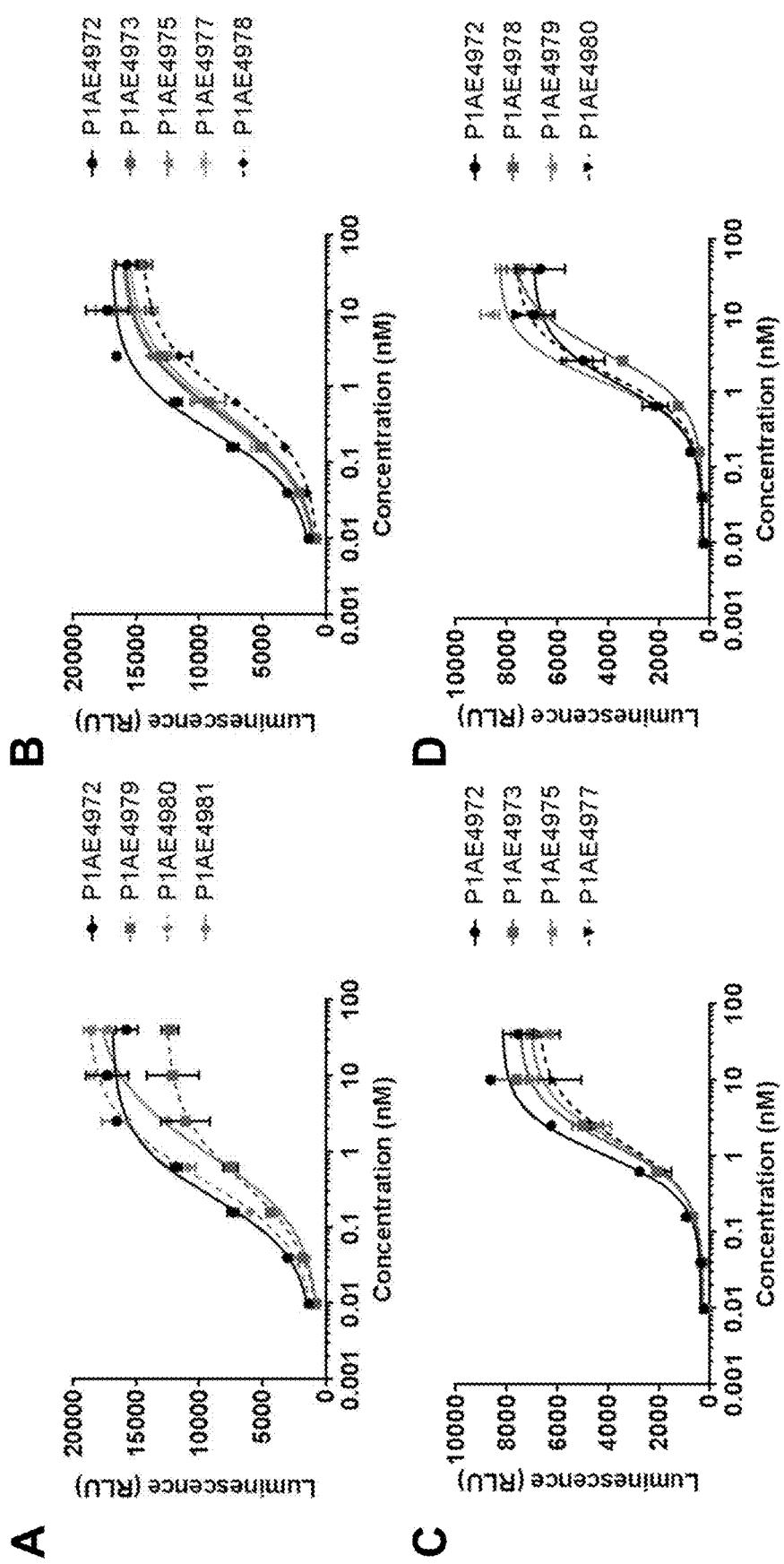
FIG. 23. Functional activity of humanized variants of anti-NKG2D antibody 395 in the bispecific M format was tested in the Jurkat NFAT NKG2D reporter cell assay on MKN-45 cells (A, B) and HT-29 cells (C, D) in combination with 5 nM CEA-TCB and compared to the activity of the respective format with the parental antibody (P1AE4972). Activation of Jurkat NFAT NKG2D reporter cells was determined by measuring luminescence after 5 hours upon treatment.

Furthermore, the functional activity of the seven humanization variants was tested in the Jurkat NFAT NKG2D reporter cell assay in combination with CEA-TCB and compared to the functional activity of the parental antibody 395 (with the C50S mutation) on the CEA high expressing tumor cell line MKN-45 (FIGS. 23 A and B) and on the CEA low expressing tumor cell line HT-29 (FIGS. 23 C and D). On both tested tumor cell lines all 395 humanization variants in the bispecific format had good activity. The activity of variant P1AE4980 was always very close to the one of the parental antibody which is in line with the binding data.

The humanized variant P1AE4980 was then selected for further characterization because it showed good binding to NKG2D and had the highest functional activity among the humanized variants and was comparable in activity to the parental antibody 395.

Figure 24:
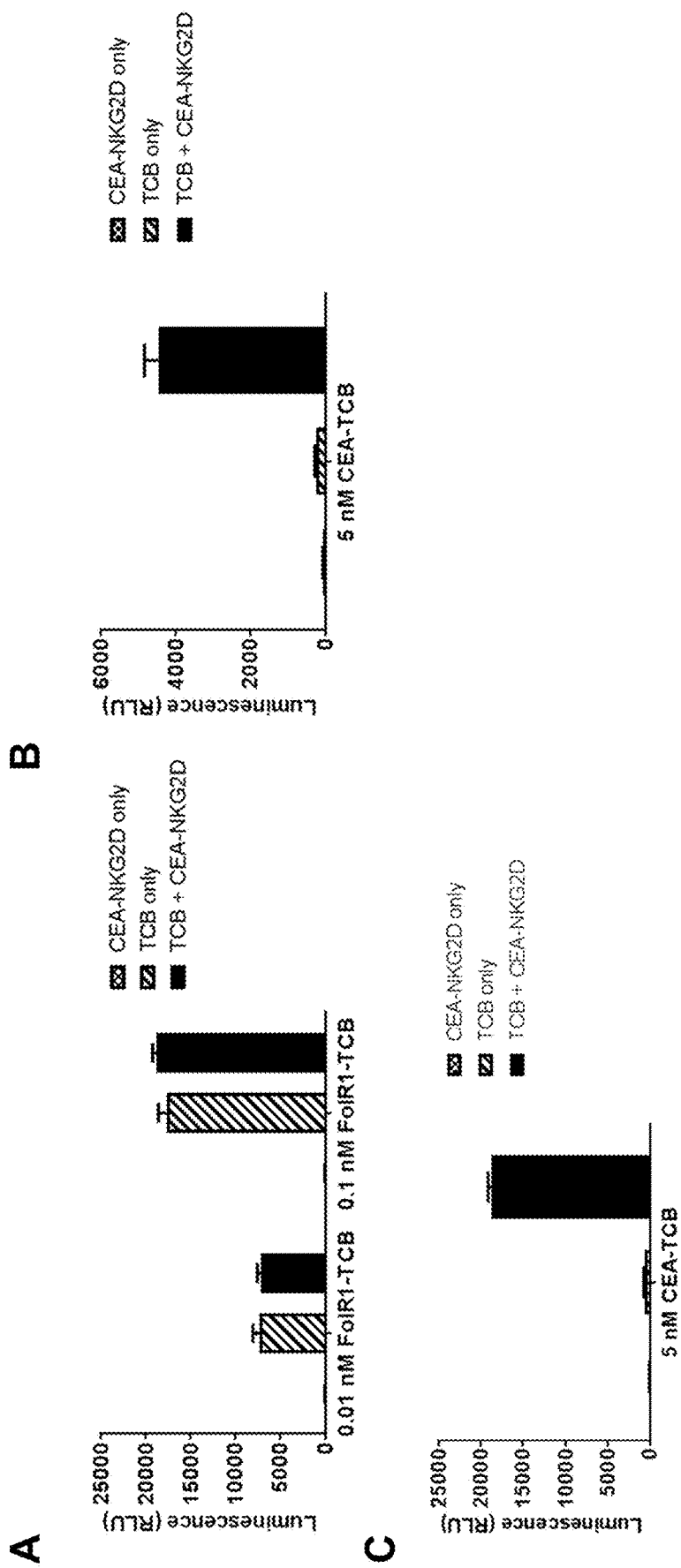
FIG. 24. Functional activity of humanized anti-NKG2D antibody variant P1AE4980 in bispecific M format in combination with a TCB was tested in the Jurkat NFAT NKG2D reporter cell assay with a CEA negative tumor cell line (HeLa (A)) and two CEA positive tumor cell lines (HT29 (B) and MKN-45 (C)). Activation of Jurkat NFAT NKG2D reporter cells was determined by measuring luminescence after 5 hours upon treatment.

In a next step we tested if the boosting of CEA-TCB activity via NKG2D engagement is dependent on crosslinking of NKG2D via CEA expressed on tumor cells. The combination of a FolR1×CD3 bispecific antibody (FolR1-TCB) with CEA-TCB was tested on CEA-negative, FolR1-positive HeLa cells in the Jurkat NFAT NKG2D reporter cell assay. In this setup signal 1 can be delivered via FolR1-TCB but the NKG2D×CEA bispecific antibody cannot be crosslinked due to missing CEA expression on HeLa cells. FolR1-TCB was able to activate the Jurkat NFAT NKG2D reporter cell assay but the activation could not be enhanced by addition of NKG2D×CEA bispecific antibody (FIG. 24A). As positive control the combination of NKG2D×CEA bispecific antibody and CEA-TCB was tested on CEA-expressing HT-29 and MKN-45 cells. Here, NKG2D×CEA bispecific antibody can be crosslinked and increased activation of Jurkat NFAT NKG2D cells measured by a strong increase in luminescence compared to CEA-TCB alone (FIGS. 24 B and C).

Then the functional activity of the NKG2D×CEA bispecific antibody was tested in the presence of shed CEA (sCEA). The combination of NKG2D×CEA bispecific antibody with CEA-TCB on MKN-45 was tested in the Jurkat NFAT NKG2D reporter cell assay in the presence of increasing concentrations of sCEA.

Figure 25:
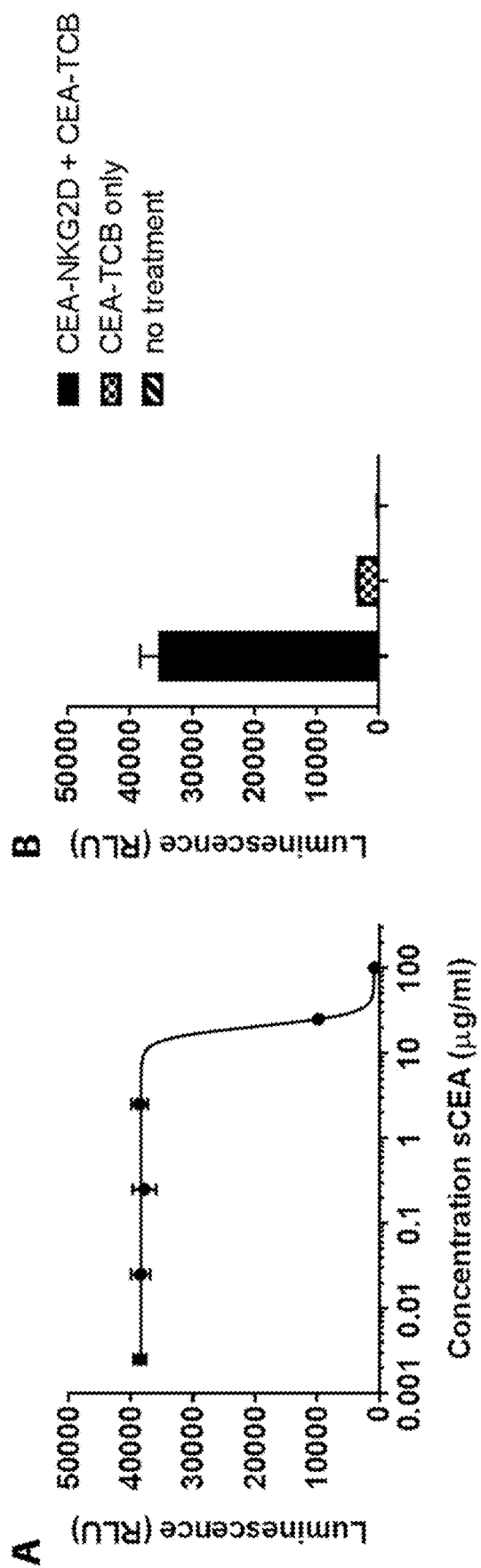
FIG. 25. Functional activity of NKG2D×CEA bispecific antibody (humanized anti-NKG2D antibody variant P1AE4980, M format) in combination with CEA-TCB was tested in the Jurkat NFAT NKG2D reporter cell assay on MKN-45 cells with increasing concentrations of shed CEA (sCEA) (A). In parallel, functional activity of NKG2D×CEA bispecific antibody in combination with CEA-TCB and CEA-TCB alone was tested as reference in the same assay (B). Activation of Jurkat NFAT NKG2D reporter cells was determined by measuring luminescence after 5 hours upon treatment.

Only at high concentrations (>5 µg/ml) sCEA had a negative impact on the activity of the NKG2D×CEA bispecific antibody (FIG. 25).

In a next step it was also tested if the presence of soluble NKG2D ligands can interfere with the activity of the NKG2D×CEA bispecific antibody in combination with CEA-TCB. Soluble MICA (sMICA; R&D Systems, #1300-MA-050) and soluble ULBP2 (sULBP2; R&D Systems, #1298-UL-050) were added to the combination of NKG2D×CEA bispecific antibody with CEA-TCB and activation of Jurkat NFAT NKG2D cells was tested and compared to the activation in the absence of soluble NKG2D ligands.

Figure 26:
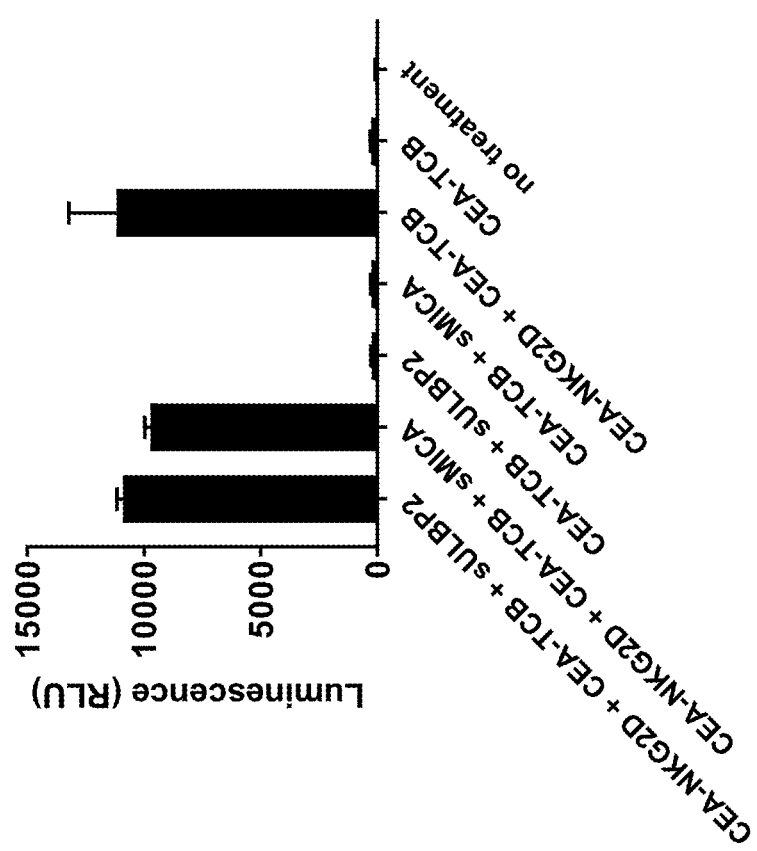
FIG. 26. The functional activity of NKG2D×CEA bispecific antibody (humanized anti-NKG2D antibody variant P1AE4980, M format) with CEA-TCB in the presence of the soluble NKG2D ligand MICA (sMICA, 10 μg/ml) or ULBP2 (sULBP2, 10 μg/ml) was compared to the activity of NKG2D×CEA bispecific antibody with CEA-TCB (in the absence of ligands) in the Jurkat NFAT NKG2D reporter cell assay on MKN-45 cells. Activation of Jurkat NFAT NKG2D reporter cells was determined by measuring luminescence after 5 hours upon treatment.

The addition of nM of either soluble MICA or soluble ULBP2 did not change the activity of the NKG2D×CEA bispecific antibody in combination with CEA-TCB in the Jurkat NFAT NKG2D reporter cell assay (FIG. 26). These results show that the activity of the NKG2D×CEA bispecific antibody is not affected/inhibited by the presence of soluble NKG2D ligands.

Example 19. Generation of NKG2D×CEA Bispecific Antibodies Using Affinity Matured Variants of Antibody huA5B7

CEA binder huA5B7 is a humanized version of antibody A5B7. Antibody A5B7 is for example disclosed by M. J. Banfield et al, Proteins 1997, 29(2), 161-171 and its structure can be found as PDB ID:1CLO in the Protein structural database PDB (www.rcsb.org, H. M. Berman et al, The Protein Data Bank, Nucleic Acids Research, 2000, 28, 235-242). The CDR and variable region sequences of A5B7 are given in SEQ ID NOs 122 (HCDR1), 162 (HCDR2), 124 (HCDR3), 125 (LCDR1), 126 (LCDR2), 127 (LCDR3), 163 (VH) and 164 (VL). The generation of huA5B7 is described in EP application no. 19182505.8 and the PCT application claiming priority thereof. The CDR and variable region sequences of huA5B7 are given in SEQ ID NOs 122 (HCDR1), 123 (HCDR2), 124 (HCDR3), 125 (LCDR1), 126 (LCDR2), 127 (LCDR3), 128 (VH) and 129 (VL).

In order to further increase the potency of the preferred molecule P1AE4980 (see Example 17 above), the CEA binder huA5B7 was replaced by affinity matured variants thereof. Affinity maturation of huA5B7 is described in EP application no. 19182505.8 and the PCT application claiming priority thereof.

The CDR and variable region sequences of selected affinity matured variants of huA5B7 are given in the sequence listing and the corresponding SEQ ID NOs are summarized in Table 16 below.

TABLE 16

CDR and variable region sequences (SEQ ID NOs) of affinity matured variants of antibody huA5B7.

| Binder | HCDR1 | HCDR2 | HCDR3 | LCDR1 | LCDR2 | LCDR3 | VH | VL |
|---|---|---|---|---|---|---|---|---|
| huA5B7 | 122 | 123 | 124 | 125 | 126 | 127 | 128 | 129 |
| P006.038 | 122 | 123 | 172 | 125 | 126 | 180 | 184 | 185 |
| P005.097 | 122 | 123 | 173 | 125 | 126 | 181 | 186 | 187 |
| P005.103 | 122 | 123 | 174 | 125 | 126 | 182 | 188 | 189 |
| P002.139 | 166 | 169 | 124 | 178 | 126 | 127 | 190 | 191 |
| P001.177 | 122 | 170 | 124 | 125 | 126 | 127 | 192 | 193 |
| P005.102 | 122 | 123 | 175 | 125 | 126 | 183 | 194 | 195 |
| P005.102-combo1 | 122 | 169 | 175 | 125 | 126 | 183 | 196 | 197 |
| P005.102-combo2 | 122 | 169 | 175 | 125 | 126 | 183 | 198 | 199 |
| P005.103-combo1 | 122 | 123 | 176 | 125 | 126 | 182 | 200 | 201 |
| P005.103-combo2 | 122 | 169 | 176 | 125 | 126 | 182 | 202 | 203 |
| P006.038-combo1 | 166 | 169 | 172 | 125 | 126 | 180 | 204 | 205 |
| P006.038-combo2 | 167 | 170 | 172 | 125 | 126 | 180 | 206 | 207 |

Figure 27:
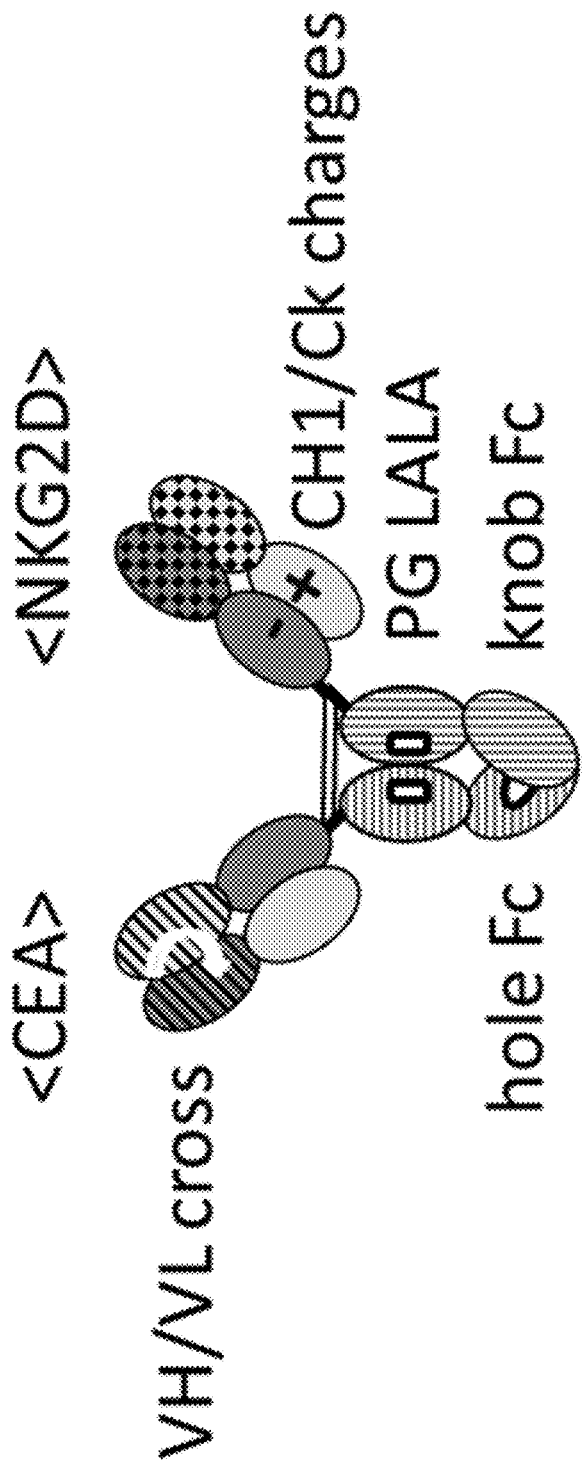
FIG. 27. Schematic illustration of the NKG2D×CEA bispecific antibodies prepared in Example 19, containing antibody P1AE4980 as NKG2D binder, and antibody huA5B7 and its affinity-matured variants as CEA binder.

The variable domains of all affinity matured variants were synthesized and cloned into plasmids coding for an IgG-like NKG2D×CEA bispecific antibody based on the knob-into-hole and the CrossMab technology (for correct heavy/heavy and heavy/light chain pairing, respectively) in combination with the PGLALA Fc domain mutations. A schematic illustration of the bispecific molecules prepared in this example is shown in FIG. 27. Heavy and light chains comprising the VH and VL sequences of huA5B7 and its affinity-matured variants (see Table 16) were combined with the heavy and light chains specific for NKG2D (comprising the VH and VL sequences of clone P1AE4980, SEQ ID NOs 112 and 80, respectively). The sequences of an exemplary such bispecific antibody, comprising the CEA binder P011.177, are given in SEQ ID NOs 213, 214, 215 and 216.

The constructs were prepared using conventional (non-PCR based) cloning techniques and expressed in transiently transfected suspension-adapted CHO K1 cells, grown in animal-component free and serum-free media. Proteins were purified from filtered cell culture supernatants referring to standard protocols. In brief, Fc containing proteins were purified from cell culture supernatants by affinity chromatography using Protein A. Elution was achieved at pH 3.0 followed by immediate neutralization of the sample. The protein was concentrated, and aggregated protein was separated from monomeric protein by size exclusion chromatography in 20 mM histidine, 140 mM sodium chloride, pH 6.0.

Figure 28:
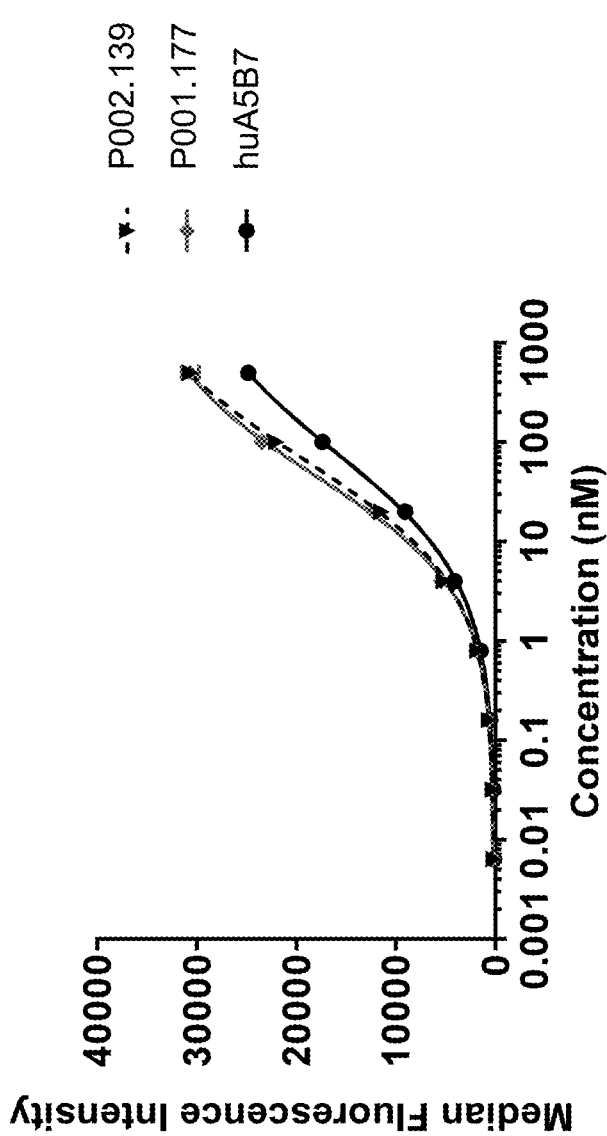
FIG. 28. Binding of bispecific NKG2D×CEA antibodies with two affinity matured variants of anti-CEA antibody huA5B7, P002.139 and P001.177, to CEA expressed on LS180 tumor cells was compared to binding of the corresponding bispecific NKG2D×CEA antibody containing the parental CEA binder huA5B7. Binding of the bispecific antibodies was detected with a fluorescently labeled secondary antibody and fluorescence was analyzed by flow cytometry.

Example 20. Characterization of Bispecific CEA×NKG2D Antibodies Comprising Affinity Matured CEA Binders The two affinity matured CEA binders P002.139 and P001.177 were converted into bispecific molecules as described in Example 19 above. Binding of these two molecules to the medium CEA expressing LS180 tumor cells was compared to binding of the corresponding molecule containing the parental humanized A5B7 CEA binder (huA5B7). Binding of the molecules to tumor cells was analyzed by flow cytometry (FIG. 28). The bispecific molecules containing the affinity matured CEA binders P002.139 and P001.177 had a slightly better binding to CEA than the corresponding molecule with the parental huA5B7 binder.

Figure 29:
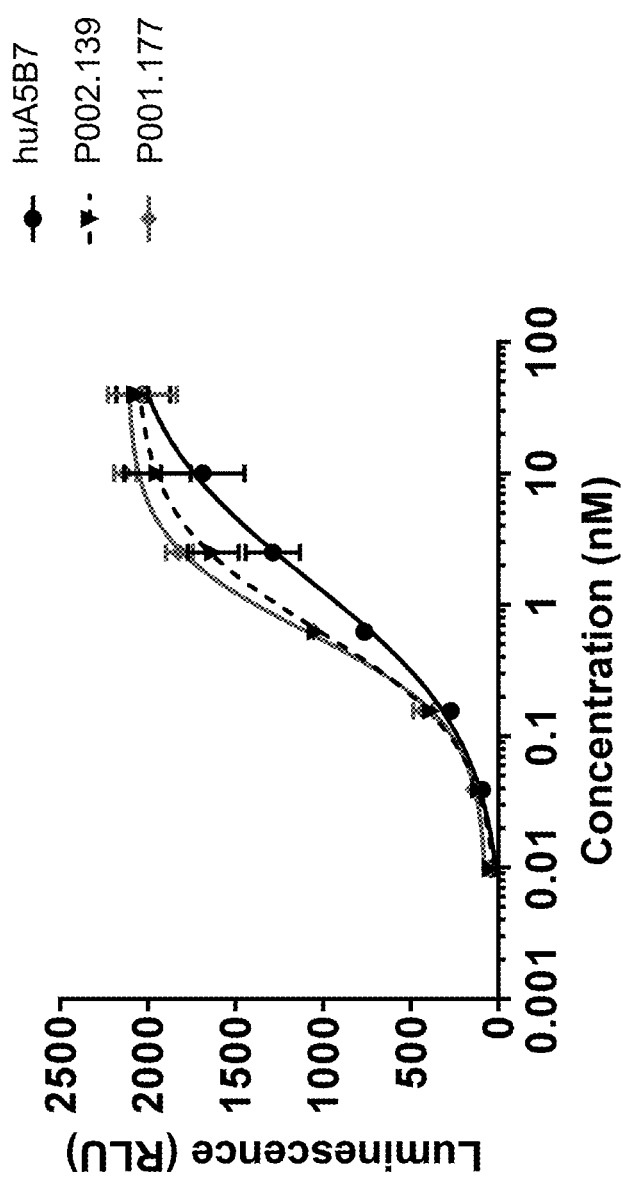
FIG. 29. The bispecific NKG2D×CEA antibodies containing huA5B7, P002.139 or P001.177 as CEA binders were tested for their functional activity in a Jurkat NFAT NKG2D reporter cell assay on high CEA expressing MKN45 cells in combination with 5 nM CEA-TCB in a 96 well plate. Activation of Jurkat NFAT NKG2D reporter cells was determined by measuring luminescence after 5 hours upon addition of treatment.
Figure 30:
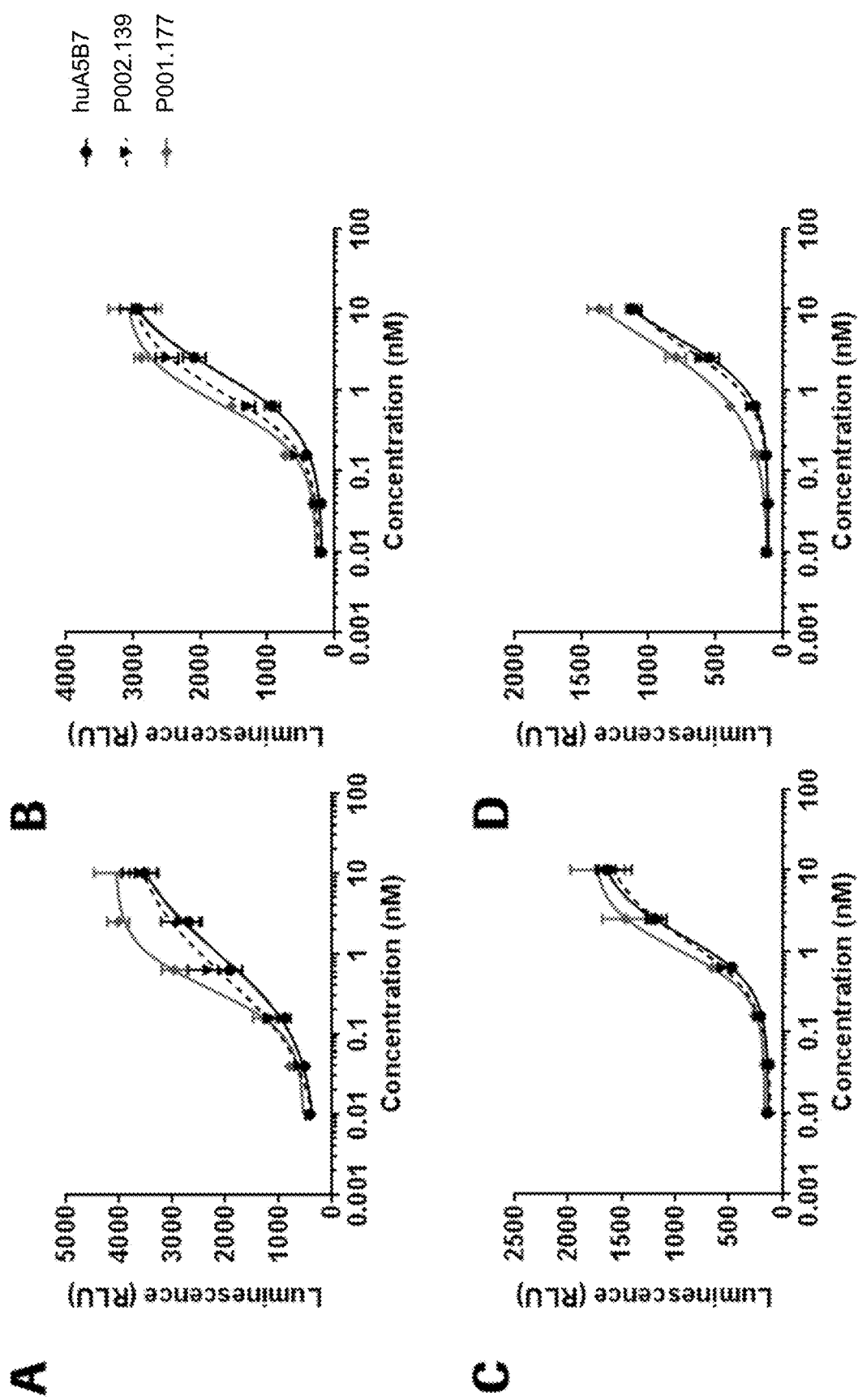
FIG. 30. The bispecific NKG2D×CEA antibodies containing huA5B7, P002.139 or P001.177 as CEA binders were tested for their functional activity in a Jurkat NFAT NKG2D reporter cell assay on medium CEA expressing LS180 cells (A, B) and on low CEA expressing HT29 cells (C, D) in combination with 5 nM CEA-TCB (A, C) or 1 nM CEA-TCB (B, D) in a 384 well plate. Activation of Jurkat NFAT NKG2D reporter cells was determined by measuring luminescence after 3 hours upon addition of treatment.

In a next step, the functional activity of these three bispecific NKG2D×CEA antibodies was determined in the Jurkat NFAT NKG2D reporter cell assay on MKN45 cells (FIG. 29) and on LS180 and HT29 cells (FIG. 30). Activity of the molecules with the affinity matured CEA binder P002.139 or P001.177 was under some conditions slightly more potent than the activity measured with the molecule comprising the huA5B7 CEA binder.

The experiments were performed as described in Example 16 above. For the Jurkat NFAT NKG2D reporter cell assay, in some instances 384 well plates were used, as follows. 10 000 target cells were seeded in a white flat bottom 384 well plate. Then the TCB and the bispecific NKG2D×CEA antibodies were added at the indicated concentrations and 15 000 Jurkat NFAT NKG2D reporter cells were added corresponding to an E:T ratio of 1.5:1.

Example 21. Cloning, Production, and Purification of Anti-NKG2D (Bispecific) Antibodies Using NKG2D Binders C26 and ADI27743

The variable domains of the anti-NKG2D antibodies C26 and ADI27743 (WO 2018/148445) were synthesized and cloned into plasmids coding for human IgG1 or bispecific molecules in the M format (FIG. 12F), each with the PGLALA Fc domain mutations. The bispecific antibodies comprised anti-CEA antibody huA5B7 as second binder. The full amino acid sequences of the molecules produced are given in SEQ ID NOs 221-222 (C26 IgG), SEQ ID NOs 223-224 (ADI27743 IgG), SEQ ID NOs 225, 226, 229 and 230 (C26 bispecific), and SEQ ID NOs 227-230 (ADI27743 bispecific).

Resulting constructs were prepared by Evitria (Switzerland) using their proprietary vector system with conventional (non-PCR based) cloning techniques and suspension-adapted CHO K1 cells (originally received from ATCC® (American Type Culture Collection) and adapted to serum-free growth in suspension culture at Evitria). For the production, Evitria's proprietary, animal-component free and serum-free media (eviGrow and eviMake2) and its proprietary transfection reagent (eviFect) were used.

Proteins were purified from filtered cell culture supernatants according to standard protocols. In brief, Fc containing proteins were purified from cell culture supernatants by affinity chromatography using Protein A. Elution was achieved at pH 3.0, followed by immediate neutralization of the sample. The protein was concentrated and aggregated protein was separated from monomeric protein by size exclusion chromatography in 20 mM histidine, 140 mM sodium chloride, pH 6.0.

Example 22. Comparison of Anti-NKG2D Antibody P1AE4980 to C26 and ADI27743

Binding to NKG2D on NK92 Cell Line

The anti-NKG2D antibodies P1AE4980, C26 and ADI27743 from Example 21 were tested for binding to NKG2D on NK92 cells.

NK92 cells were cultured in advanced RPMI 1640 medium (Gibco) containing 2% FBS, 1% GLUTAMAX™ (Gibco) and 10 ng/ml PROLEUKIN® (aldesleukin) (Novartis). Viability of NK92 cells was checked and cells were re-suspended and adjusted to a density of 1.5 mio cells/ml. 100 µl of this cell suspension (containing 0.15 mio cells) were seeded into a 96 well round bottom plate. The plate was centrifuged for 4 min at 400×g and the supernatant was removed. Then 40 µl of the diluted antibodies or FACS buffer were added to the cells and incubated for 30 min at 4° C. After the incubation the cells were washed twice with 150 µl FACS buffer per well. Then 30 µl of the diluted secondary PE anti-human Fc specific secondary antibody (Jackson ImmunoResearch, #109-116-170) was added to the cells. The cells were incubated for an additional 30 min at 4° C. To remove unbound antibody the cells were washed again twice with 150 µl per well FACS buffer. For the measurement, the cells were re-suspended in 150 µl FACS buffer. The fluorescence was measured using a BD flow cytometer.

Figure 31:
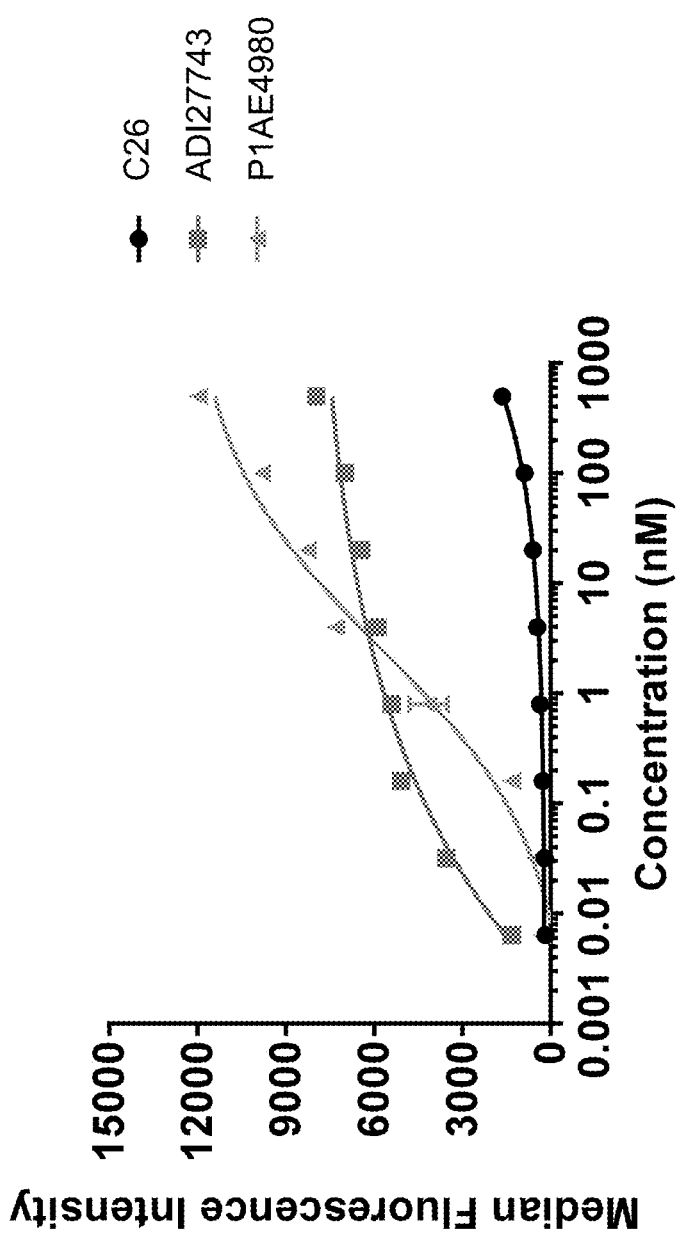
FIG. 31. The anti-NKG2D antibodies C26, ADI27743 and P1AE4980 were tested for binding to NKG2D on NK92 cells by flow cytometry. Bound antibodies were detected with a fluorescently labeled secondary antibody.

As shown in FIG. 31, the anti-NKG2D antibody P1AE4980 shows highest overall binding to NK92 cells indicating the highest number of antibodies bound to the cell compared to ADI27743 and C26. The anti-NKG2D antibody C26 binds only very weakly to NK92 at the highest tested concentrations.

The binding was also tested for the corresponding bispecific NKG2D×CEA antibodies from Example 21.

Figure 32:
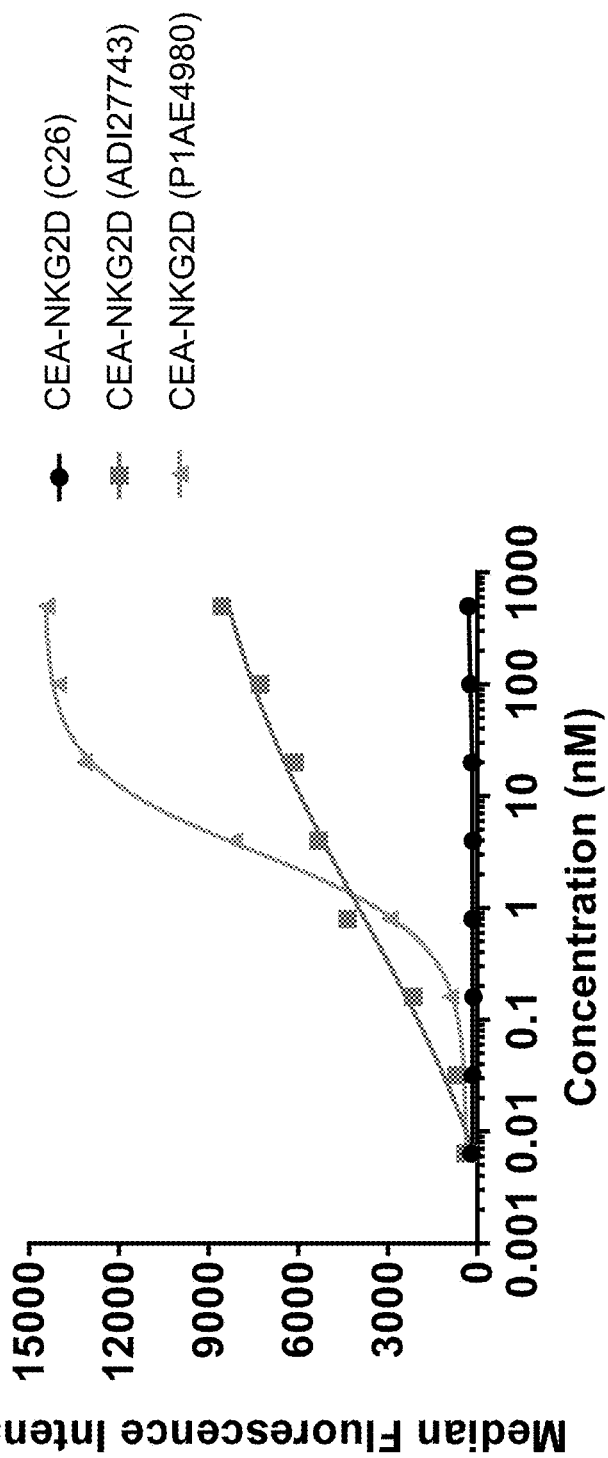
FIG. 32. The bispecific NKG2D×CEA antibodies containing C26, ADI27743 or P1AE4980 as NKG2D binders were tested for binding to NKG2D on NK92 cells by flow cytometry. Bound antibodies were detected with a fluorescently labeled secondary antibody.

As seen with the IgGs, the bispecific antibody comprising P1AE4980 as NKG2D binder shows highest overall binding to NK92 cells compared to the bispecific antibodies comprising either C26 or ADI27743 (FIG. 32).

Test of Functional Activity in the Jurkat NFAT NKG2D Reporter Cell Assay

The bispecific CEA×NKG2D antibodies comprising either C26, ADI27743 or P1AE4980 as NKG2D binders were tested in the Jurkat NFAT NKG2D reporter cell assay in combination with 5 nM CEA-TCB, with the tumor cell lines MKN45 (DSMZ ACC 409) and HT-29 (ATCC® (American Type Culture Collection) HTB-38), as described in Example 16 above.

Figure 33:
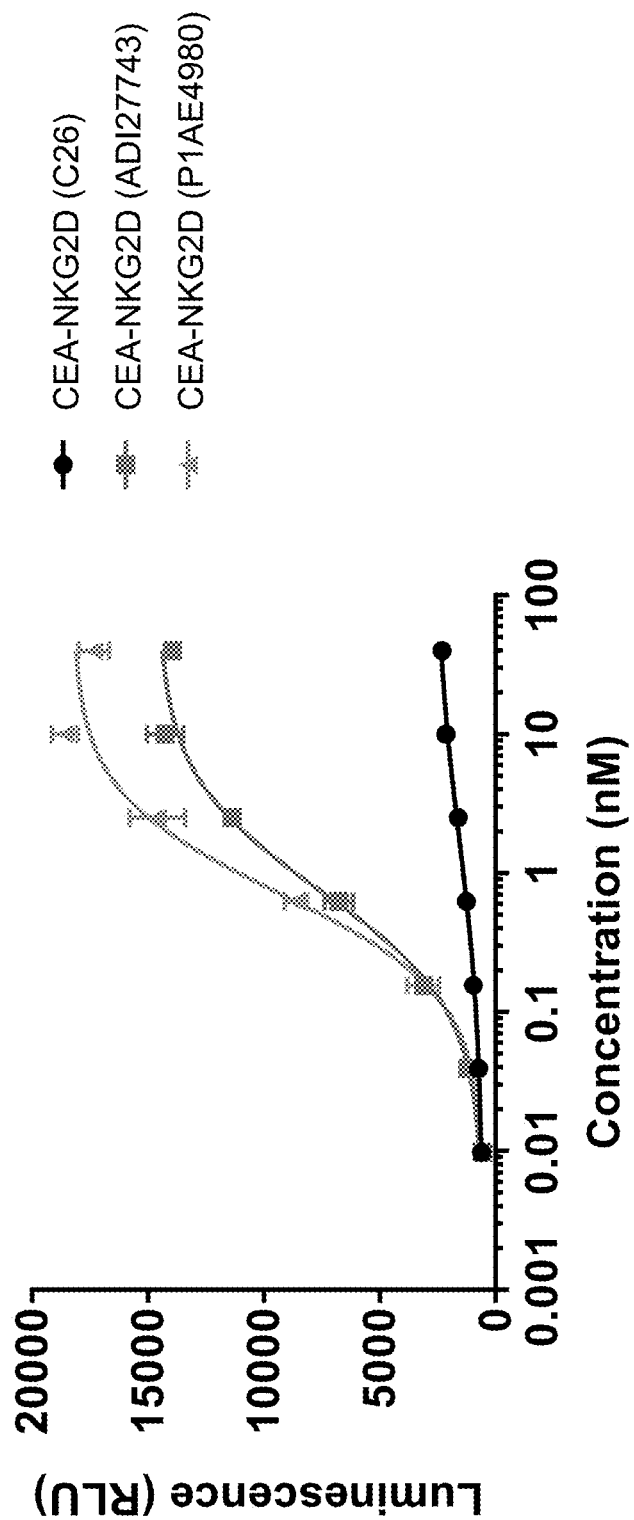
FIG. 33. The bispecific NKG2D×CEA antibodies containing C26, ADI27743 or P1AE4980 as NKG2D binders were tested in the Jurkat NFAT NKG2D reporter cell assay on the high CEA expressing MKN45 tumor cell line in combination with 5 nM CEA-TCB. Activation of Jurkat NFAT NKG2D reporter cells was determined by measuring luminescence after 6 hours upon addition of treatment.
Figure 34:
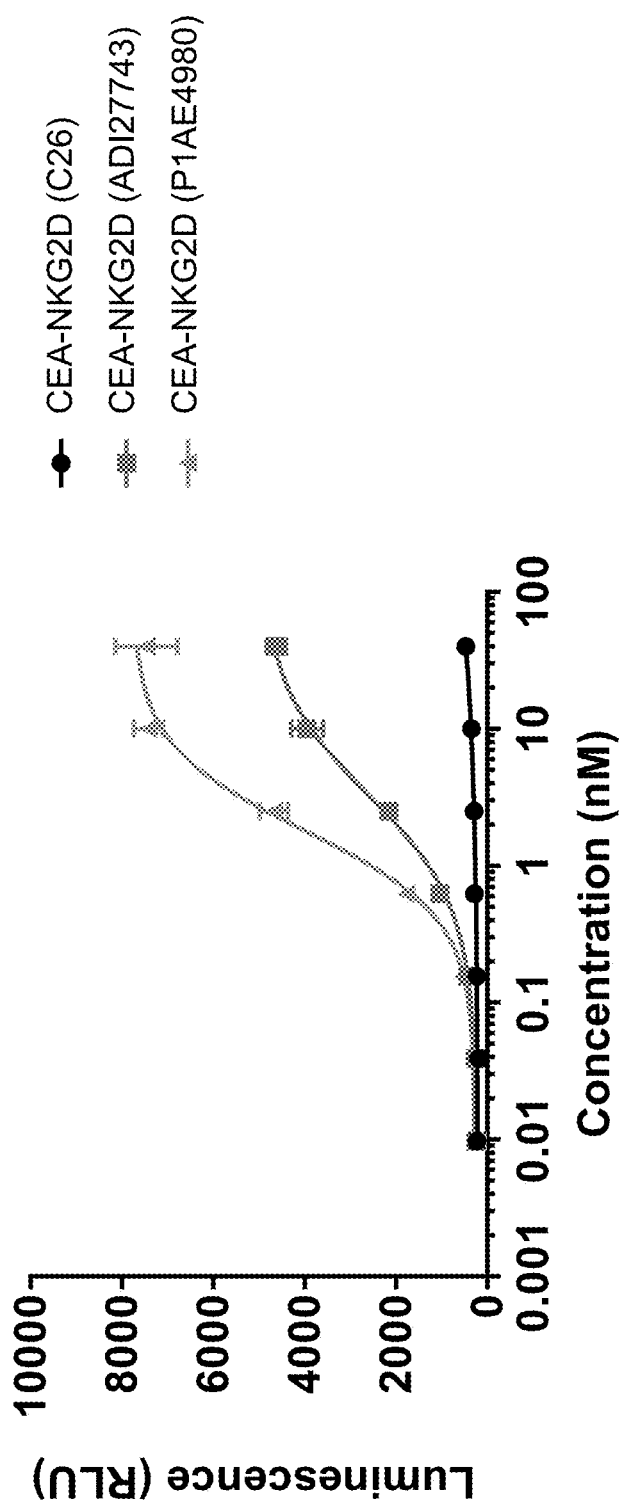
FIG. 34. The bispecific NKG2D×CEA antibodies containing C26, ADI27743 or P1AE4980 as NKG2D binders were tested in the Jurkat NFAT NKG2D reporter cell assay on the low CEA expressing HT-29 tumor cell line in combination with 5 nM CEA-TCB. Activation of Jurkat NFAT NKG2D reporter cells was determined by measuring luminescence after 6 hours upon addition of treatment.

The Jurkat NFAT NKG2D reporter cell assay in presence of MKN45 (FIG. 33) or HT-29 (FIG. 34) cells shows that the bispecific antibody comprising P1AE4980 as NKG2D binder leads to highest activation of Jurkat NFAT NKG2D cells in combination with 5 nM CEA-TCB compared to the bispecific antibodies comprising ADI27743 or C26. The bispecific antibody comprising ADI27743 activates Jurkat NFAT NKG2D cells moderately compared to the bispecific antibody comprising P1AE4980. The bispecific antibody comprising C26 only activates Jurkat NFAT NKG2D cells very weakly in presence of both tested target cell lines.

Example 23. Comparison of Anti-NKG2D Antibodies Comprising Wild-Type or Effector-Silent Fc Domains Activation of NK cells by anti-NKG2D antibodies with either wild-type or effector-silent Fc domains was assessed. For this assay, antibody P1AE4980 or 395 was used in (monospecific) human IgG$_1$ format.

PBMCs were freshly isolated from whole blood. Isolated PBMCs were counted and viability was checked. The cells were re-suspended in RPMI+10% FBS+1% GLUTA-MAX™ at a density of 3 mio cells/ml. 100 µl of the cell suspension was seeded per well in a 96-well U-bottom plate (resulting in 300 000 cells/well). 50 µl of the diluted anti-NKG2D antibodies were added to each well, resulting in a total of 150 µl/well.

The plate was incubated for 24 hours at 37° C. in the incubator and then centrifuged for 2 min at 350×g. PBMCs were harvested and seeded in another 96 well U bottom plate for analysis by flow cytometry. The cells were centrifuged for 4 min at 400×g and washed once with PBS. 50 μl of diluted Aqua LIVE/DEAD™ stain (diluted 1:1000 in PBS, Invitrogen, #L34965) was added to each well and incubated for 30 min at 4° C. Afterwards, 150 μl FACS buffer (1×PBS, 2% FBS, 1% 0.5 M EDTA pH 8, 0.25% NaN$_3$ (20%)) was added and the plate was centrifuged for 4 min at 400×g. Supernatant was removed and cells were washed again with 150 μl FACS buffer. Then, 30 μl per well of the antibody mix of FITC anti-human CD3 (BioLegend, #300406), Brilliant Violet 421™ anti-human CD56 (BioLegend, #318328), APC anti-human CD69 (BioLegend, #310910) was added to the cells. The cells were incubated for 60 min at 4° C. Afterwards, the cells were washed twice with FACS buffer and re-suspended in 100 μl FACS buffer containing 1% PFA per well for fixing the cells. The plate was incubated overnight at 4° C. Before the FACS measurement the next day, the cells were resuspended in 150 μl FACS buffer. The analysis was performed using BD LSR FORTESSA™ device.

Figure 35:
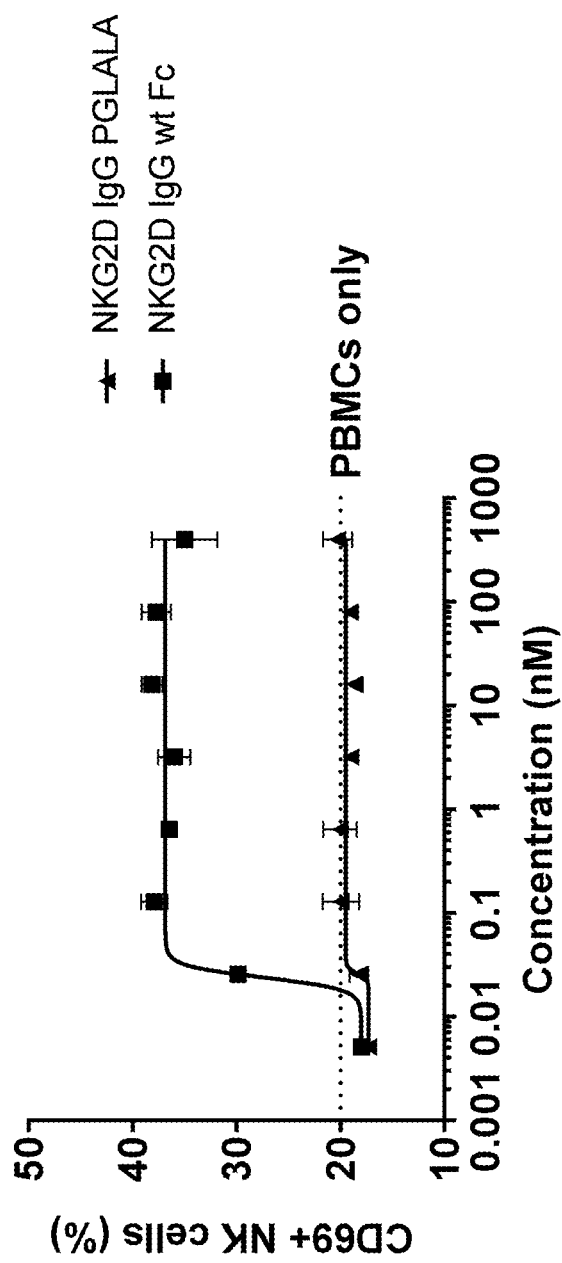
FIG. 35. PBMCs were treated for 24 h with NKG2D antibodies comprising wild-type or effector-silent Fc domains and CD69 upregulation on NK cells was subsequently determined by flow cytometry.

As shown in FIG. 35, the anti-NKG2D antibody with the wild-type Fc domain induces upregulation of CD69 on NK cells which indicates activation. In contrast, the anti-NKG2D antibody with the effector-silent Fc domain (comprising the PGLALA mutation) does not induce upregulation of CD69 on NK cells. This indicates that our agonistic anti-NKG2D antibodies will not induce systemic activation of NK or other Fcγ receptor-expressing immune cells in the absence of a functional Fc domain (but only local activation of NKG2D-expressing cells upon binding to and crosslinking via a target cell antigen).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An antibody that binds to human NKG2D, wherein the antibody comprises an NKG2D binding domain, comprising
   (i) a heavy chain variable region (VH) comprising a heavy chain complementary determining region (HCDR) 1 of SEQ ID NO: 73, a HCDR 2 of SEQ ID NO: 74, and a HCDR 3 of SEQ ID NO: 75, and a light chain variable region (VL) comprising a light chain complementarity determining region (LCDR) 1 of SEQ ID NO: 76, a LCDR 2 of SEQ ID NO: 77 and a LCDR 3 of SEQ ID NO: 78;
   (ii) a VH comprising a HCDR 1 of SEQ ID NO: 65, a HCDR 2 of SEQ ID NO: 66, and a HCDR 3 of SEQ ID NO: 67, and a VL comprising a LCDR 1 of SEQ ID NO: 68, a LCDR 2 of SEQ ID NO: 69 and a LCDR 3 of SEQ ID NO: 70;
   (iii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;
   (iv) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
   (v) a VH comprising a HCDR 1 of SEQ ID NO: 49, a HCDR 2 of SEQ ID NO: 50, and a HCDR 3 of SEQ ID NO: 51, and a VL comprising a LCDR 1 of SEQ ID NO: 52, a LCDR 2 of SEQ ID NO: 53 and a LCDR 3 of SEQ ID NO: 54;
   (vi) a VH comprising a HCDR 1 of SEQ ID NO: 57, a HCDR 2 of SEQ ID NO: 58, and a HCDR 3 of SEQ ID NO: 59, and a VL comprising a LCDR 1 of SEQ ID NO: 60, a LCDR 2 of SEQ ID NO: 61 and a LCDR 3 of SEQ ID NO: 62;
   (vii) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;
   (viii) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22;
   (ix) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;
   (x) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;
   (xi) a VH comprising a HCDR 1 of SEQ ID NO: 73, a HCDR 2 of SEQ ID NO: 102, and a HCDR 3 of SEQ ID NO: 75, and a VL comprising a LCDR 1 of SEQ ID NO: 76, a LCDR 2 of SEQ ID NO: 77 and a LCDR 3 of SEQ ID NO: 78;
   (xii) a VH comprising a HCDR 1 of SEQ ID NO: 73, a HCDR 2 of SEQ ID NO: 103, and a HCDR 3 of SEQ ID NO: 75, and a VL comprising a LCDR 1 of SEQ ID NO: 76, a LCDR 2 of SEQ ID NO: 77 and a LCDR 3 of SEQ ID NO: 78;
   (xiii) a VH comprising a HCDR 1 of SEQ ID NO: 73, a HCDR 2 of SEQ ID NO: 104, and a HCDR 3 of SEQ ID NO: 75, and a VL comprising a LCDR 1 of SEQ ID NO: 76, a LCDR 2 of SEQ ID NO: 77 and a LCDR 3 of SEQ ID NO: 78; or
   (xiv) a VH comprising a HCDR 1 of SEQ ID NO: 73, a HCDR 2 of SEQ ID NO: 105, and a HCDR 3 of SEQ ID NO: 75, and a VL comprising a LCDR 1 of SEQ ID NO: 76, a LCDR 2 of SEQ ID NO: 77 and a LCDR 3 of SEQ ID NO: 78.

2. The antibody of claim 1, wherein the NKG2D binding domain comprises
   (i) a VH comprising an amino acid sequence that is at least 95% identical to the amino acid sequence of SEQ ID NO: 79, and/or a VL comprising an amino acid sequence that is at least 95% identical to the amino acid sequence of SEQ ID NO: 80;
   (ii) a VH comprising an amino acid sequence that is at least 95% identical to the amino acid sequence of SEQ ID NO: 71, and/or a VL comprising an amino acid sequence that is at least 95% identical to the amino acid sequence of SEQ ID NO: 72;
   (iii) a VH comprising an amino acid sequence that is at least 95% identical to the amino acid sequence of SEQ ID NO: 7, and/or a VL comprising an amino acid sequence that is at least 95% identical to the amino acid sequence of SEQ ID NO: 8;
   (iv) a VH comprising an amino acid sequence that is at least 95% identical to the amino acid sequence of SEQ ID NO: 31, and/or a VL comprising an amino acid sequence that is at least 95% identical to the amino acid sequence of SEQ ID NO: 32;
   (v) a VH comprising an amino acid sequence that is at least 95% identical to the amino acid sequence of SEQ ID NO: 55, and/or a VL comprising an amino acid sequence that is at least 95% identical to the amino acid sequence of SEQ ID NO: 56;
   (vi) a VH comprising an amino acid sequence that is at least 95% identical to the amino acid sequence of SEQ ID NO: 63, and/or a VL comprising an amino acid sequence that is at least 95% identical to the amino acid sequence of SEQ ID NO: 64;
   (vii) a VH comprising an amino acid sequence that is at least 95% identical to the amino acid sequence of SEQ ID NO: 15, and/or a VL comprising an amino acid sequence that is at least 95% identical to the amino acid sequence of SEQ ID NO: 16;
   (viii) a VH comprising an amino acid sequence that is at least 95% identical to the amino acid sequence of SEQ ID NO: 23, and/or a VL comprising an amino acid sequence that is at least 95% identical to the amino acid sequence of SEQ ID NO: 24;
   (ix) a VH comprising an amino acid sequence that is at least 95% identical to the amino acid sequence of SEQ ID NO: 39, and/or a VL comprising an amino acid sequence that is at least 95% identical to the amino acid sequence of SEQ ID NO: 40;
   (x) a VH comprising an amino acid sequence that is at least 95% identical to the amino acid sequence of SEQ ID NO: 47, and/or a VL comprising an amino acid sequence that is at least 95%, identical to the amino acid sequence of SEQ ID NO: 48;
   (xi) a VH comprising an amino acid sequence that is at least 95% identical to the amino acid sequence of SEQ ID NO: 106, and/or a VL comprising an amino acid sequence that is at least 95% identical to the amino acid sequence of SEQ ID NO: 80;

(xii) a VH comprising an amino acid sequence that is at least 95% identical to the amino acid sequence of SEQ ID NO: 107, and/or a VL comprising an amino acid sequence that is at least 95% identical to the amino acid sequence of SEQ ID NO: 80;

(xiii) a VH comprising an amino acid sequence that is at least 95% identical to the amino acid sequence of SEQ ID NO: 108, and/or a VL comprising an amino acid sequence that is at least 95% identical to the amino acid sequence of SEQ ID NO: 80;

(xiv) a VH comprising an amino acid sequence that is at least 95% identical to the amino acid sequence of SEQ ID NO: 109, and/or a VL comprising an amino acid sequence that is at least 95% identical to the amino acid sequence of SEQ ID NO: 80;

(xv) a VH comprising an amino acid sequence that is at least 95% identical to the amino acid sequence of SEQ ID NO: 110, and/or a VL comprising an amino acid sequence that is at least 95% identical to the amino acid sequence of SEQ ID NO: 80;

(xvi) a VH comprising an amino acid sequence that is at least 95% identical to the amino acid sequence of SEQ ID NO: 111, and/or a VL comprising an amino acid sequence that is at least 95% identical to the amino acid sequence of SEQ ID NO: 80;

(xvii) a VH comprising an amino acid sequence that is at least 95% identical to the amino acid sequence of SEQ ID NO: 112, and/or a VL comprising an amino acid sequence that is at least 95% identical to the amino acid sequence of SEQ ID NO: 80; or (xviii) a VH comprising an amino acid sequence that is at least 95% identical to the amino acid sequence of SEQ ID NO: 113, and/or a VL comprising an amino acid sequence that is at least 95% identical to the amino acid sequence of SEQ ID NO: 80.

3. The antibody of claim 1, wherein the antibody is an IgG antibody.

4. The antibody of claim 1, wherein the antibody is a full-length antibody.

5. The antibody of claim 1, wherein the antibody is an antibody fragment selected from the group of an Fv molecule, a scFv molecule, a Fab molecule, and a F(ab')$_2$ molecule.

6. The antibody of claim 1, wherein the antibody is a multispecific antibody.

7. The antibody of claim 1, wherein the antibody further comprises a second antigen binding domain that binds to a second antigen.

8. The antibody of claim 7, wherein the second antigen is a target cell antigen.

9. The antibody of claim 1, wherein the antibody comprises an Fc domain composed of a first and a second subunit.

10. The antibody of claim 9, wherein the Fc domain is an IgG Fc domain.

11. The antibody of claim 9, wherein the Fc domain is a human Fc domain.

12. The antibody of claim 9, wherein the Fc domain comprises one or more amino acid substitution that reduces binding to an Fc receptor and/or effector function.

13. The antibody of claim 1, wherein the antibody does not bind to FcγRIIIa (CD16a).

14. The antibody of claim 7, wherein the NKG2D binding domain and/or the second antigen binding domain is a Fab molecule.

15. The antibody of claim 1, wherein the NKG2D binding domain is a Fab molecule wherein the variable domains VL and VH or the constant domains CL and CH1, of the Fab light chain and the Fab heavy chain are replaced by each other.

16. The antibody of claim 7, wherein the second antigen binding domain is a Fab molecule comprising a heavy chain comprising a heavy chain variable domain and a heavy chain constant domain comprising from the N-terminus to the C-terminus a VH domain and a CH1 domain, and a light chain comprising a light chain variable domain and a light chain constant domain comprising from the N-terminus to the C-terminus a VL domain and a CL domain.

17. The antibody of claim 7, wherein the second antigen binding domain is a Fab molecule wherein in the constant CL domain the amino acid at position 124 is substituted independently by lysine, arginine or histidine and the amino acid at position 123 is substituted independently by lysine, arginine or histidine, wherein the amino acid numbering in the constant CL domain is according to Kabat, and in the constant domain CH1 the amino acid at position 147 is substituted independently by glutamic acid, or aspartic acid and the amino acid at position 213 is substituted independently by glutamic acid, or aspartic acid, wherein the amino acid numbering in the constant domain CH1 is according to Kabat EU index.

18. The antibody of claim 7, wherein the second antigen binding domain is a Fab molecule wherein the variable domains VL and VH or the constant domains CL and CH1, of the Fab light chain and the Fab heavy chain are replaced by each other.

19. The antibody of claim 1, wherein the NKG2D antigen binding domain is a Fab molecule comprising a heavy chain comprising from the N-terminus to the C-terminus a VH domain and a CH1 domain and a light chain comprising from the N-terminus to the C-terminus a VL domain and a CL domain.

20. The antibody of claim 1, wherein the NKG2D antigen binding domain is a Fab molecule wherein in the constant CL domain the amino acid at position 124 is substituted independently by lysine, arginine or histidine and the amino acid at position 123 is substituted independently by lysine, arginine or histidine, wherein the amino acid numbering in the constant CL domain is according to Kabat, and in the constant domain CH1 the amino acid at position 147 is substituted independently by glutamic acid, or aspartic acid and the amino acid at position 213 is substituted independently by glutamic acid, or aspartic acid, wherein the amino acid numbering in the constant domain CH1 is according to Kabat EU index.

21. The antibody of claim 7, wherein the NKG2D binding domain and the second antigen binding domain are each a Fab molecule and the antibody comprises an Fc domain composed of a first and a second subunit; and (i) the NKG2D antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or (ii) the second antigen binding domain is fused at the C-terminus of the Fab heavy chain to the N-terminus of the first subunit of the Fc domain and the NKG2D antigen binding domain is fused at the C-terminus of the Fab heavy chain to the N-terminus of the second subunit of the Fc domain.

22. The antibody of claim 9, wherein the Fc domain comprises a modification promoting the association of the first and the second subunit of the Fc domain.

23. The antibody of claim 9, wherein an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable.

24. An isolated polynucleotide encoding the antibody of claim 1.

25. A host cell comprising the isolated polynucleotide of claim 24.

26. A method of producing an antibody that binds to NKG2D, comprising the steps of (a) culturing the host cell of claim 25 under conditions suitable for the expression of the antibody and optionally (b) recovering the antibody.

27. A pharmaceutical composition comprising the antibody of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 11,827,711 B2 | Page 1 of 1 |
| APPLICATION NO. | : 16/929000 | |
| DATED | : November 28, 2023 | |
| INVENTOR(S) | : Dengl et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 351 days.

Signed and Sealed this
First Day of July, 2025

Coke Morgan Stewart
*Acting Director of the United States Patent and Trademark Office*

SEQUENCE LISTING

```
<160> NUMBER OF SEQ ID NOS: 230

<210> SEQ ID NO 1
<211> LENGTH: 5
<212> TYPE: PRT
<213> ORGANISM: Artificial Sequence
<220> FEATURE:
<223> OTHER INFORMATION: Synthetic construct

<400> SEQUENCE: 1

Ser Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic construct

<400> SEQUENCE: 2

Ala Ile Ser Gly Ser Gly Gly Ser Thr Tyr Tyr Ala Asp Ser Val Lys
1               5                   10                  15

Gly

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Glu Leu Tyr Arg Glu Tyr Met Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic construct

<400> SEQUENCE: 4
```

```
Gln Gly Asp Ser Leu Arg Ser Tyr Tyr Ala Ser
1               5                  10
```

<210> SEQ ID NO 5
<211> LENGTH: 7
<212> TYPE: PRT
<213> ORGANISM: Artificial Sequence
<220> FEATURE:
<223> OTHER INFORMATION: Synthetic construct

<400> SEQUENCE: 5

```
Gly Lys Asn Asn Arg Pro Ser
1               5
```

<210> SEQ ID NO 6
<211> LENGTH: 12
<212> TYPE: PRT
<213> ORGANISM: Artificial Sequence
<220> FEATURE:
<223> OTHER INFORMATION: Synthetic construct

<400> SEQUENCE: 6

```
Asn Ser Arg Asp Ser Phe Ser Ile His Gln Asn Val
1               5                  10
```

<210> SEQ ID NO 7
<211> LENGTH: 118
<212> TYPE: PRT
<213> ORGANISM: Artificial Sequence
<220> FEATURE:
<223> OTHER INFORMATION: Synthetic construct

<400> SEQUENCE: 7

```
Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Leu Tyr Arg Glu Tyr Met Asp Tyr Trp Gly Gln Gly Thr
            100                 105                 110

Leu Val Thr Val Ser Ser
        115
```

<210> SEQ ID NO 8
<211> LENGTH: 109
<212> TYPE: PRT
<213> ORGANISM: Artificial Sequence
<220> FEATURE:
<223> OTHER INFORMATION: Synthetic construct

<400> SEQUENCE: 8

```
Ser Ser Glu Leu Thr Gln Asp Pro Ala Val Ser Val Ala Leu Gly Gln
1               5                  10                  15

Thr Val Arg Ile Thr Cys Gln Gly Asp Ser Leu Arg Ser Tyr Tyr Ala
            20                  25                  30
```

-continued

```
Ser Trp Tyr Gln Gln Lys Pro Gly Gln Ala Pro Val Leu Val Ile Tyr
         35                  40                  45
Gly Lys Asn Asn Arg Pro Ser Gly Ile Pro Asp Arg Phe Ser Gly Ser
 50                  55                  60
Ser Ser Gly Asn Thr Ala Ser Leu Thr Ile Thr Gly Ala Gln Ala Glu
 65                  70                  75                  80
Asp Glu Ala Asp Tyr Tyr Cys Asn Ser Arg Asp Ser Phe Ser Ile His
                 85                  90                  95
Gln Asn Val Phe Gly Gly Gly Thr Lys Leu Thr Val Leu
            100                 105

<210> SEQ ID NO 9
<211> LENGTH: 5
<212> TYPE: PRT
<213> ORGANISM: Artificial Sequence
<220> FEATURE:
<223> OTHER INFORMATION: Synthetic construct

<400> SEQUENCE: 9

Ser Tyr Trp Ile Gly
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic construct

<400> SEQUENCE: 10

Ile Ile Tyr Pro Gly Asp Ser Asp Thr Arg Tyr Ser Pro Ser Phe Gln
1               5                   10                  15
Gly

<210> SEQ ID NO 11
<211> LENGTH: 10
<212> TYPE: PRT
<213> ORGANISM: Artificial Sequence
<220> FEATURE:
<223> OTHER INFORMATION: Synthetic construct

<400> SEQUENCE: 11

Leu Tyr Pro Val Gly Val Tyr Phe Asp Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic construct

<400> SEQUENCE: 12

Arg Ala Ser Gln Ser Ile Ser Ser Trp Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic construct

<400> SEQUENCE: 13
```

Asp Ala Ser Ser Leu Glu Ser
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic construct

<400> SEQUENCE: 14

Gln Gln Tyr Trp Ser Tyr Trp Met
1               5

<210> SEQ ID NO 15
<211> LENGTH: 119
<212> TYPE: PRT
<213> ORGANISM: Artificial Sequence
<220> FEATURE:
<223> OTHER INFORMATION: Synthetic construct

<400> SEQUENCE: 15

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Tyr Pro Val Gly Val Tyr Phe Asp Tyr Trp Gly Gln Gly
            100                 105                 110

Thr Leu Val Thr Val Ser Ser
        115

<210> SEQ ID NO 16
<211> LENGTH: 106
<212> TYPE: PRT
<213> ORGANISM: Artificial Sequence
<220> FEATURE:
<223> OTHER INFORMATION: Synthetic construct

<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Trp Ser Tyr Trp Met
                85                  90                  95

Phe Gly Gln Gly Thr Lys Val Glu Ile Lys

```
<210> SEQ ID NO 17
<211> LENGTH: 4
<212> TYPE: PRT
<213> ORGANISM: Artificial Sequence
<220> FEATURE:
<223> OTHER INFORMATION: Synthetic construct

<400> SEQUENCE: 17

Tyr Trp Met Thr
1

<210> SEQ ID NO 18
<211> LENGTH: 18
<212> TYPE: PRT
<213> ORGANISM: Artificial Sequence
<220> FEATURE:
<223> OTHER INFORMATION: Synthetic construct

<400> SEQUENCE: 18

Cys Ile His Gly Gly Ser Ser Gly Ser Thr Tyr Tyr Ala Ser Trp Val
1               5                   10                  15

Asn Gly

<210> SEQ ID NO 19
<211> LENGTH: 12
<212> TYPE: PRT
<213> ORGANISM: Artificial Sequence
<220> FEATURE:
<223> OTHER INFORMATION: Synthetic construct

<400> SEQUENCE: 19

Pro Gly Tyr Arg Ser Trp Ser Lys Thr Phe Asp Leu
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic construct

<400> SEQUENCE: 20

Arg Ala Ser Gln Asp Ile Ser Glu Ser Leu Asn
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic construct

<400> SEQUENCE: 21

Ala Ala Ser Ser Leu Gln Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic construct

<400> SEQUENCE: 22
```

Gln Gln Ala Asn Ser Phe Pro Leu Thr
1               5

<210> SEQ ID NO 23
<211> LENGTH: 121
<212> TYPE: PRT
<213> ORGANISM: Artificial Sequence
<220> FEATURE:
<223> OTHER INFORMATION: Synthetic construct

<400> SEQUENCE: 23

Gln Gln Leu Glu Gln Ser Gly Gly Leu Val Thr Pro Gly Gly Ser
1               5                   10                  15

Leu Lys Leu Cys Cys Ile Gly Ser Gly Phe Asp Phe Asn Thr Tyr Trp
            20                  25                  30

Met Thr Trp Val Arg Gln Ala Pro Gly Lys Gly Leu Glu Trp Ile Gly
        35                  40                  45

Cys Ile His Gly Gly Ser Ser Gly Ser Thr Tyr Tyr Ala Ser Trp Val
    50                  55                  60

Asn Gly Arg Phe Thr Leu Ser Arg Asp Ile Asp Gln Ser Thr Gly Cys
65                  70                  75                  80

Leu Gln Val Asn Ser Leu Thr Ala Ala Asp Thr Ala Met Tyr Tyr Cys
                85                  90                  95

Ala Arg Pro Gly Tyr Arg Ser Trp Ser Lys Thr Phe Asp Leu Trp Gly
            100                 105                 110

Gln Gly Thr Met Val Thr Val Ser Ser
            115                 120

<210> SEQ ID NO 24
<211> LENGTH: 107
<212> TYPE: PRT
<213> ORGANISM: Artificial Sequence
<220> FEATURE:
<223> OTHER INFORMATION: Synthetic construct

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Glu Ser
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 25
<211> LENGTH: 5
<212> TYPE: PRT
<213> ORGANISM: Artificial Sequence
<220> FEATURE:
<223> OTHER INFORMATION: Synthetic construct

<400> SEQUENCE: 25

Ile Tyr Trp Met Ser

```
<210> SEQ ID NO 26
<211> LENGTH: 18
<212> TYPE: PRT
<213> ORGANISM: Artificial Sequence
<220> FEATURE:
<223> OTHER INFORMATION: Synthetic construct

<400> SEQUENCE: 26

Arg Ile Tyr Gly Gly Ser Ser Asp Tyr Thr Ala Tyr Ala Ser Trp Val
1               5                   10                  15
Asn Gly

<210> SEQ ID NO 27
<211> LENGTH: 11
<212> TYPE: PRT
<213> ORGANISM: Artificial Sequence
<220> FEATURE:
<223> OTHER INFORMATION: Synthetic construct

<400> SEQUENCE: 27

Leu Asn Pro Ser Phe Ser Arg Ser Phe Asp Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic construct

<400> SEQUENCE: 28

Arg Ala Ser Gln Gly Ile Phe Ser Trp Leu Val
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic construct

<400> SEQUENCE: 29

Gly Ala Ser Thr Leu Gln Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic construct

<400> SEQUENCE: 30

Gln Gln Gly Tyr Ser Thr Pro Tyr Thr
1               5

<210> SEQ ID NO 31
<211> LENGTH: 121
<212> TYPE: PRT
<213> ORGANISM: Artificial Sequence
<220> FEATURE:
<223> OTHER INFORMATION: Synthetic construct

<400> SEQUENCE: 31
```

```
Glu Gln Ser Gly Gly Gly Ala Gly Gly Leu Val Lys Pro Gly Gly
1               5                   10                  15

Ser Leu Glu Leu Cys Cys Lys Ala Ser Gly Phe Asp Phe Ser Ile Tyr
            20                  25                  30

Trp Met Ser Trp Val Arg Gln Ser Pro Gly Lys Gly Leu Glu Trp Ile
            35                  40                  45

Gly Arg Ile Tyr Gly Gly Ser Ser Asp Tyr Thr Ala Tyr Ala Ser Trp
            50                  55                  60

Val Asn Gly Arg Phe Thr Leu Ser Arg Asp Ile Asp Gln Ser Thr Gly
65                  70                  75                  80

Cys Leu Gln Leu Asn Ser Leu Thr Ala Ala Asp Thr Ala Met Tyr Tyr
            85                  90                  95

Cys Val Arg Leu Asn Pro Ser Phe Ser Arg Ser Phe Asp Tyr Trp Gly
            100                 105                 110

Gln Gly Thr Leu Val Thr Val Ser Ser
            115                 120
```

<210> SEQ ID NO 32
<211> LENGTH: 107
<212> TYPE: PRT
<213> ORGANISM: Artificial Sequence
<220> FEATURE:
<223> OTHER INFORMATION: Synthetic construct

<400> SEQUENCE: 32

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Phe Ser Trp
            20                  25                  30

Leu Val Trp Tyr Gln Gln Lys Pro Gly Lys Ala Pro Glu Leu Leu Met
            35                  40                  45

Tyr Gly Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Pro Tyr
            85                  90                  95

Thr Phe Gly Gln Gly Thr Lys Val Glu Ile Lys
            100                 105
```

<210> SEQ ID NO 33
<211> LENGTH: 5
<212> TYPE: PRT
<213> ORGANISM: Artificial Sequence
<220> FEATURE:
<223> OTHER INFORMATION: Synthetic construct

<400> SEQUENCE: 33

```
Ser Tyr Ala Met Ser
1               5
```

<210> SEQ ID NO 34
<211> LENGTH: 17
<212> TYPE: PRT
<213> ORGANISM: Artificial Sequence
<220> FEATURE:
<223> OTHER INFORMATION: Synthetic construct

<400> SEQUENCE: 34

```
Arg Ile Ser Asp Gly Gly Gly Thr Ile Tyr Tyr Thr Asp Ser Val Lys
```

Gly

<210> SEQ ID NO 35
<211> LENGTH: 14
<212> TYPE: PRT
<213> ORGANISM: Artificial Sequence
<220> FEATURE:
<223> OTHER INFORMATION: Synthetic construct

<400> SEQUENCE: 35

His Arg Leu Tyr Asp Ser Ile Gly Ala Tyr Ala Met Asp Val
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic construct

<400> SEQUENCE: 36

Arg Ala Ser Gln Ser Ile Ser Ser Tyr Leu Asn
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Synthetic construct

<400> SEQUENCE: 37

Asp Ala Ser Asn Leu Glu Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic construct

<400> SEQUENCE: 38

Gln Gln Ala Asn Ser Phe Pro Leu Thr
1               5

<210> SEQ ID NO 39
<211> LENGTH: 123
<212> TYPE: PRT
<213> ORGANISM: Artificial Sequence
<220> FEATURE:
<223> OTHER INFORMATION: Synthetic construct

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Asp Gly Gly Gly Thr Ile Tyr Tyr Thr Asp Ser Val
    50                  55                  60

Lys Gly Arg Phe Thr Ile Ala Arg Asp Asn Ser Lys Asn Thr Leu Tyr 65                  70                  75                  80
Leu Glu Met Lys Ser Leu Arg Ala Glu Asp Thr Ala Val Tyr Tyr Cys
                    85                  90                  95
Ala Lys His Arg Leu Tyr Asp Ser Ile Gly Ala Tyr Ala Met Asp Val
            100                 105                 110
Trp Gly Gln Gly Thr Thr Val Ala Val Ser Ser
        115                 120

<210> SEQ ID NO 40
<211> LENGTH: 107
<212> TYPE: PRT
<213> ORGANISM: Artificial Sequence
<220> FEATURE:
<223> OTHER INFORMATION: Synthetic construct

<400> SEQUENCE: 40

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Asp Ala Ser Asn Leu Glu Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro Leu
                85                  90                  95
Thr Phe Gly Pro Gly Thr Lys Val Asp Ile Lys
            100                 105

<210> SEQ ID NO 41
<211> LENGTH: 4
<212> TYPE: PRT
<213> ORGANISM: Artificial Sequence
<220> FEATURE:
<223> OTHER INFORMATION: Synthetic construct

<400> SEQUENCE: 41

Tyr Trp Met Thr
1

<210> SEQ ID NO 42
<211> LENGTH: 18
<212> TYPE: PRT
<213> ORGANISM: Artificial Sequence
<220> FEATURE:
<223> OTHER INFORMATION: Synthetic construct

<400> SEQUENCE: 42

Cys Ile His Gly Gly Asp Ser Gly Ala Thr Tyr Tyr Ala Asn Trp Val
1               5                   10                  15
Asn Gly

<210> SEQ ID NO 43
<211> LENGTH: 12
<212> TYPE: PRT
<213> ORGANISM: Artificial Sequence
<220> FEATURE:
<223> OTHER INFORMATION: Synthetic construct

<400> SEQUENCE: 43

```
Pro Gly Tyr Pro Ser Trp Ser Lys Thr Phe Asp Leu
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic construct

<400> SEQUENCE: 44

Gln Ala Ser Gln Asp Ile Ser Asn Ala Leu Asn
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic construct

<400> SEQUENCE: 45

Ala Ala Ser Thr Leu Gln Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic construct

<400> SEQUENCE: 46

Gln His Ser Asn Ser Phe Pro Leu Thr
1               5

<210> SEQ ID NO 47
<211> LENGTH: 121
<212> TYPE: PRT
<213> ORGANISM: Artificial Sequence
<220> FEATURE:
<223> OTHER INFORMATION: Synthetic construct

<400> SEQUENCE: 47

Gln Gln Leu Glu Gln Ser Gly Gly Gly Leu Val Thr Pro Gly Gly Ser
1               5                   10                  15

Leu Lys Val Cys Cys Lys Ala Ser Gly Phe Asp Phe Thr Thr Tyr Trp
            20                  25                  30

Met Thr Trp Val Arg Gln Ala Pro Glu Lys Gly Leu Glu Trp Ile Gly
        35                  40                  45

Cys Ile His Gly Gly Asp Ser Gly Ala Thr Tyr Tyr Ala Asn Trp Val
    50                  55                  60

Asn Gly Arg Phe Thr Leu Ser Arg Asp Ile Asp Gln Ser Thr Gly Cys
65                  70                  75                  80

Leu Gln Leu Asn Ser Leu Thr Ala Ala Asp Thr Ala Met Tyr Tyr Cys
                85                  90                  95

Ala Arg Pro Gly Tyr Pro Ser Trp Ser Lys Thr Phe Asp Leu Trp Gly
            100                 105                 110

Gln Gly Thr Met Val Thr Val Ser Ser
        115                 120

<210> SEQ ID NO 48
```

```
<211> LENGTH: 107
<212> TYPE: PRT
<213> ORGANISM: Artificial Sequence
<220> FEATURE:
<223> OTHER INFORMATION: Synthetic construct

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Ala
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Ser Asn Ser Phe Pro Leu
                85                  90                  95

Thr Phe Gly Gly Gly Thr Lys Val Glu Ile Lys
            100                 105

<210> SEQ ID NO 49
<211> LENGTH: 4
<212> TYPE: PRT
<213> ORGANISM: Artificial Sequence
<220> FEATURE:
<223> OTHER INFORMATION: Synthetic construct

<400> SEQUENCE: 49

Tyr Trp Met Thr
1

<210> SEQ ID NO 50
<211> LENGTH: 18
<212> TYPE: PRT
<213> ORGANISM: Artificial Sequence
<220> FEATURE:
<223> OTHER INFORMATION: Synthetic construct

<400> SEQUENCE: 50

Cys Ile His Gly Gly Gly Ser Gly Thr Thr Ser Tyr Ala Ser Trp Val
1               5                   10                  15

Asn Gly

<210> SEQ ID NO 51
<211> LENGTH: 12
<212> TYPE: PRT
<213> ORGANISM: Artificial Sequence
<220> FEATURE:
<223> OTHER INFORMATION: Synthetic construct

<400> SEQUENCE: 51

Pro Gly Tyr Arg Ser Trp Ser Lys Thr Phe Asp Leu
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic construct

<400> SEQUENCE: 52
```

Gln Ala Asn Gln Asp Ile Ser Asn Ala Leu Asn
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Synthetic construct

<400> SEQUENCE: 53

Ala Ala Ser Ser Leu Gln Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic construct

<400> SEQUENCE: 54

Gln Gln Ala Ala Ser Phe Pro Leu Thr
1               5

<210> SEQ ID NO 55
<211> LENGTH: 121
<212> TYPE: PRT
<213> ORGANISM: Artificial Sequence
<220> FEATURE:
<223> OTHER INFORMATION: Synthetic construct

<400> SEQUENCE: 55

Gln Gln Leu Glu Gln Ser Gly Gly Gly Leu Val Lys Pro Gly Gly Ser
1               5                   10                  15

Leu Glu Leu Cys Cys Ile Ala Ser Gly Phe Asp Phe Ser Thr Tyr Trp
            20                  25                  30

Met Thr Trp Val Arg Gln Ala Pro Gly Lys Gly Leu Glu Trp Ile Gly
        35                  40                  45

Cys Ile His Gly Gly Gly Ser Gly Thr Thr Ser Tyr Ala Ser Trp Val
    50                  55                  60

Asn Gly Arg Phe Thr Leu Ser Arg Asp Ile Asp Gln Ser Thr Gly Cys
65                  70                  75                  80

Leu Gln Leu Thr Ser Leu Thr Ala Ala Asp Thr Ala Met Tyr Tyr Cys
                85                  90                  95

Ala Arg Pro Gly Tyr Arg Ser Trp Ser Lys Thr Phe Asp Leu Trp Gly
            100                 105                 110

Gln Gly Thr Met Val Thr Val Ser Ser
        115                 120

<210> SEQ ID NO 56
<211> LENGTH: 107
<212> TYPE: PRT
<213> ORGANISM: Artificial Sequence
<220> FEATURE:
<223> OTHER INFORMATION: Synthetic construct

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Gln Ala Asn Gln Asp Ile Ser Asn Ala
            20                  25                  30

```
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Ala Tyr Tyr Cys Gln Gln Ala Ala Ser Phe Pro Leu
                85                  90                  95

Thr Phe Gly Gly Gly Thr Lys Val Glu Ile Lys
            100                 105
```

<210> SEQ ID NO 57
<211> LENGTH: 5
<212> TYPE: PRT
<213> ORGANISM: Artificial Sequence
<220> FEATURE:
<223> OTHER INFORMATION: Synthetic construct

<400> SEQUENCE: 57

```
Ser Tyr Ala Met Ser
1               5
```

<210> SEQ ID NO 58
<211> LENGTH: 17
<212> TYPE: PRT
<213> ORGANISM: Artificial Sequence
<220> FEATURE:
<223> OTHER INFORMATION: Synthetic construct

<400> SEQUENCE: 58

```
Ala Ile Gly Ile Gly Gly Gly Thr Tyr Tyr Ala Asp Ser Val Lys
1               5                   10                  15

Gly
```

<210> SEQ ID NO 59
<211> LENGTH: 12
<212> TYPE: PRT
<213> ORGANISM: Artificial Sequence
<220> FEATURE:
<223> OTHER INFORMATION: Synthetic construct

<400> SEQUENCE: 59

```
Gly Ala Ser Phe Asp Phe Ile Asn Phe Phe Pro Tyr
1               5                   10
```

<210> SEQ ID NO 60
<211> LENGTH: 11
<212> TYPE: PRT
<213> ORGANISM: Artificial Sequence
<220> FEATURE:
<223> OTHER INFORMATION: Synthetic construct

<400> SEQUENCE: 60

```
Arg Ala Ser Gln Gly Ile Ser Asn Asp Leu Ala
1               5                   10
```

<210> SEQ ID NO 61
<211> LENGTH: 7
<212> TYPE: PRT
<213> ORGANISM: Artificial Sequence
<220> FEATURE:
<223> OTHER INFORMATION: Synthetic construct

<400> SEQUENCE: 61

Ala Ala Ser Ser Leu Gln Ser
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic construct

<400> SEQUENCE: 62

Gln Gln Thr Tyr Ser Thr Pro Leu Thr
1               5

<210> SEQ ID NO 63
<211> LENGTH: 121
<212> TYPE: PRT
<213> ORGANISM: Artificial Sequence
<220> FEATURE:
<223> OTHER INFORMATION: Synthetic construct

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Ile Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Lys Gly Ala Ser Phe Asp Phe Ile Asn Phe Phe Pro Tyr Trp Gly
            100                 105                 110

Gln Gly Thr Leu Val Thr Val Ser Ser
        115                 120

<210> SEQ ID NO 64
<211> LENGTH: 107
<212> TYPE: PRT
<213> ORGANISM: Artificial Sequence
<220> FEATURE:
<223> OTHER INFORMATION: Synthetic construct

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gly Gly Thr Lys Val Glu Ile Lys
            100                 105

<210> SEQ ID NO 65
<211> LENGTH: 5
<212> TYPE: PRT
<213> ORGANISM: Artificial Sequence
<220> FEATURE:
<223> OTHER INFORMATION: Synthetic construct

<400> SEQUENCE: 65

Asp Tyr Ala Met Ser
1               5

<210> SEQ ID NO 66
<211> LENGTH: 17
<212> TYPE: PRT
<213> ORGANISM: Artificial Sequence
<220> FEATURE:
<223> OTHER INFORMATION: Synthetic construct

<400> SEQUENCE: 66

Tyr Asn Ser Phe Ser Val Gly Ser Thr Asp Tyr Ala Asp Ser Val Lys
1               5                   10                  15

Gly

<210> SEQ ID NO 67
<211> LENGTH: 12
<212> TYPE: PRT
<213> ORGANISM: Artificial Sequence
<220> FEATURE:
<223> OTHER INFORMATION: Synthetic construct

<400> SEQUENCE: 67

His Ser Gly Asn Tyr Tyr Thr Gly Pro Phe His Tyr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic construct

<400> SEQUENCE: 68

Arg Ala Ser Gln Gly Ile Ser Ser Tyr Leu Ala
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic construct

<400> SEQUENCE: 69

Ala Ala Ser Ser Leu Glu Ser
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic construct

<400> SEQUENCE: 70

```
Gln Gln Ser Tyr Ser Thr Pro Ile Thr
1               5
```

```
<210> SEQ ID NO 71
<211> LENGTH: 121
<212> TYPE: PRT
<213> ORGANISM: Artificial Sequence
<220> FEATURE:
<223> OTHER INFORMATION: Synthetic construct

<400> SEQUENCE: 71
```

```
Glu Val Gln Leu Leu Glu Ser Gly Gly Gly Leu Val Gln Pro Gly Gly
1               5                   10                  15

Ser Leu Arg Leu Ser Cys Ala Thr Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Tyr Asn Ser Phe Ser Val Gly Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Lys His Ser Gly Asn Tyr Tyr Thr Gly Pro Phe His Tyr Trp Gly
            100                 105                 110

Gln Gly Thr Leu Val Thr Val Ser Ser
        115                 120
```

```
<210> SEQ ID NO 72
<211> LENGTH: 107
<212> TYPE: PRT
<213> ORGANISM: Artificial Sequence
<220> FEATURE:
<223> OTHER INFORMATION: Synthetic construct

<400> SEQUENCE: 72
```

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105
```

```
<210> SEQ ID NO 73
<211> LENGTH: 5
<212> TYPE: PRT
<213> ORGANISM: Artificial Sequence
<220> FEATURE:
<223> OTHER INFORMATION: Synthetic construct

<400> SEQUENCE: 73
```

```
Thr Phe Trp Met Thr
1               5
```

<210> SEQ ID NO 74
<211> LENGTH: 17
<212> TYPE: PRT
<213> ORGANISM: Artificial Sequence
<220> FEATURE:
<223> OTHER INFORMATION: Synthetic construct

<400> SEQUENCE: 74

```
Cys Ile His Gly Gly Ser Gly Ser Arg Asp Tyr Ala Ser Trp Val Asn
1               5                   10                  15
Gly
```

<210> SEQ ID NO 75
<211> LENGTH: 12
<212> TYPE: PRT
<213> ORGANISM: Artificial Sequence
<220> FEATURE:
<223> OTHER INFORMATION: Synthetic construct

<400> SEQUENCE: 75

```
Pro Gly Tyr Arg Ser Trp Ser Lys Thr Phe Asp Leu
1               5                   10
```

<210> SEQ ID NO 76
<211> LENGTH: 11
<212> TYPE: PRT
<213> ORGANISM: Artificial Sequence
<220> FEATURE:
<223> OTHER INFORMATION: Synthetic construct

<400> SEQUENCE: 76

```
Arg Ala Ser Gln Asp Ile Ser Gly Ala Leu Asn
1               5                   10
```

<210> SEQ ID NO 77
<211> LENGTH: 7
<212> TYPE: PRT
<213> ORGANISM: Artificial Sequence
<220> FEATURE:
<223> OTHER INFORMATION: Synthetic construct

<400> SEQUENCE: 77

```
Ala Ala Ser Ser Leu Gln Ser
1               5
```

<210> SEQ ID NO 78
<211> LENGTH: 9
<212> TYPE: PRT
<213> ORGANISM: Artificial Sequence
<220> FEATURE:
<223> OTHER INFORMATION: Synthetic construct

<400> SEQUENCE: 78

```
Gln Gln Ala Asn Ser Phe Pro Leu Thr
1               5
```

<210> SEQ ID NO 79
<211> LENGTH: 121
<212> TYPE: PRT
<213> ORGANISM: Artificial Sequence
<220> FEATURE:
<223> OTHER INFORMATION: Synthetic construct

<400> SEQUENCE: 79

```
Gln Glu Gln Leu Glu Gln Ser Gly Gly Gly Leu Val Thr Pro Gly Gly
1               5                   10                  15

Ser Leu Lys Leu Cys Cys Thr Ala Ser Gly Phe Asp Phe Asn Thr Phe
            20                  25                  30

Trp Met Thr Trp Val Arg Gln Ala Pro Gly Lys Gly Leu Glu Trp Ile
        35                  40                  45

Gly Cys Ile His Gly Gly Ser Gly Ser Arg Asp Tyr Ala Ser Trp Val
    50                  55                  60

Asn Gly Arg Phe Thr Leu Ser Arg Asp Ile Asp Gln Ser Thr Ala Cys
65                  70                  75                  80

Leu Gln Val Asn Ser Leu Thr Ala Ala Asp Thr Ala Met Tyr Tyr Cys
                85                  90                  95

Ala Arg Pro Gly Tyr Arg Ser Trp Ser Lys Thr Phe Asp Leu Trp Gly
            100                 105                 110

Gln Gly Thr Met Val Thr Val Ser Ser
            115                 120
```

<210> SEQ ID NO 80
<211> LENGTH: 107
<212> TYPE: PRT
<213> ORGANISM: Artificial Sequence
<220> FEATURE:
<223> OTHER INFORMATION: Synthetic construct

<400> SEQUENCE: 80

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Gly Ala
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105
```

<210> SEQ ID NO 81
<211> LENGTH: 115
<212> TYPE: PRT
<213> ORGANISM: Artificial Sequence
<220> FEATURE:
<223> OTHER INFORMATION: Synthetic construct

<400> SEQUENCE: 81

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
```

```
                65                   70                   75                   80
Leu Gln Met Asn Ser Leu Arg Ala Glu Asp Thr Ala Val Tyr Tyr Cys
                    85                   90                   95
Ala Lys Gly Ser Gly Phe Asp Tyr Trp Gly Gln Gly Thr Leu Val Thr
                100                  105                  110
Val Ser Ser
        115
```

<210> SEQ ID NO 82
<211> LENGTH: 108
<212> TYPE: PRT
<213> ORGANISM: Artificial Sequence
<220> FEATURE:
<223> OTHER INFORMATION: Synthetic construct

<400> SEQUENCE: 82

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Leu Thr Phe Gly Gln Gly Thr Lys Val Glu Ile Lys
                100                  105
```

<210> SEQ ID NO 83
<211> LENGTH: 107
<212> TYPE: PRT
<213> ORGANISM: Homo Sapiens

<400> SEQUENCE: 83

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
                20                  25                  30
Tyr Pro Arg Glu Ala Lys Val Gln Trp Lys Val Asp Asn Ala Leu Gln
            35                  40                  45
Ser Gly Asn Ser Gln Glu Ser Val Thr Glu Gln Asp Ser Lys Asp Ser
        50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
                100                  105
```

<210> SEQ ID NO 84
<211> LENGTH: 105
<212> TYPE: PRT
<213> ORGANISM: Homo Sapiens

<400> SEQUENCE: 84

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
                35                  40                  45

Lys Ala Gly Val Glu Thr Thr Thr Pro Ser Lys Gln Ser Asn Asn Lys
50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 85
<211> LENGTH: 328
<212> TYPE: PRT
<213> ORGANISM: Homo Sapiens

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 86
<211> LENGTH: 225
<212> TYPE: PRT
<213> ORGANISM: Homo Sapiens

<400> SEQUENCE: 86

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225
```

<210> SEQ ID NO 87
<211> LENGTH: 216
<212> TYPE: PRT
<213> ORGANISM: Homo Sapiens

<400> SEQUENCE: 87

```
Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30
```

```
Arg Trp Gln Lys Gln Arg Cys Pro Val Val Lys Ser Lys Cys Arg Glu
            35                  40                  45

Asn Ala Ser Pro Phe Phe Cys Cys Phe Ile Ala Val Ala Met Gly
    50                  55                  60

Ile Arg Phe Ile Ile Met Val Ala Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
            115                 120                 125

Ser Gln Asn Ala Ser Leu Leu Lys Val Tyr Ser Lys Glu Asp Gln Asp
        130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
        195                 200                 205

Tyr Ile Cys Met Gln Arg Thr Val
            210                 215

<210> SEQ ID NO 88
<211> LENGTH: 137
<212> TYPE: PRT
<213> ORGANISM: Homo Sapiens

<400> SEQUENCE: 88

Asn Ser Leu Phe Asn Gln Glu Val Gln Ile Pro Leu Thr Glu Ser Tyr
1               5                   10                  15

Cys Gly Pro Cys Pro Lys Asn Trp Ile Cys Tyr Lys Asn Asn Cys Tyr
            20                  25                  30

Gln Phe Phe Asp Glu Ser Lys Asn Trp Tyr Glu Ser Gln Ala Ser Cys
        35                  40                  45

Met Ser Gln Asn Ala Ser Leu Leu Lys Val Tyr Ser Lys Glu Asp Gln
    50                  55                  60

Asp Leu Leu Lys Leu Val Lys Ser Tyr His Trp Met Gly Leu Val His
65                  70                  75                  80

Ile Pro Thr Asn Gly Ser Trp Gln Trp Glu Asp Gly Ser Ile Leu Ser
                85                  90                  95

Pro Asn Leu Leu Thr Ile Ile Glu Met Gln Lys Gly Asp Cys Ala Leu
            100                 105                 110

Tyr Ala Ser Ser Phe Lys Gly Tyr Ile Glu Asn Cys Ser Thr Pro Asn
        115                 120                 125

Thr Tyr Ile Cys Met Gln Arg Thr Val
    130                 135

<210> SEQ ID NO 89
<211> LENGTH: 216
<212> TYPE: PRT
<213> ORGANISM: Macaca Fascicularis

<400> SEQUENCE: 89
```

```
Met Gly Trp Ile Arg Gly Arg Pro Arg His Asn Leu Glu Met Ser
1               5                   10                  15

Glu Phe His Asn Tyr Lys Leu Gly Leu Ala Lys Ser Asp Phe Ser Thr
                20                  25                  30

Arg Cys Gln Lys Gln Arg Cys Pro Val Ile Lys Ser Lys Cys Arg Glu
            35                  40                  45

Asn Ala Ser Pro Leu Phe Phe Cys Phe Ile Ala Val Ala Met Gly
        50                  55                  60

Ile Arg Phe Ile Ile Met Val Thr Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
                100                 105                 110

Phe Phe Asn Glu Ser Lys Asn Trp Tyr Glu Ser Gln Ala Ser Cys Met
            115                 120                 125

Ser Gln Asn Ala Ser Leu Leu Lys Val Tyr Ser Lys Glu Asp Gln Asp
130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
                180                 185                 190

Ala Ser Ser Phe Lys Gly Tyr Ile Glu Asn Cys Ser Ile Pro Asn Thr
                195                 200                 205

Tyr Ile Cys Met Gln Arg Thr Val
        210                 215

<210> SEQ ID NO 90
<211> LENGTH: 137
<212> TYPE: PRT
<213> ORGANISM: Macaca Fascicularis

<400> SEQUENCE: 90

Asn Ser Leu Phe Asn Gln Glu Val Gln Ile Pro Leu Thr Glu Ser Tyr
1               5                   10                  15

Cys Gly Pro Cys Pro Lys Asn Trp Ile Cys Tyr Lys Asn Asn Cys Tyr
                20                  25                  30

Gln Phe Phe Asn Glu Ser Lys Asn Trp Tyr Glu Ser Gln Ala Ser Cys
            35                  40                  45

Met Ser Gln Asn Ala Ser Leu Leu Lys Val Tyr Ser Lys Glu Asp Gln
50                  55                  60

Asp Leu Leu Lys Leu Val Lys Ser Tyr His Trp Met Gly Leu Val His
65                  70                  75                  80

Ile Pro Thr Asn Gly Ser Trp Gln Trp Glu Asp Gly Ser Ile Leu Ser
                85                  90                  95

Pro Asn Leu Leu Thr Ile Ile Glu Met Gln Lys Gly Asp Cys Ala Leu
                100                 105                 110

Tyr Ala Ser Ser Phe Lys Gly Tyr Ile Glu Asn Cys Ser Ile Pro Asn
            115                 120                 125

Thr Tyr Ile Cys Met Gln Arg Thr Val
130                 135
```

<210> SEQ ID NO 91
<211> LENGTH: 232
<212> TYPE: PRT
<213> ORGANISM: Mus Musculus

<400> SEQUENCE: 91

Met Ala Leu Ile Arg Asp Arg Lys Ser His His Ser Glu Met Ser Lys
1               5                   10                  15

Cys His Asn Tyr Asp Leu Lys Pro Ala Lys Trp Asp Thr Ser Gln Glu
                20                  25                  30

Gln Gln Lys Gln Arg Leu Ala Leu Thr Thr Ser Gln Pro Gly Glu Asn
            35                  40                  45

Gly Ile Ile Arg Gly Arg Tyr Pro Ile Glu Lys Leu Lys Ile Ser Pro
        50                  55                  60

Met Phe Val Val Arg Val Leu Ala Ile Ala Leu Ala Ile Arg Phe Thr
65                  70                  75                  80

Leu Asn Thr Leu Met Trp Leu Ala Ile Phe Lys Glu Thr Phe Gln Pro
                85                  90                  95

Val Leu Cys Asn Lys Glu Val Pro Val Ser Ser Arg Glu Gly Tyr Cys
            100                 105                 110

Gly Pro Cys Pro Asn Asn Trp Ile Cys His Arg Asn Asn Cys Tyr Gln
        115                 120                 125

Phe Phe Asn Glu Glu Lys Thr Trp Asn Gln Ser Gln Ala Ser Cys Leu
130                 135                 140

Ser Gln Asn Ser Ser Leu Leu Lys Ile Tyr Ser Lys Glu Glu Gln Asp
145                 150                 155                 160

Phe Leu Lys Leu Val Lys Ser Tyr His Trp Met Gly Leu Val Gln Ile
                165                 170                 175

Pro Ala Asn Gly Ser Trp Gln Trp Glu Asp Gly Ser Ser Leu Ser Tyr
            180                 185                 190

Asn Gln Leu Thr Leu Val Glu Ile Pro Lys Gly Ser Cys Ala Val Tyr
        195                 200                 205

Gly Ser Ser Phe Lys Ala Tyr Thr Glu Asp Cys Ala Asn Leu Asn Thr
210                 215                 220

Tyr Ile Cys Met Lys Arg Ala Val
225                 230

<210> SEQ ID NO 92
<211> LENGTH: 133
<212> TYPE: PRT
<213> ORGANISM: Mus Musculus

<400> SEQUENCE: 92

Asn Lys Glu Val Pro Val Ser Ser Arg Glu Gly Tyr Cys Gly Pro Cys
1               5                   10                  15

Pro Asn Asn Trp Ile Cys His Arg Asn Asn Cys Tyr Gln Phe Phe Asn
                20                  25                  30

Glu Glu Lys Thr Trp Asn Gln Ser Gln Ala Ser Cys Leu Ser Gln Asn
            35                  40                  45

Ser Ser Leu Leu Lys Ile Tyr Ser Lys Glu Glu Gln Asp Phe Leu Lys
        50                  55                  60

Leu Val Lys Ser Tyr His Trp Met Gly Leu Val Gln Ile Pro Ala Asn
65                  70                  75                  80

Gly Ser Trp Gln Trp Glu Asp Gly Ser Ser Leu Ser Tyr Asn Gln Leu
                85                  90                  95

Thr Leu Val Glu Ile Pro Lys Gly Ser Cys Ala Val Tyr Gly Ser Ser

```
                    100                 105                 110
Phe Lys Ala Tyr Thr Glu Asp Cys Ala Asn Leu Asn Thr Tyr Ile Cys
        115                 120                 125

Met Lys Arg Ala Val
        130

<210> SEQ ID NO 93
<211> LENGTH: 165
<212> TYPE: PRT
<213> ORGANISM: Artificial Sequence
<220> FEATURE:
<223> OTHER INFORMATION: Synthetic construct

<400> SEQUENCE: 93

His His His His His Gly Ser Gly Leu Asn Asp Ile Phe Glu Ala
1               5                   10                  15

Gln Lys Ile Glu Trp His Glu Gly Gly Gly Ser Asn Ser Leu Phe
            20                  25                  30

Asn Gln Glu Val Gln Ile Pro Leu Thr Glu Ser Tyr Cys Gly Pro Cys
        35                  40                  45

Pro Lys Asn Trp Ile Cys Tyr Lys Asn Asn Cys Tyr Gln Phe Phe Asp
    50                  55                  60

Glu Ser Lys Asn Trp Tyr Glu Ser Gln Ala Ser Cys Met Ser Gln Asn
65                  70                  75                  80

Ala Ser Leu Leu Lys Val Tyr Ser Lys Glu Asp Gln Asp Leu Leu Lys
                85                  90                  95

Leu Val Lys Ser Tyr His Trp Met Gly Leu Val His Ile Pro Thr Asn
            100                 105                 110

Gly Ser Trp Gln Trp Glu Asp Gly Ser Ile Leu Ser Pro Asn Leu Leu
        115                 120                 125

Thr Ile Ile Glu Met Gln Lys Gly Asp Cys Ala Leu Tyr Ala Ser Ser
    130                 135                 140

Phe Lys Gly Tyr Ile Glu Asn Cys Ser Thr Pro Asn Thr Tyr Ile Cys
145                 150                 155                 160

Met Gln Arg Thr Val
                165

<210> SEQ ID NO 94
<211> LENGTH: 388
<212> TYPE: PRT
<213> ORGANISM: Artificial Sequence
<220> FEATURE:
<223> OTHER INFORMATION: Synthetic construct

<400> SEQUENCE: 94

Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95
```

Val Val Ser Val Leu Thr Val Leu His Gln Asp Trp Leu Asn Gly Lys
                100                 105                 110

Glu Tyr Lys Cys Lys Val Ser Asn Lys Ala Leu Pro Ala Pro Ile Glu
            115                 120                 125

Lys Thr Ile Ser Lys Ala Lys Gly Gln Pro Arg Glu Pro Gln Val Tyr
        130                 135                 140

Thr Leu Pro Pro Cys Arg Asp Glu Leu Thr Lys Asn Gln Val Ser Leu
145                 150                 155                 160

Trp Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
210                 215                 220

Glu Ala Leu His Asn His Tyr Thr Gln Lys Ser Leu Ser Leu Ser Pro
225                 230                 235                 240

Gly Gly Gly Gly Ser Gly Gly Gly Ser Asn Ser Leu Phe Asn
                245                 250                 255

Gln Glu Val Gln Ile Pro Leu Thr Glu Ser Tyr Cys Gly Pro Cys Pro
            260                 265                 270

Lys Asn Trp Ile Cys Tyr Lys Asn Asn Cys Tyr Gln Phe Phe Asp Glu
        275                 280                 285

Ser Lys Asn Trp Tyr Glu Ser Gln Ala Ser Cys Met Ser Gln Asn Ala
        290                 295                 300

Ser Leu Leu Lys Val Tyr Ser Lys Glu Asp Gln Asp Leu Leu Lys Leu
305                 310                 315                 320

Val Lys Ser Tyr His Trp Met Gly Leu Val His Ile Pro Thr Asn Gly
                325                 330                 335

Ser Trp Gln Trp Glu Asp Gly Ser Ile Leu Ser Pro Asn Leu Leu Thr
            340                 345                 350

Ile Ile Glu Met Gln Lys Gly Asp Cys Ala Leu Tyr Ala Ser Ser Phe
        355                 360                 365

Lys Gly Tyr Ile Glu Asn Cys Ser Thr Pro Asn Thr Tyr Ile Cys Met
    370                 375                 380

Gln Arg Thr Val
385

<210> SEQ ID NO 95
<211> LENGTH: 227
<212> TYPE: PRT
<213> ORGANISM: Artificial Sequence
<220> FEATURE:
<223> OTHER INFORMATION: Synthetic construct

<400> SEQUENCE: 95

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Phe Thr Gln Lys Ser Leu Ser Leu Ser
210                 215                 220

Pro Gly Lys
225

<210> SEQ ID NO 96
<211> LENGTH: 388
<212> TYPE: PRT
<213> ORGANISM: Artificial Sequence
<220> FEATURE:
<223> OTHER INFORMATION: Synthetic construct

<400> SEQUENCE: 96

Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
                20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
 50                  55                  60

Asp Pro Glu Val Lys Phe Asn Trp Tyr Val Asp Gly Val Glu Val His
 65                  70                  75                  80

Asn Ala Lys Thr Lys Pro Arg Glu Glu Gln Tyr Asn Ser Thr Tyr Arg
                 85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Gly Ala Pro Ile Glu
        115                 120                 125

Lys Thr Ile Ser Lys Ala Lys Gly Gln Pro Arg Glu Pro Gln Val Tyr
130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
            195                 200                 205

Lys Ser Arg Trp Gln Gln Gly Asn Val Phe Ser Cys Ser Val Met His
210                 215                 220

Glu Ala Leu His Asn His Tyr Thr Gln Lys Ser Leu Ser Leu Ser Pro
225                 230                 235                 240

Gly Gly Gly Gly Ser Gly Gly Gly Ser Asn Ser Leu Phe Asn
            245                 250                 255

Gln Glu Val Gln Ile Pro Leu Thr Glu Ser Tyr Cys Gly Pro Cys Pro
            260                 265                 270

Lys Asn Trp Ile Cys Tyr Lys Asn Asn Cys Tyr Gln Phe Phe Asp Glu
            275                 280                 285

Ser Lys Asn Trp Tyr Glu Ser Gln Ala Ser Cys Met Ser Gln Asn Ala
            290                 295                 300

Ser Leu Leu Lys Val Tyr Ser Lys Glu Asp Gln Asp Leu Leu Lys Leu
305                 310                 315                 320

Val Lys Ser Tyr His Trp Met Gly Leu Val His Ile Pro Thr Asn Gly
                325                 330                 335

Ser Trp Gln Trp Glu Asp Gly Ser Ile Leu Ser Pro Asn Leu Leu Thr
            340                 345                 350

Ile Ile Glu Met Gln Lys Gly Asp Cys Ala Leu Tyr Ala Ser Ser Phe
355                 360                 365

Lys Gly Tyr Ile Glu Asn Cys Ser Thr Pro Asn Thr Tyr Ile Cys Met
            370                 375                 380

Gln Arg Thr Val
385

<210> SEQ ID NO 97
<211> LENGTH: 388
<212> TYPE: PRT
<213> ORGANISM: Artificial Sequence
<220> FEATURE:
<223> OTHER INFORMATION: Synthetic construct

<400> SEQUENCE: 97

Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Gly Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

```
Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
210                 215                 220

Glu Ala Leu His Asn His Tyr Thr Gln Lys Ser Leu Ser Leu Ser Pro
225                 230                 235                 240

Gly Gly Gly Gly Ser Gly Gly Gly Ser Asn Ser Leu Phe Asn
                245                 250                 255

Gln Glu Val Gln Ile Pro Leu Thr Glu Ser Tyr Cys Gly Pro Cys Pro
            260                 265                 270

Lys Asn Trp Ile Cys Tyr Lys Asn Asn Cys Tyr Gln Phe Phe Asn Glu
        275                 280                 285

Ser Lys Asn Trp Tyr Glu Ser Gln Ala Ser Cys Met Ser Gln Asn Ala
    290                 295                 300

Ser Leu Leu Lys Val Tyr Ser Lys Glu Asp Gln Asp Leu Leu Lys Leu
305                 310                 315                 320

Val Lys Ser Tyr His Trp Met Gly Leu Val His Ile Pro Thr Asn Gly
                325                 330                 335

Ser Trp Gln Trp Glu Asp Gly Ser Ile Leu Ser Pro Asn Leu Leu Thr
            340                 345                 350

Ile Ile Glu Met Gln Lys Gly Asp Cys Ala Leu Tyr Ala Ser Ser Phe
        355                 360                 365

Lys Gly Tyr Ile Glu Asn Cys Ser Ile Pro Asn Thr Tyr Ile Cys Met
370                 375                 380

Gln Arg Thr Val
385

<210> SEQ ID NO 98
<211> LENGTH: 384
<212> TYPE: PRT
<213> ORGANISM: Artificial Sequence
<220> FEATURE:
<223> OTHER INFORMATION: Synthetic construct

<400> SEQUENCE: 98

Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Gly Ala Pro Ile Glu
        115                 120                 125
```

Lys Thr Ile Ser Lys Ala Lys Gly Gln Pro Arg Glu Pro Gln Val Tyr
130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
210                 215                 220

Glu Ala Leu His Asn His Tyr Thr Gln Lys Ser Leu Ser Leu Ser Pro
225                 230                 235                 240

Gly Gly Gly Gly Ser Gly Gly Gly Ser Asn Lys Glu Val Pro
                245                 250                 255

Val Ser Ser Arg Glu Gly Tyr Cys Gly Pro Cys Pro Asn Asn Trp Ile
                260                 265                 270

Cys His Arg Asn Asn Cys Tyr Gln Phe Phe Asn Glu Glu Lys Thr Trp
                275                 280                 285

Asn Gln Ser Gln Ala Ser Cys Leu Ser Gln Asn Ser Ser Leu Leu Lys
            290                 295                 300

Ile Tyr Ser Lys Glu Glu Gln Asp Phe Leu Lys Leu Val Lys Ser Tyr
305                 310                 315                 320

His Trp Met Gly Leu Val Gln Ile Pro Ala Asn Gly Ser Trp Gln Trp
                325                 330                 335

Glu Asp Gly Ser Ser Leu Ser Tyr Asn Gln Leu Thr Leu Val Glu Ile
            340                 345                 350

Pro Lys Gly Ser Cys Ala Val Tyr Gly Ser Ser Phe Lys Ala Tyr Thr
        355                 360                 365

Glu Asp Cys Ala Asn Leu Asn Thr Tyr Ile Cys Met Lys Arg Ala Val
370                 375                 380

<210> SEQ ID NO 99
<211> LENGTH: 374
<212> TYPE: PRT
<213> ORGANISM: Artificial Sequence
<220> FEATURE:
<223> OTHER INFORMATION: Synthetic construct

<400> SEQUENCE: 99

Asp Gly Cys Lys Pro Cys Ile Cys Thr Val Pro Glu Val Ser Ser Val
1               5                   10                  15

Phe Ile Phe Pro Pro Lys Pro Lys Asp Val Leu Thr Ile Thr Leu Thr
                20                  25                  30

Pro Lys Val Thr Cys Val Val Asp Ile Ser Lys Asp Ala Pro Glu
            35                  40                  45

Val Gln Phe Ser Trp Phe Val Asp Asp Val Glu Val His Thr Ala Gln
    50                  55                  60

Thr Gln Pro Arg Glu Glu Gln Phe Asn Ser Thr Phe Arg Ser Val Ser
65                  70                  75                  80

Glu Leu Pro Ile Met His Gln Asp Trp Leu Asn Gly Lys Glu Phe Lys
                85                  90                  95

Cys Arg Val Asn Ser Ala Ala Phe Gly Ala Pro Ile Glu Lys Thr Ile
                100                 105                 110

```
Ser Lys Thr Lys Gly Arg Pro Lys Ala Pro Gln Val Tyr Thr Ile Pro
            115                 120                 125

Pro Pro Lys Glu Gln Met Ala Lys Asp Lys Val Ser Leu Thr Cys Met
130                 135                 140

Ile Thr Asp Phe Phe Pro Glu Asp Ile Thr Val Glu Trp Gln Trp Asn
145                 150                 155                 160

Gly Gln Pro Ala Glu Asn Tyr Lys Asn Thr Gln Pro Ile Met Asp Thr
                165                 170                 175

Asp Gly Ser Tyr Phe Val Tyr Ser Lys Leu Asn Val Gln Lys Ser Asn
                180                 185                 190

Trp Glu Ala Gly Asn Thr Phe Thr Cys Ser Val Leu His Glu Gly Leu
            195                 200                 205

His Asn His His Thr Glu Lys Ser Leu Ser His Ser Pro Gly Gly Gly
    210                 215                 220

Gly Gly Ser Gly Gly Gly Gly Ser Gly Gly Gly Gly Ser Asn Ser Leu
225                 230                 235                 240

Phe Asn Gln Glu Val Gln Ile Pro Leu Thr Glu Ser Tyr Cys Gly Pro
                245                 250                 255

Cys Pro Lys Asn Trp Ile Cys Tyr Lys Asn Asn Cys Tyr Gln Phe Phe
                260                 265                 270

Asp Glu Ser Lys Asn Trp Tyr Glu Ser Gln Ala Ser Cys Met Ser Gln
            275                 280                 285

Asn Ala Ser Leu Leu Lys Val Tyr Ser Lys Glu Asp Gln Asp Leu Leu
    290                 295                 300

Lys Leu Val Lys Ser Tyr His Trp Met Gly Leu Val His Ile Pro Thr
305                 310                 315                 320

Asn Gly Ser Trp Gln Trp Glu Asp Gly Ser Ile Leu Ser Pro Asn Leu
                325                 330                 335

Leu Thr Ile Ile Glu Met Gln Lys Gly Asp Cys Ala Leu Tyr Ala Ser
                340                 345                 350

Ser Phe Lys Gly Tyr Ile Glu Asn Cys Ser Thr Pro Asn Thr Tyr Ile
            355                 360                 365

Cys Met Gln Arg Thr Val
    370

<210> SEQ ID NO 100
<211> LENGTH: 548
<212> TYPE: PRT
<213> ORGANISM: Artificial Sequence
<220> FEATURE:
<223> OTHER INFORMATION: Synthetic construct

<400> SEQUENCE: 100

Ala Glu Pro His Ser Leu Arg Tyr Asn Leu Met Val Leu Ser Gln Asp
1               5                   10                  15

Glu Ser Val Gln Ser Gly Phe Leu Ala Glu Gly His Leu Asp Gly Gln
            20                  25                  30

Pro Phe Leu Arg Tyr Asp Arg Gln Lys Arg Arg Ala Lys Pro Gln Gly
        35                  40                  45

Gln Trp Ala Glu Asp Val Leu Gly Ala Lys Thr Trp Asp Thr Glu Thr
    50                  55                  60

Glu Asp Leu Thr Glu Asn Gly Gln Asp Leu Arg Arg Thr Leu Thr His
65                  70                  75                  80

Ile Lys Asp Gln Lys Gly Gly Leu His Ser Leu Gln Glu Ile Arg Val
                85                  90                  95
```

```
Cys Glu Ile His Glu Asp Ser Ser Thr Arg Gly Ser Arg His Phe Tyr
                100                 105                 110
Tyr Asp Gly Glu Leu Phe Leu Ser Gln Asn Leu Glu Thr Gln Glu Ser
            115                 120                 125
Thr Val Pro Gln Ser Ser Arg Ala Gln Thr Leu Ala Met Asn Val Thr
        130                 135                 140
Asn Phe Trp Lys Glu Asp Ala Met Lys Thr Lys Thr His Tyr Arg Ala
145                 150                 155                 160
Met Gln Ala Asp Cys Leu Gln Lys Leu Gln Arg Tyr Leu Lys Ser Gly
                165                 170                 175
Val Ala Ile Arg Arg Thr Val Pro Pro Met Val Asn Val Thr Ser Ser
            180                 185                 190
Glu Val Ser Glu Gly Asn Ile Thr Val Thr Cys Arg Ala Ser Ser Phe
        195                 200                 205
Tyr Pro Arg Asn Ile Thr Leu Thr Trp Arg Gln Asp Gly Val Ser Leu
    210                 215                 220
Ser His Asn Thr Gln Gln Trp Gly Asp Val Leu Pro Asp Gly Asn Gly
225                 230                 235                 240
Thr Tyr Gln Thr Trp Val Ala Thr Arg Ile Arg Gln Gly Glu Glu Gln
                245                 250                 255
Arg Phe Thr Cys Tyr Met Glu His Ser Gly Asn His Gly Thr His Pro
            260                 265                 270
Val Pro Ser Gly Lys Val Leu Val Leu Gln Ser Gln Arg Thr Val Asp
        275                 280                 285
Ala Ser Gly Gly Ser Pro Thr Pro Thr Pro Gly Gly Gly Ser Ala
290                 295                 300
Asp Lys Thr His Thr Cys Pro Pro Cys Pro Ala Pro Glu Ala Ala Gly
305                 310                 315                 320
Gly Pro Ser Val Phe Leu Phe Pro Pro Lys Pro Lys Asp Thr Leu Met
                325                 330                 335
Ile Ser Arg Thr Pro Glu Val Thr Cys Val Val Val Asp Val Ser His
            340                 345                 350
Glu Asp Pro Glu Val Lys Phe Asn Trp Tyr Val Asp Gly Val Glu Val
        355                 360                 365
His Asn Ala Lys Thr Lys Pro Arg Glu Glu Gln Tyr Asn Ser Thr Tyr
    370                 375                 380
Arg Val Val Ser Val Leu Thr Val Leu His Gln Asp Trp Leu Asn Gly
385                 390                 395                 400
Lys Glu Tyr Lys Cys Lys Val Ser Asn Lys Ala Leu Gly Ala Pro Ile
                405                 410                 415
Glu Lys Thr Ile Ser Lys Ala Lys Gly Gln Pro Arg Glu Pro Gln Val
            420                 425                 430
Tyr Thr Leu Pro Pro Cys Arg Asp Glu Leu Thr Lys Asn Gln Val Ser
        435                 440                 445
Leu Trp Cys Leu Val Lys Gly Phe Tyr Pro Ser Asp Ile Ala Val Glu
    450                 455                 460
Trp Glu Ser Asn Gly Gln Pro Glu Asn Asn Tyr Lys Thr Thr Pro Pro
465                 470                 475                 480
Val Leu Asp Ser Asp Gly Ser Phe Phe Leu Tyr Ser Lys Leu Thr Val
                485                 490                 495
Asp Lys Ser Arg Trp Gln Gln Gly Asn Val Phe Ser Cys Ser Val Met
            500                 505                 510
His Glu Ala Leu His Asn His Tyr Thr Gln Lys Ser Leu Ser Leu Ser
```

```
                    515                 520                 525
Pro Gly Lys Ser Gly Gly Leu Asn Asp Ile Phe Glu Ala Gln Lys Ile
    530                 535                 540
Glu Trp His Glu
545
```

<210> SEQ ID NO 101
<211> LENGTH: 227
<212> TYPE: PRT
<213> ORGANISM: Artificial Sequence
<220> FEATURE:
<223> OTHER INFORMATION: Synthetic construct

<400> SEQUENCE: 101

```
Asp Lys Thr His Thr Cys Pro Pro Cys Pro Ala Pro Glu Ala Ala Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Gly Ala Pro Ile
            100                 105                 110
Glu Lys Thr Ile Ser Lys Ala Lys Gly Gln Pro Arg Glu Pro Gln Val
        115                 120                 125
Cys Thr Leu Pro Pro Ser Arg Asp Glu Leu Thr Lys Asn Gln Val Ser
130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn Arg Phe Thr Gln Lys Ser Leu Ser Leu Ser
    210                 215                 220
Pro Gly Lys
225
```

<210> SEQ ID NO 102
<211> LENGTH: 17
<212> TYPE: PRT
<213> ORGANISM: Artificial Sequence
<220> FEATURE:
<223> OTHER INFORMATION: Synthetic construct

<400> SEQUENCE: 102

```
Ser Ile His Gly Gly Ser Gly Ser Arg Asp Tyr Ala Ser Trp Val Asn
1               5                   10                  15
Gly
```

<210> SEQ ID NO 103
<211> LENGTH: 17
<212> TYPE: PRT
<213> ORGANISM: Artificial Sequence
<220> FEATURE:
<223> OTHER INFORMATION: Synthetic construct

<400> SEQUENCE: 103

Ser Ile His Gly Gly Ser Gly Ser Arg Asp Tyr Ala Asp Ser Val Lys
1               5                   10                  15
Gly

<210> SEQ ID NO 104
<211> LENGTH: 17
<212> TYPE: PRT
<213> ORGANISM: Artificial Sequence
<220> FEATURE:
<223> OTHER INFORMATION: Synthetic construct

<400> SEQUENCE: 104

Ser Ile His Gly Gly Ser Gly Ser Arg Asp Tyr Ser Pro Ser Phe Gln
1               5                   10                  15
Gly

<210> SEQ ID NO 105
<211> LENGTH: 17
<212> TYPE: PRT
<213> ORGANISM: Artificial Sequence
<220> FEATURE:
<223> OTHER INFORMATION: Synthetic construct

<400> SEQUENCE: 105

Ser Ile His Gly Gly Ser Gly Ser Arg Asp Tyr Asn Pro Ser Leu Lys
1               5                   10                  15
Ser

<210> SEQ ID NO 106
<211> LENGTH: 121
<212> TYPE: PRT
<213> ORGANISM: Artificial Sequence
<220> FEATURE:
<223> OTHER INFORMATION: Synthetic construct

<400> SEQUENCE: 106

Gln Glu Gln Leu Glu Gln Ser Gly Gly Gly Leu Val Thr Pro Gly Gly
1               5                   10                  15

Ser Leu Lys Leu Cys Cys Thr Ala Ser Gly Phe Asp Phe Asn Thr Phe
            20                  25                  30

Trp Met Thr Trp Val Arg Gln Ala Pro Gly Lys Gly Leu Glu Trp Ile
        35                  40                  45

Gly Ser Ile His Gly Gly Ser Gly Ser Arg Asp Tyr Ala Ser Trp Val
    50                  55                  60

Asn Gly Arg Phe Thr Leu Ser Arg Asp Ile Asp Gln Ser Thr Ala Cys
65                  70                  75                  80

Leu Gln Val Asn Ser Leu Thr Ala Ala Asp Thr Ala Met Tyr Tyr Cys
                85                  90                  95

Ala Arg Pro Gly Tyr Arg Ser Trp Ser Lys Thr Phe Asp Leu Trp Gly
            100                 105                 110

Gln Gly Thr Met Val Thr Val Ser Ser
        115                 120

```
<210> SEQ ID NO 107
<211> LENGTH: 121
<212> TYPE: PRT
<213> ORGANISM: Artificial Sequence
<220> FEATURE:
<223> OTHER INFORMATION: Synthetic construct

<400> SEQUENCE: 107
```

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Asp | Phe | Asn | Thr | Phe |
|     |     |     | 20  |     |     |     |     | 25  |     |     |     |     | 30  |     |     |

| Trp | Met | Thr | Trp | Val | Arg | Gln | Ala | Pro | Gly | Lys | Gly | Leu | Glu | Trp | Val |
|     |     | 35  |     |     |     |     | 40  |     |     |     |     | 45  |     |     |     |

| Gly | Ser | Ile | His | Gly | Gly | Ser | Gly | Ser | Arg | Asp | Tyr | Ala | Asp | Ser | Val |
|     | 50  |     |     |     |     | 55  |     |     |     |     | 60  |     |     |     |     |

| Lys | Gly | Arg | Phe | Thr | Ile | Ser | Arg | Asp | Asn | Ser | Lys | Asn | Thr | Leu | Tyr |
| 65  |     |     |     |     | 70  |     |     |     |     | 75  |     |     |     |     | 80  |

| Leu | Gln | Met | Asn | Ser | Leu | Arg | Ala | Glu | Asp | Thr | Ala | Val | Tyr | Tyr | Cys |
|     |     |     |     | 85  |     |     |     |     | 90  |     |     |     |     | 95  |     |

| Ala | Arg | Pro | Gly | Tyr | Arg | Ser | Trp | Ser | Lys | Thr | Phe | Asp | Leu | Trp | Gly |
|     |     |     | 100 |     |     |     |     | 105 |     |     |     |     | 110 |     |     |

| Gln | Gly | Thr | Thr | Val | Thr | Val | Ser | Ser |
|     |     |     | 115 |     |     |     |     | 120 |

```
<210> SEQ ID NO 108
<211> LENGTH: 121
<212> TYPE: PRT
<213> ORGANISM: Artificial Sequence
<220> FEATURE:
<223> OTHER INFORMATION: Synthetic construct

<400> SEQUENCE: 108
```

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Asp | Phe | Asn | Thr | Phe |
|     |     |     | 20  |     |     |     |     | 25  |     |     |     |     | 30  |     |     |

| Trp | Met | Thr | Trp | Val | Arg | Gln | Ala | Pro | Gly | Lys | Gly | Leu | Glu | Trp | Val |
|     |     | 35  |     |     |     |     | 40  |     |     |     |     | 45  |     |     |     |

| Gly | Ser | Ile | His | Gly | Gly | Ser | Gly | Ser | Arg | Asp | Tyr | Ala | Asp | Ser | Val |
|     | 50  |     |     |     |     | 55  |     |     |     |     | 60  |     |     |     |     |

| Lys | Gly | Arg | Phe | Thr | Ile | Ser | Arg | Asp | Asn | Ser | Lys | Asn | Thr | Ala | Tyr |
| 65  |     |     |     |     | 70  |     |     |     |     | 75  |     |     |     |     | 80  |

| Leu | Gln | Met | Asn | Ser | Leu | Arg | Ala | Glu | Asp | Thr | Ala | Val | Tyr | Tyr | Cys |
|     |     |     |     | 85  |     |     |     |     | 90  |     |     |     |     | 95  |     |

| Ala | Arg | Pro | Gly | Tyr | Arg | Ser | Trp | Ser | Lys | Thr | Phe | Asp | Leu | Trp | Gly |
|     |     |     | 100 |     |     |     |     | 105 |     |     |     |     | 110 |     |     |

| Gln | Gly | Thr | Thr | Val | Thr | Val | Ser | Ser |
|     |     |     | 115 |     |     |     |     | 120 |

```
<210> SEQ ID NO 109
<211> LENGTH: 121
<212> TYPE: PRT
<213> ORGANISM: Artificial Sequence
<220> FEATURE:
<223> OTHER INFORMATION: Synthetic construct

<400> SEQUENCE: 109
```

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ser Leu Arg Leu Ser Cys Ala Ala Ser Gly Phe Asp Phe Asn Thr Phe
            20                  25                  30

Trp Met Thr Trp Val Arg Gln Ala Pro Gly Lys Gly Leu Glu Trp Val
        35                  40                  45

Gly Ser Ile His Gly Gly Ser Gly Ser Arg Asp Tyr Ala Asp Ser Val
    50                  55                  60

Lys Gly Arg Phe Thr Ile Ser Arg Asp Ile Asp Gln Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr Arg Ser Trp Ser Lys Thr Phe Asp Leu Trp Gly
            100                 105                 110

Gln Gly Thr Thr Val Thr Val Ser Ser
            115                 120

<210> SEQ ID NO 110
<211> LENGTH: 121
<212> TYPE: PRT
<213> ORGANISM: Artificial Sequence
<220> FEATURE:
<223> OTHER INFORMATION: Synthetic construct

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Asn Thr Phe
            20                  25                  30

Trp Met Thr Trp Val Arg Gln Ala Pro Gly Lys Gly Leu Glu Trp Val
        35                  40                  45

Gly Ser Ile His Gly Gly Ser Gly Ser Arg Asp Tyr Ala Asp Ser Val
    50                  55                  60

Lys Gly Arg Phe Thr Ile Ser Ala Asp Ile Asp Gln Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr Arg Ser Trp Ser Lys Thr Phe Asp Leu Trp Gly
            100                 105                 110

Gln Gly Thr Thr Val Thr Val Ser Ser
            115                 120

<210> SEQ ID NO 111
<211> LENGTH: 121
<212> TYPE: PRT
<213> ORGANISM: Artificial Sequence
<220> FEATURE:
<223> OTHER INFORMATION: Synthetic construct

<400> SEQUENCE: 111

Gln Glu Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Thr Phe
            20                  25                  30

Trp Met Thr Trp Val Arg Gln Ala Pro Gly Lys Gly Leu Glu Trp Val
        35                  40                  45

Gly Ser Ile His Gly Gly Ser Gly Ser Arg Asp Tyr Ala Asp Ser Val
    50                  55                  60

Lys Gly Arg Phe Thr Ile Ser Arg Asp Ile Asp Gln Ser Thr Ala Tyr

```
                65                  70                  75                  80
Leu Gln Met Asn Ser Leu Arg Ala Glu Asp Thr Ala Val Tyr Tyr Cys
                    85                  90                  95

Ala Arg Pro Gly Tyr Arg Ser Trp Ser Lys Thr Phe Asp Leu Trp Gly
                100                 105                 110

Gln Gly Thr Thr Val Thr Val Ser Ser
        115                 120
```

```
<210> SEQ ID NO 112
<211> LENGTH: 121
<212> TYPE: PRT
<213> ORGANISM: Artificial Sequence
<220> FEATURE:
<223> OTHER INFORMATION: Synthetic construct

<400> SEQUENCE: 112

Gln Glu Gln Leu Val Gln Ser Gly Ala Glu Val Lys Lys Pro Gly Glu
1               5                   10                  15

Ser Leu Lys Ile Ser Cys Lys Gly Ser Gly Phe Asp Phe Asn Thr Phe
                20                  25                  30

Trp Met Thr Trp Val Arg Gln Met Pro Gly Lys Gly Leu Glu Trp Met
            35                  40                  45

Gly Ser Ile His Gly Gly Ser Gly Ser Arg Asp Tyr Ser Pro Ser Phe
        50                  55                  60

Gln Gly Gln Val Thr Ile Ser Ala Asp Ile Asp Gln Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Pro Gly Tyr Arg Ser Trp Ser Lys Thr Phe Asp Leu Trp Gly
                100                 105                 110

Gln Gly Thr Thr Val Thr Val Ser Ser
        115                 120
```

```
<210> SEQ ID NO 113
<211> LENGTH: 121
<212> TYPE: PRT
<213> ORGANISM: Artificial Sequence
<220> FEATURE:
<223> OTHER INFORMATION: Synthetic construct

<400> SEQUENCE: 113

Gln Glu Gln Leu Gln Glu Ser Gly Pro Gly Leu Val Lys Pro Ser Glu
1               5                   10                  15

Thr Leu Ser Leu Thr Cys Thr Val Ser Gly Phe Asp Phe Asn Thr Phe
                20                  25                  30

Trp Met Thr Trp Ile Arg Gln Pro Pro Gly Lys Gly Leu Glu Trp Ile
            35                  40                  45

Gly Ser Ile His Gly Gly Ser Gly Ser Arg Asp Tyr Asn Pro Ser Leu
        50                  55                  60

Lys Ser Arg Val Thr Ile Ser Val Asp Ile Asp Gln Asn Gln Phe Ser
65                  70                  75                  80

Leu Lys Leu Ser Ser Val Thr Ala Ala Asp Thr Ala Val Tyr Tyr Cys
                85                  90                  95

Ala Arg Pro Gly Tyr Arg Ser Trp Ser Lys Thr Phe Asp Leu Trp Gly
                100                 105                 110

Gln Gly Thr Thr Val Thr Val Ser Ser
        115                 120
```

<210> SEQ ID NO 114
<211> LENGTH: 5
<212> TYPE: PRT
<213> ORGANISM: Artificial Sequence
<220> FEATURE:
<223> OTHER INFORMATION: Synthetic construct

<400> SEQUENCE: 114

Ser Tyr Trp Met His
1               5

<210> SEQ ID NO 115
<211> LENGTH: 19
<212> TYPE: PRT
<213> ORGANISM: Artificial Sequence
<220> FEATURE:
<223> OTHER INFORMATION: Synthetic construct

<400> SEQUENCE: 115

Phe Ile Arg Asn Lys Ala Asn Gly Gly Thr Thr Glu Tyr Ala Ala Ser
1               5                   10                  15

Val Lys Gly

<210> SEQ ID NO 116
<211> LENGTH: 10
<212> TYPE: PRT
<213> ORGANISM: Artificial Sequence
<220> FEATURE:
<223> OTHER INFORMATION: Synthetic construct

<400> SEQUENCE: 116

Asp Arg Gly Leu Arg Phe Tyr Phe Asp Tyr
1               5                   10

<210> SEQ ID NO 117
<211> LENGTH: 14
<212> TYPE: PRT
<213> ORGANISM: Artificial Sequence
<220> FEATURE:
<223> OTHER INFORMATION: Synthetic construct

<400> SEQUENCE: 117

Thr Leu Arg Arg Gly Ile Asn Val Gly Ala Tyr Ser Ile Tyr
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic construct

<400> SEQUENCE: 118

Tyr Lys Ser Asp Ser Asp Lys Gln Gln Gly Ser
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Synthetic construct

<400> SEQUENCE: 119

Met Ile Trp His Ser Gly Ala Ser Ala Val
1               5                   10

<210> SEQ ID NO 120
<211> LENGTH: 120
<212> TYPE: PRT
<213> ORGANISM: Artificial Sequence
<220> FEATURE:
<223> OTHER INFORMATION: Synthetic construct

<400> SEQUENCE: 120

Val Gln Leu Val Glu Ser Gly Gly Gly Leu Val Gln Pro Gly Arg Ser
1               5                   10                  15

Leu Arg Leu Ser Cys Ala Ala Ser Gly Phe Thr Val Ser Ser Tyr Trp
            20                  25                  30

Met His Trp Val Arg Gln Ala Pro Gly Lys Gly Leu Glu Trp Val Gly
        35                  40                  45

Phe Ile Arg Asn Lys Ala Asn Gly Gly Thr Thr Glu Tyr Ala Ala Ser
    50                  55                  60

Val Lys Gly Arg Phe Thr Ile Ser Arg Asp Asp Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Arg Gly Leu Arg Phe Tyr Phe Asp Tyr Trp Gly Gln
            100                 105                 110

Gly Thr Thr Val Thr Val Ser Ser
        115                 120

<210> SEQ ID NO 121
<211> LENGTH: 116
<212> TYPE: PRT
<213> ORGANISM: Artificial Sequence
<220> FEATURE:
<223> OTHER INFORMATION: Synthetic construct

<400> SEQUENCE: 121

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110

Leu Thr Val Leu
        115

<210> SEQ ID NO 122
<211> LENGTH: 5
<212> TYPE: PRT
<213> ORGANISM: Artificial Sequence
<220> FEATURE:
<223> OTHER INFORMATION: Synthetic construct

<400> SEQUENCE: 122

```
Asp Tyr Tyr Met Asn
1               5

<210> SEQ ID NO 123
<211> LENGTH: 19
<212> TYPE: PRT
<213> ORGANISM: Artificial Sequence
<220> FEATURE:
<223> OTHER INFORMATION: Synthetic construct

<400> SEQUENCE: 123

Phe Ile Gly Asn Lys Ala Asn Ala Tyr Thr Thr Glu Tyr Ser Ala Ser
1               5                   10                  15

Val Lys Gly

<210> SEQ ID NO 124
<211> LENGTH: 10
<212> TYPE: PRT
<213> ORGANISM: Artificial Sequence
<220> FEATURE:
<223> OTHER INFORMATION: Synthetic construct

<400> SEQUENCE: 124

Asp Arg Gly Leu Arg Phe Tyr Phe Asp Tyr
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Synthetic construct

<400> SEQUENCE: 125

Arg Ala Ser Ser Ser Val Thr Tyr Ile His
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Synthetic construct

<400> SEQUENCE: 126

Ala Thr Ser Asn Leu Ala Ser
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic construct

<400> SEQUENCE: 127

Gln His Trp Ser Ser Lys Pro Pro Thr
1               5

<210> SEQ ID NO 128
<211> LENGTH: 121
<212> TYPE: PRT
<213> ORGANISM: Artificial Sequence
<220> FEATURE:
<223> OTHER INFORMATION: Synthetic construct

<400> SEQUENCE: 128
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Asn Trp Val Arg Gln Ala Pro Gly Lys Gly Leu Glu Trp Leu
        35                  40                  45

Gly Phe Ile Gly Asn Lys Ala Asn Ala Tyr Thr Thr Glu Tyr Ser Ala
    50                  55                  60

Ser Val Lys Gly Arg Phe Thr Ile Ser Arg Asp Lys Ser Lys Asn Thr
65              70                  75                  80

Leu Tyr Leu Gln Met Asn Ser Leu Arg Ala Glu Asp Thr Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Val Thr Val Ser Ser
            115                 120

<210> SEQ ID NO 129
<211> LENGTH: 106
<212> TYPE: PRT
<213> ORGANISM: Artificial Sequence
<220> FEATURE:
<223> OTHER INFORMATION: Synthetic construct

<400> SEQUENCE: 129

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Thr Tyr Ile
            20                  25                  30

His Trp Tyr Gln Gln Lys Pro Gly Gln Ala Pro Arg Ser Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65              70                  75                  80

Asp Phe Ala Val Tyr Tyr Cys Gln His Trp Ser Ser Lys Pro Pro Thr
                85                  90                  95

Phe Gly Gln Gly Thr Lys Leu Glu Ile Lys
            100                 105

<210> SEQ ID NO 130
<211> LENGTH: 5
<212> TYPE: PRT
<213> ORGANISM: Artificial Sequence
<220> FEATURE:
<223> OTHER INFORMATION: Synthetic construct

<400> SEQUENCE: 130

Thr Tyr Ala Met Asn
1               5

<210> SEQ ID NO 131
<211> LENGTH: 19
<212> TYPE: PRT
<213> ORGANISM: Artificial Sequence
<220> FEATURE:
<223> OTHER INFORMATION: Synthetic construct

<400> SEQUENCE: 131

```
Arg Ile Arg Ser Lys Tyr Asn Asn Tyr Ala Thr Tyr Tyr Ala Asp Ser
1               5                   10                  15

Val Lys Gly

<210> SEQ ID NO 132
<211> LENGTH: 14
<212> TYPE: PRT
<213> ORGANISM: Artificial Sequence
<220> FEATURE:
<223> OTHER INFORMATION: Synthetic construct

<400> SEQUENCE: 132

His Gly Asn Phe Gly Asn Ser Tyr Val Ser Trp Phe Ala Tyr
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Synthetic construct

<400> SEQUENCE: 133

Gly Ser Ser Thr Gly Ala Val Thr Thr Ser Asn Tyr Ala Asn
1               5                   10

<210> SEQ ID NO 134
<211> LENGTH: 7
<212> TYPE: PRT
<213> ORGANISM: Artificial Sequence
<220> FEATURE:
<223> OTHER INFORMATION: Synthetic construct

<400> SEQUENCE: 134

Gly Thr Asn Lys Arg Ala Pro
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic construct

<400> SEQUENCE: 135

Ala Leu Trp Tyr Ser Asn Leu Trp Val
1               5

<210> SEQ ID NO 136
<211> LENGTH: 125
<212> TYPE: PRT
<213> ORGANISM: Artificial Sequence
<220> FEATURE:
<223> OTHER INFORMATION: Synthetic construct

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60
```

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
             85                  90                  95

Tyr Cys Val Arg His Gly Asn Phe Gly Asn Ser Tyr Val Ser Trp Phe
        100                 105                 110

Ala Tyr Trp Gly Gln Gly Thr Leu Val Thr Val Ser Ser
        115                 120                 125

<210> SEQ ID NO 137
<211> LENGTH: 109
<212> TYPE: PRT
<213> ORGANISM: Artificial Sequence
<220> FEATURE:
<223> OTHER INFORMATION: Synthetic construct

<400> SEQUENCE: 137

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
             20                  25                  30

Asn Tyr Ala Asn Trp Val Gln Glu Lys Pro Gly Gln Ala Phe Arg Gly
         35                  40                  45

Leu Ile Gly Gly Thr Asn Lys Arg Ala Pro Gly Thr Pro Ala Arg Phe
     50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
             85                  90                  95

Leu Trp Val Phe Gly Gly Gly Thr Lys Leu Thr Val Leu
        100                 105

<210> SEQ ID NO 138
<211> LENGTH: 5
<212> TYPE: PRT
<213> ORGANISM: Artificial Sequence
<220> FEATURE:
<223> OTHER INFORMATION: Synthetic construct

<400> SEQUENCE: 138

Glu Phe Gly Met Asn
 1               5

<210> SEQ ID NO 139
<211> LENGTH: 17
<212> TYPE: PRT
<213> ORGANISM: Artificial Sequence
<220> FEATURE:
<223> OTHER INFORMATION: Synthetic construct

<400> SEQUENCE: 139

Trp Ile Asn Thr Lys Thr Gly Glu Ala Thr Tyr Val Glu Glu Phe Lys
 1               5                  10                  15

Gly

<210> SEQ ID NO 140
<211> LENGTH: 12
<212> TYPE: PRT
<213> ORGANISM: Artificial Sequence
<220> FEATURE:
<223> OTHER INFORMATION: Synthetic construct

```
<400> SEQUENCE: 140

Trp Asp Phe Ala Tyr Tyr Val Glu Ala Met Asp Tyr
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Synthetic construct

<400> SEQUENCE: 141

Lys Ala Ser Ala Ala Val Gly Thr Tyr Val Ala
1               5                   10

<210> SEQ ID NO 142
<211> LENGTH: 7
<212> TYPE: PRT
<213> ORGANISM: Artificial Sequence
<220> FEATURE:
<223> OTHER INFORMATION: Synthetic construct

<400> SEQUENCE: 142

Ser Ala Ser Tyr Arg Lys Arg
1               5

<210> SEQ ID NO 143
<211> LENGTH: 10
<212> TYPE: PRT
<213> ORGANISM: Artificial Sequence
<220> FEATURE:
<223> OTHER INFORMATION: Synthetic construct

<400> SEQUENCE: 143

His Gln Tyr Tyr Thr Tyr Pro Leu Phe Thr
1               5                   10

<210> SEQ ID NO 144
<211> LENGTH: 121
<212> TYPE: PRT
<213> ORGANISM: Artificial Sequence
<220> FEATURE:
<223> OTHER INFORMATION: Synthetic construct

<400> SEQUENCE: 144

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
        115                 120
```

<210> SEQ ID NO 145
<211> LENGTH: 108
<212> TYPE: PRT
<213> ORGANISM: Artificial Sequence
<220> FEATURE:
<223> OTHER INFORMATION: Synthetic construct

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105

<210> SEQ ID NO 146
<211> LENGTH: 5
<212> TYPE: PRT
<213> ORGANISM: Artificial Sequence
<220> FEATURE:
<223> OTHER INFORMATION: Synthetic construct

<400> SEQUENCE: 146

Asp Thr Tyr Met His
1               5

<210> SEQ ID NO 147
<211> LENGTH: 17
<212> TYPE: PRT
<213> ORGANISM: Artificial Sequence
<220> FEATURE:
<223> OTHER INFORMATION: Synthetic construct

<400> SEQUENCE: 147

Arg Ile Asp Pro Ala Asn Gly Asn Ser Lys Tyr Val Pro Lys Phe Gln
1               5                   10                  15

Gly

<210> SEQ ID NO 148
<211> LENGTH: 12
<212> TYPE: PRT
<213> ORGANISM: Artificial Sequence
<220> FEATURE:
<223> OTHER INFORMATION: Synthetic construct

<400> SEQUENCE: 148

Phe Gly Tyr Tyr Val Ser Asp Tyr Ala Met Ala Tyr
1               5                   10

<210> SEQ ID NO 149
<211> LENGTH: 15
<212> TYPE: PRT
<213> ORGANISM: Artificial Sequence
<220> FEATURE:
<223> OTHER INFORMATION: Synthetic construct

```
<400> SEQUENCE: 149

Arg Ala Gly Glu Ser Val Asp Ile Phe Gly Val Gly Phe Leu His
1               5                   10                  15

<210> SEQ ID NO 150
<211> LENGTH: 7
<212> TYPE: PRT
<213> ORGANISM: Artificial Sequence
<220> FEATURE:
<223> OTHER INFORMATION: Synthetic construct

<400> SEQUENCE: 150

Arg Ala Ser Asn Arg Ala Thr
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic construct

<400> SEQUENCE: 151

Gln Gln Thr Asn Glu Asp Pro Tyr Thr
1               5

<210> SEQ ID NO 152
<211> LENGTH: 121
<212> TYPE: PRT
<213> ORGANISM: Artificial Sequence
<220> FEATURE:
<223> OTHER INFORMATION: Synthetic construct

<400> SEQUENCE: 152

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser
        115                 120

<210> SEQ ID NO 153
<211> LENGTH: 111
<212> TYPE: PRT
<213> ORGANISM: Artificial Sequence
<220> FEATURE:
<223> OTHER INFORMATION: Synthetic construct

<400> SEQUENCE: 153

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
```

```
                    20                  25                  30
Gly Val Gly Phe Leu His Trp Tyr Gln Gln Lys Pro Gly Gln Ala Pro
                35                  40                  45

Arg Leu Leu Ile Tyr Arg Ala Ser Asn Arg Ala Thr Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys
                100                 105                 110

<210> SEQ ID NO 154
<211> LENGTH: 694
<212> TYPE: PRT
<213> ORGANISM: Artificial Sequence
<220> FEATURE:
<223> OTHER INFORMATION: Synthetic construct

<400> SEQUENCE: 154

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
                35                  40                  45

Gly Trp Ile Asn Thr Lys Thr Gly Glu Ala Thr Tyr Val Glu Glu Phe
 50                  55                  60

Lys Gly Arg Val Thr Phe Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
                100                 105                 110

Gln Gly Thr Thr Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
                210                 215                 220

Asp Gly Gly Gly Gly Ser Gly Gly Gly Ser Glu Val Gln Leu Leu
225                 230                 235                 240

Glu Ser Gly Gly Gly Leu Val Gln Pro Gly Gly Ser Leu Arg Leu Ser
                245                 250                 255

Cys Ala Ala Ser Gly Phe Thr Phe Ser Thr Tyr Ala Met Asn Trp Val
                260                 265                 270

Arg Gln Ala Pro Gly Lys Gly Leu Glu Trp Val Ser Arg Ile Arg Ser
```

```
                275                 280                 285
Lys Tyr Asn Asn Tyr Ala Thr Tyr Tyr Ala Asp Ser Val Lys Gly Arg
    290                 295                 300
Phe Thr Ile Ser Arg Asp Asp Ser Lys Asn Thr Leu Tyr Leu Gln Met
305                 310                 315                 320
Asn Ser Leu Arg Ala Glu Asp Thr Ala Val Tyr Tyr Cys Val Arg His
                325                 330                 335
Gly Asn Phe Gly Asn Ser Tyr Val Ser Trp Phe Ala Tyr Trp Gly Gln
                340                 345                 350
Gly Thr Leu Val Thr Val Ser Ser Ala Ser Val Ala Ala Pro Ser Val
                355                 360                 365
Phe Ile Phe Pro Pro Ser Asp Glu Gln Leu Lys Ser Gly Thr Ala Ser
                370                 375                 380
Val Val Cys Leu Leu Asn Asn Phe Tyr Pro Arg Glu Ala Lys Val Gln
385                 390                 395                 400
Trp Lys Val Asp Asn Ala Leu Gln Ser Gly Asn Ser Gln Glu Ser Val
                405                 410                 415
Thr Glu Gln Asp Ser Lys Asp Ser Thr Tyr Ser Leu Ser Ser Thr Leu
                420                 425                 430
Thr Leu Ser Lys Ala Asp Tyr Glu Lys His Lys Val Tyr Ala Cys Glu
                435                 440                 445
Val Thr His Gln Gly Leu Ser Ser Pro Val Thr Lys Ser Phe Asn Arg
                450                 455                 460
Gly Glu Cys Asp Lys Thr His Thr Cys Pro Pro Cys Pro Ala Pro Glu
465                 470                 475                 480
Ala Ala Gly Gly Pro Ser Val Phe Leu Phe Pro Pro Lys Pro Lys Asp
                485                 490                 495
Thr Leu Met Ile Ser Arg Thr Pro Glu Val Thr Cys Val Val Val Asp
                500                 505                 510
Val Ser His Glu Asp Pro Glu Val Lys Phe Asn Trp Tyr Val Asp Gly
                515                 520                 525
Val Glu Val His Asn Ala Lys Thr Lys Pro Arg Glu Glu Gln Tyr Asn
                530                 535                 540
Ser Thr Tyr Arg Val Val Ser Val Leu Thr Val Leu His Gln Asp Trp
545                 550                 555                 560
Leu Asn Gly Lys Glu Tyr Lys Cys Lys Val Ser Asn Lys Ala Leu Gly
                565                 570                 575
Ala Pro Ile Glu Lys Thr Ile Ser Lys Ala Lys Gly Gln Pro Arg Glu
                580                 585                 590
Pro Gln Val Tyr Thr Leu Pro Pro Cys Arg Asp Glu Leu Thr Lys Asn
                595                 600                 605
Gln Val Ser Leu Trp Cys Leu Val Lys Gly Phe Tyr Pro Ser Asp Ile
                610                 615                 620
Ala Val Glu Trp Glu Ser Asn Gly Gln Pro Glu Asn Asn Tyr Lys Thr
625                 630                 635                 640
Thr Pro Pro Val Leu Asp Ser Asp Gly Ser Phe Phe Leu Tyr Ser Lys
                645                 650                 655
Leu Thr Val Asp Lys Ser Arg Trp Gln Gln Gly Asn Val Phe Ser Cys
                660                 665                 670
Ser Val Met His Glu Ala Leu His Asn His Tyr Thr Gln Lys Ser Leu
                675                 680                 685
Ser Leu Ser Pro Gly Lys
                690
```

<210> SEQ ID NO 155
<211> LENGTH: 451
<212> TYPE: PRT
<213> ORGANISM: Artificial Sequence
<220> FEATURE:
<223> OTHER INFORMATION: Synthetic construct

<400> SEQUENCE: 155

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365
```

```
Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 156
<211> LENGTH: 214
<212> TYPE: PRT
<213> ORGANISM: Artificial Sequence
<220> FEATURE:
<223> OTHER INFORMATION: Synthetic construct

<400> SEQUENCE: 156

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 157
<211> LENGTH: 215
<212> TYPE: PRT
<213> ORGANISM: Artificial Sequence
<220> FEATURE:
<223> OTHER INFORMATION: Synthetic construct
```

<400> SEQUENCE: 157

```
Asp Ile Gln Met Thr Gln Ser Pro Ser Leu Ser Ala Ser Val Gly
1               5                   10                  15

Asp Arg Val Thr Ile Thr Cys Lys Ala Ser Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215
```

<210> SEQ ID NO 158
<211> LENGTH: 674
<212> TYPE: PRT
<213> ORGANISM: Artificial Sequence
<220> FEATURE:
<223> OTHER INFORMATION: Synthetic construct

<400> SEQUENCE: 158

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
```

```
                130                 135                 140
Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
                195                 200                 205

Lys Pro Ser Asn Thr Lys Val Asp Glu Lys Val Glu Pro Lys Ser Cys
210                 215                 220

Asp Gly Gly Gly Ser Gly Gly Gly Ser Gln Ala Val Val Thr
225                 230                 235                 240

Gln Glu Pro Ser Leu Thr Val Ser Pro Gly Gly Thr Val Thr Leu Thr
                245                 250                 255

Cys Gly Ser Ser Thr Gly Ala Val Thr Thr Ser Asn Tyr Ala Asn Trp
            260                 265                 270

Val Gln Glu Lys Pro Gly Gln Ala Phe Arg Gly Leu Ile Gly Gly Thr
            275                 280                 285

Asn Lys Arg Ala Pro Gly Thr Pro Ala Arg Phe Ser Gly Ser Leu Leu
290                 295                 300

Gly Gly Lys Ala Ala Leu Thr Leu Ser Gly Ala Gln Pro Glu Asp Glu
305                 310                 315                 320

Ala Glu Tyr Tyr Cys Ala Leu Trp Tyr Ser Asn Leu Trp Val Phe Gly
                325                 330                 335

Gly Gly Thr Lys Leu Thr Val Leu Ser Ser Ala Ser Thr Lys Gly Pro
            340                 345                 350

Ser Val Phe Pro Leu Ala Pro Ser Ser Lys Ser Thr Ser Gly Gly Thr
            355                 360                 365

Ala Ala Leu Gly Cys Leu Val Lys Asp Tyr Phe Pro Glu Pro Val Thr
            370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                405                 410                 415

Val Pro Ser Ser Ser Leu Gly Thr Gln Thr Tyr Ile Cys Asn Val Asn
            420                 425                 430

His Lys Pro Ser Asn Thr Lys Val Asp Lys Lys Val Glu Pro Lys Ser
            435                 440                 445

Cys Asp Lys Thr His Thr Cys Pro Pro Cys Pro Ala Pro Glu Ala Ala
450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
            500                 505                 510

Val His Asn Ala Lys Thr Lys Pro Arg Glu Glu Gln Tyr Asn Ser Thr
            515                 520                 525

Tyr Arg Val Val Ser Val Leu Thr Val Leu His Gln Asp Trp Leu Asn
530                 535                 540

Gly Lys Glu Tyr Lys Cys Lys Val Ser Asn Lys Ala Leu Gly Ala Pro
545                 550                 555                 560
```

```
Ile Glu Lys Thr Ile Ser Lys Ala Lys Gly Gln Pro Arg Glu Pro Gln
                565                 570                 575

Val Tyr Thr Leu Pro Pro Cys Arg Asp Glu Leu Thr Lys Asn Gln Val
            580                 585                 590

Ser Leu Trp Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
            660                 665                 670

Ser Pro
```

<210> SEQ ID NO 159
<211> LENGTH: 449
<212> TYPE: PRT
<213> ORGANISM: Artificial Sequence
<220> FEATURE:
<223> OTHER INFORMATION: Synthetic construct

<400> SEQUENCE: 159

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Ala Ala Gly
225                 230                 235                 240
```

```
Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 160
<211> LENGTH: 232
<212> TYPE: PRT
<213> ORGANISM: Artificial Sequence
<220> FEATURE:
<223> OTHER INFORMATION: Synthetic construct

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
```

```
                145                 150                 155                 160
Glu Ala Lys Val Gln Trp Lys Val Asp Asn Ala Leu Gln Ser Gly Asn
                    165                 170                 175

Ser Gln Glu Ser Val Thr Glu Gln Asp Ser Lys Asp Ser Thr Tyr Ser
                180                 185                 190

Leu Ser Ser Thr Leu Thr Leu Ser Lys Ala Asp Tyr Glu Lys His Lys
                    195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 161
<211> LENGTH: 218
<212> TYPE: PRT
<213> ORGANISM: Artificial Sequence
<220> FEATURE:
<223> OTHER INFORMATION: Synthetic construct

<400> SEQUENCE: 161

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
                20                  25                  30

Gly Val Gly Phe Leu His Trp Tyr Gln Gln Lys Pro Gly Gln Ala Pro
            35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Arg Lys
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 162
<211> LENGTH: 19
<212> TYPE: PRT
<213> ORGANISM: Artificial Sequence
<220> FEATURE:
<223> OTHER INFORMATION: Synthetic construct

<400> SEQUENCE: 162
```

```
Phe Ile Gly Asn Lys Ala Asn Gly Tyr Thr Thr Glu Tyr Ser Ala Ser
1               5                   10                  15

Val Lys Gly
```

<210> SEQ ID NO 163
<211> LENGTH: 121
<212> TYPE: PRT
<213> ORGANISM: Artificial Sequence
<220> FEATURE:
<223> OTHER INFORMATION: Synthetic construct

<400> SEQUENCE: 163

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Asn Trp Val Arg Gln Pro Pro Gly Lys Ala Leu Glu Trp Leu
        35                  40                  45

Gly Phe Ile Gly Asn Lys Ala Asn Gly Tyr Thr Thr Glu Tyr Ser Ala
    50                  55                  60

Ser Val Lys Gly Arg Phe Thr Ile Ser Arg Asp Lys Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Leu Thr Val Ser Ser
        115                 120
```

<210> SEQ ID NO 164
<211> LENGTH: 106
<212> TYPE: PRT
<213> ORGANISM: Artificial Sequence
<220> FEATURE:
<223> OTHER INFORMATION: Synthetic construct

<400> SEQUENCE: 164

```
Gln Thr Val Leu Ser Gln Ser Pro Ala Ile Leu Ser Ala Ser Pro Gly
1               5                   10                  15

Glu Lys Val Thr Met Thr Cys Arg Ala Ser Ser Ser Val Thr Tyr Ile
            20                  25                  30

His Trp Tyr Gln Gln Lys Pro Gly Ser Ser Pro Lys Ser Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln His Trp Ser Ser Lys Pro Pro Thr
                85                  90                  95

Phe Gly Gly Gly Thr Lys Leu Glu Ile Lys
            100                 105
```

<210> SEQ ID NO 165
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE

```
<222> LOCATION: (3)..(3)
<223> OTHER INFORMATION: X is Y or A or E

<400> SEQUENCE: 165

Asp Tyr Xaa Met Asn
1               5

<210> SEQ ID NO 166
<211> LENGTH: 5
<212> TYPE: PRT
<213> ORGANISM: Artificial Sequence
<220> FEATURE:
<223> OTHER INFORMATION: Synthetic construct

<400> SEQUENCE: 166

Asp Tyr Ala Met Asn
1               5

<210> SEQ ID NO 167
<211> LENGTH: 5
<212> TYPE: PRT
<213> ORGANISM: Artificial Sequence
<220> FEATURE:
<223> OTHER INFORMATION: Synthetic construct

<400> SEQUENCE: 167

Asp Tyr Glu Met Asn
1               5

<210> SEQ ID NO 168
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is F or V
<220> FEATURE:
<221> NAME/KEY: MISC_FEATURE
<222> LOCATION: (3)..(3)
<223> OTHER INFORMATION: X is G or S

<400> SEQUENCE: 168

Xaa Ile Xaa Asn Lys Ala Asn Ala Tyr Thr Thr Glu Tyr Ser Ala Ser
1               5                   10                  15

Val Lys Gly

<210> SEQ ID NO 169
<211> LENGTH: 19
<212> TYPE: PRT
<213> ORGANISM: Artificial Sequence
<220> FEATURE:
<223> OTHER INFORMATION: Synthetic construct

<400> SEQUENCE: 169

Val Ile Ser Asn Lys Ala Asn Ala Tyr Thr Thr Glu Tyr Ser Ala Ser
1               5                   10                  15

Val Lys Gly

<210> SEQ ID NO 170
<211> LENGTH: 19
<212> TYPE: PRT
<213> ORGANISM: Artificial Sequence
<220> FEATURE:
<223> OTHER INFORMATION: Synthetic construct
```

```
<400> SEQUENCE: 170

Phe Ile Ser Asn Lys Ala Asn Ala Tyr Thr Thr Glu Tyr Ser Ala Ser
1               5                   10                  15

Val Lys Gly

<210> SEQ ID NO 171
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: X is L or I
<220> FEATURE:
<221> NAME/KEY: MISC_FEATURE
<222> LOCATION: (7)..(7)
<223> OTHER INFORMATION: X is Y or G or Q or S

<400> SEQUENCE: 171

Asp Arg Gly Xaa Arg Phe Xaa Phe Asp Tyr
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Synthetic construct

<400> SEQUENCE: 172

Asp Arg Gly Ile Arg Phe Gly Phe Asp Tyr
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Synthetic construct

<400> SEQUENCE: 173

Asp Arg Gly Leu Arg Phe Ser Phe Asp Tyr
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Synthetic construct

<400> SEQUENCE: 174

Asp Arg Gly Ile Arg Phe Tyr Phe Asp Tyr
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Synthetic construct

<400> SEQUENCE: 175

Asp Arg Gly Ile Arg Phe Gln Phe Asp Tyr
```

```
<210> SEQ ID NO 176
<211> LENGTH: 10
<212> TYPE: PRT
<213> ORGANISM: Artificial Sequence
<220> FEATURE:
<223> OTHER INFORMATION: Synthetic construct

<400> SEQUENCE: 176

Asp Arg Gly Ile Arg Phe Ser Phe Asp Tyr
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is R or H

<400> SEQUENCE: 177

Xaa Ala Ser Ser Ser Val Thr Tyr Ile His
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Synthetic construct

<400> SEQUENCE: 178

His Ala Ser Ser Ser Val Thr Tyr Ile His
1               5                   10

<210> SEQ ID NO 179
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: X is K or V or Q or I
<220> FEATURE:
<221> NAME/KEY: MISC_FEATURE
<222> LOCATION: (7)..(7)
<223> OTHER INFORMATION: X is P or S

<400> SEQUENCE: 179

Gln His Trp Ser Ser Xaa Xaa Pro Thr
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic construct

<400> SEQUENCE: 180

Gln His Trp Ser Ser Val Pro Pro Thr
1               5
```

<210> SEQ ID NO 181
<211> LENGTH: 9
<212> TYPE: PRT
<213> ORGANISM: Artificial Sequence
<220> FEATURE:
<223> OTHER INFORMATION: Synthetic construct

<400> SEQUENCE: 181

Gln His Trp Ser Ser Gln Pro Pro Thr
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic construct

<400> SEQUENCE: 182

Gln His Trp Ser Ser Ile Ser Pro Thr
1               5

<210> SEQ ID NO 183
<211> LENGTH: 9
<212> TYPE: PRT
<213> ORGANISM: Artificial Sequence
<220> FEATURE:
<223> OTHER INFORMATION: Synthetic construct

<400> SEQUENCE: 183

Gln His Trp Ser Ser Lys Ser Pro Thr
1               5

<210> SEQ ID NO 184
<211> LENGTH: 121
<212> TYPE: PRT
<213> ORGANISM: Artificial Sequence
<220> FEATURE:
<223> OTHER INFORMATION: Synthetic construct

<400> SEQUENCE: 184

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Asn Trp Val Arg Gln Ala Pro Gly Lys Gly Leu Glu Trp Leu
        35                  40                  45

Gly Phe Ile Gly Asn Lys Ala Asn Ala Tyr Thr Thr Glu Tyr Ser Ala
    50                  55                  60

Ser Val Lys Gly Arg Phe Thr Ile Ser Arg Asp Lys Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Thr Arg Asp Arg Gly Ile Arg Phe Gly Phe Asp Tyr Trp Gly
            100                 105                 110

Gln Gly Thr Thr Val Thr Val Ser Ser
        115                 120

<210> SEQ ID NO 185
<211> LENGTH: 106
<212> TYPE: PRT
<213> ORGANISM: Artificial Sequence
<220> FEATURE:

<223> OTHER INFORMATION: Synthetic construct

<400> SEQUENCE: 185

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Thr Tyr Ile
            20                  25                  30

His Trp Tyr Gln Gln Lys Pro Gly Gln Ala Pro Arg Ser Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln His Trp Ser Ser Val Pro Pro Thr
                85                  90                  95

Phe Gly Gln Gly Thr Lys Leu Glu Ile Lys
            100                 105
```

<210> SEQ ID NO 186
<211> LENGTH: 121
<212> TYPE: PRT
<213> ORGANISM: Artificial Sequence
<220> FEATURE:
<223> OTHER INFORMATION: Synthetic construct

<400> SEQUENCE: 186

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Asn Trp Val Arg Gln Ala Pro Gly Lys Gly Leu Glu Trp Leu
        35                  40                  45

Gly Phe Ile Gly Asn Lys Ala Asn Ala Tyr Thr Thr Glu Tyr Ser Ala
    50                  55                  60

Ser Val Lys Gly Arg Phe Thr Ile Ser Arg Asp Lys Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Thr Arg Asp Arg Gly Leu Arg Phe Ser Phe Asp Tyr Trp Gly
            100                 105                 110

Gln Gly Thr Thr Val Thr Val Ser Ser
        115                 120
```

<210> SEQ ID NO 187
<211> LENGTH: 106
<212> TYPE: PRT
<213> ORGANISM: Artificial Sequence
<220> FEATURE:
<223> OTHER INFORMATION: Synthetic construct

<400> SEQUENCE: 187

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Thr Tyr Ile
            20                  25                  30

His Trp Tyr Gln Gln Lys Pro Gly Gln Ala Pro Arg Ser Trp Ile Tyr
        35                  40                  45

Ala Thr Ser Asn Leu Ala Ser Gly Ile Pro Ala Arg Phe Ser Gly Ser
```

-continued

```
                50                  55                  60
Gly Ser Gly Thr Asp Phe Thr Leu Thr Ile Ser Ser Leu Glu Pro Glu
 65                  70                  75                  80

Asp Phe Ala Val Tyr Tyr Cys Gln His Trp Ser Ser Gln Pro Pro Thr
                 85                  90                  95

Phe Gly Gln Gly Thr Lys Leu Glu Ile Lys
                100                 105

<210> SEQ ID NO 188
<211> LENGTH: 121
<212> TYPE: PRT
<213> ORGANISM: Artificial Sequence
<220> FEATURE:
<223> OTHER INFORMATION: Synthetic construct

<400> SEQUENCE: 188

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
                 20                  25                  30

Tyr Met Asn Trp Val Arg Gln Ala Pro Gly Lys Gly Leu Glu Trp Leu
             35                  40                  45

Gly Phe Ile Gly Asn Lys Ala Asn Ala Tyr Thr Thr Glu Tyr Ser Ala
 50                  55                  60

Ser Val Lys Gly Arg Phe Thr Ile Ser Arg Asp Lys Ser Lys Asn Thr
 65                  70                  75                  80

Leu Tyr Leu Gln Met Asn Ser Leu Arg Ala Glu Asp Thr Ala Thr Tyr
                 85                  90                  95

Tyr Cys Thr Arg Asp Arg Gly Ile Arg Phe Tyr Phe Asp Tyr Trp Gly
                100                 105                 110

Gln Gly Thr Thr Val Thr Val Ser Ser
            115                 120

<210> SEQ ID NO 189
<211> LENGTH: 106
<212> TYPE: PRT
<213> ORGANISM: Artificial Sequence
<220> FEATURE:
<223> OTHER INFORMATION: Synthetic construct

<400> SEQUENCE: 189

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Ser Val Thr Tyr Ile
                 20                  25                  30

His Trp Tyr Gln Gln Lys Pro Gly Gln Ala Pro Arg Ser Trp Ile Tyr
             35                  40                  45

Ala Thr Ser Asn Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln His Trp Ser Ser Ile Ser Pro Thr
                 85                  90                  95

Phe Gly Gln Gly Thr Lys Leu Glu Ile Lys
                100                 105

<210> SEQ ID NO 190
<211> LENGTH: 121
```

```
<212> TYPE: PRT
<213> ORGANISM: Artificial Sequence
<220> FEATURE:
<223> OTHER INFORMATION: Synthetic construct

<400> SEQUENCE: 190
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Tyr Phe Thr Asp Tyr
            20                  25                  30

Ala Met Asn Trp Val Arg Gln Ala Pro Gly Lys Gly Leu Glu Trp Leu
        35                  40                  45

Gly Val Ile Ser Asn Lys Ala Asn Ala Tyr Thr Thr Glu Tyr Ser Ala
    50                  55                  60

Ser Val Lys Gly Arg Phe Thr Ile Ser Arg Asp Lys Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Val Thr Val Ser Ser
            115                 120

```
<210> SEQ ID NO 191
<211> LENGTH: 106
<212> TYPE: PRT
<213> ORGANISM: Artificial Sequence
<220> FEATURE:
<223> OTHER INFORMATION: Synthetic construct

<400> SEQUENCE: 191
```

Glu Ile Val Leu Thr Gln Ser Pro Ala Thr Leu Ser Leu Ser Pro Gly
1               5                   10                  15

Glu Arg Ala Thr Leu Ser Cys His Ala Ser Ser Ser Val Thr Tyr Ile
            20                  25                  30

His Trp Tyr Gln Gln Lys Pro Gly Gln Ala Pro Arg Ser Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln His Trp Ser Ser Lys Pro Pro Thr
                85                  90                  95

Phe Gly Gln Gly Thr Lys Leu Glu Ile Lys
            100                 105

```
<210> SEQ ID NO 192
<211> LENGTH: 121
<212> TYPE: PRT
<213> ORGANISM: Artificial Sequence
<220> FEATURE:
<223> OTHER INFORMATION: Synthetic construct

<400> SEQUENCE: 192
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Tyr Phe Thr Asp Tyr
            20                  25                  30

Tyr Met Asn Trp Val Arg Gln Ala Pro Gly Lys Gly Leu Glu Trp Leu

```
                35                  40                  45
Gly Phe Ile Ser Asn Lys Ala Asn Ala Tyr Thr Thr Glu Tyr Ser Ala
            50                  55                  60
Ser Val Lys Gly Arg Phe Thr Ile Ser Arg Asp Lys Ser Lys Asn Thr
65                  70                  75                  80
Leu Tyr Leu Gln Met Asn Ser Leu Arg Ala Glu Asp Thr Ala Thr Tyr
                85                  90                  95
Tyr Cys Thr Arg Asp Arg Gly Leu Arg Phe Tyr Phe Asp Tyr Trp Gly
            100                 105                 110
Gln Gly Thr Thr Val Thr Val Ser Ser
        115                 120

<210> SEQ ID NO 193
<211> LENGTH: 106
<212> TYPE: PRT
<213> ORGANISM: Artificial Sequence
<220> FEATURE:
<223> OTHER INFORMATION: Synthetic construct

<400> SEQUENCE: 193

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Ser Ser Val Thr Tyr Ile
            20                  25                  30
His Trp Tyr Gln Gln Lys Pro Gly Gln Ala Pro Arg Ser Trp Ile Tyr
                35                  40                  45
Ala Thr Ser Asn Leu Ala Ser Gly Ile Pro Ala Arg Phe Ser Gly Ser
            50                  55                  60
Gly Ser Gly Thr Asp Phe Thr Leu Thr Ile Ser Ser Leu Glu Pro Glu
65                  70                  75                  80
Asp Phe Ala Val Tyr Tyr Cys Gln His Trp Ser Ser Lys Pro Pro Thr
                85                  90                  95
Phe Gly Gln Gly Thr Lys Leu Glu Ile Lys
            100                 105

<210> SEQ ID NO 194
<211> LENGTH: 121
<212> TYPE: PRT
<213> ORGANISM: Artificial Sequence
<220> FEATURE:
<223> OTHER INFORMATION: Synthetic construct

<400> SEQUENCE: 194

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Thr Asp Tyr
            20                  25                  30
Tyr Met Asn Trp Val Arg Gln Ala Pro Gly Lys Gly Leu Glu Trp Leu
                35                  40                  45
Gly Phe Ile Gly Asn Lys Ala Asn Ala Tyr Thr Thr Glu Tyr Ser Ala
            50                  55                  60
Ser Val Lys Gly Arg Phe Thr Ile Ser Arg Asp Lys Ser Lys Asn Thr
65                  70                  75                  80
Leu Tyr Leu Gln Met Asn Ser Leu Arg Ala Glu Asp Thr Ala Thr Tyr
                85                  90                  95
Tyr Cys Thr Arg Asp Arg Gly Ile Arg Phe Gln Phe Asp Tyr Trp Gly
            100                 105                 110
```

Gln Gly Thr Thr Val Thr Val Ser Ser
            115                 120

<210> SEQ ID NO 195
<211> LENGTH: 106
<212> TYPE: PRT
<213> ORGANISM: Artificial Sequence
<220> FEATURE:
<223> OTHER INFORMATION: Synthetic construct

<400> SEQUENCE: 195

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Thr Tyr Ile
            20                  25                  30

His Trp Tyr Gln Gln Lys Pro Gly Gln Ala Pro Arg Ser Trp Ile Tyr
            35                  40                  45

Ala Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln His Trp Ser Ser Lys Ser Pro Thr
                85                  90                  95

Phe Gly Gln Gly Thr Lys Leu Glu Ile Lys
            100                 105

<210> SEQ ID NO 196
<211> LENGTH: 121
<212> TYPE: PRT
<213> ORGANISM: Artificial Sequence
<220> FEATURE:
<223> OTHER INFORMATION: Synthetic construct

<400> SEQUENCE: 196

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Tyr Phe Thr Asp Tyr
            20                  25                  30

Tyr Met Asn Trp Val Arg Gln Ala Pro Gly Lys Gly Leu Glu Trp Leu
            35                  40                  45

Gly Val Ile Ser Asn Lys Ala Asn Ala Tyr Thr Thr Glu Tyr Ser Ala
        50                  55                  60

Ser Val Lys Gly Arg Phe Thr Ile Ser Arg Asp Lys Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Thr Arg Asp Arg Gly Ile Arg Phe Gln Phe Asp Tyr Trp Gly
            100                 105                 110

Gln Gly Thr Thr Val Thr Val Ser Ser
            115                 120

<210> SEQ ID NO 197
<211> LENGTH: 106
<212> TYPE: PRT
<213> ORGANISM: Artificial Sequence
<220> FEATURE:
<223> OTHER INFORMATION: Synthetic construct

<400> SEQUENCE: 197

Glu Ile Val Leu Thr Gln Ser Pro Ala Thr Leu Ser Leu Ser Pro Gly

```
                1               5                  10                 15
Glu Arg Ala Thr Leu Ser Cys Arg Ala Ser Ser Ser Val Thr Tyr Ile
                20                  25                 30

His Trp Tyr Gln Gln Lys Pro Gly Gln Ala Pro Arg Ser Trp Ile Tyr
                35                  40                 45

Ala Thr Ser Asn Leu Ala Ser Gly Ile Pro Ala Arg Phe Ser Gly Ser
            50                  55                 60

Gly Ser Gly Thr Asp Phe Thr Leu Thr Ile Ser Ser Leu Glu Pro Glu
65                  70                  75                 80

Asp Phe Ala Val Tyr Tyr Cys Gln His Trp Ser Ser Lys Ser Pro Thr
                    85                  90                 95

Phe Gly Gln Gly Thr Lys Leu Glu Ile Lys
                100                 105
```

<210> SEQ ID NO 198
<211> LENGTH: 121
<212> TYPE: PRT
<213> ORGANISM: Artificial Sequence
<220> FEATURE:
<223> OTHER INFORMATION: Synthetic construct

<400> SEQUENCE: 198

```
Glu Val Gln Leu Leu Glu Ser Gly Gly Gly Leu Val Gln Pro Gly Gly
1               5                  10                 15

Ser Leu Arg Leu Ser Cys Ala Ala Ser Gly Phe Tyr Phe Ser Asp Tyr
                20                  25                 30

Tyr Met Asn Trp Val Arg Gln Ala Pro Gly Lys Gly Leu Glu Trp Leu
                35                  40                 45

Gly Val Ile Ser Asn Lys Ala Asn Ala Tyr Thr Thr Glu Tyr Ser Ala
            50                  55                 60

Ser Val Lys Gly Arg Phe Thr Ile Ser Arg Asp Lys Ser Lys Asn Thr
65                  70                  75                 80

Leu Tyr Leu Gln Met Asn Ser Leu Arg Ala Glu Asp Thr Ala Thr Tyr
                    85                  90                 95

Tyr Cys Thr Arg Asp Arg Gly Ile Arg Phe Gln Phe Asp Tyr Trp Gly
                100                 105                110

Gln Gly Thr Thr Val Thr Val Ser Ser
        115                 120
```

<210> SEQ ID NO 199
<211> LENGTH: 106
<212> TYPE: PRT
<213> ORGANISM: Artificial Sequence
<220> FEATURE:
<223> OTHER INFORMATION: Synthetic construct

<400> SEQUENCE: 199

```
Glu Ile Val Leu Thr Gln Ser Pro Ala Thr Leu Ser Leu Ser Pro Gly
1               5                  10                 15

Glu Arg Ala Thr Leu Ser Cys Arg Ala Ser Ser Ser Val Thr Tyr Ile
                20                  25                 30

His Trp Tyr Gln Gln Lys Pro Gly Gln Ala Pro Arg Ser Trp Ile Tyr
                35                  40                 45

Ala Thr Ser Asn Leu Ala Ser Gly Ile Pro Ala Arg Phe Ser Gly Ser
            50                  55                 60

Gly Ser Gly Thr Asp Phe Thr Leu Thr Ile Ser Ser Leu Glu Pro Glu
65                  70                  75                 80
```

Asp Phe Ala Val Tyr Tyr Cys Gln His Trp Ser Ser Lys Ser Pro Thr
                85                  90                  95

Phe Gly Gln Gly Thr Lys Leu Glu Ile Lys
            100                 105

<210> SEQ ID NO 200
<211> LENGTH: 121
<212> TYPE: PRT
<213> ORGANISM: Artificial Sequence
<220> FEATURE:
<223> OTHER INFORMATION: Synthetic construct

<400> SEQUENCE: 200

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Asn Trp Val Arg Gln Ala Pro Gly Lys Gly Leu Glu Trp Leu
        35                  40                  45

Gly Phe Ile Gly Asn Lys Ala Asn Ala Tyr Thr Thr Glu Tyr Ser Ala
    50                  55                  60

Ser Val Lys Gly Arg Phe Thr Ile Ser Arg Asp Lys Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Thr Arg Asp Arg Gly Ile Arg Phe Ser Phe Asp Tyr Trp Gly
            100                 105                 110

Gln Gly Thr Thr Val Thr Val Ser Ser
        115                 120

<210> SEQ ID NO 201
<211> LENGTH: 106
<212> TYPE: PRT
<213> ORGANISM: Artificial Sequence
<220> FEATURE:
<223> OTHER INFORMATION: Synthetic construct

<400> SEQUENCE: 201

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Thr Tyr Ile
            20                  25                  30

His Trp Tyr Gln Gln Lys Pro Gly Gln Ala Pro Arg Ser Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln His Trp Ser Ser Ile Ser Pro Thr
                85                  90                  95

Phe Gly Gln Gly Thr Lys Leu Glu Ile Lys
            100                 105

<210> SEQ ID NO 202
<211> LENGTH: 121
<212> TYPE: PRT
<213> ORGANISM: Artificial Sequence
<220> FEATURE:
<223> OTHER INFORMATION: Synthetic construct

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Tyr Phe Thr Asp Tyr
            20                  25                  30

Tyr Met Asn Trp Val Arg Gln Ala Pro Gly Lys Gly Leu Glu Trp Leu
        35                  40                  45

Gly Val Ile Ser Asn Lys Ala Asn Ala Tyr Thr Thr Glu Tyr Ser Ala
    50                  55                  60

Ser Val Lys Gly Arg Phe Thr Ile Ser Arg Asp Lys Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Thr Arg Asp Arg Gly Ile Arg Phe Ser Phe Asp Tyr Trp Gly
            100                 105                 110

Gln Gly Thr Thr Val Thr Val Ser Ser
        115                 120

<210> SEQ ID NO 203
<211> LENGTH: 106
<212> TYPE: PRT
<213> ORGANISM: Artificial Sequence
<220> FEATURE:
<223> OTHER INFORMATION: Synthetic construct

<400> SEQUENCE: 203

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Thr Tyr Ile
            20                  25                  30

His Trp Tyr Gln Gln Lys Pro Gly Gln Ala Pro Arg Ser Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln His Trp Ser Ser Ile Ser Pro Thr
                85                  90                  95

Phe Gly Gln Gly Thr Lys Leu Glu Ile Lys
            100                 105

<210> SEQ ID NO 204
<211> LENGTH: 121
<212> TYPE: PRT
<213> ORGANISM: Artificial Sequence
<220> FEATURE:
<223> OTHER INFORMATION: Synthetic construct

<400> SEQUENCE: 204

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Tyr Phe Thr Asp Tyr
            20                  25                  30

Ala Met Asn Trp Val Arg Gln Ala Pro Gly Lys Gly Leu Glu Trp Leu
        35                  40                  45

Gly Val Ile Ser Asn Lys Ala Asn Ala Tyr Thr Thr Glu Tyr Ser Ala
    50                  55                  60

```
Ser Val Lys Gly Arg Phe Thr Ile Ser Arg Asp Lys Ser Lys Asn Thr
 65                  70                  75                  80

Leu Tyr Leu Gln Met Asn Ser Leu Arg Ala Glu Asp Thr Ala Thr Tyr
                 85                  90                  95

Tyr Cys Thr Arg Asp Arg Gly Ile Arg Phe Gly Phe Asp Tyr Trp Gly
            100                 105                 110

Gln Gly Thr Thr Val Thr Val Ser Ser
        115                 120

<210> SEQ ID NO 205
<211> LENGTH: 106
<212> TYPE: PRT
<213> ORGANISM: Artificial Sequence
<220> FEATURE:
<223> OTHER INFORMATION: Synthetic construct

<400> SEQUENCE: 205

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Ser Ser Val Thr Tyr Ile
                 20                  25                  30

His Trp Tyr Gln Gln Lys Pro Gly Gln Ala Pro Arg Ser Trp Ile Tyr
             35                  40                  45

Ala Thr Ser Asn Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln His Trp Ser Ser Val Pro Pro Thr
                 85                  90                  95

Phe Gly Gln Gly Thr Lys Leu Glu Ile Lys
            100                 105

<210> SEQ ID NO 206
<211> LENGTH: 121
<212> TYPE: PRT
<213> ORGANISM: Artificial Sequence
<220> FEATURE:
<223> OTHER INFORMATION: Synthetic construct

<400> SEQUENCE: 206

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
                 20                  25                  30

Glu Met Asn Trp Val Arg Gln Ala Pro Gly Lys Gly Leu Glu Trp Leu
             35                  40                  45

Gly Phe Ile Ser Asn Lys Ala Asn Ala Tyr Thr Thr Glu Tyr Ser Ala
 50                  55                  60

Ser Val Lys Gly Arg Phe Thr Ile Ser Arg Asp Lys Ser Lys Asn Thr
 65                  70                  75                  80

Leu Tyr Leu Gln Met Asn Ser Leu Arg Ala Glu Asp Thr Ala Thr Tyr
                 85                  90                  95

Tyr Cys Thr Arg Asp Arg Gly Ile Arg Phe Gly Phe Asp Tyr Trp Gly
            100                 105                 110

Gln Gly Thr Thr Val Thr Val Ser Ser
        115                 120

<210> SEQ ID NO 207
```

<211> LENGTH: 106
<212> TYPE: PRT
<213> ORGANISM: Artificial Sequence
<220> FEATURE:
<223> OTHER INFORMATION: Synthetic construct

<400> SEQUENCE: 207

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Thr Tyr Ile
            20                  25                  30

His Trp Tyr Gln Gln Lys Pro Gly Gln Ala Pro Arg Ser Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln His Trp Ser Ser Val Pro Pro Thr
                85                  90                  95

Phe Gly Gln Gly Thr Lys Leu Glu Ile Lys
            100                 105

<210> SEQ ID NO 208
<211> LENGTH: 420
<212> TYPE: PRT
<213> ORGANISM: Artificial Sequence
<220> FEATURE:
<223> OTHER INFORMATION: Synthetic construct

<400> SEQUENCE: 208

Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
            20                  25                  30

Trp Tyr Lys Gly Glu Arg Val Asp Gly Asn Arg Gln Ile Val Gly Tyr
        35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Phe Ile Thr Ser Asn Asn Ser Asn Pro Val Glu Asp Glu Asp Ala
        115                 120                 125

Val Ala Leu Thr Cys Glu Pro Glu Ile Gln Asn Thr Thr Tyr Leu Trp
    130                 135                 140

Trp Val Asn Asn Gln Ser Leu Pro Val Ser Pro Arg Leu Gln Leu Ser
145                 150                 155                 160

Asn Asp Asn Arg Thr Leu Thr Leu Leu Ser Val Thr Arg Asn Asp Val
                165                 170                 175

Gly Pro Tyr Glu Cys Gly Ile Gln Asn Lys Leu Ser Val Asp His Ser
            180                 185                 190

Asp Pro Val Ile Leu Asn Val Leu Tyr Gly Pro Asp Asp Pro Thr Ile
        195                 200                 205

Ser Pro Ser Tyr Thr Tyr Tyr Arg Pro Gly Val Asn Leu Ser Leu Ser

-continued

```
            210                 215                 220
Cys His Ala Ala Ser Asn Pro Pro Ala Gln Tyr Ser Trp Leu Ile Asp
225                 230                 235                 240

Gly Asn Ile Gln Gln His Thr Gln Glu Leu Phe Ile Ser Asn Ile Thr
                245                 250                 255

Glu Lys Asn Ser Gly Leu Tyr Thr Cys Gln Ala Asn Asn Ser Ala Ser
            260                 265                 270

Gly His Ser Arg Thr Thr Val Lys Thr Ile Thr Val Ser Ala Leu Ser
            275                 280                 285

Pro Val Val Ala Lys Pro Gln Ile Lys Ala Ser Lys Thr Thr Val Thr
        290                 295                 300

Gly Asp Lys Asp Ser Val Asn Leu Thr Cys Ser Thr Asn Asp Thr Gly
305                 310                 315                 320

Ile Ser Ile Arg Trp Phe Phe Lys Asn Gln Ser Leu Pro Ser Ser Glu
                325                 330                 335

Arg Met Lys Leu Ser Gln Gly Asn Ile Thr Leu Ser Ile Asn Pro Val
            340                 345                 350

Lys Arg Glu Asp Ala Gly Thr Tyr Trp Cys Glu Val Phe Asn Pro Ile
            355                 360                 365

Ser Lys Asn Gln Ser Asp Pro Ile Met Leu Asn Val Asn Tyr Asn Ala
        370                 375                 380

Leu Pro Gln Glu Asn Leu Ile Asn Val Asp Gly Ser Gly Leu Asn Asp
385                 390                 395                 400

Ile Phe Glu Ala Gln Lys Ile Glu Trp His Glu Ala Arg Ala His His
                405                 410                 415

His His His His
        420

<210> SEQ ID NO 209
<211> LENGTH: 435
<212> TYPE: PRT
<213> ORGANISM: Artificial Sequence
<220> FEATURE:
<223> OTHER INFORMATION: Synthetic construct

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Gly Ala
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
```

```
            145                 150                 155                 160
Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Lys Val Glu Pro Lys
        195                 200                 205

Ser Cys Asp Lys Thr His Thr Cys Pro Pro Cys Pro Ala Pro Glu Ala
    210                 215                 220

Ala Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Gly Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Cys Arg Asp Glu Leu Thr Lys Asn Gln
            340                 345                 350

Val Ser Leu Trp Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro
        435

<210> SEQ ID NO 210
<211> LENGTH: 449
<212> TYPE: PRT
<213> ORGANISM: Artificial Sequence
<220> FEATURE:
<223> OTHER INFORMATION: Synthetic construct

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Asn Trp Val Arg Gln Ala Pro Gly Lys Gly Leu Glu Trp Leu
        35                  40                  45

Gly Phe Ile Gly Asn Lys Ala Asn Ala Tyr Thr Thr Glu Tyr Ser Ala
    50                  55                  60

Ser Val Lys Gly Arg Phe Thr Ile Ser Arg Asp Lys Ser Lys Asn Thr
```

```
            65                  70                  75                  80
Leu Tyr Leu Gln Met Asn Ser Leu Arg Ala Glu Asp Thr Ala Thr Tyr
                85                  90                  95

Tyr Cys Thr Arg Asp Arg Gly Leu Arg Phe Tyr Phe Asp Tyr Trp Gly
                100                 105                 110

Gln Gly Thr Thr Val Thr Val Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Glu Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
                340                 345                 350

Cys Thr Leu Pro Pro Ser Arg Asp Glu Leu Thr Lys Asn Gln Val Ser
                355                 360                 365

Leu Ser Cys Ala Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro

<210> SEQ ID NO 211
<211> LENGTH: 228
<212> TYPE: PRT
<213> ORGANISM: Artificial Sequence
<220> FEATURE:
```

<223> OTHER INFORMATION: Synthetic construct

<400> SEQUENCE: 211

```
Gln Glu Gln Leu Val Gln Ser Gly Ala Glu Val Lys Lys Pro Gly Glu
1               5                   10                  15

Ser Leu Lys Ile Ser Cys Lys Gly Ser Gly Phe Asp Phe Asn Thr Phe
            20                  25                  30

Trp Met Thr Trp Val Arg Gln Met Pro Gly Lys Gly Leu Glu Trp Met
        35                  40                  45

Gly Ser Ile His Gly Gly Ser Gly Ser Arg Asp Tyr Ser Pro Ser Phe
    50                  55                  60

Gln Gly Gln Val Thr Ile Ser Ala Asp Ile Asp Gln Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Pro Gly Tyr Arg Ser Trp Ser Lys Thr Phe Asp Leu Trp Gly
            100                 105                 110

Gln Gly Thr Thr Val Thr Val Ser Ser Ala Ser Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly Glu Cys
225
```

<210> SEQ ID NO 212
<211> LENGTH: 213
<212> TYPE: PRT
<213> ORGANISM: Artificial Sequence
<220> FEATURE:
<223> OTHER INFORMATION: Synthetic construct

<400> SEQUENCE: 212

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Thr Tyr Ile
            20                  25                  30

His Trp Tyr Gln Gln Lys Pro Gly Gln Ala Pro Arg Ser Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln His Trp Ser Ser Lys Pro Pro Thr
                85                  90                  95

Phe Gly Gln Gly Thr Lys Leu Glu Ile Lys Arg Thr Val Ala Ala Pro
            100                 105                 110
```

```
Ser Val Phe Ile Phe Pro Pro Ser Asp Arg Lys Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 213
<211> LENGTH: 449
<212> TYPE: PRT
<213> ORGANISM: Artificial Sequence
<220> FEATURE:
<223> OTHER INFORMATION: Synthetic construct

<400> SEQUENCE: 213

Gln Glu Gln Leu Val Gln Ser Gly Ala Glu Val Lys Lys Pro Gly Glu
1               5                   10                  15

Ser Leu Lys Ile Ser Cys Lys Gly Ser Gly Phe Asp Phe Asn Thr Phe
            20                  25                  30

Trp Met Thr Trp Val Arg Gln Met Pro Gly Lys Gly Leu Glu Trp Met
        35                  40                  45

Gly Ser Ile His Gly Gly Ser Gly Ser Arg Asp Tyr Ser Pro Ser Phe
    50                  55                  60

Gln Gly Gln Val Thr Ile Ser Ala Asp Ile Asp Gln Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Pro Gly Tyr Arg Ser Trp Ser Lys Thr Phe Asp Leu Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 214
<211> LENGTH: 436
<212> TYPE: PRT
<213> ORGANISM: Artificial Sequence
<220> FEATURE:
<223> OTHER INFORMATION: Synthetic construct

<400> SEQUENCE: 214

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Thr Tyr Ile
            20                  25                  30

His Trp Tyr Gln Gln Lys Pro Gly Gln Ala Pro Arg Ser Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln His Trp Ser Ser Lys Pro Pro Thr
                85                  90                  95

Phe Gly Gln Gly Thr Lys Leu Glu Ile Lys Ser Ser Ala Ser Thr Lys
            100                 105                 110

Gly Pro Ser Val Phe Pro Leu Ala Pro Ser Ser Lys Ser Thr Ser Gly
        115                 120                 125

Gly Thr Ala Ala Leu Gly Cys Leu Val Lys Asp Tyr Phe Pro Glu Pro
    130                 135                 140

Val Thr Val Ser Trp Asn Ser Gly Ala Leu Thr Ser Gly Val His Thr
145                 150                 155                 160
```

Phe Pro Ala Val Leu Gln Ser Ser Gly Leu Tyr Ser Leu Ser Ser Val
                165                 170                 175

Val Thr Val Pro Ser Ser Leu Gly Thr Gln Thr Tyr Ile Cys Asn
            180                 185                 190

Val Asn His Lys Pro Ser Asn Thr Lys Val Asp Lys Lys Val Glu Pro
        195                 200                 205

Lys Ser Cys Asp Lys Thr His Thr Cys Pro Pro Cys Pro Ala Pro Glu
    210                 215                 220

Ala Ala Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Gly
305                 310                 315                 320

Ala Pro Ile Glu Lys Thr Ile Ser Lys Ala Lys Gly Gln Pro Arg Glu
                325                 330                 335

Pro Gln Val Cys Thr Leu Pro Pro Ser Arg Asp Glu Leu Thr Lys Asn
            340                 345                 350

Gln Val Ser Leu Ser Cys Ala Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Val Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro
        435

<210> SEQ ID NO 215
<211> LENGTH: 214
<212> TYPE: PRT
<213> ORGANISM: Artificial Sequence
<220> FEATURE:
<223> OTHER INFORMATION: Synthetic construct

<400> SEQUENCE: 215

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Gly Ala
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 216
<211> LENGTH: 228
<212> TYPE: PRT
<213> ORGANISM: Artificial Sequence
<220> FEATURE:
<223> OTHER INFORMATION: Synthetic construct

<400> SEQUENCE: 216

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Tyr Phe Thr Asp Tyr
            20                  25                  30

Tyr Met Asn Trp Val Arg Gln Ala Pro Gly Lys Gly Leu Glu Trp Leu
        35                  40                  45

Gly Phe Ile Ser Asn Lys Ala Asn Ala Tyr Thr Thr Glu Tyr Ser Ala
    50                  55                  60

Ser Val Lys Gly Arg Phe Thr Ile Ser Arg Asp Lys Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Val Thr Val Ser Ser Ala Ser Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly Glu Cys
225

<210> SEQ ID NO 217
<211> LENGTH: 117
<212> TYPE: PRT
<213> ORGANISM: Artificial Sequence
<220> FEATURE:
<223> OTHER INFORMATION: Synthetic construct

<400> SEQUENCE: 217

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 218
<211> LENGTH: 107
<212> TYPE: PRT
<213> ORGANISM: Artificial Sequence
<220> FEATURE:
<223> OTHER INFORMATION: Synthetic construct

<400> SEQUENCE: 218

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Ile
                85                  90                  95

Thr Phe Gly Gly Gly Thr Lys Val Glu Ile Lys
            100                 105

<210> SEQ ID NO 219
<211> LENGTH: 117
<212> TYPE: PRT
<213> ORGANISM: Artificial Sequence
<220> FEATURE:
<223> OTHER INFORMATION: Synthetic construct

<400> SEQUENCE: 219

Gln Val Gln Leu Gln Gln Trp Gly Ala Gly Leu Leu Lys Pro Ser Glu

```
                1               5                  10                 15
            Thr Leu Ser Leu Thr Cys Ala Val Tyr Gly Gly Ser Phe Ser Gly Tyr
                        20                  25                 30

Tyr Trp Ser Trp Ile Arg Gln Pro Pro Gly Lys Gly Leu Glu Trp Ile
                        35                  40                 45

Gly Glu Ile Asp His Ser Gly Ser Thr Asn Tyr Asn Pro Ser Leu Lys
                        50                  55                 60

Ser Arg Val Thr Ile Ser Val Asp Thr Ser Lys Asn Gln Phe Ser Leu
            65                  70                  75                 80

Lys Leu Ser Ser Val Thr Ala Ala Asp Thr Ala Val Tyr Tyr Cys Ala
                        85                  90                 95

Arg Ala Arg Gly Pro Trp Ser Phe Asp Pro Trp Gly Gln Gly Thr Leu
                        100                 105                110

Val Thr Val Ser Ser
                        115

<210> SEQ ID NO 220
<211> LENGTH: 106
<212> TYPE: PRT
<213> ORGANISM: Artificial Sequence
<220> FEATURE:
<223> OTHER INFORMATION: Synthetic construct

<400> SEQUENCE: 220

Asp Ile Gln Met Thr Gln Ser Pro Ser Thr Leu Ser Ala Ser Val Gly
1               5                  10                 15

Asp Arg Val Thr Ile Thr Cys Arg Ala Ser Gln Ser Ile Ser Ser Trp
            20                  25                 30

Leu Ala Trp Tyr Gln Gln Lys Pro Gly Lys Ala Pro Lys Leu Leu Ile
            35                  40                 45

Tyr Lys Ala Ser Ser Leu Glu Ser Gly Val Pro Ser Arg Phe Ser Gly
            50                  55                 60

Ser Gly Ser Gly Thr Glu Phe Thr Leu Thr Ile Ser Ser Leu Gln Pro
65                  70                  75                 80

Asp Asp Phe Ala Thr Tyr Tyr Cys Gln Gln Tyr Asn Ser Tyr Pro Thr
            85                  90                 95

Phe Gly Gly Gly Thr Lys Val Glu Ile Lys
            100                 105

<210> SEQ ID NO 221
<211> LENGTH: 447
<212> TYPE: PRT
<213> ORGANISM: Artificial Sequence
<220> FEATURE:
<223> OTHER INFORMATION: Synthetic construct

<400> SEQUENCE: 221

Gln Val Gln Leu Gln Gln Trp Gly Ala Gly Leu Leu Lys Pro Ser Glu
1               5                  10                 15

Thr Leu Ser Leu Thr Cys Ala Val Tyr Gly Gly Ser Phe Ser Gly Tyr
            20                  25                 30

Tyr Trp Ser Trp Ile Arg Gln Pro Pro Gly Lys Gly Leu Glu Trp Ile
            35                  40                 45

Gly Glu Ile Asp His Ser Gly Ser Thr Asn Tyr Asn Pro Ser Leu Lys
            50                  55                 60

Ser Arg Val Thr Ile Ser Val Asp Thr Ser Lys Asn Gln Phe Ser Leu
65                  70                  75                 80
```

```
Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 222
<211> LENGTH: 214
<212> TYPE: PRT
<213> ORGANISM: Artificial Sequence
<220> FEATURE:
<223> OTHER INFORMATION: Synthetic construct

<400> SEQUENCE: 222
```

-continued

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Ile
            85                  90                  95

Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 223
<211> LENGTH: 447
<212> TYPE: PRT
<213> ORGANISM: Artificial Sequence
<220> FEATURE:
<223> OTHER INFORMATION: Synthetic construct

<400> SEQUENCE: 223

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Ala Arg Gly Pro Trp Ser Phe Asp Pro Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140
```

-continued

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 224
<211> LENGTH: 213
<212> TYPE: PRT
<213> ORGANISM: Artificial Sequence
<220> FEATURE:
<223> OTHER INFORMATION: Synthetic construct

<400> SEQUENCE: 224

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Pro Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
            210

<210> SEQ ID NO 225
<211> LENGTH: 439
<212> TYPE: PRT
<213> ORGANISM: Artificial Sequence
<220> FEATURE:
<223> OTHER INFORMATION: Synthetic construct

<400> SEQUENCE: 225

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Gly Ser Phe Pro Ile
                 85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
            130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
                180                 185                 190

Asn Val Asn His Lys Pro Ser Asn Thr Lys Val Asp Lys Lys Val Glu
                195                 200                 205
```

Pro Lys Ser Cys Asp Lys Thr His Thr Cys Pro Pro Cys Pro Ala Pro
210                 215                 220

Glu Ala Ala Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
                260                 265                 270

Gly Val Glu Val His Asn Ala Lys Thr Lys Pro Arg Glu Glu Gln Tyr
                275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Ala Leu
305                 310                 315                 320

Gly Ala Pro Ile Glu Lys Thr Ile Ser Lys Ala Lys Gly Gln Pro Arg
                325                 330                 335

Glu Pro Gln Val Cys Thr Leu Pro Pro Ser Arg Asp Glu Leu Thr Lys
                340                 345                 350

Asn Gln Val Ser Leu Ser Cys Ala Val Lys Gly Phe Tyr Pro Ser Asp
                355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Val Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
                420                 425                 430

Leu Ser Leu Ser Pro Gly Lys
            435

<210> SEQ ID NO 226
<211> LENGTH: 224
<212> TYPE: PRT
<213> ORGANISM: Artificial Sequence
<220> FEATURE:
<223> OTHER INFORMATION: Synthetic construct

<400> SEQUENCE: 226

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
                100                 105                 110

Val Thr Val Ser Ser Ala Ser Val Ala Ala Pro Ser Val Phe Ile Phe
            115                 120                 125

```
Pro Pro Ser Asp Glu Gln Leu Lys Ser Gly Thr Ala Ser Val Val Cys
            130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
            195                 200                 205

Gln Gly Leu Ser Ser Pro Val Thr Lys Ser Phe Asn Arg Gly Glu Cys
210                 215                 220
```

<210> SEQ ID NO 227
<211> LENGTH: 438
<212> TYPE: PRT
<213> ORGANISM: Artificial Sequence
<220> FEATURE:
<223> OTHER INFORMATION: Synthetic construct

<400> SEQUENCE: 227

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Thr
                85                  90                  95

Phe Gly Gly Gly Thr Lys Val Glu Ile Lys Ser Ser Ala Ser Thr Lys
            100                 105                 110

Gly Pro Ser Val Phe Pro Leu Ala Pro Ser Ser Lys Ser Thr Ser Gly
        115                 120                 125

Gly Thr Ala Ala Leu Gly Cys Leu Val Lys Asp Tyr Phe Pro Glu Pro
130                 135                 140

Val Thr Val Ser Trp Asn Ser Gly Ala Leu Thr Ser Gly Val His Thr
145                 150                 155                 160

Phe Pro Ala Val Leu Gln Ser Ser Gly Leu Tyr Ser Leu Ser Ser Val
                165                 170                 175

Val Thr Val Pro Ser Ser Ser Leu Gly Thr Gln Thr Tyr Ile Cys Asn
            180                 185                 190

Val Asn His Lys Pro Ser Asn Thr Lys Val Asp Lys Val Glu Pro
        195                 200                 205

Lys Ser Cys Asp Lys Thr His Thr Cys Pro Pro Cys Pro Ala Pro Glu
210                 215                 220

Ala Ala Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270
```

Val Glu Val His Asn Ala Lys Thr Lys Pro Arg Glu Gln Tyr Asn
            275                 280                 285

Ser Thr Tyr Arg Val Val Ser Val Leu Thr Val Leu His Gln Asp Trp
        290                 295                 300

Leu Asn Gly Lys Glu Tyr Lys Cys Lys Val Ser Asn Lys Ala Leu Gly
305                 310                 315                 320

Ala Pro Ile Glu Lys Thr Ile Ser Lys Ala Lys Gly Gln Pro Arg Glu
                325                 330                 335

Pro Gln Val Cys Thr Leu Pro Pro Ser Arg Asp Glu Leu Thr Lys Asn
            340                 345                 350

Gln Val Ser Leu Ser Cys Ala Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Val Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys
            435

<210> SEQ ID NO 228
<211> LENGTH: 224
<212> TYPE: PRT
<213> ORGANISM: Artificial Sequence
<220> FEATURE:
<223> OTHER INFORMATION: Synthetic construct

<400> SEQUENCE: 228

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
    130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
                195                 200                 205

Gln Gly Leu Ser Ser Pro Val Thr Lys Ser Phe Asn Arg Gly Glu Cys
    210                 215                 220

<210> SEQ ID NO 229
<211> LENGTH: 451
<212> TYPE: PRT
<213> ORGANISM: Artificial Sequence
<220> FEATURE:
<223> OTHER INFORMATION: Synthetic construct

<400> SEQUENCE: 229

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Asn Trp Val Arg Gln Ala Pro Gly Lys Gly Leu Glu Trp Leu
        35                  40                  45

Gly Phe Ile Gly Asn Lys Ala Asn Ala Tyr Thr Thr Glu Tyr Ser Ala
    50                  55                  60

Ser Val Lys Gly Arg Phe Thr Ile Ser Arg Asp Lys Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

```
Glu Lys Thr Ile Ser Lys Ala Lys Gly Gln Pro Arg Glu Pro Gln Val
                340                 345                 350

Tyr Thr Leu Pro Pro Cys Arg Asp Glu Leu Thr Lys Asn Gln Val Ser
            355                 360                 365

Leu Trp Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 230
<211> LENGTH: 213
<212> TYPE: PRT
<213> ORGANISM: Artificial Sequence
<220> FEATURE:
<223> OTHER INFORMATION: Synthetic construct

<400> SEQUENCE: 230

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Thr Tyr Ile
            20                  25                  30

His Trp Tyr Gln Gln Lys Pro Gly Gln Ala Pro Arg Ser Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln His Trp Ser Ser Lys Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Arg Lys Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```